(12) United States Patent
Nakamura et al.

(10) Patent No.: US 8,093,241 B2
(45) Date of Patent: Jan. 10, 2012

(54) ACID AMIDE DERIVATIVES, PROCESS FOR THEIR PRODUCTION AND PESTICIDES CONTAINING THEM

(75) Inventors: Yuji Nakamura, Shiga (JP); Masayuki Morita, Shiga (JP); Tetsuo Yoneda, Shiga (JP); Kenji Izakura, Shiga (JP)

(73) Assignee: Ishihara Sangyo Kaisha, Ltd., Osaka-shi (JP)

( * ) Notice: Subject to any disclaimer, the term of this patent is extended or adjusted under 35 U.S.C. 154(b) by 76 days.

(21) Appl. No.: 12/640,140

(22) Filed: Dec. 17, 2009

(65) Prior Publication Data
US 2010/0093707 A1   Apr. 15, 2010

Related U.S. Application Data

(62) Division of application No. 10/489,778, filed as application No. PCT/JP02/09560 on Sep. 18, 2002, now Pat. No. 7,683,096.

(30) Foreign Application Priority Data

Sep. 18, 2001 (JP) ................................ 2001-283969

(51) Int. Cl.
| | |
|---|---|
| A01N 43/84 | (2006.01) |
| A01N 37/18 | (2006.01) |
| A01N 43/60 | (2006.01) |
| A01N 43/40 | (2006.01) |
| A01N 43/56 | (2006.01) |
| A01N 43/42 | (2006.01) |
| C07C 233/64 | (2006.01) |
| C07D 409/02 | (2006.01) |
| C07D 231/10 | (2006.01) |
| C07D 213/46 | (2006.01) |
| C07D 215/14 | (2006.01) |
| C07D 263/54 | (2006.01) |

(52) U.S. Cl. ...................... 514/224.2; 564/185; 514/617; 514/336; 514/332; 514/311; 514/375; 514/230.5; 544/405; 544/105; 546/280.4; 546/168; 548/217

(58) Field of Classification Search ............... 514/224.2, 514/617, 336, 406, 354; 564/185; 544/405; 546/280.4, 328, 262; 548/374.1
See application file for complete search history.

(56) References Cited

U.S. PATENT DOCUMENTS

| 3,716,573 A | 2/1973 | Pives |
| 7,439,366 B2 | 10/2008 | Nakamura et al. |
| 2003/0153464 A1 | 8/2003 | Nakamura et al. |
| 2008/0318779 A1 | 12/2008 | Nakamura et al. |

FOREIGN PATENT DOCUMENTS

| EP | 0 600 629 | 6/1994 |
| EP | 0 816 330 | 1/1998 |
| EP | 0 816 348 A1 | 1/1998 |
| JP | 05-70350 | 3/1993 |
| JP | 2001-302606 | 10/2001 |
| WO | WO 98/08838 | 3/1998 |
| WO | WO 01/60783 | 8/2001 |

OTHER PUBLICATIONS

U.S. Appl. No. 12/740,121, filed Apr. 28, 2010, Mitani, et al.
Garcia et al., Combined solidprand solution synthesis of a library of a, a-disubstituted-a-acylaminoketones, Tetrahedron Letters 43 (2002) 7495-7498.
Von Ulf Fischer, et al., "97.1,3-Dipolare Addition von 2-Benzonitrilio-2-propanid an 7-Methylthieno [2,3-c]pyridin-1,1-dioxid und Folgereaktionen", Helvetica Chimica Acta, vol. 66, No. 3, 1983,1 front page, pp. 971-988.
Seemon H. Pines, et al., "3-Aryl-2methylserines III. Synthesis Via Alanine Azlactone", Tetrahedron Letters, No. 9, 1969, pp. 727-728.
Seemon H. Pines, et al., "3-aryl-2-methylserines. I. A New Synthesis", The Journal of Organic Chemistry, vol. 33, No. 5, May 1968, pp. 1758-1761.
Shozo Ueda, et al., "Novel Base-Induced Reactions of Substituted (1, 2-Benzisoxazol-3-yl) acetates", Journal of the Chemical Society Perkin Transactions I, No. 5, 1988, pp. 1013-1021. Rene J. Lachicotte et al., "C-acylation of hippurate and related esters utilizing multiple anion intermediates and ethyl 4-aminobenzoate", Synthetic Communications, 1990, vol. 20, No. 1, pp. 63-69.
U.S. Appl. No. 12/095,517, filed May 30, 2008, Nakamura, et al.
U.S. Appl. No. 12/822,204, filed Jun. 24, 2010, Nakamura, et al.
U.S. Appl. No. 12/822,206, filed Jun. 24, 2010, Nakamura, et al.

*Primary Examiner* — Robert A Wax
*Assistant Examiner* — Aradhana Sasan
(74) *Attorney, Agent, or Firm* — Oblon, Spivak, McClelland, Maier & Neustadt, L.L.P.

(57) ABSTRACT

The present invention relates to an acid amid derivative of the formula (I) or a salt thereof:

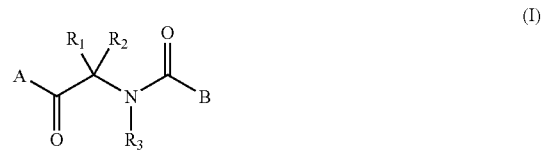

(I)

wherein A is phenyl which may be substituted by X, benzyl which may be substituted by X, naphthyl which may be substituted by X, a heterocyclic group which may be substituted by X, a fused heterocyclic group which may be substituted by X, indanyl (the indanyl may be substituted by halogen, alkyl or alkoxy) or tetrahydronaphthyl (the tetrahydronaphthyl may be substituted by halogen, alkyl or alkoxy), B is alkyl, cycloalkyl, phenyl which may be substituted by Y, a heterocyclic group which may be substituted by Y, or a condensed heterocyclic group which may be substituted by Y, each of $R_1$ and $R_2$ is alkyl, cyano or $-CO_2R_{14}$, or $R_1$ and $R_2$ may together form a 3- to 6-membered saturated carbocyclic ring, $R_3$ is hydrogen, alkyl, alkoxyalkyl, alkylthioalkyl, $-COR_{15}$, $-S(O)mR_{16}$ or $-S(O)nNR_{17}R_{18}$, which is useful as an active ingredient of pesticides.

11 Claims, No Drawings

ACID AMIDE DERIVATIVES, PROCESS FOR THEIR PRODUCTION AND PESTICIDES CONTAINING THEM

This application is a Divisional of U.S. application Ser. No. 10/489,778, filed on Mar. 17, 2004, which is a National Stage of PCT/JP02/09560, filed on Sep. 18, 2002.

TECHNICAL FIELD

The present invention relates to novel acid amide derivatives useful as active ingredients for pesticides.

BACKGROUND ART

WO 2001/60783 discloses phenacylamine derivatives, a process for their production and pesticides containing them, but there is no specific disclosure relating to acid amide derivatives of the formula (I) given hereinafter.

DISCLOSURE OF THE INVENTION

Over the years, a number of pesticides have been used, but many of them have various problems such that the effects are inadequate, their use is restricted as the pests have acquired resistance, they have high toxicity against human, animal, fish, etc., and their residual effects disturb the ecological system. Accordingly, it is desired to develop novel pesticides having high safety without such drawbacks.

Further, parasites on animals are parasitic on the body surfaces, stomachs, intestinal tracts, lungs, hearts, livers, blood vessels, subcutis and lymphatic tissues of domestic animals or companion animals and thus cause various animal diseases, such as anemia, malnutrition, asthenia, weight loss or disorders of intestinal tract walls, organs or other tissues. Accordingly, it is desired to control such parasites.

The present inventors have conducted various studies on acid amide derivatives to find a superior pesticide. As a result, it has been found that novel acid amide derivatives and their salts have very high controlling effects against pests at low doses, and they show no substantial adverse effects against mammals, fish, etc. The present invention has been accomplished on the basis of this discovery. That is the present invention provides an acid amide derivative of the formula (I) or a salt thereof:

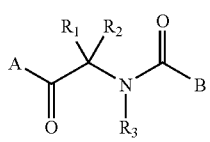

(I)

wherein A is phenyl which may be substituted by X, benzyl which may be substituted by X, naphthyl which may be substituted by X, a heterocyclic group which may be substituted by X, a fused heterocyclic group which may be substituted by X, indanyl (the indanyl may be substituted by halogen, alkyl or alkoxy) or tetrahydronaphthyl (the tetrahydronaphthyl may be substituted by halogen, alkyl or alkoxy), B is alkyl, cycloalkyl, phenyl which may be substituted by Y, a heterocyclic group which may be substituted by Y, or a fused heterocyclic group which may be substituted by Y, X is halogen, alkyl, haloalkyl, alkenyl, haloalkenyl, alkynyl, haloalkynyl, alkoxy, haloalkoxy, alkoxyalkoxy, haloalkoxyalkoxy, alkoxyhaloalkoxy, haloalkoxyhaloalkoxy, alkenyloxy, haloalkenyloxy, alkynyloxy, haloalkynyloxy, alkylthio, haloalkylthio, alkenylthio, haloalkenylthio, alkynylthio, haloalkynylthio, alkylsulfinyl, haloalkylsulfinyl, alkylsulfonyl, haloalkylsulfonyl, dialkylaminosulfonyl, nitro, cyano, phenyl which may be substituted by Y, phenoxy which may be substituted by Y, benzyloxy which may be substituted by Y, pyridyloxy which may be substituted by Y, —$OR_4$, —$SR_5$, —$NR_6R_7$, —$CO_2R_8$, —$C(=O)NR_9R_{10}$ or an unsaturated heterocyclic group (the unsaturated heterocyclic ring may be substituted by halogen, alkyl, haloalkyl, alkoxy or haloalkoxy), Y is halogen, alkyl, haloalkyl, alkoxy, haloalkoxy, alkylthio, haloalkylthio, alkylsulfinyl, haloalkylsulfinyl, alkylsulfonyl, haloalkylsulfonyl, dialkylaminosulfonyl, nitro, cyano, —$OR_4$, —$CO_2R_{11}$, —$CONR_{12}R_{13}$ or an unsaturated heterocyclic group (the unsaturated heterocyclic ring may be substituted by halogen, alkyl, haloalkyl, alkoxy or haloalkoxy), each of $R_1$ and $R_2$ is alkyl, cyano or —$CO_2R_{14}$, or $R_1$ and $R_2$ may together form a 3- to 6-membered saturated carbocyclic ring, $R_3$ is hydrogen, alkyl, alkoxyalkyl, alkylthioalkyl, —$COR_{15}$, —$S(O)mR_{16}$ or —$S(O)nNR_{17}R_{18}$, each of $R_4$ and $R_6$ is hydrogen, —$C(=W)R_{19}$, —$C(=W)OR_{20}$, —$C(=W)SR_{21}$, —$C(=W)NR_{22}R_{23}$, —$S(O)qR_{24}$ or —$S(O)rNR_{25}R_{26}$, $R_5$ is hydrogen, —$C(=W)R_{19}$, —$C(=W)OR_{20}$, —$C(=W)SR_{21}$ or —$C(=W)NR_{22}R_{23}$, $R_7$ is hydrogen, alkyl or haloalkyl, each of $R_8$, $R_9$, $R_{10}$, $R_{11}$, $R_{12}$, $R_{13}$ and $R_{14}$ is hydrogen or alkyl, $R_{15}$ is hydrogen, alkyl or alkoxy, each of $R_{16}$, $R_{17}$, $R_{18}$, $R_{19}$, $R_{20}$, $R_{21}$, $R_{22}$, $R_{23}$, $R_{24}$, $R_{25}$ and $R_{26}$ is alkyl, haloalkyl or phenyl (the phenyl which may be substituted by halogen, alkyl, haloalkyl, alkoxy or haloalkoxy), each of m, n, q and r is from 0 to 2, W is oxygen or sulfur, provided that (1) a case where A is phenyl which may be substituted by $X_1$, B is alkyl, cycloalkyl, phenyl which may be substituted by $Y_1$, pyridyl which may be substituted by $Y_1$ or pyrazolyl which may be substituted by $Y_1$, each of $R_1$ and $R_2$ is alkyl, or $R_1$ and $R_2$ together form a 3- to 6-membered saturated carbocyclic ring, $R_3$ is hydrogen, alkyl, alkoxyalkyl, alkylthioalkyl, alkylcarbonyl or alkoxycarbonyl, $X_1$ is halogen, alkyl, haloalkyl, alkenyl, haloalkenyl, alkynyl, haloalkynyl, alkoxy, haloalkoxy, alkenyloxy, haloalkenyloxy, alkynyloxy, haloalkynyloxy, alkylthio, haloalkylthio, alkenylthio, haloalkenylthio, alkynylthio, haloalkynylthio, alkylsulfinyl, haloalkylsulfinyl, alkylsulfonyl, haloalkylsulfonyl, dialkylaminosulfonyl, nitro, cyano, phenyl which may be substituted by $Y_1$, phenoxy which may be substituted by $Y_1$, benzyloxy which may be substituted by $Y_1$ or pyridyloxy which may be substituted by $Y_1$, and $Y_1$ is halogen, alkyl, haloalkyl, alkoxy, haloalkoxy, alkylthio, haloalkylthio, alkylsulfinyl, haloalkylsulfinyl, alkylsulfonyl, haloalkylsulfonyl, dialkylaminosulfonyl, nitro or cyano, and (2) N-[1-methyl-1-(2'-methylisonicotinoyl)ethyl]benzamide, are excluded; a process for its production; and a pesticide containing it.

The number of substituents X in the phenyl which may be substituted by X, the benzyl which may be substituted by X, the naphthyl which may be substituted by X, the heterocyclic group which may be substituted by X or the fused heterocyclic group which may be substituted by X, in A, may be one or more, and in the case of more than one, such substituents may be the same or different, and the number of substituents Y in the phenyl which may be substituted by Y, the heterocyclic group which may be substituted by Y or the fused heterocyclic group which may be substituted by Y, in B, or the number of substituents Y in the phenyl which may be substituted by Y, the phenoxy which may be substituted by Y, the benzyloxy which may be substituted by Y or the pyridyloxy which may be substituted by Y, in X, may be one or more, and in the case of more than one, such substituents may be the same or different. The number of halogen, alkyl or alkoxy which is substituent of indanyl or tetrahydronaphthyl, may be one or more, and in the case of more than one, such substituents may be the same or different. The number of the substituent of the unsaturated heterocyclic group in X or Y, or the number of the substituent of the phenyl in $R_{16}$ to $R_{26}$, may be one or more, and in the case of more than one, such substituents may be the same or different.

The heterocyclic group in A or B, is a 5- or 6-membered heterocyclic group containing from 1 to 4 atoms of at least one type selected from the group consisting of O, S and N, such as furyl, tetrahydrofuryl, thienyl, pyrrolyl, pyrrolinyl, pyrrolidinyl, dioxolanyl, oxazolyl, isoxazolyl, thiazolyl, isothiazolyl, imidazolyl, imidazolinyl, imidazolidinyl, pyrazolyl, pyrazolinyl, pyrazolidinyl, triazolyl, oxadiazolyl, thiadiazolyl, tetrazolyl, pyranyl, pyridyl, piperidinyl, dioxanyl, oxazinyl, morpholinyl, thiazinyl, pyridazinyl, pyrimidinyl, pyrazinyl, piperazinyl or triazinyl.

The fused heterocyclic group in A or B, is a 8- to 10-membered fused heterocyclic group containing from 1 to 4 atoms of at least one type selected from the group consisting of O, S and N, such as benzofuranyl, isobenzofuranyl, dihydrobenzofuranyl, dihydroisobenzofuranyl, benzothienyl, isobenzothienyl, dihydrobenzothienyl, dihydroisobenzothienyl, tetrahydrobenzothienyl, indolyl, isoindolyl, benzoxazolyl, benzothiazolyl, indazolyl, benzimidazolyl, benzodioxolanyl, benzodioxanyl, chromenyl, chromanyl, isochromanyl, chromonyl, chromanonyl, quinolyl, isoquinolyl, cinnolinyl, phthalazinyl, quinazolinyl, quinoxalinyl, indolizinyl, quinolizinyl, imidazopyridyl, naphthyridinyl, pteridinyl, dihydrobenzoxazinyl, dihydrobenzoxazolinonyl, dihydrobenzoxazinonyl or benzothioxanyl.

The unsaturated heterocyclic group in X or Y, is a 5- to 6-membered unsaturated heterocyclic group containing from 1 to 4 atoms of at least one type selected from the group consisting of O, S and N, such as furyl, thienyl, pyrrolyl, pyrrolinyl, oxazolyl, isoxazolyl, thiazolyl, isothiazolyl, imidazolyl, imidazolinyl, pyrazolyl, pyrazolinyl, triazolyl, oxadiazolyl, thiadiazolyl, tetrazolyl, pyranyl, pyridyl, oxazinyl, thiazinyl, pyridazinyl, pyrimidinyl, pyrazinyl, or triazinyl.

The alkyl or alkyl moiety in B, X, Y, $R_1$ to $R_3$ or $R_7$ to $R_{26}$, the alkyl or alkyl moiety as a substituent of indanyl or tetrahydronaphthyl, in A, the alkyl or alkyl moiety as a substituent of unsaturated heterocyclic group in X or Y, or, the alkyl or alkyl moiety as a substituent of phenyl in $R_{16}$ to $R_{26}$, may be linear or branched one having from 1 to 6 carbon atoms, such as methyl, ethyl, propyl, isopropyl, butyl, tert-butyl, pentyl or hexyl.

The cycloalkyl in B may be one having from 3 to 6 carbon atoms, such as cyclopropyl, cyclopentyl or cyclohexyl.

The alkenyl or alkenyl moiety in X may be linear or branched one having from 2 to 7 carbon atoms, such as vinyl, 1-propenyl, allyl, isopropenyl, 1-butenyl, 1,3-butadienyl, 1-hexenyl or 1-heptenyl. Further, the alkynyl or alkynyl moiety in X may be linear or branched one having from 2 to 7 carbon atoms, such as ethynyl, 2-butynyl, 2-pentynyl, 3-hexynyl or 4-dimethyl-2-pentynyl.

As the halogen or the halogen as a substituent in A, X, Y, $R_7$ or $R_{16}$ to $R_{26}$ (include halogen as a substituent of indanyl or tetrahydronaphthyl, in A, halogen as a substituent of unsaturated heterocyclic group in X and Y, and halogen as a substituent of phenyl in $R_{16}$ to $R_{26}$), an atom of fluorine, chlorine, bromine or iodine may be mentioned. The number of halogens as substituents may be one or more, and in a case where it is more than one, the respective halogens may be the same or different. Further, such halogens may be substituted at any position.

The salt of the acid amide derivative of the above formula (I) may be any salt so long as it is agriculturally acceptable. For example, it may be an alkali metal salt such as a sodium salt or a potassium salt; an alkaline earth metal salt such as a magnesium salt or a calcium salt; an ammonium salt such as a dimethylamine salt or a triethylamine salt; an inorganic salt such as a hydrochloride, a perchlorate, a sulfate or a nitrate; or an organic salt such as an acetate or a methanesulfonate.

The acid amide derivative of the above formula (I) has various isomers such as optical isomers and tautomeric isomers, and the present invention includes both isomers and mixtures of such isomers. Further, the present invention also includes various isomers other than the above isomers within the common knowledge in the technical field concerned.

The acid amide derivative of the above formula (I) or a salt thereof (hereinafter referred to simply as the compound of the present invention) can be produced by the following reactions (A) to (K), or by a usual process for producing a salt.

Reaction A

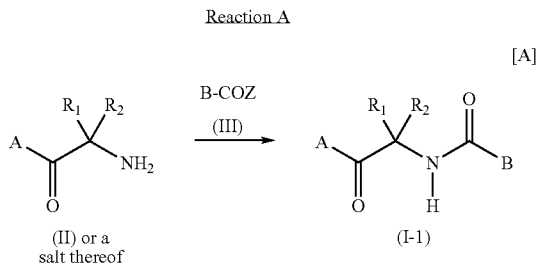

[A]

(II) or a salt thereof (I-1)

In the reaction (A), A, B, $R_1$, and $R_2$, are as defined above. Z is hydroxy, alkoxy or halogen, and the halogen may be an atom of fluorine, chlorine, bromine or iodine.

Reaction (A) is carried out usually in the presence of a base and a solvent.

The base may be one or more suitably selected from e.g. an alkali metal such as sodium or potassium; an alkali metal alcoholate such as sodium methylate, sodium ethylate or potassium tertiary butoxide; a carbonate such as sodium carbonate or potassium carbonate; a bicarbonate such as sodium bicarbonate or potassium bicarbonate; a metal hydroxide such as sodium hydroxide or potassium hydroxide; a metal hydride such as sodium hydride or potassium hydride; an amine such as monomethylamine, dimethylamine or triethylamine; and a pyridine such as pyridine or 4-dimethylaminopyridine. The base is used in an amount of from 1 to 3 mols, preferably from 1 to 2 mols, per mol of the compound of the formula (II).

The solvent may be any solvent so long as it is a solvent inert to the reaction. For example, it may be one or more suitably selected from e.g. an aromatic hydrocarbon such as benzene, toluene, xylene or chlorobenzene; an aliphatic hydrocarbon such as carbon tetrachloride, methyl chloride, chloroform, dichloromethane, dichloroethane, trichloroethane, hexane or cyclohexane; an ether such as dioxane, tetrahydrofuran, diethyl ether or dimethoxyethane; an ester such as methyl acetate or ethyl acetate; a polar aprotic solvent such as dimethyl sulfoxide, sulfolane, dimethylacetamide, dimethylformamide, N-methylpyrrolidone or pyridine; a nitrile such as acetonitrile, propionitrile or acrylonitrile and a ketone such as acetone or methyl ethyl ketone.

Reaction (A) is carried out, if necessary, in the presence of a dehydration condensation agent. The dehydration condensation agent may, for example, be N,N'-dicyclohexylcarbodiimide, chlorosulfonyl isocyanate, N,N'-carbonyldiimidazole and trifluoroacetic anhydride.

The reaction temperature for reaction (A) is usually from 0 to 100° C., preferably from 0 to 50° C., and the reaction time is usually from 0.5 to 48 hours, preferably from 1 to 24 hours.

Reaction B

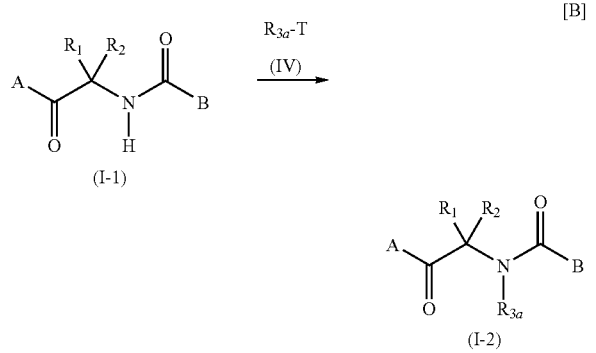

In reaction (B), A, B, $R_1$ and $R_2$ are as defined above, and $R_{3a}$ is alkyl, alkoxyalkyl, alkylthioalkyl, —$COR_{15}$, —$S(O)_m R_{16}$ or —$S(O)_n NR_{17}R_{18}$ (wherein $R_{15}$, $R_{16}$, $R_{17}$, $R_{18}$, m and n are as defined above), and T is halogen, and the halogen may be an atom of fluorine, chlorine, bromine or iodine.

Reaction (B) is carried out usually in the presence of a base and a solvent.

The base may be one or more suitably selected from e.g. an alkali metal such as sodium or potassium; an alkali metal alcoholate such as sodium methylate, sodium ethylate or potassium tertiary butoxide; a carbonate such as sodium carbonate or potassium carbonate; a bicarbonate such as sodium bicarbonate or potassium bicarbonate; a metal hydroxide such as sodium hydroxide or potassium hydroxide; a metal hydride such as sodium hydride or potassium hydride; an amine such as monomethylamine, dimethylamine or triethylamine; and a pyridine such as pyridine or 4-dimethylaminopyridine. The base is used in an amount of from 1 to 3 mols, preferably from 1 to 1.5 mols, per mol of the compound of the formula (I-1).

The solvent may be any solvent so long as it is a solvent inert to the reaction. For example, it may be one or more suitably selected from e.g. an aromatic hydrocarbon such as benzene, toluene, xylene or chlorobenzene; an aliphatic hydrocarbon such as carbon tetrachloride, methyl chloride, chloroform, dichloromethane, dichloroethane, trichloroethane, hexane or cyclohexane; an ether such as dioxane, tetrahydrofuran, diethyl ether or dimethoxyethane; an ester such as methyl acetate or ethyl acetate; a polar aprotic solvent such as dimethyl sulfoxide, sulfolane, dimethylacetamide, dimethylformamide, N-methylpyrrolidone or pyridine; a nitrile such as acetonitrile, propionitrile or acrylonitrile; and a ketone such as acetone or methyl ethyl ketone.

The reaction temperature for reaction (B) is usually from 0 to 100° C., preferably from 0 to 50° C., and the reaction time is usually from 1 to 300 hours, preferably from 1 to 150 hours.

Reaction (C)

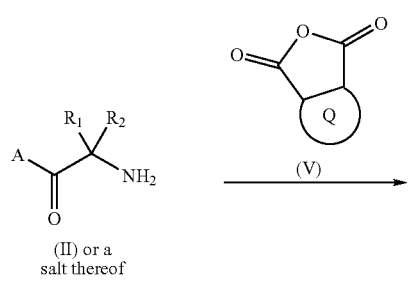

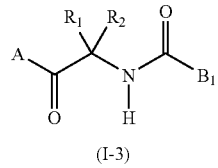

In reaction (C), A, $R_1$ and $R_2$ are as defined above, and $B_1$ is phenyl substituted by —$CO_2H$, a heterocyclic group substituted by —$CO_2H$, or a fused heterocyclic group substituted by —$CO_2H$. The formula (V) is anhydrous dicarboxylic acid of Q (phenyl, a heterocyclic group or a fused heterocyclic group).

Reaction (C) is carried out usually in the presence of a solvent. The solvent may be any solvent so long as it is a solvent inert to the reaction. For example, it may be one or more suitably selected from e.g. an aromatic hydrocarbon such as benzene, toluene, xylene or chlorobenzene; an aliphatic hydrocarbon such as carbon tetrachloride, methyl chloride, chloroform, dichloromethane, dichloroethane, trichloroethane, hexane or cyclohexane; an ether such as dioxane, tetrahydrofuran, diethyl ether or dimethoxy ethane; an ester such as methyl acetate or ethyl acetate; a polar aprotic solvent such as dimethyl sulfoxide, sulfolane, dimethylacetamide, dimethylformamide, N-methylpyrrolidone or pyridine; a nitrile such as acetonitrile, propionitrile or acrylonitrile; a ketone such as acetone or methyl ethyl ketone; and an alcohol such as methanol, ethanol, propanol or tert-butanol.

Reaction (C) is carried out, if necessary, in the presence of a base. The base may be one or more suitably selected from e.g. an alkali metal such as sodium or potassium; an alkali metal alcoholate such as sodium methylate, sodium ethylate or potassium tertiary butoxide; a carbonate such as sodium carbonate or potassium carbonate; a bicarbonate such as sodium bicarbonate or potassium bicarbonate; a metal hydroxide such as sodium hydroxide or potassium hydroxide; a metal hydride such as sodium hydride or potassium hydride; an amine such as monomethylamine, dimethylamine or triethylamine; and a pyridine such as pyridine or 4-dimethylaminopyridine. The base is used in an amount of from 1 to 3 mols, preferably from 1 to 1.5 mols, per mol of the compound of the formula (II).

The reaction temperature for reaction (C) is usually from 0 to 150° C., preferably from 0 to 80° C. The reaction time is usually from 0.5 to 96 hours, preferably from 1 to 48 hours.

Reaction D

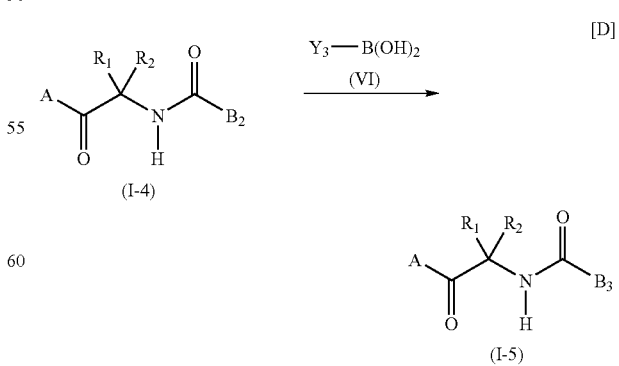

In reaction (D), A, $R_1$ and $R_2$ are as defined above. $B_2$ is phenyl substituted by $Y_2$, a heterocyclic group substituted by $Y_2$, or a fused heterocyclic group substituted by $Y_2$, $B_3$ is phenyl substituted by $Y_3$, a heterocyclic group substituted by $Y_3$, or a fused heterocyclic group substituted by $Y_3$, $Y_2$ is an atom of chlorine, bromine or iodine, and $Y_3$ is an unsaturated heterocyclic group (the unsaturated heterocyclic ring may be substituted by halogen, alkyl, haloalkyl, alkoxy or haloalkoxy).

Reaction (D) is carried out usually in the presence of a catalyst, a base, a solvent and an inert gas.

The catalyst may be one or more suitably selected from e.g. palladium complexes such as tetrakis(triphenylphosphine)palladium(0), bis(dibenzylideneacetone)palladium(0), and tris(dibenzylideneacetone)dipalladium(0).

The base may be one or more suitably selected from e.g. a carbonate such as sodium carbonate, potassium carbonate or calcium carbonate; a bicarbonate such as sodium bicarbonate or potassium bicarbonate; and a metal hydroxide such as sodium hydroxide or potassium hydroxide. The base is used in an amount of from 1 to 20 mols, preferably from 1 to 10 mols, per mol of the compound of the formula (I-4).

The solvent may be any solvent so long as it is a solvent inert to the reaction. For example, it may be one or more suitably selected from e.g. an aromatic hydrocarbon such as benzene, toluene, xylene or chlorobenzene; an aliphatic hydrocarbon such as carbon tetrachloride, methyl chloride, chloroform, dichloromethane, dichloroethane, trichloroethane, hexane or cyclohexane; an ether such as dioxane, tetrahydrofuran, diethyl ether or dimethoxyethane; an ester such as methyl acetate or ethyl acetate; a polar aprotic solvent such as dimethyl sulfoxide, sulfolane, dimethylacetamide, dimethylformamide, N-methylpyrrolidone or pyridine; a nitrile such as acetonitrile, propionitrile or acrylonitrile; a ketone such as acetone or methyl ethyl ketone; an alcohol such as methanol, ethanol, propanol or tert-butanol; and water.

The inert gas may, for example, be nitrogen gas or argon gas.

The reaction temperature for reaction (D) is usually from 0 to 150° C., preferably from 15 to 100° C. The reaction time is usually from 0.5 to 96 hours, preferably from 1 to 48 hours.

Reaction E

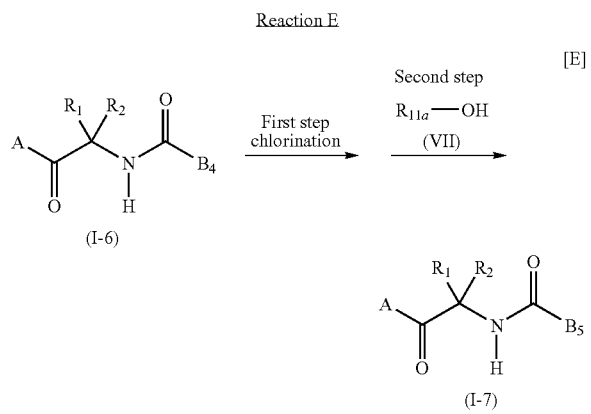

[E]

In reaction (E), A, $R_1$ and $R_2$ are as defined above, and $B_4$ is phenyl substituted by —$CO_2H$, a heterocyclic group substituted by —$CO_2H$, or a fused heterocyclic group substituted by —$CO_2H$, $B_5$ is phenyl substituted by —$CO_2R_{11a}$, a heterocyclic group substituted by —$CO_2R_{11a}$, or a fused heterocyclic group substituted by —$CO_2R_{11a}$, and $R_{11a}$ is alkyl.

The first step in reaction (E) is carried out in the presence of a chlorination agent. The chlorination agent may be one or more suitably selected from e.g. thionyl chloride, oxalyl chloride and phosphorus pentachloride.

The first step in reaction (E) is carried out, if necessary, in the presence of a solvent. The solvent may be any solvent so long as it is a solvent inert to the reaction. For example, it may be one or more suitably selected from e.g. an aromatic hydrocarbon such as benzene, toluene, xylene or chlorobenzene; an aliphatic hydrocarbon such as carbon tetrachloride, methyl chloride, chloroform, dichloromethane, dichloroethane, trichloroethane, hexane or cyclohexane; an ether such as dioxane, tetrahydrofuran, diethyl ether or dimethoxyethane; and an ester such as methyl acetate or ethyl acetate.

The reaction temperature for the first step in reaction (E) is usually from 0 to 200° C., preferably from 15 to 150° C. The reaction time is usually from 0.1 to 72 hours, preferably from 0.5 to 3 hours.

The second step in reaction (E) is carried out, if necessary, in the presence of a base. The base may be one or more suitably selected from e.g. an alkali metal such as sodium or potassium; an alkali metal alcoholate such as sodium methylate, sodium ethylate or potassium tertiary butoxide; a carbonate such as sodium carbonate or potassium carbonate; a bicarbonate such as sodium bicarbonate or potassium bicarbonate; a metal hydroxide such as sodium hydroxide or potassium hydroxide; a metal hydride such as sodium hydride or potassium hydride; an amine such as monomethylamine, dimethylamine or triethylamine; and a pyridine such as pyridine or 4-dimethylaminopyridine. The base is used in an amount of from 1 to 5 mols, preferably from 1 to 2 mols, per mol of the compound of the formula (I-6).

The second step in reaction (E) is carried out, if necessary, in the presence of a solvent. The solvent may be any solvent so long as it is a solvent inert to the reaction. For example, it may be one or more suitably selected from e.g. an aromatic hydrocarbon such as benzene, toluene, xylene or chlorobenzene; an aliphatic hydrocarbon such as carbon tetrachloride, methyl chloride, chloroform, dichloromethane, dichloroethane, trichloroethane, hexane or cyclohexane; an ether such as dioxane, tetrahydrofuran, diethyl ether or dimethoxyethane; an ester such as methyl acetate or ethyl acetate; a polar aprotic solvent such as dimethyl sulfoxide, sulfolane, dimethylacetamide, dimethylformamide, N-methylpyrrolidone or pyridine; a nitrile such as acetonitrile, propionitrile or acrylonitrile; and a ketone such as acetone or methyl ethyl ketone. Further, in this reaction, the compound of the formula (VII) may serve also as a solvent if used excessively.

The reaction temperature for the second step in reaction (E) is usually from 0 to 100° C., preferably from 0 to 50° C. The reaction time is usually from 0.1 to 48 hours, preferably from 0.5 to 6 hours.

Reaction F

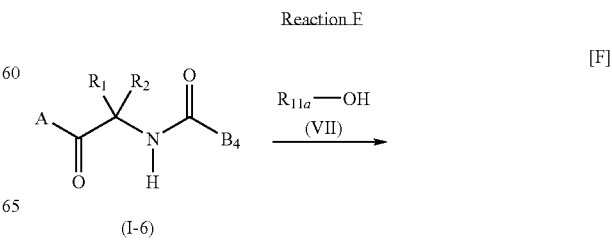

[F]

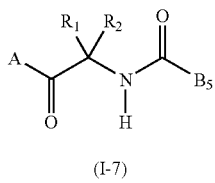

(I-7)

In reaction (F), A, $B_4B_5$, $R_1$, $R_2$ and $B_{11a}$ are as defined above.

Reaction (F) is carried out usually in the presence of a catalyst or a dehydration condensation agent.

The catalyst may be one or more suitably selected from e.g. a mineral acid such as hydrochloric acid or sulfuric acid; an organic acid such as paratoluene sulfonic acid; and a Lewis acid such as boron trifluoride etherate.

The dehydration condensation agent may be one or more suitably selected from e.g. N,N'-dicyclohexylcarbodiimide, chlorosulfonyl isocyanate, N,N'-carbonyldiimidazole and trifluoroacetic anhydride.

Reaction (F) is carried out, if necessary, in the presence of a solvent. The solvent may be any solvent so long as it is a solvent inert to the reaction. For example, it may be one or more suitably selected from e.g. an aromatic hydrocarbon such as benzene, toluene, xylene or chlorobenzene; an aliphatic hydrocarbon such as carbon tetrachloride, methyl chloride, chloroform, dichloromethane, dichloroethane, trichloroethane, hexane or cyclohexane; an ether such as dioxane, tetrahydrofuran, diethyl ether or dimethoxyethane; an ester such as methyl acetate or ethyl acetate; a polar aprotic solvent such as dimethyl sulfoxide, sulfolane, dimethylacetamide, dimethylformamide, N-methylpyrrolidone or pyridine; a nitrile such as acetonitrile, propionitrile or acrylonitrile; a ketone such as acetone or methyl ethyl ketone; and an alcohol such as methanol, ethanol, propanol or tert-butanol. Further, in this reaction, the compound of the formula (VII) may serve also as a solvent if used excessively.

The reaction temperature for reaction (F) is usually from 0 to 200° C., preferably from 0 to 100° C. The reaction time is usually from 0.1 to 96 hours, preferably from 0.5 to 24 hours.

heterocyclic group substituted by —$CONR_{12}R_{13}$ (wherein $R_{12}$ and $R_{13}$ are as defined above).

The first step in reaction (G) is carried out in accordance with the first step in the above-described reaction (E).

The second step in the reaction (G) is carried out, if necessary, in the presence of a base. The base may be one or more suitably selected from e.g. an alkali metal such as sodium or potassium; an alkali metal alcoholate such as sodium methylate, sodium ethylate or potassium tertiary butoxide; a carbonate such as sodium carbonate or potassium carbonate; a bicarbonate such as sodium bicarbonate or potassium bicarbonate; a metal hydroxide such as sodium hydroxide or potassium hydroxide; a metal hydride such as sodium hydride or potassium hydride; an amine such as monomethylamine, dimethylamine or triethylamine; and a pyridine such as pyridine or 4-dimethylaminopyridine. The base is used in an amount of from 1 to 10 mols, preferably from 1 to 2 mols, per mol of the compound of the formula (I-6).

The second step in reaction (G) is carried out, if necessary, in the presence of a solvent. The solvent may be any solvent so long as it is a solvent inert to the reaction. For example, it may be one or more suitably selected from e.g. an aromatic hydrocarbon such as benzene, toluene, xylene or chlorobenzene; an aliphatic hydrocarbon such as carbon tetrachloride, methyl chloride, chloroform, dichloromethane, dichloroethane, trichloroethane, hexane or cyclohexane; an ether such as dioxane, tetrahydrofuran, diethyl ether or dimethoxyethane; an ester such as methyl acetate or ethyl acetate; a polar aprotic solvent such as dimethyl sulfoxide, sulfolane, dimethylacetamide, dimethylformamide, N-methylpyrrolidone or pyridine; a nitrile such as acetonitrile, propionitrile or acrylonitrile; a ketone such as acetone or methyl ethyl ketone; and water.

The reaction temperature for the second step in reaction (G) is usually from 0 to 100° C., preferably from 0 to 50° C. The reaction time is usually from 0.1 to 48 hours, preferably from 0.5 to 6 hours.

Reaction G

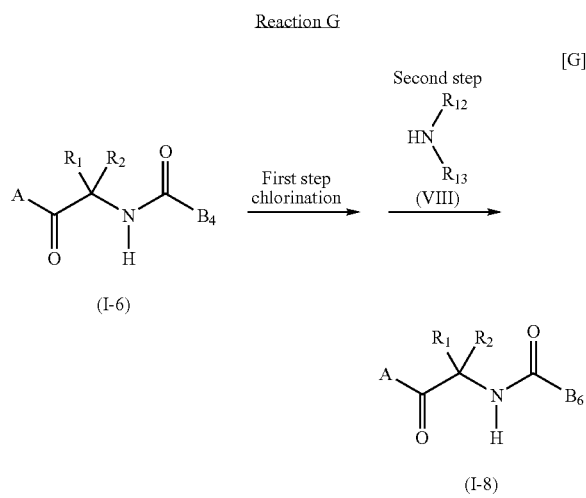

Reaction H

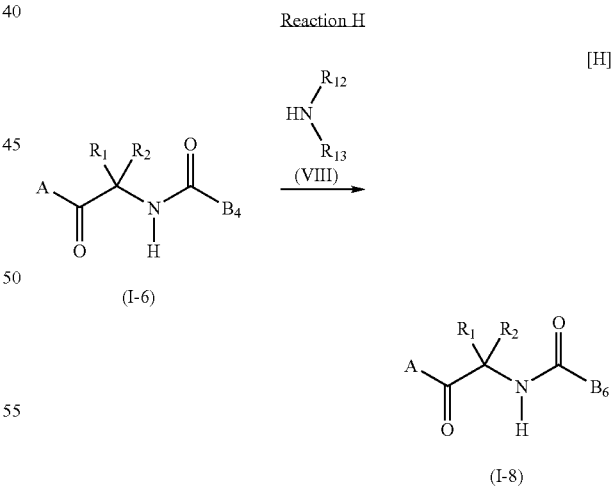

In reaction (G), A, $B_4$, $R_1$, $R_2$, $R_{12}$ and $R_{13}$ are as defined above, and $B_6$ is phenyl substituted by —$CONR_{12}R_{13}$, a heterocyclic group substituted by —$CONR_{12}R_{13}$, or a fused In reaction (H), A, $B_4$, $B_6$, $R_1$, $R_2$, $R_{12}$ and $B_{13}$ are as defined above.

Reaction (H) is carried out usually in the presence of a dehydration condensation agent and a solvent.

The dehydration condensation agent may be one or more suitably selected from e.g. N,N'-dicyclohexylcarbodiimide, chlorosulfonyl isocyanate, N,N'-carbonyldiimidazole and trifluoroacetic anhydride.

The solvent may be any solvent so long as it is a solvent inert to the reaction. For example, it may be one or more suitably selected from e.g. an aromatic hydrocarbon such as benzene, toluene, xylene or chlorobenzene; an aliphatic hydrocarbon such as carbon tetrachloride, methyl chloride, chloroform, dichloromethane, dichloroethane, trichloroethane, hexane or cyclohexane; an ether such as dioxane, tetrahydrofuran, diethyl ether or dimethoxyethane; an ester such as methyl acetate or ethyl acetate; a polar aprotic solvent such as dimethyl sulfoxide, sulfolane, dimethylacetamide, dimethylformamide, N-methylpyrrolidone or pyridine; a nitrile such as acetonitrile, propionitrile or acrylonitrile; and a ketone such as acetone or methyl ethyl ketone.

The reaction temperature for the reaction (H) is usually from 0 to 200° C., preferably from 0 to 100° C. The reaction time is usually from 0.1 to 96 hours, preferably from 0.5 to 24 hours.

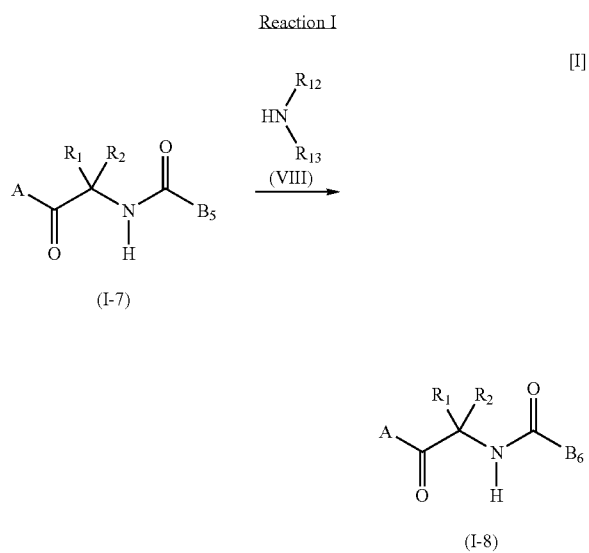

In reaction (I), A, $B_5$, $B_6$, $R_1$, $R_2$, $R_{12}$ and $R_{13}$ are as defined above.

Reaction (I) is carried out usually in the presence of a solvent. The solvent may be any solvent so long as it is a solvent inert to the reaction. For example, it may be one or more suitably selected from e.g. an aromatic hydrocarbon such as benzene, toluene, xylene or chlorobenzene; an aliphatic hydrocarbon such as carbon tetrachloride, methyl chloride, chloroform, dichloromethane, dichloroethane, trichloroethane, hexane or cyclohexane; an ether such as dioxane, tetrahydrofuran, diethyl ether or dimethoxyethane; an ester such as methyl acetate or ethyl acetate; a polar aprotic solvent such as dimethyl sulfoxide, sulfolane, dimethylacetamide, dimethylformamide, N-methylpyrrolidone or pyridine; a nitrile such as acetonitrile, propionitrile or acrylonitrile; a ketone such as acetone or methyl ethyl ketone; an alcohol such as methanol, ethanol, propanol or tert-butanol; and water. Further, in this reaction, the compound of the formula (VIII) may serve also as a solvent if used excessively.

The reaction temperature for the reaction (I) is usually from 0 to 150° C., preferably from 0 to 80° C. The reaction time is usually from 0.1 to 48 hours, preferably from 0.5 to 24 hours.

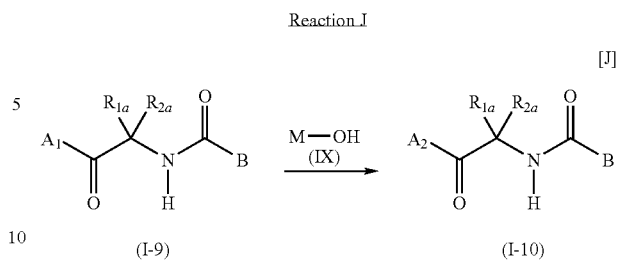

In reaction (J), B is as defined above, $A_1$ is phenyl substituted by $—OR_{4a}$, benzyl substituted by $—OR_{4a}$, naphthyl substituted by $—OR_{4a}$, a heterocyclic group substituted by $—OR_{4a}$ or a fused heterocyclic group substituted by $—OR_{4a}$, $A_2$ is phenyl substituted by $—OH$, benzyl substituted by $—OH$, naphthyl substituted by $—OH$, a heterocyclic group substituted by $—OH$ or a fused heterocyclic group substituted by $—OH$, each of $R_{1a}$ and $R_{2a}$ is alkyl or cyano. $R_{1a}$ and $R_{2a}$ may together form a 3- to 6-membered saturated carbocycle, $R_{4a}$ is $—C(=W)R_{19}$, $—C(=W)OR_{20}$, $—C(=W)SR_{21}$, $—C(=W)NR_{22}R_{23}$, $—S(O)qR_{24}$ or $—S(O)rNR_{25}R_{26}$ (wherein $R_{19}$ to $R_{26}$, W, q and r are as defined above), and M is sodium or potassium.

Reaction (J) is usually carried out in the presence of a solvent. The solvent may be any solvent so long as it is a solvent inert to the reaction. For example, it may be one or more suitably selected from e.g. an aromatic hydrocarbon such as benzene, toluene, xylene or chlorobenzene; an aliphatic hydrocarbon such as carbon tetrachloride, methyl chloride, chloroform, dichloromethane, dichloroethane, trichloroethane, hexane or cyclohexane; an ether such as dioxane, tetrahydrofuran, diethyl ether or dimethoxyethane; a polar aprotic solvent such as dimethyl sulfoxide, sulfolane, dimethylacetamide, dimethylformamide, N-methylpyrrolidone or pyridine; a nitrile such as acetonitrile, propionitrile or acrylonitrile; a ketone such as acetone or methyl ethyl ketone; an alcohol such as methanol, ethanol, propanol or tert-butanol; and water.

The reaction temperature for reaction (J) is usually from 0 to 100° C., preferably from 20 to 80° C. The reaction time is usually from 0.1 to 24 hours, preferably from 0.1 to 12 hours.

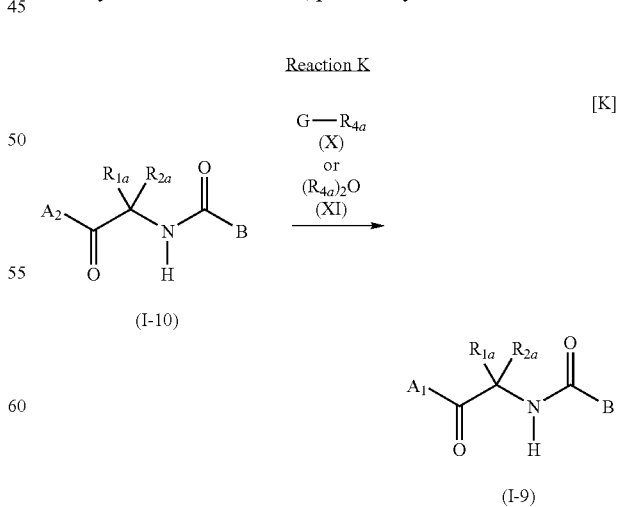

In reaction (K), $A_1$, $A_2$, B, $R_{1a}$, $R_{2a}$ and $R_{4a}$ are as defined above, G is an atom of chlorine, bromine or iodine.

Reaction (K) is usually carried out in the presence of a base and a solvent.

The base may be one or more suitably selected from e.g. an alkali metal alcoholate such as sodium methylate, sodium ethylate or potassium tertiary butoxide; a carbonate such as sodium carbonate or potassium carbonate; a bicarbonate such as sodium bicarbonate or potassium bicarbonate; a metal hydroxide such as sodium hydroxide or potassium hydroxide; a metal hydride such as sodium hydride or potassium hydride; an amine such as monomethylamine, dimethylamine or triethylamine; and a pyridine such as pyridine or 4-dimethylaminopyridine. The base is used in an amount of from 1 to 2 mols, preferably from 1 to 1.5 mols, per mol of the compound of the formula (I-10).

The solvent may be any solvent so long as it is a solvent inert to the reaction. For example, it may be one or more suitably selected from e.g. an aromatic hydrocarbon such as benzene, toluene, xylene or chlorobenzene; an aliphatic hydrocarbon such as carbon tetrachloride, methyl chloride, chloroform, dichloromethane, dichloroethane, trichloroethane, hexane or cyclohexane; an ether such as dioxane, tetrahydrofuran, diethyl ether or dimethoxyethane; an ester such as methyl acetate or ethyl acetate; a polar aprotic solvent such as dimethyl sulfoxide, sulfolane, dimethylacetamide, dimethylformamide, N-methylpyrrolidone or pyridine; a nitrile such as acetonitrile, propionitrile or acrylonitrile; and a ketone such as acetone or methyl ethyl ketone.

The reaction temperature for reaction (K) is usually from −20 to 100° C., preferably from 0 to 50° C. The reaction time is usually from 0.1 to 24 hours, preferably from 0.1 to 12 hours.

The compound of the formula (II) to be used in the above reaction (A) or (C) is novel and can be produced by the following reactions (L) to (N).

Reaction (L)

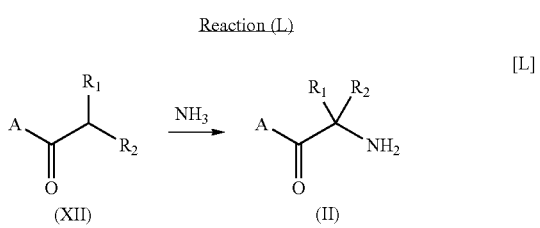

In reaction (L), A, $R_1$ and $R_2$ are as defined above. In reaction (L), a salt of the compound (II) can be produced by post treatment of the reaction or in accordance with a usual reaction for forming a salt.

Reaction (L) is carried out usually in the presence of an oxidizing agent and a solvent.

The oxidizing agent may, for example, be potassium ferricyanide. The oxidizing agent is used in an amount of from 1 to 10 mols, preferably from 1 to 5 mols, per mol of the compound of the formula (XII).

The solvent may be any solvent so long as it is inert to the reaction. For example, it may be one or more suitably selected from e.g. an ether such as dioxane, tetrahydrofuran, diethyl ether or dimethoxyethane; an ester such as methyl acetate or ethyl acetate; a polar aprotic solvent such as dimethyl sulfoxide, sulfolane, dimethylacetamide, dimethylformamide, N-methylpyrrolidone or pyridine; a nitrile such as acetonitrile, propionitrile or acrylonitrile; a ketone such as acetone or methyl ethyl ketone; and water.

The reaction temperature for reaction (L) is usually from 20 to 150° C., preferably from 50 to 100° C. The reaction time is usually from 0.5 to 30 hours, preferably from 1 to 20 hours.

Reaction (M)

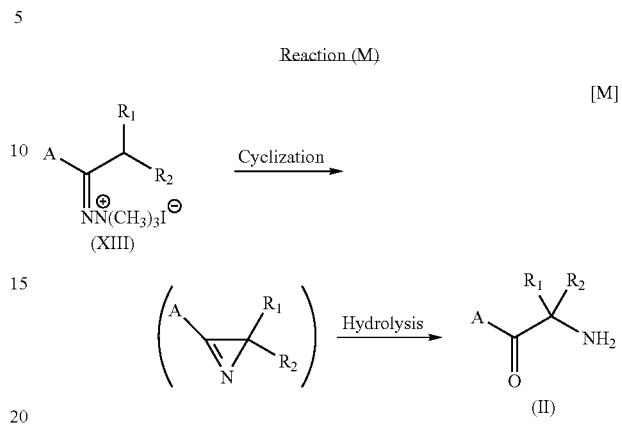

In reaction (M), A, $R_1$ and $R_2$ are as defined above. In reaction (M), a salt of the compound (II) can be produced by post treatment of the reaction or in accordance with a usual reaction for forming a salt.

The cyclization reaction in reaction (M) is carried out usually in the presence of a base and a solvent.

The base may be one or more suitably selected from e.g. an alkali metal such as sodium or potassium; an alkali metal alcoholate such as sodium methylate, sodium ethylate or potassium tert-butoxide; and a metal hydride such as sodium hydride or potassium hydride. The base is used in an amount of from 1 to 3 mols, preferably from 1 to 1.5 mols per mol of the compound of the formula (XIII).

The solvent may be any solvent so long as it is inert to the reaction. For example, it may be one or more suitably selected from e.g. an aromatic hydrocarbon such as benzene, toluene, xylene or chlorobenzene; an ether such as dioxane, tetrahydrofuran, diethyl ether or dimethoxyethane; an alcohol such as methanol, ethanol, propanol or tert-butanol; and a nitrile such as acetonitrile, propionitrile or acrylonitrile.

The reaction temperature for the cyclization reaction in reaction (M) is usually from 0 to 150° C., preferably from 30 to 100° C. The reaction time is usually from 0.5 to 24 hours, preferably from 1 to 12 hours.

The hydrolytic reaction in reaction (M) may be carried out in accordance with a common hydrolytic reaction and is carried out usually in the presence of an acid or base and a solvent.

The acid may, for example, be hydrogen chloride or sulfuric acid. The base may, for example, be a metal hydroxide such as sodium hydroxide or potassium hydroxide.

The solvent may be any solvent so long as it is inert to the reaction. For example, it may be one or more suitably selected e.g. an alcohol such as methanol, ethanol, propanol or tert-butanol; a nitrile such as acetonitrile, propionitrile or acrylonitrile; a ketone such as acetone or methyl ethyl ketone; and water.

The reaction temperature for the hydrolytic reaction in reaction (M) is usually from 0 to 100° C., preferably from 20 to 80° C. The reaction time is usually from 0.1 to 12 hours, preferably from 0.1 to 1 hour.

Reaction (N)

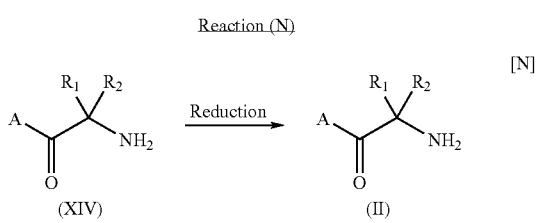

In reaction (N), A, $R_1$ and $R_2$ are as defined above. In reaction (N), a salt of the compound (II) can be produced by post treatment of the reaction or in accordance with a usual reaction for forming a salt.

The reduction reaction in reaction (N) may, for example, be catalytic reduction, reduction by a metal hydride (such as sodium boron hydride, or lithium aluminum hydride) or reduction by e.g. triphenylphosphine or sulfide. The catalytic reduction is usually carried out by reacting with hydrogen, formic acid, ammonium formate, an alcohol, cyclohexane, triethylammonium formate or ammonium chloride, in the presence of a catalyst. The catalyst may be one or more suitably selected from e.g. platinum, platinum oxide, platinum black, Raney Nickel, palladium, palladium-carbon, rhodium, rhodium-alumina, iron and copper.

Reaction (N) is carried out usually in the presence of a solvent. The solvent may be any solvent so long as it is a solvent inert to the reaction. For example, it may be one or more suitably selected from e.g. an aromatic hydrocarbon such as benzene, toluene or xylene; an aliphatic hydrocarbon such as hexane or cyclohexane; an ether such as dioxane, tetrahydrofuran, diethyl ether or dimethoxyethane; an ester such as methyl acetate or ethyl acetate; a polar aprotic solvent such as dimethyl sulfoxide, sulfolane, dimethylacetamide, dimethylformamide, N-methylpyrrolidone or pyridine; a nitrile such as acetonitrile, propionitrile or acrylonitrile; a ketone such as acetone or methyl ethyl ketone; an alcohol such as methanol, ethanol, propanol or tert-butanol; and water.

The reaction temperature in reaction (N) is usually from 0 to 150° C., preferably from 0 to 80° C. The reaction time is usually from 0.5 to 96 hours, preferably from 1 to 48 hours.

The compound of the formula (XIII) to be used in the above reaction (M) is novel and can be produced by the following reaction (O).

Reaction (O)

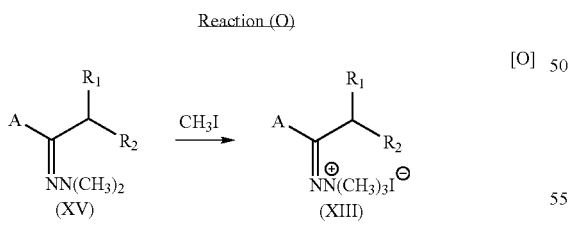

In reaction (O), A, $R_1$ and $R_2$ are as defined above.

Reaction (O) may be carried out, if necessary, in the presence of a solvent. The solvent may be any solvent so long as it is inert to the reaction, and for example, it may be one or more suitably selected from e.g. an aromatic hydrocarbon such as benzene, toluene, xylene or chlorobenzene; an aliphatic hydrocarbon such as carbon tetrachloride, chloroform, dichloromethane, dichloroethane, trichloroethane, hexane or cyclohexane; an ether such as dioxane, tetrahydrofuran, diethyl ether or dimethyoxyethane; an ester such as methyl acetate or ethyl acetate; an alcohol such as methanol, ethanol, propanol or tert-butanol; a nitrile such as acetonitrile, propionitrile or acrylonitrile; and a ketone such as acetone or methyl ethyl ketone.

Methyl iodide in reaction (O) is used in an amount of from 1 to 10 mols, preferably from 1 to 3 mols, per mol of the compound of the formula (XV). Further, methyl iodide may serve also as a solvent if used excessively.

The reaction temperature for reaction (O) is usually from 0 to 100° C., preferably from 10 to 50° C. The reaction time is usually from 0.5 to 48 hours, preferably from 1 to 24 hours.

The compound of the formula (XIV) to be used in the above reaction (N) is novel and can be produced by the following reaction (P).

Reaction (P)

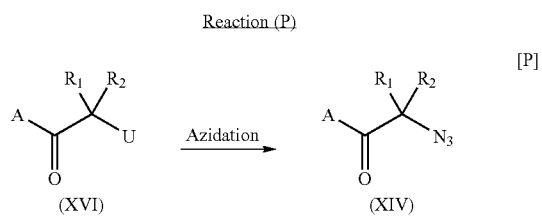

In reaction (P), A, $R_1$ and $R_2$ are as defined above, U is an atom of chlorine or bromine.

Reaction (P) is carried out in the presence of an azidation agent. The azidation agent may be one or more suitably selected from e.g. sodium azide, potassium azide and trimethylsilyl azide.

Reaction (P) is carried out usually in the presence of a solvent. The solvent may be any solvent so long as it is a solvent inert to the reaction. For example, it may be one or more suitably selected from e.g. an aromatic hydrocarbon such as benzene, toluene, xylene or chlorobenzene; an aliphatic hydrocarbon such as carbon tetrachloride, methyl chloride, chloroform, dichloromethane, dichloroethane, trichloroethane, hexane or cyclohexane; an ether such as dioxane, tetrahydrofuran, diethyl ether or dimethoxyethane; an ester such as methyl acetate or ethyl acetate; a polar aprotic solvent such as dimethyl sulfoxide, sulfolane, dimethylacetamide, dimethylformamide, N-methylpyrrolidone or pyridine; a nitrile such as acetonitrile, propionitrile or acrylonitrile; a ketone such as acetone or methyl ethyl ketone; an alcohol such as methanol, ethanol, propanol or tert-butanol; and water.

The reaction temperature for reaction (P) is usually from 0 to 150° C., preferably from 20 to 90° C. The reaction time is usually from 0.1 to 96 hours, preferably from 0.5 to 12 hours.

The compound of the formula (XV) to be used in the above reaction (O) is novel and can be produced by the following reaction (Q).

Reaction (Q)

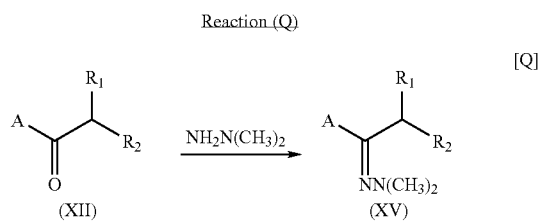

In reaction (Q), A, $R_1$ and $R_2$ are as defined above.

Reaction (Q) can be carried out in accordance with a common hydrazone synthetic reaction and, if necessary, in the presence of a dehydrating agent and/or a catalyst.

As the dehydrating agent, molecular sieve may, for example, be mentioned. The dehydrating agent may be used usually from 1 to 30 times, preferably from 5 to 10 times relative to the weight of the compound of the formula (XII).

The catalyst may, for example, be titanium tetrachloride.

Dimethylhydrazine for reaction (Q) is used usually in an amount of from 1 to 30 mols, preferably from 5 to 10 mols, per mol of the compound of the formula (XII).

The reaction temperature for reaction (Q) is usually from 20 to 150° C., preferably from 50 to 120° C.

The reaction time is usually from 5 to 200 hours, preferably from 24 to 120 hours.

The compound of the formula (XVI) to be used in the above reaction (P) is novel and can be produced by the following reaction (R).

Reaction (R)

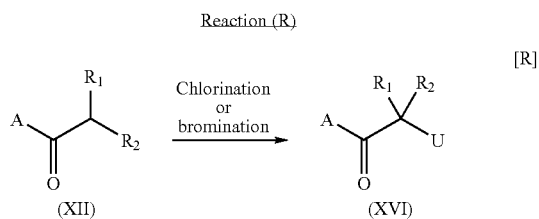

[R]

In reaction (R), A, $R_1$, $R_2$ and U are as defined above.

Reaction (R) is carried out in the presence of a chlorination agent or a bromination agent. The chlorination agent may be one or more suitably selected from e.g. chlorine and N-chlorosuccinimide. The bromination agent may be one or more suitably selected from e.g. bromine, N-bromosuccinimide and phenyltrimethyl ammonium tribromide.

Reaction (R) is carried out usually in the presence of a solvent. The solvent may be any solvent so long as it is a solvent inert to the reaction. For example, it may be one or more suitably selected from e.g. an aromatic hydrocarbon such as benzene, toluene, xylene or chlorobenzene; an aliphatic hydrocarbon such as carbon tetrachloride, methyl chloride, chloroform, dichloromethane, dichloroethane, trichloroethane, hexane or cyclohexane; an ether such as dioxane, tetrahydrofuran, diethyl ether or dimethoxyethane; an ester such as methyl acetate or ethyl acetate; a polar aprotic solvent such as dimethyl sulfoxide, sulfolane, dimethylacetamide, dimethylformamide, N-methylpyrrolidone or pyridine; an organic acid such as acetic acid or propionic acid; and water.

Reaction (R) is carried out, if necessary, in the presence of a base or an acid.

The base may, for example, be lithium diisopropylamide. The base is used in an amount of from 1 to 2 mols, preferably from 1 to 1.2 mols, per mol of the compound of the formula (XII).

The acid may be one or more suitably selected from e.g. an organic acid such as acetic acid or propionic acid, and aluminum chloride. The acid is usually used in a catalytic amount. Further, an organic acid as a solvent may serve as both a solvent and an acid if used excessively.

The reaction temperature for reaction (R) is usually from −100 to 150° C., preferably from −78 to 110° C. The reaction time is usually from 0.1 to 48 hours, preferably from 0.5 to 24 hours. However, if it is carried out in the presence of a base, the reaction temperature is usually from −100 to 0° C., preferably from −78 to −20° C., and the reaction time is usually from 0.1 to 12 hours, preferably from 0.5 to 6 hours. If it is carried out in the presence of an acid, the reaction temperature is usually from 0 to 150° C., preferably from 20 to 110° C., and the reaction time is usually from 0.1 to 48 hours, preferably from 1 to 24 hours.

The compound of the formula (XII) to be used in the above reaction (Q) is a known compound, or can be produced by the following reactions (S) to (T) or by methods in accordance therewith.

Reaction (S)

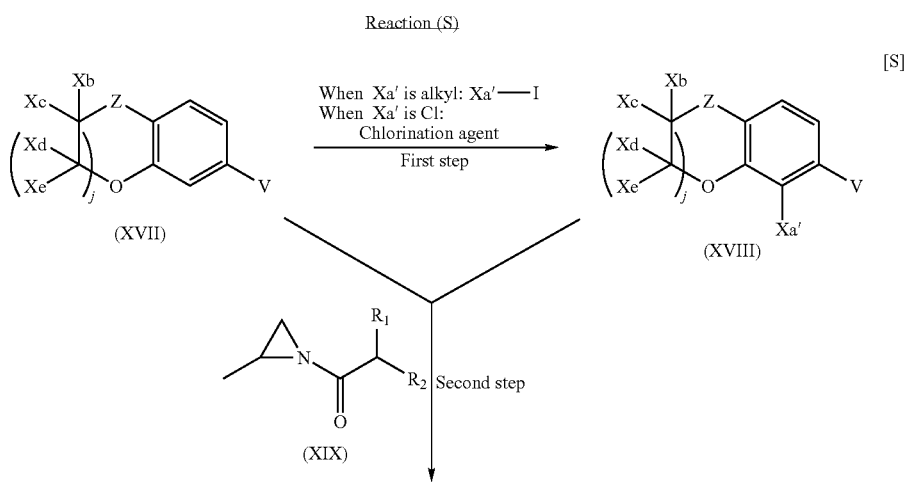

[S]

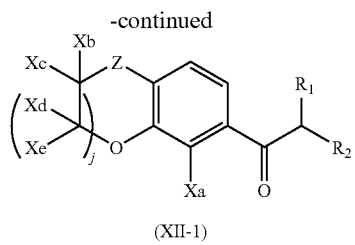

(XII-1)

In reaction (S), $R_1$ and $R_2$ are as defined above, and Z is an oxygen atom or —C($G_1$)$G_2$-, Xa is an hydrogen atom, chlorine atom or alkyl, Xa' is a chlorine atom or alkyl, each of Xb, Xc, Xd, Xe, $G_1$ and $G_2$ is an atom of hydrogen, fluorine or chlorine, V is an atom of bromine or iodine, and j is 0 or 1.

The first step in reaction (S) is carried out in the presence of a base and a solvent.

The base may be suitably selected from an organic lithium compound such as lithium diisopropylamide. The base is used in an amount of from 1 to 2 mols, preferably from 1 to 1.5 mols, per mol of the compound of the formula (XVII).

The solvent may be any solvent so long as it is a solvent inert to the reaction. For example, it may be one or more suitably selected from e.g. an ether such as dioxane, tetrahydrofuran and diethyl ether.

The chlorination agent to be used for the first step in reaction (S) may, for example, be N-chlorosuccinimide.

The formula: Xa'-I to be used for the first step in reaction (S) is used in an amount of from 1 to 10 mols, preferably from 1 to 5 mols, per mol of the compound of the formula (XVII). Further, the chlorination agent to be used for the first step in reaction (S) is used in an amount of from 1 to 5 mols, preferably from 1 to 3 mols, per mol of the compound of the formula (XVII).

The first step in reaction (S) is carried out, if necessary, in the presence of an inert gas. The inert gas may be suitably selected from e.g. nitrogen gas or argon gas.

The reaction temperature for the first step in reaction (S) is usually from −100 to 50° C., preferably from −70 to 25° C. The reaction time is usually from 1 to 48 hours, preferably from 1 to 20 hours.

The second step in reaction (S) is carried out, usually in the presence of a base and a solvent.

The base may be one or more suitably selected from e.g. organic lithium compounds such as methyllithium and n-butyllithium. The base is used in an amount of from 1 to 2 mols, preferably from 1 to 1.5 mols, per mol of the compound of the formula (XVII) or (XVIII).

The solvent may be any solvent so long as it is a solvent inert to the reaction. For example, it may be one or more suitably selected from e.g. ethers such as dioxane, tetrahydrofuran and diethyl ether.

The compound of the formula (XIX) to be used for the second step in reaction (S) is used in an amount of from 1 to 3 mols, preferably from 1 to 1.5 mols, per mol of the compound of the formula (XVII) or (XVIII).

The second step in reaction (S) is carried out, if necessary, in the presence of an inert gas. The inert gas may be suitably selected from e.g. nitrogen gas and argon gas.

The reaction temperature for the second step in reaction (S) is usually from −100 to 50° C., preferably from −70 to 25° C. The reaction time is usually from 1 to 48 hours, preferably from 1 to 20 hours.

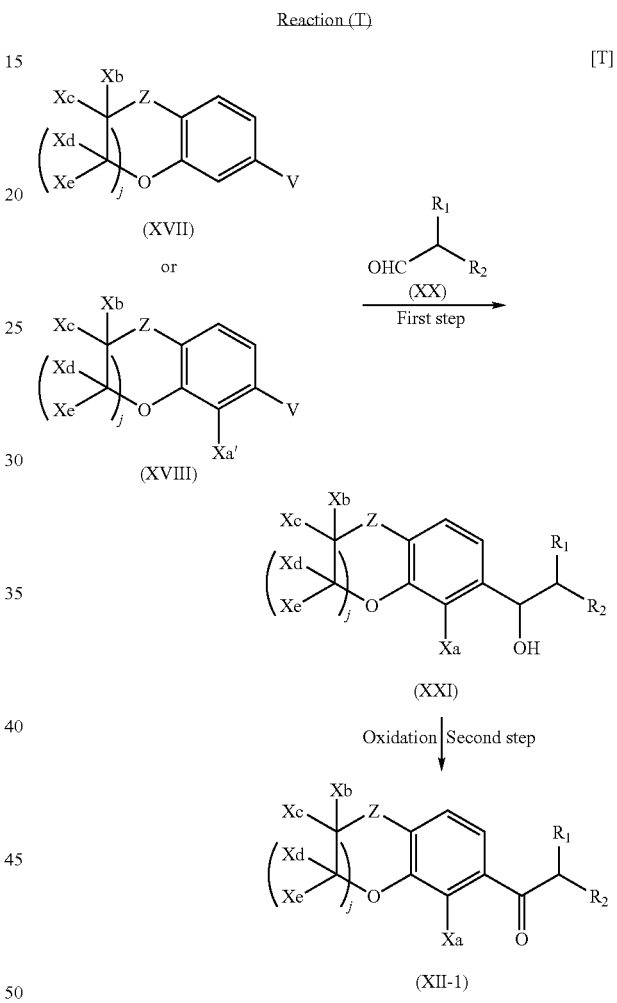

In reaction (T), $R_1$, $R_2$, Z, Xa, Xa', Xb, Xc, Xd, Xe, V and j are as defined above.

The first step in reaction (T) is carried out usually in the presence of a base and a solvent.

The base may be one or more suitably selected from e.g. organic lithium compounds such as methyllithium and n-butyllithium.

The base is used in an amount of from 1 to 2 mols, preferably from 1 to 1.5 mols, per mol of the compound of the formula (XVII) or (XVIII).

The solvent may be any solvent so long as it is a solvent inert to the reaction. For example, it may be one or more suitably selected from e.g. an ether such as dioxane, tetrahydrofuran and diethyl ether.

The compound of the formula (XX) to be used for the first step in reaction (T) is used in an amount of from 1 to 3 mols, preferably from 1 to 1.5 mols, per mol of the compound of the formula (XVII) or (XVIII).

The first step in reaction (T) is carried out, if necessary, in the presence of an inert gas. The inert gas may be suitably selected from e.g. nitrogen gas and argon gas.

The reaction temperature for the first step in reaction (T) is usually from −100 to 50° C., preferably from −70 to 25° C. The reaction time is usually from 1 to 48 hours, preferably from 1 to 20 hours.

The second step for reaction (T) is carried out usually in the presence of an oxidizing agent and a solvent.

The oxidizing agent may be one or more suitably selected from e.g. pyridinium chlorochromate and manganese dioxide. The oxidizing agent is used in an amount of from 1 to 10 mols, preferably from 1 to 3 mols, per mol of the compound of the formula (XXI).

The solvent may be any solvent so long as it is a solvent inert to the reaction. For example, it may be one or more suitably selected from e.g. an aromatic hydrocarbon such as benzene, toluene, xylene or chlorobenzene; and an aliphatic hydrocarbon such as carbon tetrachloride, methyl chloride, chloroform, dichloromethane, dichloroethane, trichloroethane, hexane or cyclohexane.

The reaction temperature for the second step in reaction (T) is usually from 0 to 150° C., preferably from 20 to 100° C. The reaction time is usually from 0.5 to 24 hours, preferably from 1 to 12 hours.

Preferred embodiments of pesticides containing the compounds of the present invention will now be described.

The pesticides containing the compounds of the present invention are particularly useful as an insecticide, a miticide, a nematicide and a soil pesticide, and they are effective for controlling plant parasitic mites such as two-spotted spider mite (*Tetranychus urticae*), carmine spider mite (*Tetranychus cinnabarinus*), kanzawa spider mite (*Tetranychus kanzawai*), citrus red mite (*Panonychus citri*), European red mite (*Panonychus ulmi*), broad mite (*Polyphagotarsonemus latus*), pink citrus rust mite (*Aculops pelekassi*) and bulb mite (*Rhizoglyphus echinopus*); agricultural insect pests such as aphids such as green peach aphid (*Myzus persicae*) and cotton aphid (*Aphis gossypii*), diamondback moth (*Plutella xylostella*), cabbage armyworm (*Mamestra brassicae*), common cutworm (*Spodoptera litura*), codling moth (*Laspeyresia pomonella*), bollworm (*Heliothis zea*), tobacco budworm (*Heliothis virescens*), gypsy moth (*Lymantria dispar*), rice leafroller (*Cnaphalocrocis medinalis*), *Adoxophyes* sp., colorado potato beetle (*Leptinotarsa decemlineata*), cucurbit leaf beetle (*Aulacophora femoralis*), boll weevil (*Anthonomus grandis*), planthoppers, leafhoppers, scales, bugs, whiteflies, thrips, grasshoppers, anthomyiid flies, scarabs, black cutworm (*Agrotis ipsilon*), cutworm (*Agrotis segetum*) and ants; plant parasitic nematodes such as root-knot nematodes, cyst nematodes, root-lesion nematodes, rice white-tip nematode (*Aphelenchoides besseyi*), strawberry bud nematode (*Nothotylenchus acris*), pine wood nematode (*Bursaphelenchus lignicolus*); gastropods such as slugs and snails; soil pests such as isopods such as pillbugs (*Armadilidium vulgare*) and pillbugs (*Porcellio scaber*); hygienic insect pests such as tropical rat mite (*Ornithonyssus bacoti*), cockroachs, housefly (*Musca domestica*) and house mosquito (*Culex pipiens*); stored grain insect pests such as angoumois grai moth (*Sitotroga cerealella*), adzuki bean weevil (*Callosobruchus chinensis*), red flour beetle (*Tribolium castaneum*) and mealworms; household goods insect pests such as casemaking clothes moth (*Tinea pellionella*), black carpet beetle (*Anthrenus scrophularidae*) and subterranean termites; domestic mites such as mold mite (*Tyrophagus putrescentiae*), *Dermatophagoides farinae* and *Chelacaropsis moorei*. Among them, the pesticides containing the compounds of the present invention are particularly effective for controlling agricultural insect pests, plant parasitic nematodes or the like. Further, they are effective against insect pests having acquired resistance to organophosphorus, carbamate and/or synthetic pyrethroid insecticides. Moreover, the compounds of the present invention have excellent systemic properties, and by the application of the compounds of the present invention to soil treatment, not only noxious insects, noxious mites, noxious nematodes, noxious gastropods and noxious isopods in soil but also foliage pests can be controlled.

Another preferred embodiments of the pesticides containing compounds of the present invention may be agricultural and horticultural pesticides which collectively control the above-mentioned plant parasitic mites, agricultural insect pests, plant parasitic nematodes, gastropods and soil pests.

The pesticide containing the compound of the present invention, is usually formulated by mixing the compound with various agricultural adjuvants and used in the form of a formulation such as a dust, granules, water-dispersible granules, a wettable powder, a water-based suspension concentrate, an oil-based suspension concentrate, water soluble granules, an emulsifiable concentrate, a soluble concentrate, a paste, an aerosol or an ultra low-volume formulation. However, so long as it is suitable for the purpose of the present invention, it may be formulated into any type of formulation which is commonly used in this field. Such agricultural adjuvants include solid carriers such as diatomaceous earth, slaked lime, calcium carbonate, talc, white carbon, kaoline, bentonite, a mixture of kaolinite and sericite, clay, sodium carbonate, sodium bicarbonate, mirabilite, zeolite and starch; solvents such as water, toluene, xylene, solvent naphtha, dioxane, acetone, isophorone, methyl isobutyl ketone, chlorobenzene, cyclohexane, dimethylsulfoxide, dimethylformamide, dimethylacetamide, N-methyl-2-pyrrolidone, and alcohol; anionic surfactants and spreaders such as a salt of fatty acid, a benzoate, an alkylsulfosuccinate, a dialkylsulfosuccinate, a polycarboxylate, a salt of alkylsulfuric acid ester, an alkyl sulfate, an alkylaryl sulfate, an alkyl diglycol ether sulfate, a salt of alcohol sulfuric acid ester, an alkyl sulfonate, an alkylaryl sulfonate, an aryl sulfonate, a lignin sulfonate, an alkyldiphenyl ether disulfonate, a polystyrene sulfonate, a salt of alkylphosphoric acid ester, an alkylaryl phosphate, a styrylaryl phosphate, a salt of polyoxyethylene alkyl ether sulfuric acid ester, a polyoxyethylene alkylaryl ether sulfate, a salt of polyoxyethylene alkylaryl ether sulfuric acid ester, a polyoxyethylene alkyl ether phosphate, a salt of polyoxyethylene alkylaryl phosphoric acid ester, and a salt of a condensate of naphthalene sulfonate with formalin; nonionic surfactants and spreaders such as a sorbitan fatty acid ester, a glycerin fatty acid ester, a fatty acid polyglyceride, a fatty acid alcohol polyglycol ether, acetylene glycol, acetylene alcohol, an oxyalkylene block polymer, a polyoxyethylene alkyl ether, a polyoxyethylene alkylaryl ether, a polyoxyethylene styrylaryl ether, a polyoxyethylene glycol alkyl ether, a polyoxyethylene fatty acid ester, a polyoxyethylene sorbitan fatty acid ester, a polyoxyethylene glycerin fatty acid ester, a polyoxyethylene hydrogenated castor oil, and a polyoxypropylene fatty acid ester; and vegetable and mineral oils such as olive oil, kapok oil, castor oil, palm oil, camellia oil, coconut oil, sesame oil, corn oil, rice bran oil, peanut oil, cottonseed oil, soybean oil, rapeseed oil, linseed oil, tung oil, and liquid paraffins. Such adjuvants may be selected for use among those known in this field, so long as the purpose of the present invention can thereby be accomplished. Further, various additives which are commonly used, such as a filler, a thickener, an anti-settling agent, an anti-freezing agent, a dispersion stabilizer, a phytotoxicity reducing agent, and an anti-mold agent, may also be employed.

The weight ratio of the compound of the present invention to the various agricultural adjuvants is usually from 0.001:99.999 to 95:5, preferably from 0.005:99.995 to 90:10.

In the actual application of such a formulation, it may be used as it is, or may be diluted to a predetermined concentration with a diluent such as water, and various spreaders may be added thereto, as the case requires.

The application of the pesticide containing the compound of the present invention can not generally be defined, as it varies depending upon the weather conditions, the type of the formulation, the application season, the application site or the types or degree of outbreak of the pest insects. However, it is usually applied in a concentration of the active ingredient being from 0.05 to 800,000 ppm, preferably from 0.5 to 500,000 ppm, and the dose per unit area is such that the compound of the present invention is from 0.05 to 50,000 g, preferably from 1 to 30,000 g, per hectare. Further, agricultural and horticultural pesticides as another preferred embodiment of pesticides containing the compounds of the present invention may be applied in accordance with the above-described application of pesticides. The present invention includes such a method for controlling pests, particularly for controlling agricultural insect pests or plant parasitic nematodes by such applications.

Various formulations of pesticides containing the compounds of the present invention or their diluted compositions may be applied by conventional methods for application which are commonly employed, such as spraying (e.g. spraying, jetting, misting, atomizing, powder or grain scattering or dispersing in water), soil application (e.g. mixing or drenching), surface application (e.g. coating, powdering or covering) or impregnation to obtain poisonous feed. Further, it is possible to feed domestic animals with a food containing the above active ingredient and to control the outbreak or growth of pests, particularly insect pests, with their excrements. Furthermore, the active ingredient may also be applied by a so-called ultra low-volume application method. In this method, the composition may be composed of 100% of the active ingredient.

Further, the pesticides containing compounds of the present invention may be mixed with or may be used in combination with other agricultural chemicals, fertilizers or phytotoxicity-reducing agents, whereby synergistic effects or activities may sometimes be obtained. Such other agricultural chemicals include, for example, a herbicide, an insecticide, a miticide, a nematicide, a soil pesticide, a fungicide, an antivirus agent, an attractant, an antibiotic, a plant hormone and a plant growth regulating agent. Especially, with a mixed pesticide having a compound of the present invention mixed with or used in combination with one or more active compounds of other agricultural chemicals, the application range, the application time, the pesticidal activities, etc. may be improved to preferred directions. The compound of the present invention and the active compounds of other agricultural chemicals may separately be formulated so that they may be mixed for use at the time of application, or they may be formulated together. The present invention includes such a mixed pesticidal composition.

The mixing ratio of the compound of the present invention to the active compounds of other agricultural chemicals can not generally be defined, since it varies depending upon the weather conditions, the types of formulations, the application time, the application site, the types or degree of outbreak of insect pests, etc., but it is usually within a range of from 1:300 to 300:1, preferably from 1:100 to 100:1, by weight. Further, the dose for the application is such that the total amount of the active compounds is from 0.1 to 50,000 g, preferably from 1 to 30,000 g, per hectare. The present invention includes a method for controlling pests by an application of such a mixed pesticide composition.

The active compounds of pest control agents such as insecticides, miticides, nematicides or soil pesticides in the above-mentioned other agricultural chemicals, include, for example, (by common names, some of them are still in an application stage) organic phosphate compounds such as Profenofos, Dichlorvos, Fenamiphos, Fenitrothion, EPN, Diazinon, Chlorpyrifos-methyl, Acephate, Prothiofos, Fosthiazate, Phosphocarb, Cadusafos, Disulfoton, Chlorpyrifos, Demeton-S-methyl, Dimethoate, and Methamidophos; carbamate compounds such as Carbaryl, Propoxur, Aldicarb, Carbofuran, Thiodicarb, Methomyl, Oxamyl, Ethiofencarb, Pirimicarb, Fenobucarb, Carbosulfan, and Benfuracarb; nereistoxin derivatives such as Cartap, Thiocyclam and Bensultap; organic chlorine compounds such as Dicofol, and Tetradifon; organometallic compounds such as Fenbutatin Oxide; pyrethroid compounds such as Fenvalerate, Permethrin, Cypermethrin, Deltamethrin, Cyhalothrin, Tefluthrin, Ethofenprox and Bifenthrin; benzoylurea compounds such as Diflubenzuron, Chlorfluazuron, Teflubenzuron, Flufenoxuron, Lufenuron, and Novaluron; juvenile hormone-like compounds such as Methoprene, Pyriproxyfen, and Fenoxycarb; pyridazinone compounds such as Pyridaben; pyrazole compounds such as Fenpyroximate, Fipronil, Tebufenpyrad, Ethiprole, Tolfenpyrad, and Acetoprole; neonicotinoids such as Imidacloprid, Nitenpyram, Acetamiprid, Thiacloprid, Thiamethoxam, Clothianidin, and Dinotefuran; hydrazine compounds such as Tebufenozide, Methoxyfenozide, and Chromafenozide; dinitro compounds; organic sulfur compounds; urea compounds; triazine compounds; hydrazone compounds; and other compounds, such as Flonicamid, Buprofezin, Hexythiazox, Amitraz, Chlordimeform, Silafluofen, Triazamate, Pymetrozine, Pyrimidifen, Chlorfenapyr, Indoxacarb, Acequinocyl, Etoxazole, Cyromazine, 1,3-dichloropropene, Diafenthiuron, Benclothiaz, Flufenerim, Pyridalyl, and Spirodiclofen. Further, microbial agricultural chemicals such as BT agents, insect viruses, entomopathogenic fungi, and nematophagous fungi or antibiotics such as Avermectin, Milbemectin, Spinosad, Ivermectin, and Emamectin-benzoate may be used in admixture or in combination.

The active compounds of fungicides among the above-mentioned other agricultural chemicals include, for example, (by common names, some of which are still in an application stage) pyrimidinamine compounds such as Mepanipyrim, Pyrimethanil, and Cyprodinil; azole compounds such as Triadimefon, Bitertanol, Triflumizole, Etaconazole, Propiconazole, Penconazole, Flusilazole, Myclobutanil, Cyproconazole, Terbuconazole, Hexaconazole, Furconazole-cis, Prochloraz, Metconazole, Epoxiconazole, Tetraconazole, Oxpoconazole, and Sipconazole; quinoxaline compounds such as Quinomethionate; dithiocarbamate compounds such as Maneb, Zineb, Mancozeb, Polycarbamate, Propineb; organic chlorine compounds such as Fthalide, Chlorothalonil, and Quintozene; imidazole compounds such as Benomyl, Thiophanate-Methyl, Carbendazim, and Cyazofamid; pyridinamine compounds such as Fluazinam; cyanoacetamide compounds such as Cymoxanil; phenylamide compounds such as Metalaxyl, Oxadixyl, Ofurace, Benalaxyl, Furalaxyl, and Cyprofuram; sulfenic acid compounds such as Dichlofluanid; copper compounds such as cupric hydroxide, and Oxine Copper; isoxazole compounds such as Hydroxyisoxazole; organophosphorus compounds such as Fosetyl-Al, Tolclofos-Methyl, S-benzyl O,O-diisopropylphosphorothioate, O-ethyl S,S-diphenylphosphorodithioate, and aluminumethylhydrogen phosphonate; N-halogenothioalkyl compounds such as Captan, Captafol, and Folpet; dicarboximide compounds such as Procymidone, Iprodione, and Vinclozolin; benzanilide compounds such as Flutolanil, Mepronil, and Zoxamide; piperazine compounds such as Triforine; pyrizine compounds such as Pyrifenox; carbinol compounds such as Fenarimol; and Flutriafol; piperidine compounds such as Fenpropidine; morpholine compounds such as Fenpropimorph; organotin compounds such as Fentin Hydroxide, and Fentin Acetate; urea compounds such as Pencycuron; cinnamic acid compounds such as Dimethomorph; phenylcarbamate compounds such as Diethofencarb; cyanopyrrole compounds such as Fludioxonil, and Fenpiclonil; Strobilurin compounds such as Azoxystrobin, Kresoxim-Methyl, Metominofen, Trifloxystrobin, and Picoxystrobin; oxazolidinedione compounds such as Famoxadone; thiazole carboxamide compounds such as Ethaboxam; silyl amide compounds such as Silthiopham; aminoacid amidecarbamate compounds such as Iprovalicarb; imidazolidine compound such as Fenamidone; hydroxyanilide compounds such as Fenhexamid; benzene sulfonamide compounds such as Flusulfamide; Strobilurin compounds such as Pyraclostrobin; anthraquinone compounds; crotonic acid compounds; antibiotics; and other compounds, such as Isoprothiolane, Tricyclazole, Pyroquilon, Diclomezine, Pro. benazole, Quinoxyfen, Propamocarb Hydrochloride, Spiroxamine, Chloropicrin, Dazomet, and Metam-Sodium.

Further, agricultural chemicals which may be used in admixture with or in combination with the compounds of the present invention, may, for example, be the active ingredient compounds in the herbicides as disclosed in Farm Chemicals Handbook (1998 edition), particularly those of soil treatment type.

Further, pesticides containing the compounds of the present invention are useful as agents for controlling parasites on animals, particularly as agents for controlling parasites in the bodies of animals, or as agents for controlling animal diseases caused by such parasites.

For example, they are effective for controlling (1) parasites parasitic on the exterior of a host animal, such as, acarus such as mange mite, mesostigmatid mites, sarcoptic mange mite (*Sarcoptes scabiei*), trombiculid mites, New Zealand cattle tick (*Haemaphyalis longicornis*) and southern cattle tick (*Boophilus microplus*); fleas such as cat flea (*Ctenocephalides felis*), dog flea (*Ctenocephalides canis*), northern rat flea (*Nosopsyllus fasciatus*), oriental rat flea (*Xenopsylla cheopis*) and human flea (*Pulex irritans*); sucking lice such as short-nosed cattle louse (*Haematopinus eurysternus*), horse sucking louse (*Haematopinus asini*), sheep lice, long-nosed cattle louse (*Linognathus vituli*) and head louse (*Pediculus capitis*); biting lice such as dog biting louse (*Trichodectes canis*); blood-sucking dipterous insects such as horse fly (*Tabanus trigonus*), biting midges (*Culicoides schultzei*) and blackfly (*Simulium ornatum*); and (2) parasites parasitic in the body of a host animal, such as, nematodes such as lung worms, whipworm (*Trichuris trichiura*), tuberous worm, gastric parasites, ascaris and filarioidea; tapeworms; flukes; and protozoa such as coccidia, malarial parasite (*Plasmodium malariae*), intestinal sarcocyst, Toxoplasma and cryptosporidium.

The compound of the present invention is usually formulated together with a suitable vehicle into a formulation such as a powder, a granule, a parvule, a tablet, a dusting powder, a capsule, a solution or an emulsion. The suitable vehicle may be one which is commonly used as a feed additive, and it may, for example, be lactose, sucrose, glucose, starch, wheat powder, corn powder, soybean meal, degreased rice bran, calcium carbonate or other commercially available feed material. Further, the compound of the present invention can be used, together with a vehicle, in combination with various vitamins, minerals, amino acids, enzyme drugs, antifebriles, sedatives, antiphlogistics, bactericides, colorants, aromatizing agents, preservatives, etc. The dose of the compound of the present invention varies depending upon the parasites as the object of control, the administration method, the purpose of administration, the diseased degree, etc. However, it is usually administered as mixed in a feed in a concentration of at least 0.1 ppm.

The compound of the present invention exhibits an effect for controlling parasites on animals, such as fleas, coccidia and filarioidea, by a test in accordance with the test method disclosed in e.g. JP-A-5-70350 or JP-A-11-500439.

Preferred embodiments in the present invention are as follows. However, it should be understood that the present invention is by no means restricted to such specific embodiments.

(1) An acid amide derivative of the above formula (I) or a salt thereof, wherein A is phenyl which may be substituted by X'; benzyl which may be substituted by X, naphthyl which may be substituted by X, a heterocyclic group which may be substituted by X, a fused heterocyclic group which may be substituted by X, indanyl (the indanyl may be substituted by halogen, alkyl or alkoxy) or tetrahydronaphthyl (the tetrahydronaphthyl may be substituted by halogen, alkyl or alkoxy), X' is alkoxyalkoxy, haloalkoxyalkoxy, alkoxyhaloalkoxy, haloalkoxyhaloalkoxy, phenyl which may be substituted by Y', phenoxy which may be substituted by Y', benzyloxy which may be substituted by Y', pyridyloxy which may be substituted by Y', —$OR_4$, —$SR_5$, —$NR_6R_7$, —$CO_2R_8$, —C(=O)$NR_9R_{10}$ or an unsaturated heterocyclic group (the unsaturated heterocyclic ring may be substituted by halogen, alkyl, haloalkyl, alkoxy or haloalkoxy), Y' is —$OR_4$, —$CO_2R_{11}$, —$CONR_{12}R_{13}$ or an unsaturated heterocyclic group (the unsaturated heterocyclic ring may be substituted by halogen, alkyl, haloalkyl, alkoxy or haloalkoxy).

(2) The acid amide derivative or a salt thereof according to the above (1), wherein A is phenyl which may be substituted by X'.

(3) The acid amide derivative or a salt thereof according to the above (1), wherein A is benzyl which may be substituted by X, naphthyl which may be substituted by X, a heterocyclic group which may be substituted by X, a fused heterocyclic group which may be substituted by X, indanyl (the indanyl may be substituted by halogen, alkyl or alkoxy), or tetrahydronaphthyl (the tetrahydronaphthyl may be substituted by halogen, alkyl or alkoxy).

(4) The acid amide derivative or a salt thereof according to the above (3), wherein A is benzyl which may be substituted by X, naphthyl which may be substituted by X.

(5) The acid amide derivative or a salt thereof according to the above (3), wherein A is a heterocyclic group which may be substituted by X, or a fused heterocyclic group which may be substituted by X.

(6) The acid amide derivative or a salt thereof according to the above (5), wherein the heterocyclic group is a 5- or 6-membered heterocyclic group containing from 1 to 4 atoms of at least one type selected from the group consisting of O, S and N, and the fused heterocyclic group is a 8- to 10-membered fused heterocyclic group containing from 1 to 4 atoms of at least one type selected from the group consisting of O, S and N.

(7) The acid amide derivative or a salt thereof according to the above (6), wherein the heterocyclic group is furyl, tetrahydrofuryl, thienyl, pyrrolyl, pyrrolinyl, pyrrolidinyl, dioxolanyl, oxazolyl, isoxazolyl, thiazolyl, isothiazolyl, imidazolyl, imidazolinyl, imidazolidinyl, pyrazolyl, pyrazolinyl, pyrazolidinyl, triazolyl, oxadiazolyl, thiadiazolyl, tetrazolyl, pyranyl, pyridyl, piperidinyl, dioxanyl, oxazinyl, morpholinyl, thiazinyl, pyridazinyl, pyrimidinyl, pyrazinyl, piperazinyl or triazinyl, and the fused heterocyclic group is benzofuranyl, isobenzofuranyl, dihydrobenzofuranyl, dihydroisobenzofuranyl, benzothienyl, isobenzothienyl, dihydrobenzothienyl, dihydroisobenzothienyl, tetrahydrobenzothienyl, indolyl, isoindolyl, benzoxazolyl, benzothiazolyl, indazolyl, benzimidazolyl, benzodioxolanyl, benzodioxanyl, chromenyl, chromanyl, isochromanyl, chromonyl, chromanonyl, quinolyl, isoquinolyl, cinnolinyl, phthalazinyl, quinazolinyl, quinoxalinyl, indolizinyl, quinolizinyl, imidazopyridyl, naphthyridinyl, pteridinyl, dihydrobenzoxazinyl, dihydrobenzoxazolinonyl, dihydrobenzoxazinonyl or benzothioxanyl.

(8) The acid amide derivative or a salt thereof according to the (3), wherein A is indanyl (the indanyl may be substituted by halogen, alkyl or alkoxy), or tetrahydronaphthyl (the tetrahydronaphthyl may be substituted by halogen, alkyl or alkoxy).

(9) The acid amide derivative or a salt thereof according to the above (1) or (3) to (7), wherein X is at least one type selected from the group consisting of halogen, alkyl, haloalkyl, alkoxy or haloalkoxy.

(10) The acid amide derivative or a salt thereof according to the above (1) to (8), wherein B is phenyl which may be substituted by Y.

(11) The acid amide derivative or a salt thereof according to the above (1) to (8), wherein each of $R_1$ and $R_2$ is alkyl, $R_3$ is a hydrogen atom.

(12) The acid amide derivative or a salt thereof according to the above (1) to (8), wherein B is phenyl which may be substituted by Y, each of $R_1$ and $R_2$ is alkyl, and $R_3$ is a hydrogen atom.

(13) The acid amide derivative or a salt thereof according to the above (10) or (12), wherein Y is at least one type selected from the group consisting of halogen, alkyl or haloalkyl.

Further, other preferred embodiments in the present invention are as follows. However, the present invention is not limited to them.

An acid amid derivative of the above formula (I) or a salt thereof, wherein A is phenyl which may be substituted by X, benzyl which may be substituted by X, naphthyl which may be substituted by X, a heterocyclic group which may be substituted by X, or a fused heterocyclic group which may be substituted by X, B is alkyl, cycloalkyl, phenyl which may be substituted by Y, a heterocyclic group which may be substituted by Y, or a fused heterocyclic group which may be substituted by Y, X is halogen, alkyl, haloalkyl, alkenyl, haloalkenyl, alkynyl, haloalkynyl, alkoxy, haloalkoxy, alkenyloxy, haloalkenyloxy, alkynyloxy, haloalkynyloxy, alkylthio, haloalkylthio, alkenylthio, haloalkenylthio, alkynylthio, haloalkynylthio, alkylsulfinyl, haloalkylsulfinyl, alkylsulfonyl, haloalkylsulfonyl, dialkylaminosulfonyl, nitro, cyano, phenyl which may be substituted by Y, phenoxy which may be substituted by Y, benzyloxy which may be substituted by Y, pyridyloxy which may be substituted by Y, $-OR_4$, $-SR_5$, $-NR_6R_7$, $-CO_2R_8$, $-C(=O)NR_9R_{10}$ or an unsaturated heterocyclic group (the unsaturated heterocyclic ring may be substituted by halogen, alkyl, haloalkyl, alkoxy or haloalkoxy), Y is halogen, alkyl, haloalkyl, alkoxy, haloalkoxy, alkylthio, haloalkylthio, alkylsulfinyl, haloalkylsulfinyl, alkylsulfonyl, haloalkylsulfonyl, dialkylaminosulfonyl, nitro, cyano, $-CO_2R_{11}$, $-CONR_{12}R_{13}$ or an unsaturated heterocyclic group (the unsaturated heterocyclic ring may be substituted by halogen, alkyl, haloalkyl, alkoxy or haloalkoxy), each of $R_1$ and $R_2$ is alkyl, cyano or $-CO_2R_{14}$, or $R_1$ and $R_2$ may together form a 3- to 6-membered saturated carbocyclic ring, $R_3$ is hydrogen, alkyl, alkoxyalkyl, alkylthioalkyl, $-COR_{15}$, $-S(O)mR_{16}$ or $-S(O)nNR_{17}R_{18}$, each of $R_4$ and $R_6$ is hydrogen, $-C(=W)R_{19}$, $-C(=W)OR_{20}$, $-C(=W)SR_{21}$, $-C(=W)NR_{22}R_{23}$, $-S(O)qR_{24}$ or $-S(O)rNR_{25}R_{26}$, $R_5$ is hydrogen, $-C(=W)R_{19}$, $-C(=W)OR_{20}$, $-C(=W)SR_{21}$ or $-C(=W)NR_{22}R_{23}$, $R_7$ is hydrogen, alkyl or haloalkyl, each of $R_8$, $R_9$, $R_{10}$, $R_{11}$, $R_{12}$, $R_{13}$ and $R_{14}$ is hydrogen or alkyl, $R_{15}$ is hydrogen, alkyl or alkoxy, each of $R_{16}$, $R_{17}$, $R_{18}$, $R_{19}$, $R_{20}$, $R_{21}$, $R_{22}$, $R_{23}$, $R_{24}$, $R_{25}$ and $R_{26}$ is alkyl, haloalkyl or phenyl (the phenyl which may be substituted by halogen, alkyl, haloalkyl, alkoxy or haloalkoxy), each of m, n, q and r is from 0 to 2, W is oxygen or sulfur.

Now, Examples of the present invention will be described. However, it should be understood that the present invention is by no means restricted to such specific Examples. Firstly, Preparation Examples for the compounds of the present invention will be described.

PREPARATION EXAMPLE 1

Preparation of 2-hydroxycarbonyl-N-[(4'-chloro-1,1-dimethyl)phenacyl]benzamide (The After-Mentioned Compound No. 1-120)

0.83 g of triethylamine was added to a mixture comprising 1.92 g of α-amino-4-chloroisobutyrophenone hydrochloride and 20 ml of tetrahydrofuran at room temperature, and a mixed solution of 1.21 g of phthalic anhydride and 30 ml of tetrahydrofuran was added thereto, followed by a reaction at room temperature for 16 hours. After completion of the reaction, the reaction mixture was concentrated, and 70 ml of water was added to the residue, followed by acidification by 10% hydrochloric acid, and then by stirring for 30 minutes. The precipitated crystal was collected by filtration, washed with water, dissolved in ethyl acetate, and then dried over anhydrous magnesium sulfate, followed by concentration under reduced pressure to obtain 1.84 g of the desired product having a melting point of from 212 to 214° C. The NMR spectrum data of this product were as follows.

$^1$H-NMR δppm (Solvent: DMSO/400 MHz)

1.53 (s, 6H), 7.00 (d, 1H), 7.48 (t, 1H), 7.52-7.55 (m, 3H), 7.75 (d, 1H), 8.05 (d, 2H), 9.11 (s, 1H), 12.96 (brs, 1 H)

PREPARATION EXAMPLE 2

Preparation of 2-(3-thienyl)-N-[(4'-chloro-1,1-dimethyl)phenacyl]benzamide (The After-Mentioned Compound No. 1-80)

0.24 g of 3-thiopheneboric acid, 0.51 g of sodium carbonate, 5 ml of water and 0.1 g of tetrakis(triphenylphosphine) palladium(0) were added to a mixed solution comprising 0.35 g of 2-bromo-N-[(4'-chloro-1,1-dimethyl)phenacyl]benzamide and 5 ml of 1,2-dimethoxyethane, followed by a reaction under heating and refluxing for 8 hours under nitrogen atmosphere. After completion of the reaction, the reaction mixture was allowed to cool and added to 40 ml of water, then 20 ml of t-butyl methyl ether was added and stirred, followed by neutralization with 30% sulfuric acid, and then by extraction with ethyl acetate. The organic layer was washed with an aqueous sodium chloride solution, then dried over anhydrous sodium sulfate, followed by concentration under reduced pressure. The obtained residue was purified by silica gel column chromatography (eluent: ethyl acetate/n-hexane=3/7) to obtain 0.14 g of the desired product having a melting point of from 170 to 173° C. The NMR spectrum data of this product were as follows.

$^1$H-NMR δppm (Solvent: CDCl$_3$/400 MHz)
1.48 (s, 6H), 6.09 (brs, 1H), 7.13 (dd, 1H), 7.32-7.48 (m, 8H), 7.84 (dd, 2H)

PREPARATION EXAMPLE 3

Preparation of 2,6-difluoro-N-[1-methyl-1-(3-thenoyl)ethyl]benzamide (The After-Mentioned Compound No. 6-5)

(1) 2.88 g of phenyltrimethylammonium tribromide was added to a mixed solution comprising 1.54 g of 2-(3-thenoyl)propane and 30 ml of tetrahydrofuran, followed by a reaction at room temperature for 15 hours. After completion of the reaction, the precipitate was separated by filtration and concentrated, and then purified by silica gel column chromatography (eluent: ethyl acetate/n-hexane=2/8-4/6) to obtain 0.87 of 2-bromo-2-(3-thenoyl)propane. The NMR spectrum data of this product were as follows.

$^1$H-NMR δppm (Solvent: CDCl$_3$/400 MHz)
2.06 (s, 6H), 7.27-7.31 (m, 1H), 7.74 (dd, 1H), 8.40 (dd, 1H)

(2) 0.87 of 2-bromo-2-(3-thenoyl)propane was dissolved in 5 ml of dimethyl sulfoxide, then 0.44 g of sodium azide was added thereto and reacted at 70° C. for 1 hour. After completion of the reaction, the reaction mixture was allowed to cool and put into 200 ml of water, and then extracted with ethyl ether. The organic layer was washed with water, then dried over magnesium sulfate, followed by concentration to obtain 0.70 g of 2-azido-2-(3-thenoyl)propane. The NMR spectrum data of this product were as follows.

$^1$H-NMR δppm (Solvent: CDCl$_3$/400 MHz)
1.58 (s, 6H), 7.27-7.32 (m, 1H), 7.69 (dd, 1H), 8.45 (dd, 1H)

(3) 4 ml of tetrahydrofuran and 0.08 ml of water were added to 0.68 g of 2-azido-2-(3-thenoyl)propane, then 1.10 g of triphenylphosphine was gradually added thereto with stirring at room temperature, and after completion of addition, a reaction was carried out for 18 hours. 15 ml of tetrahydrofuran was added to the reaction mixture, then 0.30 g of triethylamine was added, followed by cooling with ice, and a mixed solution of 0.46 g of 2,6-difluorobenzoyl chloride and 5 ml of tetrahydrofuran was dropwise added thereto. After completion of the dropwise addition, a reaction was carried out for 30 minutes under cooling with ice, and then a further reaction was carried out for 2.5 hours at room temperature. After completion of the reaction, the reaction mixture was put into 100 ml of water and extracted by ethyl acetate. The organic layer was dried over sodium sulfate, concentrated and purified by silica gel column chromatography (eluent: ethyl acetate/n-hexane=4/6) to obtain 0.60 g of the desired product having a melting point of from 139 to 142° C. The NMR spectrum data of this product were as follows. $^1$H-NMR δppm (Solvent: CDCl$_3$/400 MHz)
1.81 (s, 6H), 6.92 (t, 2H), 7.12 (br, 1H), 7.29-7.38 (m, 2H), 7.66 (dd, 1H), 8.24 (dd, 1H)

PREPARATION EXAMPLE 4

Preparation of 2,6-difluoro-N-[(1,1-dimethyl-4'-methylsulfonyloxy)phenacyl]benzamide (Compound No. 1-25)

(1) 0.85 g of phenyltrimethylammonium tribromide was added to a mixture comprising 0.55 g of 4-methylsulfonyloxy isobutyrophenone and 10 ml of tetrahydrofuran, followed by a reaction at room temperature for 6 hours. After completion of the reaction, the reaction mixture was subjected to filtration, and the filtrate was concentrated under reduced pressure to obtain 0.68 g of oily α-bromo-4-methylsulfonyloxyisobutyrophenone. The NMR spectrum data of this product were as follows.

$^1$H-NMR δppm (Solvent: CDCl$_3$/400 MHz)
2.04 (s, 6H), 3.24 (s, 3H), 7.35 (d, 2H), 8.23 (d, 2H)

(2) 0.28 g of sodium azide was added to a mixture comprising 0.68 g of α-bromo-4-methylsulfonyloxyisobutyrophenone and 4 ml of dimethyl sulfoxide, followed by a reaction at 50° C. for 3 hours. After completion of the reaction, the reaction mixture was put into water and then extracted with ethyl ether, followed by washing with water. The organic layer was dried over anhydrous magnesium sulfate, followed by concentration under reduced pressure to obtain 0.55 g of α-azido-4-methylsulfonyloxyisobutyrophenone. The NMR spectrum data of this product were as follows.

$^1$H-NMR δppm (Solvent: CDCl$_3$/400 MHz)
1.61 (s, 6H), 3.20 (s, 3H), 7.39 (d, 2H), 8.21 (d, 2H)

(3) 0.61 g of triphenylphosphine was added to a mixture comprising 0.55 g of α-azido-4-methylsulfonyloxyisobutyrophenone, 12.7 ml of tetrahydrofuran and 0.3 ml of water, followed by a reaction at room temperature for 16 hours. After completion of the reaction, the reaction mixture was concentrated under reduced pressure, and the residue was weakly acidified by adding water and then hydrochloric acid, and then washed with ethyl acetate. The aqueous layer was neutralized with an aqueous NaOH solution and extracted with methylene chloride, followed by drying over anhydrous sodium sulfate and concentration under reduced pressure to obtain 0.40 g of oily α-amino-4-methylsulfonyloxyisobutyrophenone.

(4) 0.19 g of triethylamine was added to a mixture comprising 0.40 g of α-amino-4-methylsulfonyloxyisobutyrophenone and 15 ml of tetrahydrofuran, and then 0.27 g of 2,6-difluorobenzoyl chloride was dropwise added thereto under cooling with ice. After completion of the dropwise addition, the mixture was reacted at room temperature for 2 hours. After completion of the reaction, the reaction mixture was washed with water and dried over anhydrous sodium sulfate, followed by concentration under reduced pressure. The obtained residue was purified by silica gel column chromatography (eluent: ethyl acetate/n-hexane=3/7) to obtain 0.50 g of the desired product having a melting point of from 158 to 162° C. The NMR spectrum data of this product were as follows.

$^1$H-NMR δppm (Solvent: CDCl$_3$/400 MHz)
1.78 (s, 6H), 3.15 (s, 3H), 6.89 (s, 1H), 6.91 (t, 2H), 7.32 (d, 2H), 7.32-7.42 (m, 1H), 8.09 (d, 2H)

PREPARATION EXAMPLE 5

Preparation of 2,6-difluoro-N-[(1,1-dimethyl-4'-hydroxy)phenacyl]benzamide (Compound No. 1-2)

At room temperature, a mixture comprising 0.3 g of sodium hydroxide and 15 ml of water was added to a mixture comprising 0.49 g of 2,6-difluoro-N-[(1,1-dimethyl-4'-methylsufonyloxy)phenacyl]benzamide and 30 ml of methanol, followed by a reaction under refluxing for 1 hour. After completion of the reaction, the reaction mixture was concentrated under reduced pressure, then the residue was diluted with water and weakly acidified with hydrochloric acid, and then the precipitated solid was collected by filtration, followed by drying to obtain 0.35 g of the desired product having a melting point of from 107 to 114° C. The NMR spectrum data of this product were as follows.

$^1$H-NMR δppm (Solvent: CDCl$_3$/400 MHz)

1.86 (s, 6H), 6.77 (s, 1H), 6.83 (d, 2H), 6.93 (t, 2H), 7.06 (s, 1H), 7.30-7.40 (m, 1H), 8.02 (d, 2H)

PREPARATION EXAMPLE 6

Preparation of 2,6-difluoro-N-[(1,1-dimethyl-4'-trifluoromethylsulfonyloxy)phenacyl]benzamide (Compound No. 1-26)

0.102 g of trifluoromethanesulfonate anhydride was added to a mixture comprising 0.115 g of 2,6-difluoro-N-[(1,1-dimethyl-4'-hydroxy)phenacyl]benzamide, 7 ml of dichloroethane and 44 mg of triethylamine under cooling with ice, followed by a reaction at room temperature for 2 hours. After completion of the reaction, the reaction mixture was diluted with methylene chloride and washed with water, and then dried over anhydrous sodium sulfate, followed by concentration under reduced pressure. The obtained residue was purified by silica gel column chromatography (eluent: ethyl acetate/n-hexane=3/7) to obtain 0.14 g of the desired product having a melting point of from 117 to 123° C. The NMR spectrum data of this product were as follows.

$^1$H-NMR δppm (Solvent: CDCl$_3$/400 MHz)

1.78 (s, 6H), 6.60 (s, 1H), 6.91 (t, 2H), 7.31 (d, 2H), 7.31-7.41 (m, 1H), 8.10 (d, 2H)

PREPARATION EXAMPLE 7

Preparation of 2-methoxycarbonyl-N-[(4'-chloro-1,1-dimethyl)phenacyl]benzamide (The After-Mentioned Compound No. 1-121)

A catalytic amount of concentrated sulfuric acid was added at room temperature to a mixed solution comprising 1.4 g of 2-hydroxycarbonyl-N-[(4'-chloro-1,1-dimethyl)phenacyl]benzamide and 100 ml of methanol, and the mixture was reacted under heating refluxing for 6 hours. After completion of the reaction, the methanol was distilled off and then 150 ml of water was added to the residue, followed by extraction with ethyl acetate. The organic layer was dried over anhydrous magnesium sulfate, followed by concentration under reduced pressure. The obtained residue was purified by silica gel column chromatography (eluent: ethyl acetate/n-hexane=2/8-4/6) to obtain 0.86 g of the desired product having a melting point of from 166 to 168° C. The NMR spectrum data of this product were as follows.

$^1$H-NMR δppm (Solvent: CDCl$_3$/400 MHz)

1.80 (s, 6H), 3.84 (s, 3H), 6.77 (brs, 1H), 7.18 (dd, 1H), 7.41 (dd, 2H), 7.43-7.51 (m, 2H), 7.86 (dd, 1H), 7.98 (dd, 2H)

PREPARATION EXAMPLE 8

Preparation of 2-aminocarbonyl-N-[(4'-chloro-1,1-dimethyl)phenacyl]benzamide (The After-Mentioned Compound No. 1-122)

10 ml of 28% aqueous ammonia was added at room temperature to a mixed solution comprising 0.58 g of 2-methoxycarbonyl-N-[(4'-chloro-1,1-dimethyl)phenacyl]benzamide and 15 ml of methanol, and the mixture was reacted overnight at room temperature. After completion of the reaction, the methanol was distilled off, and then 200 ml of water was added to the residue, followed by neutralization with 30% sulfuric acid, then by extraction with ethyl acetate and then by washing with a saturated sodium chloride aqueous solution. The organic layer was dried over anhydrous magnesium sulfate, followed by concentration under reduced pressure. The obtained residue was purified by silica gel column chromatography (eluent: ethyl acetate/n-hexane=1/1-8/2) to obtain 0.39 g of the desired product having a melting point of from 205 to 206° C. The NMR spectrum data of this product were as follows.

$^1$H-NMR δppm (Solvent: DMSO/400 MHz)

1.52 (s, 6H), 7.17-7.21 (m, 1H), 7.34 (brs, 1H), 7.41-7.49 (m, 3H), 7.52 (dd, 2H), 7.68 (brs, 1H), 8.05 (dd, 2H), 9.09 (s, 1H)

PREPARATION EXAMPLE 9

Preparation of 2-fluoro-N-[2-[(2,2,3,3,-tetrafluoro-5-methyl-1,4-benzodioxan-6-yl)carbonyl]-2-propyl] benzamide (The After-Mentioned Compound No. 16-37)

(1) Under nitrogen atmosphere, 11.7 ml of n-butyllithium (1.57 M-n-hexane solution) was dropwise added at −20° C. to a mixture of 1.85 g of diisopropylamine and 50 ml of tetrahydrofuran, and then the mixture was stirred at the same temperature for 30 minutes. 5.0 g of 6-bromo-2,2,3,3,-tetrafluoro-1,4-benzodioxane was dropwise added thereto at a temperature of at most −50° C., followed by stirring at the same temperature for 30 minutes. Then, 5.5 ml of methyl iodide was dropwise added thereto at a temperature of at most −70° C., and then the temperature was raised to room temperature, followed by a reaction for 15 hours. After completion of the reaction, the reaction mixture was put into water and then weakly acidified by an addition of hydrochloric acid. Then, the mixture was extracted with ethyl ether, and the extract was washed with water and dried over magnesium sulfate, followed by concentration under reduced pressure. The obtained residue was purified by silica gel column chromatography (eluent: n-hexane) to obtain 3.40 g of oily 6-bromo-2,2,3,3,-tetrafluoro-5-methyl-1,4-benzodioxane. The NMR spectrum data of this product were as follows.

$^1$H-NMR δppm (Solvent: CDCl$_3$/400 MHz)

2.39 (s, 3H), 6.89 (d, 1H), 6.91 (t, 2H), 7.35 (d, 1H)

(2) Under nitrogen atmosphere, 7.8 ml of n-butyllithium (1.57 M-n-hexane solution) was dropwise added at −50° C. to a mixture comprising 3.36 g of 6-bromo-2,2,3,3,-tetrafluoro-5-methyl-1,4-benzodioxane and 40.6 ml of ethyl ether, and then the mixture was stirred at the same temperature for 30 minutes. 0.89 g of isobutylaldehyde was dropwise added thereto at a temperature of at most −70° C., and the temperature was raised to room temperature followed by a reaction for 15 hours. After completion of the reaction, the reaction mixture was put into water, and then weakly acidified by an addition of hydrochloric acid. Then the mixture was extracted with ether, and the extract was washed with water and dried over magnesium sulfate, followed by concentration under reduced pressure. The obtained residue was purified by silica gel column chromatography (eluent: ethyl acetate/n-hexane=1/9) to obtain 1.90 g of oily 1-(2,2,3,3,-tetrafluoro-5-methyl-1,4-benzodioxan-6-yl)-2-methylpropanol. The NMR spectrum data of this product were as follows.

$^1$H-NMR δppm (Solvent: CDCl$_3$/400 MHz)

0.87 (d, 3H), 1.00 (d, 3H), 1.94 (m, 1H), 2.29 (s, 3H), 4.65 (d, 1H), 7.00 (d, 1H), 7.27 (d, 1H)

(3) At room temperature, a mixture of 1.82 g of 1-(2,2,3,3-tetrafluoro-5-methyl-1,4-benzodioxan-6-yl)-2-methylpropanol and 7 ml of methylene chloride was added to a mixture of 2.0 g of pyridinium chlorochromate, 1.01 g of sodium acetate and 20 ml of methylene chloride, followed by a reaction at the same temperature for 2 hours. After completion of the reaction, the reaction mixture was filtrated by cerite, and the filtrate was concentrated under reduced pressure. The obtained residue was purified by silica gel column chromatography (eluent: ethyl acetate/n-hexane=1/19) to obtain 1.70 g of oily 6-(2,2,3,3-tetrafluoro-5-methyl-1,4-benzodioxanyl) 2-propyl ketone. The NMR spectrum data of this product were as follows.

$^1$H-NMR δppm (Solvent: CDCl$_3$/400 MHz)

1.17 (d, 6H), 2.36 (s, 3H), 3.26 (m, 1H), 7.04 (d, 1H), 7.31 (d, 1H)

(4) 2.15 g of phenyltrimethylammonium tribromide was added to a mixture comprising 1.67 g of 6-(2,2,3,3-tetrafluoro-5-methyl-1,4-benzodioxanyl) 2-propyl ketone and 20 ml of tetrahydrofuran, followed by a reaction at room temperature for 2 hours. After completion of the reaction, the reaction mixture was filtrated, and the filtrate was concentrated under reduced pressure to obtain 1.90 g of oily 6-(2,2, 3,3-tetrafluoro-5-methyl-1,4-benzodioxanyl) 2-bromo-2-propyl ketone.

(5) 0.74 g of sodium azide was added to a mixture comprising 1.90 g of 6-(2,2,3,3-tetrafluoro-5-methyl-1,4-benzodioxanyl) 2-bromo-2-propyl ketone and 11 ml of dimethyl sulfoxide, followed by a reaction at 50° C. for 2 hours. After completion of the reaction, the reaction mixture was put into water and extracted with ethyl ether, and then washed with water. The organic layer was dried over anhydrous magnesium sulfate, followed by concentration under reduced pressure. The obtained residue was purified by silica gel column chromatography (eluent: ethyl acetate/n-hexane=1/19) to obtain 0.90 g of the oily 6-(2,2,3,3-tetrafluoro-5-methyl-1,4-benzodioxanyl) 2-azido-2-propyl ketone. The NMR spectrum data of this product were as follows.

$^1$H-NMR δppm (Solvent: CDCl$_3$/400 MHz)

1.56 (s, 6H), 2.25 (s, 3H), 7.03 (d, 1H), 7.27 (d, 1H)

(6) A mixture comprising 0.90 g of 6-(2,2,3,3-tetrafluoro-5-methyl-1,4-benzodioxanyl) 2-azido-2-propyl ketone, 20 ml of methanol and 50 mg of 5% palladium-carbon, was reacted at room temperature for 1 hour under hydrogen atmosphere. After completion of the reaction, the reaction mixture was filtrated by cerite, and then the filtrate was concentrated under reduced pressure, to obtain 0.70 g of oily 6-(2,2,3,3-tetrafluoro-5-methyl-1,4-benzodioxanyl) 2-amino-2-propyl ketone.

(7) 0.10 g of triethylamine was added to a mixture comprising 0.20 g of 6-(2,2,3,3-tetrafluoro-5-methyl-1,4-benzodioxanyl) 2-amino-2-propyl ketone and 7 ml of tetrahydrofuran. 0.11 g of 2-fluorobenzoyl chloride was dropwise added thereto under cooling with ice. After completion of the dropwise addition, a reaction was carried out at room temperature for 2 hours. After completion of the reaction, the reaction mixture was washed with water, and then dried over anhydrous sodium sulfate, followed by concentration under reduced pressure. The obtained residue was purified by silica gel column chromatography (eluent: ethyl acetate/n-hexane=3/7) to obtain 0.25 g of the desired product having a melting point of from 110 to 112° C. The NMR spectrum data of this product were as follows. $^1$H-NMR δppm (Solvent: CDCl$_3$/400 MHz)

1.74 (s, 6H), 2.35 (s, 3H), 6.94 (d, 1H), 7.14 (dq, 1H), 7.23 (dt, 1H), 7.30 (s, 1H), 7.42 (d, 1H), 7.44-7.50 (m, 1H), 7.92 (dt, 1H)

PREPARATION EXAMPLE 10

Preparation of 2,6-difluoro-N-[(3'-methoxycarbonyl-1,1-dimethyl)phenacyl]benzamide (The After-Mentioned Compound No. 1-221)

(1) A mixture comprising 2.48 g of m-iodobenzoic acid and 40 ml of tetrahydrofuran was cooled to −70° C., then 13.8 ml of n-butyllithium (1.6 M-n-hexane solution) was dropwise added over a period of 10 minutes, followed by stirring at the same temperature for 30 minutes. Then, a mixture comprising 1.5 g of N-isobutyrylpropyleneimine and 5 ml of tetrahydrofuran was added thereto at −70° C., and then the temperature was raised to room temperature, and a reaction was carried out overnight. After completion of the reaction, the reaction mixture was added to 100 ml of water and stirred, and then hexane was added thereto, followed by liquid separation. The aqueous layer was acidified by concentrated hydrochloric acid and then extracted with ethyl acetate. The extract was dried over anhydrous sodium sulfate, followed by concentration under reduced pressure to obtain a crude product of m-isobutyrylbenzoic acid.

(2) 100 ml of toluene and 5 g of thionyl chloride were added to the crude product of m-isobutyrylbenzoic acid obtained in the above step (1), and the mixture was reacted under refluxing for 1 hour. After completion of the reaction, excess thionyl chloride was distilled off to obtain a toluene solution of crude m-isobutyrylbenzoic acid chloride.

(3) The toluene solution of crude m-isobutyrylbenzoic acid chloride obtained in the above step (2) was dropwise added under cooing with ice to a mixture comprising 5 g of triethylamine and 100 ml of methanol, and the mixture was heated to room temperature and reacted for 1 hour. After completion of the reaction, methanol and toluene were distilled off under reduced pressure. Then, 200 ml of water was added thereto, followed by extraction with ethyl acetate, and then the extract was dried over anhydrous sodium sulfate, followed by concentration under reduced pressure to obtain 1.5 g of a crude product of methyl m-isobutyrylbenzoate.

(4) 0.8 g of phenyltrimethylammonium tribromide was added to a mixture comprising 1.5 g of the crude product of methyl m-isobutyrylbenzoate obtained in the above step (3) and 20 ml of tetrahydrofuran, and followed by a reaction at room temperature overnight. After completion of the reaction, the precipitated crystal was separated by filtration, then tetrahydrofuran was distilled off. The residue was dissolved in ethyl acetate, then washed with a saturated sodium chloride aqueous solution, followed by drying over anhydrous sodium sulfate. Then, concentration under reduced pressure was carried out, and then, rough purification was carried out by silica gel column chromatography to obtain 0.27 g of crude 3'-methoxycarbonyl-2-bromo-2-methylpropiophenone. The NMR spectrum data of this product were as follows.

$^1$H-NMR δppm (Solvent: CDCl$_3$/400 MHz)

2.05 (s, 6H), 3.98 (s, 3H), 7.52-7.57 (m, 1H), 8.19-8.25 (m, 1H), 8.31-8.34 (m, 1H), 8.78 (t, 1H)

(5) 17 mg of a crude product containing the desired product was obtained by employing 0.27 g of the crude 3'-methoxycarbonyl-2-bromo-2-methylpropiophenone obtained in the above step (4), in accordance with the steps (5) to (7) in Preparation Example 9. The NMR spectrum data of this product were as follows.

$^1$H-NMR δppm (Solvent: CDCl$_3$/400 MHz)

1.81 (s, 6H), 3.93 (s, 3H), 6.85-6.91 (m, 3H), 7.27-7.34 (m, 1H), 7.47-7.53 (m, 1H), 8.16-8.20 (m, 2H), 8.65 (t, 1H)

PREPARATION EXAMPLE 11

Preparation of 2,6-difluoro-N-[2-(5-trifluoromethyl-2-pyridylcarbonyl)-2-propyl]benzamide (The After-Mentioned Compound No. 8-43)

10 mg of a crude product containing the desired product was obtained by employing 2.26 g of 2-bromo-5-trifluoromethylpyridine, in accordance with the steps (1), (4) and (5) in Preparation Example 10. The NMR spectrum data of this product were as follows.

$^1$H-NMR δppm (Solvent: CDCl$_3$/400 MHz)

1.89 (s, 6H), 6.71 (br, 1H), 6.83-6.88 (m, 2H), 7.26-7.36 (m, 1H), 8.04-8.11 (m, 1H), 8.76 (s, 1H)

Now, typical examples of the compound of the present invention of the above formula (I) will be given in Tables 1 to 53. These compounds can be prepared in accordance with the above Preparation Examples or by the above-described various processes for the production of the compounds of the present invention.

In the table, Me indicates a methyl group, Et an ethyl group, Bu a butyl group, and Ph a phenyl group. Further, Ph(2-F) indicates that a fluorine atom is substituted at the 2-position. The same applies to other expressions.

TABLE 1

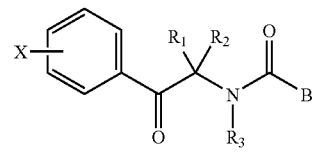

| Compound No. | R$_1$ | R$_2$ | R$_3$ | X | B | Physical properties (mp ° C.) |
|---|---|---|---|---|---|---|
| 1-1 | Me | Me | H | 4-OH | Ph(2-F) | |
| 1-2 | Me | Me | H | 4-OH | Ph(2,6-F$_2$) | 107-114 |
| 1-3 | Me | Me | H | 4-OH | Ph(2-Cl) | |
| 1-4 | Me | Me | H | 4-OH | Ph(2-CF$_3$) | |
| 1-5 | Me | Me | H | 4-OCOMe | Ph(2-F) | |
| 1-6 | Me | Me | H | 4-OCOMe | Ph(2,6-F$_2$) | |
| 1-7 | Me | Me | H | 4-OCOCF$_3$ | Ph(2-F) | |
| 1-8 | Me | Me | H | 4-OCOCF$_3$ | Ph(2,6-F$_2$) | |
| 1-9 | Me | Me | H | 4-OCO$_2$Me | Ph(2-F) | |
| 1-10 | Me | Me | H | 4-OCO$_2$Me | Ph(2,6-F$_2$) | 46-51 |
| 1-11 | Me | Me | H | 4-OCONMe$_2$ | Ph(2-F) | |
| 1-12 | Me | Me | H | 4-OCONMe$_2$ | Ph(2,6-F$_2$) | 136-142 |
| 1-13 | Me | Me | H | 4-OCOSPh | Ph(2-F) | |
| 1-14 | Me | Me | H | 4-OCOSMe | Ph(2,6-F$_2$) | 82-88 |
| 1-15 | Me | Me | H | 4-OCSOMe | Ph(2-F) | |
| 1-16 | Me | Me | H | 4-OCSOMe | Ph(2,6-F$_2$) | |
| 1-17 | Me | Me | H | 4-OCS$_2$Me | Ph(2-F) | |
| 1-18 | Me | Me | H | 4-OCS$_2$Me | Ph(2,6-F$_2$) | |
| 1-19 | Me | Me | H | 4-OCSNMe$_2$ | Ph(2-F) | |
| 1-20 | Me | Me | H | 4-OCSNMe$_2$ | Ph(2,6-F$_2$) | |
| 1-21 | Me | Me | H | 4-OCS$_2$Me | Ph(2-F) | |
| 1-22 | Me | Me | Na | 4-OCS$_2$Me | Ph(2,6-F$_2$) | |
| 1-23 | Me | Me | H | 4-OSCCl$_3$ | Ph(2-F) | |
| 1-24 | Me | Me | H | 4-OSOMe | Ph(2,6-F$_2$) | |
| 1-25 | Me | Me | H | 4-OSO$_2$Me | Ph(2,6-F$_2$) | 158-162 |
| 1-26 | Me | Me | H | 4-OSO$_2$CF$_3$ | Ph(2,6-F$_2$) | 117-123 |
| 1-27 | Me | Me | H | 4-OSO$_2$Ph | Ph(2-F) | |
| 1-28 | Me | Me | H | 4-OSO$_2$Ph | Ph(2,6-F$_2$) | |
| 1-29 | Me | Me | H | 4-OSNMe$_2$ | Ph(2,6-F$_2$) | |
| 1-30 | Me | Me | H | 4-OSO$_2$NMe$_2$ | Ph(2-F) | |
| 1-31 | Me | Me | H | 4-OSO$_2$NMe$_2$ | Ph(2,6-F$_2$) | Oil |
| 1-32 | Me | Me | H | 14-NH$_2$ | Ph(2-F) | |
| 1-33 | Me | Me | H | 4-NH$_2$ | Ph(2,6-F$_2$) | 170-180 |
| 1-34 | Me | Me | H | 4-NH$_2$•HCl | Ph(2,6-F$_2$) | 142-155 |
| 1-35 | Me | Me | H | 4-NHCOMe | Ph(2-F) | |
| 1-36 | Me | Me | H | 4-NHCOBu(t) | Ph(2,6-F$_2$) | 275-281 |
| 1-37 | Me | Me | H | 4-NHCOCF$_3$ | Ph(2-F) | |
| 1-38 | Me | Me | H | 4-NHCOCF$_3$ | Ph(2,6-F$_2$) | |
| 1-39 | Me | Me | H | 4-NHCO$_2$Me | Ph(2-F) | |
| 1-40 | Me | Me | H | 4-NHCO$_2$Me | Ph(2,6-F$_2$) | |
| 1-41 | Me | Me | H | 4-N(Me)CO$_2$Me | Ph(2-F) | |
| 1-42 | Me | Me | H | 4-NHCONMe$_2$ | Ph(2,6-F$_2$) | |
| 1-43 | Me | Me | H | 4-NHCOSMe | Ph(2-F) | |
| 1-44 | Me | Me | H | 4-NHCOSMe | Ph(2,6-F$_2$) | |
| 1-45 | Me | Me | H | 4-NHCSOMe | Ph(2-F) | |
| 1-46 | Me | Me | H | 4-NHCSOMe | Ph(2,6-F$_2$) | |
| 1-47 | Me | Me | H | 4-NHCS$_2$Me | Ph(2-F) | |
| 1-48 | Me | Me | H | 4-NHCS$_2$Me | Ph(2,6-F$_2$) | |
| 1-49 | Me | Me | H | 4-NHCSNMe$_2$ | Ph(2-F) | |
| 1-50 | Me | Me | H | 4-NHCSNMe$_2$ | Ph(2,6-F$_2$) | |
| 1-51 | Me | Me | H | 4-NHCS$_2$Ph | Ph(2-F) | |

TABLE 1-continued

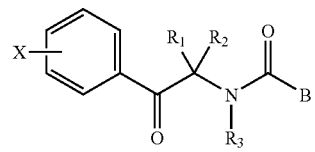

| Compound No. | $R_1$ | $R_2$ | $R_3$ | X | B | Physical properties (mp ° C.) |
|---|---|---|---|---|---|---|
| 1-52 | Me | Me | H | 4-NHCS$_2$Ph | Ph(2,6-F$_2$) | |
| 1-53 | Me | Me | H | 4-NHSCCl$_3$ | Ph(2-F) | |
| 1-54 | Me | Me | H | 4-NHSOMe | Ph(2,6-F$_2$) | |
| 1-55 | Me | Me | H | 4-NHSO$_2$Me | Ph(2-F) | |
| 1-56 | Me | Me | H | 4-NHSO$_2$Me | Ph(2,6-F$_2$) | 195-233 |
| 1-57 | Me | Me | H | 4-NHSO$_2$Ph | Ph(2-F) | |
| 1-58 | Me | Me | H | 4-NHCOPh | Ph(2,6-F$_2$) | 270-283 |
| 1-59 | Me | Me | SCCl$_3$ | 4-F | Ph(2-F) | |
| 1-60 | Me | Me | SCCl$_3$ | 4-Cl | Ph(2,6-F$_2$) | |
| 1-61 | Me | Me | SPh | 4-Br | Ph(2-F) | |
| 1-62 | Me | Me | SPh | 4-F | Ph(2,6-F$_2$) | |
| 1-63 | Me | Me | SOPh | 4-Cl | Ph(2,6-F$_2$) | |
| 1-64 | Me | Me | SO$_2$Me | 4-Br | Ph(2-F) | |
| 1-65 | Me | Me | SO$_2$Me | 4-F | Ph(2,6-F$_2$) | |
| 1-66 | Me | Me | SO$_2$Ph | 4-Cl | Ph(2-F) | |
| 1-67 | Me | Me | SO$_2$Ph | 4-Br | Ph(2,6-F$_2$) | |
| 1-68 | Me | Me | SO$_2$NMe$_2$ | 4-F | Ph(2-F) | |
| 1-69 | Me | Me | SO$_2$NMe$_2$ | 4-Cl | Ph(2,6-F$_2$) | |
| 1-70 | Me | Me | SO$_2$CF$_3$ | 4-Br | Ph(2-F) | |
| 1-71 | Me | Me | SO$_2$CF$_3$ | 4-F | Ph(2,6-F$_2$) | |
| 1-72 | Me | Me | H | 4-CO$_2$H | Ph(2,6-F$_2$) | 215-218 |
| 1-73 | Me | Me | H | 4-CO$_2$Me | Ph(2,6-F$_2$) | 58-60 |
| 1-74 | Me | Me | H | 4-CO$_2$Et | Ph(2,6-F$_2$) | |
| 1-75 | Me | Me | H | 4-CONH$_2$ | Ph(2,6-F$_2$) | >250 |
| 1-76 | Me | Me | H | 4-CONHMe | Ph(2,6-F$_2$) | 244-259 |
| 1-77 | Me | Me | H | 4-CONMe$_2$ | Ph(2,6-F$_2$) | 158-160 |
| 1-78 | Me | Me | H | 4-Cl | Ph(2-CO$_2$H) | 212-214 |
| 1-79 | Me | Me | H | 4-Cl | Ph(2-(2-thienyl)) | |
| 1-80 | Me | Me | H | 4-Cl | Ph(2-(3-thienyl)) | 170-173 |
| 1-81 | Me | Me | H | 4-Cl | Ph(2-(2-pyridyl)) | |
| 1-82 | Me | Me | H | 4-Cl | Ph(2-(3-pyridyl)) | |
| 1-83 | Me | Me | H | 4-Cl | Ph(2-(4-pyridyl)) | |
| 1-84 | Me | Me | H | 4-Br | Ph(2-CO$_2$H) | 197-199 |
| 1-85 | Me | Me | H | 4-Br | Ph(2-(2-thienyl)) | |
| 1-86 | Me | Me | H | 4-Br | Ph(2-(3-thienyl)) | |
| 1-87 | Me | Me | H | 4-Br | Ph(2-(2-pyridyl)) | |
| 1-88 | Me | Me | H | 4-Br | Ph(2-(3-pyridyl)) | |
| 1-89 | Me | Me | H | 4-Br | Ph(2-(4-pyridyl)) | |
| 1-90 | Me | Me | H | 4-(2-pyridyl) | Ph(2,6-F$_2$) | |
| 1-91 | Me | Me | H | 4-(3-pyridyl) | Ph(2,6-F$_2$) | |
| 1-92 | Me | Me | H | 4-(4-pyridyl) | Ph(2,6-F$_2$) | |
| 1-93 | Me | Me | H | 4-(2-thienyl) | Ph(2-F) | 110-112 |
| 1-94 | Me | Me | H | 4-(3-thienyl) | Ph(2-F) | 143-145 |
| 1-95 | Me | Me | H | 4-(2-thienyl) | Ph(2,6-F$_2$) | |
| 1-96 | Me | Me | H | 4-(3-thienyl) | Ph(2,6-F$_2$) | |
| 1-97 | Me | Me | H | 4-Cl | Ph(2-CO$_2$Me) | |
| 1-98 | Me | Me | H | H | Ph(2-CO$_2$Me) | |
| 1-99 | Me | CO$_2$Et | H | H | Ph(2-F) | 122-123 |
| 1-100 | Me | CO$_2$Et | H | H | Ph(2,6-F$_2$) | 117-119 |
| 1-101 | Me | CN | H | H | Ph(2-F) | Oil |
| 1-102 | Me | CN | H | H | Ph(2,6-F$_2$) | 45-48 |
| 1-103 | Me | Me | H | 4-Br | 1-naphthyl | |
| 1-104 | Me | Me | H | 4-Br | 2-naphthyl | |
| 1-105 | Me | Me | H | 4-Br | 2-thienyl | 235-240 |
| 1-106 | Me | Me | H | 4-Br | 3-thienyl | 245-247 |
| 1-107 | Me | Me | H | 4-Br | 2-pyrazinyl | 122-125 |
| 1-108 | Me | Me | H | 4-Br | 2-quinolyl | |
| 1-109 | Me | Me | H | 4-Br | 3-quinolyl | 192-195 |
| 1-110 | Me | Me | H | 4-Br | Indol-2-yl | |
| 1-111 | Me | Me | H | 4-Br | Indol-3-yl | |
| 1-112 | Me | Me | H | 4-Br | 3-furyl | |
| 1-113 | Me | Me | H | 4-Br | 2,5-dimethyl-3-furyl | 183-185 |
| 1-114 | Me | Me | H | 4-Br | 2-furyl | |
| 1-115 | Me | Me | H | 4-Br | 5-nitro-2-furyl | 132-134 |
| 1-116 | Me | Me | H | 4-Br | Benzofuran-2-yl | 164-166 |

TABLE 1-continued

| Compound No. | R₁ | R₂ | R₃ | X | B | Physical properties (mp ° C.) |
|---|---|---|---|---|---|---|
| 1-117 | Me | Me | H | 4-Br | 2,3-dihydrobenzofuran-2-yl | 145-147 |
| 1-118 | Me | Me | H | 4-Br | 1,4-benzodioxane-2-yl | 45-47 |
| 1-119 | Me | Me | H | 4-Br | N-methylindol-2-yl | 50-58 |
| 1-120 | Me | Me | H | 4-Cl | Ph(2-CO$_2$H) | 212-214 |
| 1-121 | Me | Me | H | 4-Cl | Ph(2-CO$_2$Me) | 166-168 |
| 1-122 | Me | Me | H | 4-Cl | Ph(2-CONH$_2$) | 205-206 |
| 1-123 | Me | Me | H | 4-OSO$_2$Me | Ph(2-F) | 130-133 |
| 1-124 | Me | Me | H | 4-OSO$_2$Me | Ph(2-Cl) | |
| 1-125 | Me | Me | H | 4-OSO$_2$CF$_3$ | Ph(2-F) | 72-75 |
| 1-126 | Me | Me | H | 4-OSO$_2$CF$_3$ | Ph(2-Cl) | |
| 1-127 | Me | Me | H | 4-SCH$_2$CF$_3$ | Ph(2,6-F$_2$) | 110-112 |
| 1-128 | Me | Me | H | 4-SCH$_2$CF$_3$ | Ph(2-F) | Oil |
| 1-129 | Me | Me | H | 4-SCH$_2$CF$_3$ | Ph(2-Cl) | |
| 1-130 | Me | Me | H | 4-SCHF$_2$ | Ph(2,6-F$_2$) | 108-110 |
| 1-131 | Me | Me | H | 4-SCHF$_2$ | Ph(2-F) | 77-79 |
| 1-132 | Me | Me | H | 4-SCHF$_2$ | Ph(2-Cl) | |
| 1-133 | Me | Me | H | 4-SO$_2$CH$_2$CF$_3$ | Ph(2,6-F$_2$) | 175-178 |
| 1-134 | Me | Me | H | 4-SO$_2$CH$_2$CF$_3$ | Ph(2-F) | 135-139 |
| 1-135 | Me | Me | H | 4-SO$_2$CH$_2$CF$_3$ | Ph(2-Cl) | |
| 1-136 | Me | Me | H | 4-SO$_2$CHF$_2$ | Ph(2,6-F$_2$) | 140-144 |
| 1-137 | Me | Me | H | 4-SO$_2$CHF$_2$ | Ph(2-F) | 85-88 |
| 1-138 | Me | Me | H | 4-SO$_2$CHF$_2$ | Ph(2-Cl) | |
| 1-139 | Me | Me | H | 2-Me-4-OSO$_2$Me | Ph(2,6-F$_2$) | 112-115 |
| 1-140 | Me | Me | H | 2-Me-4-OSO$_2$CF$_3$ | Ph(2,6-F$_2$) | 108-110 |
| 1-141 | Me | Me | H | 2-Me-4-OCF$_2$CHFOCF$_3$ | Ph(2-F) | |
| 1-142 | Me | Me | H | 2-Me-4-OCF$_2$CHFOCF$_3$ | Ph(2,6-F$_2$) | |
| 1-143 | Me | Me | H | 2-Me-4-OCF$_2$CHFOCF$_3$ | Ph(2-Cl) | |
| 1-144 | Me | Me | H | 2-Me-4-OCF$_2$CHFOCF$_3$ | Ph(2-Me) | |
| 1-145 | Me | Me | H | 2-Me-4-OCF$_2$CHFOCF$_3$ | Ph(2-CF$_3$) | |
| 1-146 | Me | Me | H | 2-Me-4-OCF$_2$CHFOCF$_3$ | Ph(2-F-6-Cl) | |
| 1-147 | Me | Me | H | 2-Cl-4-OCF$_2$CHFOCF$_3$ | Ph(2-F) | |
| 1-148 | Me | Me | H | 2-Cl-4-OCF$_2$CHFOCF$_3$ | Ph(2,6-F$_2$) | |
| 1-149 | Me | Me | H | 2-Cl-4-OCF$_2$CHFOCF$_3$ | Ph(2-Cl) | |
| 1-150 | Me | Me | H | 2-Cl-4-OCF$_2$CHFOCF$_3$ | Ph(2-Me) | |
| 1-151 | Me | Me | H | 2-Cl-4-OCF$_2$CHFOCF$_3$ | Ph(2-CF$_3$) | |
| 1-152 | Me | Me | H | 2-Cl-4-OCF$_2$CHFOCF$_3$ | Ph(2-F-6-Cl) | |
| 1-153 | Me | Me | H | 2,3-Me$_2$-4-OCF$_2$CHFOCF$_3$ | Ph(2-F) | |
| 1-154 | Me | Me | H | 2,3-Me$_2$-4-OCF$_2$CHFOCF$_3$ | Ph(2,6-F$_2$) | |
| 1-155 | Me | Me | H | 2,3-Me$_2$-4-OCF$_2$CHFOCF$_3$ | Ph(2-Cl) | |
| 1-156 | Me | Me | H | 2,3-Me$_2$-4-OCF$_2$CHFOCF$_3$ | Ph(2-Me) | |
| 1-157 | Me | Me | H | 2,3-Me$_2$-4-OCF$_2$CHFOCF$_3$ | Ph(2-CF$_3$) | |
| 1-158 | Me | Me | H | 2,3-Me$_2$-4-OCF$_2$CHFOCF$_3$ | Ph(2-F-6-Cl) | |
| 1-159 | Me | Me | H | 2-Me-3-OMe-4-OCF$_2$CHFOCF$_3$ | Ph(2-F) | |
| 1-160 | Me | Me | H | 2-Me-3-OMe-4-OCF$_2$CHFOCF$_3$ | Ph(2,6-F$_2$) | |
| 1-161 | Me | Me | H | 2-Me-3-OMe-4-OCF$_2$CHFOCF$_3$ | Ph(2-Cl) | |
| 1-162 | Me | Me | H | 2-Me-3-OMe-4-OCF$_2$CHFOCF$_3$ | Ph(2-Me) | |
| 1-163 | Me | Me | H | 2-Me-3-OMe-4-OCF$_2$CHFOCF$_3$ | Ph(2-CF$_3$) | |
| 1-164 | Me | Me | H | 2-Me-3-OMe-4-OCF$_2$CHFOCF$_3$ | Ph(2-F-6-Cl) | |
| 1-165 | Me | Me | H | 2-Me-3-OCHF$_2$-4-OCF$_2$CHFOCF$_3$ | Ph(2-F) | |
| 1-166 | Me | Me | H | 2-Me-3-OCHF$_2$-4-OCF$_2$CHFOCF$_3$ | Ph(2,6-F$_2$) | |
| 1-167 | Me | Me | H | 2-Me-3-OCHF$_2$-4-OCF$_2$CHFOCF$_3$ | Ph(2-Cl) | |
| 1-168 | Me | Me | H | 2-Me-3-OCHF$_2$-4-OCF$_2$CHFOCF$_3$ | Ph(2-Me) | |
| 1-169 | Me | Me | H | 2-Me-3-OCHF$_2$-4-OCF$_2$CHFOCF$_3$ | Ph(2-CF$_3$) | |
| 1-170 | Me | Me | H | 2-Me-3-OCHF$_2$-4-OCF$_2$CHFOCF$_3$ | Ph(2-F-6-Cl) | |
| 1-171 | Me | Me | H | 4-Br | Ph(2-CONHCH$_2$CH(Me)$_2$) | 253-254 |
| 1-172 | Me | Me | H | 4-Br | Ph(2-CONHMe) | 252-255 |
| 1-173 | Me | Me | H | 4-Br | Ph(2-CONH$_2$) | 193-196 |
| 1-174 | Me | Me | H | 4-Br | Ph(2-OCOMe) | 163-166 |
| 1-175 | Me | Me | H | 4-Br | Ph(2-CO$_2$Me) | 151-154 |
| 1-176 | Me | Me | H | 4-Cl | Ph(2-CO$_2$Me) | 166-168 |
| 1-177 | Me | Me | H | 4-Cl | Ph(2-CONH$_2$) | 205-206 |
| 1-178 | Me | Me | H | 2-CO$_2$H | Ph(2-F) | |
| 1-179 | Me | Me | H | 2-CO$_2$H | Ph(2,6-F$_2$) | |

TABLE 1-continued

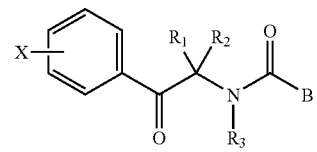

| Compound No. | $R_1$ | $R_2$ | $R_3$ | X | B | Physical properties (mp ° C.) |
|---|---|---|---|---|---|---|
| 1-180 | Me | Me | H | 2-CO$_2$H | Ph(2-Cl) | |
| 1-181 | Me | Me | H | 2-CO$_2$H | Ph(2-Me) | |
| 1-182 | Me | Me | H | 2-CO$_2$H | Ph(2-CF$_3$) | |
| 1-183 | Me | Me | H | 2-CO$_2$H | Ph(2-F-6-Cl) | |
| 1-184 | Me | Me | H | 2-CO$_2$Me | Ph(2-F) | |
| 1-185 | Me | Me | H | 2-CO$_2$Me | Ph(2,6-F$_2$) | |
| 1-186 | Me | Me | H | 2-CO$_2$Me | Ph(2-Cl) | |
| 1-187 | Me | Me | H | 2-CO$_2$Me | Ph(2-Me) | |
| 1-188 | Me | Me | H | 2-CO$_2$Me | Ph(2-CF$_3$) | |
| 1-189 | Me | Me | H | 2-CO$_2$Me | Ph(2-F-6-Cl) | |
| 1-190 | Me | Me | H | 2-CO$_2$Et | Ph(2-F) | |
| 1-191 | Me | Me | H | 2-CO$_2$Et | Ph(2,6-F$_2$) | |
| 1-192 | Me | Me | H | 2-CO$_2$Et | Ph(2-Cl) | |
| 1-193 | Me | Me | H | 2-CO$_2$Et | Ph(2-Me) | |
| 1-194 | Me | Me | H | 2-CO$_2$Et | Ph(2-CF$_3$) | |
| 1-195 | Me | Me | H | 2-CO$_2$Et | Ph(2-F-6-Cl) | |
| 1-196 | Me | Me | H | 2-CONH$_2$ | Ph(2-F) | |
| 1-197 | Me | Me | H | 2-CONH$_2$ | Ph(2,6-F$_2$) | |
| 1-198 | Me | Me | H | 2-CONH$_2$ | Ph(2-Cl) | |
| 1-199 | Me | Me | H | 2-CONH$_2$ | Ph(2-Me) | |
| 1-200 | Me | Me | H | 2-CONH$_2$ | Ph(2-CF$_3$) | |
| 1-201 | Me | Me | H | 2-CONH$_2$ | Ph(2-F-6-Cl) | |
| 1-202 | Me | Me | H | 2-CONHMe | Ph(2-F) | |
| 1-203 | Me | Me | H | 2-CONHMe | Ph(2,6-F$_2$) | |
| 1-204 | Me | Me | H | 2-CONHMe | Ph(2-Cl) | |
| 1-205 | Me | Me | H | 2-CONHMe | Ph(2-Me) | |
| 1-206 | Me | Me | H | 2-CONHMe | Ph(2-CF$_3$) | |
| 1-207 | Me | Me | H | 2-CONHMe | Ph(2-F-6-Cl) | |
| 1-208 | Me | Me | H | 2-CONMe$_2$ | Ph(2-F) | |
| 1-209 | Me | Me | H | 2-CONMe$_2$ | Ph(2,6-F$_2$) | |
| 1-210 | Me | Me | H | 2-CONMe$_2$ | Ph(2-Cl) | |
| 1-211 | Me | Me | H | 2-CONMe$_2$ | Ph(2-Me) | |
| 1-212 | Me | Me | H | 2-CONMe$_2$ | Ph(2-CF$_3$) | |
| 1-213 | Me | Me | H | 2-CONMe$_2$ | Ph(2-F-6-Cl) | |
| 1-214 | Me | Me | H | 3-CO$_2$H | Ph(2-F) | |
| 1-215 | Me | Me | H | 3-CO$_2$H | Ph(2,6-F$_2$) | |
| 1-216 | Me | Me | H | 3-CO$_2$H | Ph(2-Cl) | |
| 1-217 | Me | Me | H | 3-CO$_2$H | Ph(2-Me) | |
| 1-218 | Me | Me | H | 3-CO$_2$H | Ph(2-CF$_3$) | |
| 1-219 | Me | Me | H | 3-CO$_2$H | Ph(2-F-6-Cl) | |
| 1-220 | Me | Me | H | 3-CO$_2$Me | Ph(2-F) | |
| 1-221 | Me | Me | H | 3-CO$_2$Me | Ph(2,6-F$_2$) | Oil |
| 1-222 | Me | Me | H | 3-CO$_2$Me | Ph(2-Cl) | |
| 1-223 | Me | Me | H | 3-CO$_2$Me | Ph(2-Me) | |
| 1-224 | Me | Me | H | 3-CO$_2$Me | Ph(2-CF$_3$) | |
| 1-225 | Me | Me | H | 3-CO$_2$Me | Ph(2-F-6-Cl) | |
| 1-226 | Me | Me | H | 3-CO$_2$Et | Ph(2-F) | |
| 1-227 | Me | Me | H | 3-CO$_2$Et | Ph(2,6-F$_2$) | |
| 1-228 | Me | Me | H | 3-CO$_2$Et | Ph(2-Cl) | |
| 1-229 | Me | Me | H | 3-CO$_2$Et | Ph(2-Me) | |
| 1-230 | Me | Me | H | 3-CO$_2$Et | Ph(2-CF$_3$) | |
| 1-231 | Me | Me | H | 3-CO$_2$Et | Ph(2-F-6-Cl) | |
| 1-232 | Me | Me | H | 3-CONH$_2$ | Ph(2-F) | |
| 1-233 | Me | Me | H | 3-CONH$_2$ | Ph(2,6-F$_2$) | |
| 1-234 | Me | Me | H | 3-CONH$_2$ | Ph(2-Cl) | |
| 1-235 | Me | Me | H | 3-CONH$_2$ | Ph(2-Me) | |
| 1-236 | Me | Me | H | 3-CONH$_2$ | Ph(2-CF$_3$) | |
| 1-237 | Me | Me | H | 3-CONH$_2$ | Ph(2-F-6-Cl) | |
| 1-238 | Me | Me | H | 3-CONHMe | Ph(2-F) | |
| 1-239 | Me | Me | H | 3-CONHMe | Ph(2,6-F$_2$) | |
| 1-240 | Me | Me | H | 3-CONHMe | Ph(2-Cl) | |
| 1-241 | Me | Me | H | 3-CONHMe | Ph(2-Me) | |
| 1-242 | Me | Me | H | 3-CONHMe | Ph(2-CF$_3$) | |
| 1-243 | Me | Me | H | 3-CONHMe | Ph(2-F-6-Cl) | |
| 1-244 | Me | Me | H | 3-CONMe$_2$ | Ph(2-F) | |
| 1-245 | Me | Me | H | 3-CONMe$_2$ | Ph(2,6-F$_2$) | |
| 1-246 | Me | Me | H | 3-CONMe$_2$ | Ph(2-Cl) | |

TABLE 1-continued

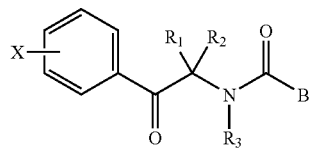

| Compound No. | R₁ | R₂ | R₃ | X | B | Physical properties (mp ° C.) |
|---|---|---|---|---|---|---|
| 1-247 | Me | Me | H | 3-CONMe₂ | Ph(2-Me) | |
| 1-248 | Me | Me | H | 3-CONMe₂ | Ph(2-CF₃) | |
| 1-249 | Me | Me | H | 3-CONMe₂ | Ph(2-F-6-Cl) | |

TABLE 2

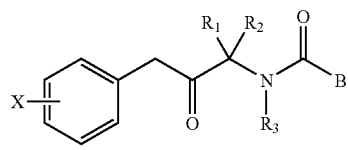

| Compound No. | R₁ | R₂ | R₃ | X | B | Physical properties (mp ° C.) |
|---|---|---|---|---|---|---|
| 2-1 | Me | Me | H | 4-Cl | Ph(2-F) | |
| 2-2 | Me | Et | H | 4-Cl | Ph(2-F) | |
| 2-3 | —(CH₂)₂— | | H | 4-Cl | Ph(2-F) | |
| 2-4 | Me | Me | H | 4-Cl | Ph(2,6-F₂) | 144-153 |
| 2-5 | Me | Me | H | 4-Cl | Ph(2-Cl) | |
| 2-6 | Me | Et | H | 4-Cl | Ph(2-Cl) | |
| 2-7 | Me | Me | COMe | 4-Cl | Ph(2-Cl) | |
| 2-8 | —(CH₂)₂— | | H | 4-Cl | Ph(2-Cl) | |
| 2-9 | —(CH₂)₄— | | H | 4-Cl | Ph(2-Cl) | |
| 2-10 | Me | Me | H | 4-Cl | Ph(2-CF₃) | |
| 2-11 | Me | Me | H | 4-Br | Ph(2-F) | |
| 2-12 | Me | Me | H | 4-Br | Ph(2,6-F₂) | |
| 2-13 | Me | Me | H | 4-Br | Ph(2-Cl) | |
| 2-14 | Me | Me | H | 4-Br | Ph(2-CF₃) | |
| 2-15 | Me | Me | H | 4-F | Ph(2-F) | |
| 2-16 | Me | Me | H | 4-F | Ph(2,6-F₂) | |
| 2-17 | Me | Me | H | 4-F | Ph(2-Cl) | |
| 2-18 | Me | Me | H | 4-F | Ph(2-CF₃) | |
| 2-19 | Me | Me | H | 4-CF₃ | Ph(2-F) | |
| 2-20 | Me | Me | H | 4-CF₃ | Ph(2,6-F₂) | |
| 2-21 | Me | Me | H | 4-CF₃ | Ph(2-Cl) | |
| 2-22 | Me | Me | H | 4-CF₃ | Ph(2-CF₃) | |
| 2-23 | Me | Me | H | 3,4-Cl₂ | Ph(2-F) | |
| 2-24 | Me | Me | H | 3,4-Cl₂ | Ph(2,6-F₂) | |
| 2-25 | —(CH₂)₂— | | H | 3,4-Cl₂ | Ph(2-Cl) | |
| 2-26 | —(CH₂)₅— | | H | 3,4-Cl₂ | Ph(2-CF₃) | |
| 2-27 | Me | Me | Me | 2,4-Cl₂ | Ph(2-F) | |
| 2-28 | Me | Me | H | 2,4-Cl₂ | Ph(2-F) | |
| 2-29 | Me | Me | H | 2,4-Cl₂ | Ph(2,6-F₂) | |
| 2-30 | Me | Me | H | 2,4-Cl₂ | Ph(2-Cl) | |
| 2-31 | Me | Me | H | 2,4-Cl₂ | Ph(2-CF₃) | |
| 2-32 | Me | Me | H | 2,4-F₂ | Ph(2-F) | |
| 2-33 | Me | Me | H | 2,4-F₂ | Ph(2,6-F₂) | |
| 2-34 | Me | Me | H | 4-OCF₃ | Ph(2-F) | |
| 2-35 | Me | Me | H | 4-OCF₃ | Ph(2,6-F₂) | |
| 2-36 | Me | Me | H | 4-OCF₃ | Ph(2-Cl) | |
| 2-37 | Me | Me | H | 4-OCF₃ | Ph(2-Me) | |
| 2-38 | Me | Me | H | 4-OCF₃ | Ph(2-CF₃) | |
| 2-39 | Me | Me | H | 4-OCF₃ | Ph(2-F-6-Cl) | |
| 2-40 | Me | Me | H | 4-OCHF₂ | Ph(2-F) | |
| 2-41 | Me | Me | H | 4-OCHF₂ | Ph(2,6-F₂) | |
| 2-42 | Me | Me | H | 4-OCHF₂ | Ph(2-Cl) | |
| 2-43 | Me | Me | H | 4-OCHF₂ | Ph(2-Me) | |
| 2-44 | Me | Me | H | 4-OCHF₂ | Ph(2-CF₃) | |
| 2-45 | Me | Me | H | 4-OCHF₂ | Ph(2-F-6-Cl) | |
| 2-46 | Me | Me | H | 4-OCH₂CF₃ | Ph(2-F) | |
| 2-47 | Me | Me | H | 4-OCH₂CF₃ | Ph(2,6-F₂) | |
| 2-48 | Me | Me | H | 4-OCH₂CF₃ | Ph(2-Cl) | |

TABLE 2-continued

| Compound No. | $R_1$ | $R_2$ | $R_3$ | X | B | Physical properties (mp ° C.) |
|---|---|---|---|---|---|---|
| 2-49 | Me | Me | H | 4-OCH$_2$CF$_3$ | Ph(2-Me) | |
| 2-50 | Me | Me | H | 4-OCH$_2$CF$_3$ | Ph(2-CF$_3$) | |
| 2-51 | Me | Me | H | 4-OCH$_2$CF$_3$ | Ph(2-F-6-Cl) | |
| 2-52 | Me | Me | H | 2-Me-4-Cl | Ph(2-F) | |
| 2-53 | Me | Me | H | 2-Me-4-Cl | Ph(2,6-F$_2$) | |
| 2-54 | Me | Me | H | 2-Me-4-Cl | Ph(2-Cl) | |
| 2-55 | Me | Me | H | 2-Me-4-Cl | Ph(2-Me) | |
| 2-56 | Me | Me | H | 2-Me-4-Cl | Ph(2-CF$_3$) | |
| 2-57 | Me | Me | H | 2-Me-4-Cl | Ph(2-F-6-Cl) | |
| 2-58 | Me | Me | H | 2-Me-4-Br | Ph(2-F) | |
| 2-59 | Me | Me | H | 2-Me-4-Br | Ph(2,6-F$_2$) | |
| 2-60 | Me | Me | H | 2-Me-4-Br | Ph(2-Cl) | |
| 2-61 | Me | Me | H | 2-Me-4-Br | Ph(2-Me) | |
| 2-62 | Me | Me | H | 2-Me-4-Br | Ph(2-CF$_3$) | |
| 2-63 | Me | Me | H | 2-Me-4-Br | Ph(2-F-6-Cl) | |
| 2-64 | Me | Me | H | 2-Me-4-OCF$_3$ | Ph(2-F) | |
| 2-65 | Me | Me | H | 2-Me-4-OCF$_3$ | Ph(2,6-F$_2$) | |
| 2-66 | Me | Me | H | 2-Me-4-OCF$_3$ | Ph(2-Cl) | |
| 2-67 | Me | Me | H | 2-Me-4-OCF$_3$ | Ph(2-Me) | |
| 2-68 | Me | Me | H | 2-Me-4-OCF$_3$ | Ph(2-CF$_3$) | |
| 2-69 | Me | Me | H | 2-Me-4-OCF$_3$ | Ph(2-F-6-Cl) | |
| 2-70 | Me | Me | H | 2-Me-4-OCHF$_2$ | Ph(2-F) | |
| 2-71 | Me | Me | H | 2-Me-4-OCHF$_2$ | Ph(2,6-F$_2$) | |
| 2-72 | Me | Me | H | 2-Me-4-OCHF$_2$ | Ph(2-Cl) | |
| 2-73 | Me | Me | H | 2-Me-4-OCHF$_2$ | Ph(2-Me) | |
| 2-74 | Me | Me | H | 2-Me-4-OCHF$_2$ | Ph(2-CF$_3$) | |
| 2-75 | Me | Me | H | 2-Me-4-OCHF$_2$ | Ph(2-F-6-Cl) | |
| 2-76 | Me | Me | H | 2-Me-4-OCH$_2$CF$_3$ | Ph(2-F) | |
| 2-77 | Me | Me | H | 2-Me-4-OCH$_2$CF$_3$ | Ph(2,6-F$_2$) | |
| 2-78 | Me | Me | H | 2-Me-4-OCH$_2$CF$_3$ | Ph(2-Cl) | |
| 2-79 | Me | Me | H | 2-Me-4-OCH$_2$CF$_3$ | Ph(2-Me) | |
| 2-80 | Me | Me | H | 2-Me-4-OCH$_2$CF$_3$ | Ph(2-CF$_3$) | |
| 2-81 | Me | Me | H | 2-Me-4-OCH$_2$CF$_3$ | Ph(2-F-6-Cl) | |
| 2-82 | Me | Me | H | 2-Me-4-CF$_3$ | Ph(2-F) | |
| 2-83 | Me | Me | H | 2-Me-4-CF$_3$ | Ph(2,6-F$_2$) | |
| 2-84 | Me | Me | H | 2-Me-4-CF$_3$ | Ph(2-Cl) | |
| 2-85 | Me | Me | H | 2-Me-4-CF$_3$ | Ph(2-Me) | |
| 2-86 | Me | Me | H | 2-Me-4-CF$_3$ | Ph(2-CF$_3$) | |
| 2-87 | Me | Me | H | 2-Me-4-CF$_3$ | Ph(2-F-6-Cl) | |
| 2-88 | Me | Me | H | 2-Cl-4-Br | Ph(2-F) | |
| 2-89 | Me | Me | H | 2-Cl-4-Br | Ph(2,6-F$_2$) | |
| 2-90 | Me | Me | H | 2-Cl-4-Br | Ph(2-Cl) | |
| 2-91 | Me | Me | H | 2-Cl-4-Br | Ph(2-Me) | |
| 2-92 | Me | Me | H | 2-Cl-4-Br | Ph(2-CF$_3$) | |
| 2-93 | Me | Me | H | 2-Cl-4-Br | Ph(2-F-6-Cl) | |
| 2-94 | Me | Me | H | 2-Cl-4-OCF$_3$ | Ph(2-F) | |
| 2-95 | Me | Me | H | 2-Cl-4-OCF$_3$ | Ph(2,6-F$_2$) | |
| 2-96 | Me | Me | H | 2-Cl-4-OCF$_3$ | Ph(2-Cl) | |
| 2-97 | Me | Me | H | 2-Cl-4-OCF$_3$ | Ph(2-Me) | |
| 2-98 | Me | Me | H | 2-Cl-4-OCF$_3$ | Ph(2-CF$_3$) | |
| 2-99 | Me | Me | H | 2-Cl-4-OCF$_3$ | Ph(2-F-6-Cl) | |
| 2-100 | Me | Me | H | 2-Cl-4-OCHF$_2$ | Ph(2-F) | |
| 2-101 | Me | Me | H | 2-Cl-4-OCHF$_2$ | Ph(2,6-F$_2$) | |
| 2-102 | Me | Me | H | 2-Cl-4-OCHF$_2$ | Ph(2-Cl) | |
| 2-103 | Me | Me | H | 2-Cl-4-OCHF$_2$ | Ph(2-Me) | |
| 2-104 | Me | Me | H | 2-Cl-4-OCHF$_2$ | Ph(2-CF$_3$) | |
| 2-105 | Me | Me | H | 2-Cl-4-OCHF$_2$ | Ph(2-F-6-Cl) | |
| 2-106 | Me | Me | H | 2-Cl-4-OCH$_2$CF$_3$ | Ph(2-F) | |
| 2-107 | Me | Me | H | 2-Cl-4-OCH$_2$CF$_3$ | Ph(2,6-F$_2$) | |
| 2-108 | Me | Me | H | 2-Cl-4-OCH$_2$CF$_3$ | Ph(2-Cl) | |
| 2-109 | Me | Me | H | 2-Cl-4-OCH$_2$CF$_3$ | Ph(2-Me) | |
| 2-110 | Me | Me | H | 2-Cl-4-OCH$_2$CF$_3$ | Ph(2-CF$_3$) | |
| 2-111 | Me | Me | H | 2-Cl-4-OCH$_2$CF$_3$ | Ph(2-F-6-Cl) | |

TABLE 3

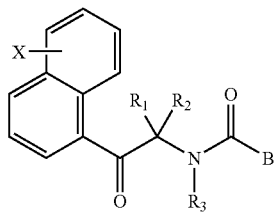

| Compound No. | R$_1$ | R$_2$ | R$_3$ | X | B | Physical properties (mp ° C.) |
|---|---|---|---|---|---|---|
| 3-1 | Me | Me | H | H | Ph | |
| 3-2 | Me | Me | H | H | Ph(2-F) | <30 yellow resin |
| 3-3 | Me | Me | H | H | Ph(2-Cl) | |
| 3-4 | Me | Me | H | H | Ph(2-OMe) | |
| 3-5 | Me | Me | H | H | Ph(2,6-F$_2$) | |
| 3-6 | Me | Me | H | H | Ph(2,6-Cl$_2$) | |
| 3-7 | Me | Me | H | H | Ph(2,6-OMe$_2$) | |
| 3-8 | Me | Me | H | 6-Cl | Ph | |
| 3-9 | Me | Me | H | 6-Cl | Ph(2-F) | |
| 3-10 | Me | Me | H | 6-Cl | Ph(2-Cl) | |
| 3-11 | Me | Me | H | 6-Cl | Ph(2,6-F$_2$) | |
| 3-12 | Me | Me | H | 6-Cl | Ph(2,6-Cl$_2$) | |
| 3-13 | Me | Me | H | 6-Br | Ph | |
| 3-14 | Me | Me | H | 6-Br | Ph(2-F) | |
| 3-15 | Me | Me | H | 6-Br | Ph(2-Cl) | |
| 3-16 | Me | Me | H | 6-Br | Ph(2,6-F$_2$) | |
| 3-17 | Me | Me | H | 6-Br | Ph(2,6-Cl$_2$) | |
| 3-18 | Me | Me | H | 6-CF$_3$ | Ph(2,6-F$_2$) | |
| 3-19 | Me | Me | H | 6-CN | Ph(2,6-F$_2$) | |
| 3-20 | Me | CN | H | H | Ph(2,6-F$_2$) | |
| 3-21 | Me | CO$_2$Et | H | H | Ph(2,6-F$_2$) | |
| 3-22 | Me | CN | H | 6-Cl | Ph(2,6-F$_2$) | |
| 3-23 | Me | CO$_2$Et | H | 6-Cl | Ph(2,6-F$_2$) | |
| 3-24 | Me | Et | H | H | Ph(2,6-F$_2$) | |
| 3-25 | Me | Me | COMe | H | Ph(2,6-F$_2$) | |
| 3-26 | Me | Me | CH$_2$OMe | H | Ph(2,6-F$_2$) | |
| 3-27 | Me | Me | H | H | 1-naphthyl | |
| 3-28 | Me | Me | H | H | 2-naphthyl | |
| 3-29 | Me | Me | H | H | 2-thienyl | |
| 3-30 | Me | Me | H | H | 3-thienyl | |
| 3-31 | Me | Me | H | H | 2-pyrazinyl | |
| 3-32 | Me | Me | H | H | 2-pyridyl | |
| 3-33 | Me | Me | H | H | 3-pyridyl | |
| 3-34 | Me | Me | H | H | 4-trifluoromethyl-3-pyridyl | |
| 3-35 | Me | Me | H | H | 4-pyridyl | |
| 3-36 | Me | Me | H | H | 2-furyl | |
| 3-37 | Me | Me | H | H | 3-furyl | |
| 3-38 | Me | Me | H | 2-Cl | Ph(2-F) | |
| 3-39 | Me | Me | H | 2-Cl | Ph(2,6-F$_2$) | |
| 3-40 | Me | Me | H | 2-Cl | Ph(2-Cl) | |
| 3-41 | Me | Me | H | 2-Cl | Ph(2-Me) | |
| 3-42 | Me | Me | H | 2-Cl | Ph(2-CF$_3$) | |
| 3-43 | Me | Me | H | 2-Cl | Ph(2-F-6-Cl) | |
| 3-44 | Me | Me | H | 2-Br | Ph(2-F) | |
| 3-45 | Me | Me | H | 2-Br | Ph(2,6-F$_2$) | |
| 3-46 | Me | Me | H | 2-Br | Ph(2-Cl) | |
| 3-47 | Me | Me | H | 2-Br | Ph(2-Me) | |
| 3-48 | Me | Me | H | 2-Br | Ph(2-CF$_3$) | |
| 3-49 | Me | Me | H | 2-Br | Ph(2-F-6-Cl) | |
| 3-50 | Me | Me | H | 2-CF$_3$ | Ph(2-F) | |
| 3-51 | Me | Me | H | 2-CF$_3$ | Ph(2,6-F$_2$) | |
| 3-52 | Me | Me | H | 2-CF$_3$ | Ph(2-Cl) | |
| 3-53 | Me | Me | H | 2-CF$_3$ | Ph(2-Me) | |
| 3-54 | Me | Me | H | 2-CF$_3$ | Ph(2-CF$_3$) | |
| 3-55 | Me | Me | H | 2-CF$_3$ | Ph(2-F-6-Cl) | |
| 3-56 | Me | Me | H | 2-OCF$_3$ | Ph(2-F) | |
| 3-57 | Me | Me | H | 2-OCF$_3$ | Ph(2,6-F$_2$) | |
| 3-58 | Me | Me | H | 2-OCF$_3$ | Ph(2-Cl) | |
| 3-59 | Me | Me | H | 2-OCF$_3$ | Ph(2-Me) | |
| 3-60 | Me | Me | H | 2-OCF$_3$ | Ph(2-CF$_3$) | |
| 3-61 | Me | Me | H | 2-OCF$_3$ | Ph(2-F-6-Cl) | |
| 3-62 | Me | Me | H | 2-OCHF$_2$ | Ph(2-F) | |
| 3-63 | Me | Me | H | 2-OCHF$_2$ | Ph(2,6-F$_2$) | |
| 3-64 | Me | Me | H | 2-OCHF$_2$ | Ph(2-Cl) | |
| 3-65 | Me | Me | H | 2-OCHF$_2$ | Ph(2-Me) | |

TABLE 3-continued

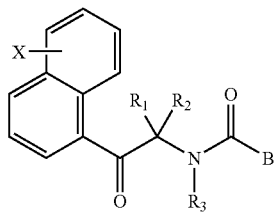

| Compound No. | R$_1$ | R$_2$ | R$_3$ | X | B | Physical properties (mp ° C.) |
|---|---|---|---|---|---|---|
| 3-66 | Me | Me | H | 2-OCHF$_2$ | Ph(2-CF$_3$) | |
| 3-67 | Me | Me | H | 2-OCHF$_2$ | Ph(2-F-6-Cl) | |
| 3-68 | Me | Me | H | 2-OCH$_2$CF$_3$ | Ph(2-F) | |
| 3-69 | Me | Me | H | 2-OCH$_2$CF$_3$ | Ph(2,6-F$_2$) | |
| 3-70 | Me | Me | H | 2-OCH$_2$CF$_3$ | Ph(2-Cl) | |
| 3-71 | Me | Me | H | 2-OCH$_2$CF$_3$ | Ph(2-Me) | |
| 3-72 | Me | Me | H | 2-OCH$_2$CF$_3$ | Ph(2-CF$_3$) | |
| 3-73 | Me | Me | H | 2-OCH$_2$CF$_3$ | Ph(2-F-6-Cl) | |
| 3-74 | Me | Me | H | 2-CN | Ph(2-F) | |
| 3-75 | Me | Me | H | 2-CN | Ph(2,6-F$_2$) | |
| 3-76 | Me | Me | H | 2-CN | Ph(2-Cl) | |
| 3-77 | Me | Me | H | 2-CN | Ph(2-Me) | |
| 3-78 | Me | Me | H | 2-CN | Ph(2-CF$_3$) | |
| 3-79 | Me | Me | H | 2-CN | Ph(2-F-6-Cl) | |
| 3-80 | Me | Me | H | 3-Cl | Ph(2-F) | |
| 3-81 | Me | Me | H | 3-Cl | Ph(2,6-F$_2$) | |
| 3-82 | Me | Me | H | 3-Cl | Ph(2-Cl) | |
| 3-83 | Me | Me | H | 3-Cl | Ph(2-Me) | |
| 3-84 | Me | Me | H | 3-Cl | Ph(2-CF$_3$) | |
| 3-85 | Me | Me | H | 3-Cl | Ph(2-F-6-Cl) | |
| 3-86 | Me | Me | H | 3-Br | Ph(2-F) | |
| 3-87 | Me | Me | H | 3-Br | Ph(2,6-F$_2$) | |
| 3-88 | Me | Me | H | 3-Br | Ph(2-Cl) | |
| 3-89 | Me | Me | H | 3-Br | Ph(2-Me) | |
| 3-90 | Me | Me | H | 3-Br | Ph(2-CF$_3$) | |
| 3-91 | Me | Me | H | 3-Br | Ph(2-F-6-Cl) | |
| 3-92 | Me | Me | H | 3-CF$_3$ | Ph(2-F) | |
| 3-93 | Me | Me | H | 3-CF$_3$ | Ph(2,6-F$_2$) | |
| 3-94 | Me | Me | H | 3-CF$_3$ | Ph(2-Cl) | |
| 3-95 | Me | Me | H | 3-CF$_3$ | Ph(2-Me) | |
| 3-96 | Me | Me | H | 3-CF$_3$ | Ph(2-CF$_3$) | |
| 3-97 | Me | Me | H | 3-CF$_3$ | Ph(2-F-6-Cl) | |
| 3-98 | Me | Me | H | 2-OCF$_3$ | Ph(2-F) | |
| 3-99 | Me | Me | H | 2-OCF$_3$ | Ph(2,6-F$_2$) | |
| 3-100 | Me | Me | H | 2-OCF$_3$ | Ph(2-Cl) | |
| 3-101 | Me | Me | H | 2-OCF$_3$ | Ph(2-Me) | |
| 3-102 | Me | Me | H | 2-OCF$_3$ | Ph(2-CF$_3$) | |
| 3-103 | Me | Me | H | 2-OCF$_3$ | Ph(2-F-6-Cl) | |
| 3-104 | Me | Me | H | 3-OCHF$_2$ | Ph(2-F) | |
| 3-105 | Me | Me | H | 3-OCHF$_2$ | Ph(2,6-F$_2$) | |
| 3-106 | Me | Me | H | 3-OCHF$_2$ | Ph(2-Cl) | |
| 3-107 | Me | Me | H | 3-OCHF$_2$ | Ph(2-Me) | |
| 3-108 | Me | Me | H | 3-OCHF$_2$ | Ph(2-CF$_3$) | |
| 3-109 | Me | Me | H | 3-OCHF$_2$ | Ph(2-F-6-Cl) | |
| 3-110 | Me | Me | H | 3-OCH$_2$CF$_3$ | Ph(2-F) | |
| 3-111 | Me | Me | H | 3-OCH$_2$CF$_3$ | Ph(2,6-F$_2$) | |
| 3-112 | Me | Me | H | 3-OCH$_2$CF$_3$ | Ph(2-Cl) | |
| 3-113 | Me | Me | H | 3-OCH$_2$CF$_3$ | Ph(2-Me) | |
| 3-114 | Me | Me | H | 3-OCH$_2$CF$_3$ | Ph(2-CF$_3$) | |
| 3-115 | Me | Me | H | 3-OCH$_2$CF$_3$ | Ph(2-F-6-Cl) | |
| 3-116 | Me | Me | H | 3-CN | Ph(2-F) | |
| 3-117 | Me | Me | H | 3-CN | Ph(2,6-F$_2$) | |
| 3-118 | Me | Me | H | 3-CN | Ph(2-Cl) | |
| 3-119 | Me | Me | H | 3-CN | Ph(2-Me) | |
| 3-120 | Me | Me | H | 3-CN | Ph(2-CF$_3$) | |
| 3-121 | Me | Me | H | 3-CN | Ph(2-F-6-Cl) | |
| 3-122 | Me | Me | H | 4-Cl | Ph(2-F) | |
| 3-123 | Me | Me | H | 4-Cl | Ph(2,6-F$_2$) | |
| 3-124 | Me | Me | H | 4-Cl | Ph(2-Cl) | |
| 3-125 | Me | Me | H | 4-Cl | Ph(2-Me) | |
| 3-126 | Me | Me | H | 4-Cl | Ph(2-CF$_3$) | |
| 3-127 | Me | Me | H | 4-Cl | Ph(2-F-6-Cl) | |
| 3-128 | Me | Me | H | 4-Br | Ph(2-F) | |
| 3-129 | Me | Me | H | 4-Br | Ph(2,6-F$_2$) | |
| 3-130 | Me | Me | H | 4-Br | Ph(2-Cl) | |
| 3-131 | Me | Me | H | 4-Br | Ph(2-Me) | |

TABLE 3-continued

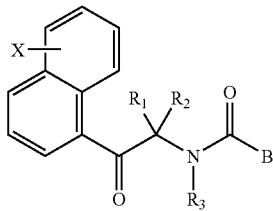

| Compound No. | R₁ | R₂ | R₃ | X | B | Physical properties (mp ° C.) |
|---|---|---|---|---|---|---|
| 3-132 | Me | Me | H | 4-Br | Ph(2-CF$_3$) | |
| 3-133 | Me | Me | H | 4-Br | Ph(2-F-6-Cl) | |
| 3-134 | Me | Me | H | 4-CF$_3$ | Ph(2-F) | |
| 3-135 | Me | Me | H | 4-CF$_3$ | Ph(2,6-F$_2$) | |
| 3-136 | Me | Me | H | 4-CF$_3$ | Ph(2-Cl) | |
| 3-137 | Me | Me | H | 4-CF$_3$ | Ph(2-Me) | |
| 3-138 | Me | Me | H | 4-CF$_3$ | Ph(2-CF$_3$) | |
| 3-139 | Me | Me | H | 4-CF$_3$ | Ph(2-F-6-Cl) | |
| 3-140 | Me | Me | H | 4-OCF$_3$ | Ph(2-F) | |
| 3-141 | Me | Me | H | 4-OCF$_3$ | Ph(2,6-F$_2$) | |
| 3-142 | Me | Me | H | 4-OCF$_3$ | Ph(2-Cl) | |
| 3-143 | Me | Me | H | 4-OCF$_3$ | Ph(2-Me) | |
| 3-144 | Me | Me | H | 4-OCF$_3$ | Ph(2-CF$_3$) | |
| 3-145 | Me | Me | H | 4-OCF$_3$ | Ph(2-F-6-Cl) | |
| 3-146 | Me | Me | H | 4-OCHF$_2$ | Ph(2-F) | |
| 3-147 | Me | Me | H | 4-OCHF$_2$ | Ph(2,6-F$_2$) | |
| 3-148 | Me | Me | H | 4-OCHF$_2$ | Ph(2-Cl) | |
| 3-149 | Me | Me | H | 4-OCHF$_2$ | Ph(2-Me) | |
| 3-150 | Me | Me | H | 4-OCHF$_2$ | Ph(2-CF$_3$) | |
| 3-151 | Me | Me | H | 4-OCHF$_2$ | Ph(2-F-6-Cl) | |
| 3-152 | Me | Me | H | 4-OCH$_2$CF$_3$ | Ph(2-F) | |
| 3-153 | Me | Me | H | 4-OCH$_2$CF$_3$ | Ph(2,6-F$_2$) | |
| 3-154 | Me | Me | H | 4-OCH$_2$CF$_3$ | Ph(2-Cl) | |
| 3-155 | Me | Me | H | 4-OCH$_2$CF$_3$ | Ph(2-Me) | |
| 3-156 | Me | Me | H | 4-OCH$_2$CF$_3$ | Ph(2-CF$_3$) | |
| 3-157 | Me | Me | H | 4-OCH$_2$CF$_3$ | Ph(2-F-6-Cl) | |
| 3-158 | Me | Me | H | 4-CN | Ph(2-F) | |
| 3-159 | Me | Me | H | 4-CN | Ph(2,6-F$_2$) | |
| 3-160 | Me | Me | H | 4-CN | Ph(2-Cl) | |
| 3-161 | Me | Me | H | 4-CN | Ph(2-Me) | |
| 3-162 | Me | Me | H | 4-CN | Ph(2-CF$_3$) | |
| 3-163 | Me | Me | H | 4-CN | Ph(2-F-6-Cl) | |
| 3-164 | Me | Me | H | 5-Cl | Ph(2-F) | |
| 3-165 | Me | Me | H | 5-Cl | Ph(2,6-F$_2$) | |
| 3-166 | Me | Me | H | 5-Cl | Ph(2-Cl) | |
| 3-167 | Me | Me | H | 5-Cl | Ph(2-Me) | |
| 3-168 | Me | Me | H | 5-Cl | Ph(2-CF$_3$) | |
| 3-169 | Me | Me | H | 5-Cl | Ph(2-F-6-Cl) | |
| 3-170 | Me | Me | H | 5-Br | Ph(2-F) | |
| 3-171 | Me | Me | H | 5-Br | Ph(2,6-F$_2$) | |
| 3-172 | Me | Me | H | 5-Br | Ph(2-Cl) | |
| 3-173 | Me | Me | H | 5-Br | Ph(2-Me) | |
| 3-174 | Me | Me | H | 5-Br | Ph(2-CF$_3$) | |
| 3-175 | Me | Me | H | 5-Br | Ph(2-F-6-Cl) | |
| 3-176 | Me | Me | H | 5-CF$_3$ | Ph(2-F) | |
| 3-177 | Me | Me | H | 5-CF$_3$ | Ph(2,6-F$_2$) | |
| 3-178 | Me | Me | H | 5-CF$_3$ | Ph(2-Cl) | |
| 3-179 | Me | Me | H | 5-CF$_3$ | Ph(2-Me) | |
| 3-180 | Me | Me | H | 5-CF$_3$ | Ph(2-CF$_3$) | |
| 3-181 | Me | Me | H | 5-CF$_3$ | Ph(2-F-6-Cl) | |
| 3-182 | Me | Me | H | 5-OCF$_3$ | Ph(2-F) | |
| 3-183 | Me | Me | H | 5-OCF$_3$ | Ph(2,6-F$_2$) | |
| 3-184 | Me | Me | H | 5-OCF$_3$ | Ph(2-Cl) | |
| 3-185 | Me | Me | H | 5-OCF$_3$ | Ph(2-Me) | |
| 3-186 | Me | Me | H | 5-OCF$_3$ | Ph(2-CF$_3$) | |
| 3-187 | Me | Me | H | 5-OCF$_3$ | Ph(2-F-6-Cl) | |
| 3-188 | Me | Me | H | 5-OCHF$_2$ | Ph(2-F) | |
| 3-189 | Me | Me | H | 5-OCHF$_2$ | Ph(2,6-F$_2$) | |
| 3-190 | Me | Me | H | 5-OCHF$_2$ | Ph(2-Cl) | |
| 3-191 | Me | Me | H | 5-OCHF$_2$ | Ph(2-Me) | |
| 3-192 | Me | Me | H | 5-OCHF$_2$ | Ph(2-CF$_3$) | |
| 3-193 | Me | Me | H | 5-OCHF$_2$ | Ph(2-F-6-Cl) | |
| 3-194 | Me | Me | H | 5-OCH$_2$CF$_3$ | Ph(2-F) | |
| 3-195 | Me | Me | H | 5-OCH$_2$CF$_3$ | Ph(2,6-F$_2$) | |
| 3-196 | Me | Me | H | 5-OCH$_2$CF$_3$ | Ph(2-Cl) | |
| 3-197 | Me | Me | H | 5-OCH$_2$CF$_3$ | Ph(2-Me) | |

TABLE 3-continued

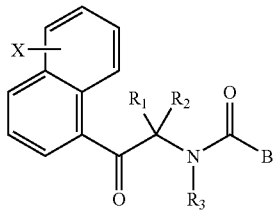

| Compound No. | R$_1$ | R$_2$ | R$_3$ | X | B | Physical properties (mp ° C.) |
|---|---|---|---|---|---|---|
| 3-198 | Me | Me | H | 5-OCH$_2$CF$_3$ | Ph(2-CF$_3$) | |
| 3-199 | Me | Me | H | 5-OCH$_2$CF$_3$ | Ph(2-F-6-Cl) | |
| 3-200 | Me | Me | H | 5-CN | Ph(2-F) | |
| 3-201 | Me | Me | H | 5-CN | Ph(2,6-F$_2$) | |
| 3-202 | Me | Me | H | 5-CN | Ph(2-Cl) | |
| 3-203 | Me | Me | H | 5-CN | Ph(2-Me) | |
| 3-204 | Me | Me | H | 5-CN | Ph(2-CF$_3$) | |
| 3-205 | Me | Me | H | 5-CN | Ph(2-F-6-Cl) | |
| 3-206 | Me | Me | H | 6-Cl | Ph(2-F) | |
| 3-207 | Me | Me | H | 6-Cl | Ph(2,6-F$_2$) | |
| 3-208 | Me | Me | H | 6-Cl | Ph(2-Cl) | |
| 3-209 | Me | Me | H | 6-Cl | Ph(2-Me) | |
| 3-210 | Me | Me | H | 6-Cl | Ph(2-CF$_3$) | |
| 3-211 | Me | Me | H | 6-Cl | Ph(2-F-6-Cl) | |
| 3-212 | Me | Me | H | 6-Br | Ph(2-F) | |
| 3-213 | Me | Me | H | 6-Br | Ph(2,6-F$_2$) | |
| 3-214 | Me | Me | H | 6-Br | Ph(2-Cl) | |
| 3-215 | Me | Me | H | 6-Br | Ph(2-Me) | |
| 3-216 | Me | Me | H | 6-Br | Ph(2-CF$_3$) | |
| 3-217 | Me | Me | H | 6-Br | Ph(2-F-6-Cl) | |
| 3-218 | Me | Me | H | 6-CF$_3$ | Ph(2-F) | |
| 3-219 | Me | Me | H | 6-CF$_3$ | Ph(2,6-F$_2$) | |
| 3-220 | Me | Me | H | 6-CF$_3$ | Ph(2-Cl) | |
| 3-221 | Me | Me | H | 6-CF$_3$ | Ph(2-Me) | |
| 3-222 | Me | Me | H | 6-CF$_3$ | Ph(2-CF$_3$) | |
| 3-223 | Me | Me | H | 6-CF$_3$ | Ph(2-F-6-Cl) | |
| 3-224 | Me | Me | H | 6-OCF$_3$ | Ph(2-F) | |
| 3-225 | Me | Me | H | 6-OCF$_3$ | Ph(2,6-F$_2$) | |
| 3-226 | Me | Me | H | 6-OCF$_3$ | Ph(2-Cl) | |
| 3-227 | Me | Me | H | 6-OCF$_3$ | Ph(2-Me) | |
| 3-228 | Me | Me | H | 6-OCF$_3$ | Ph(2-CF$_3$) | |
| 3-229 | Me | Me | H | 6-OCF$_3$ | Ph(2-F-6-Cl) | |
| 3-230 | Me | Me | H | 6-OCHF$_2$ | Ph(2-F) | |
| 3-231 | Me | Me | H | 6-OCHF$_2$ | Ph(2,6-F$_2$) | |
| 3-232 | Me | Me | H | 6-OCHF$_2$ | Ph(2-Cl) | |
| 3-233 | Me | Me | H | 6-OCHF$_2$ | Ph(2-Me) | |
| 3-234 | Me | Me | H | 6-OCHF$_2$ | Ph(2-CF$_3$) | |
| 3-235 | Me | Me | H | 6-OCHF$_2$ | Ph(2-F-6-Cl) | |
| 3-236 | Me | Me | H | 6-OCH$_2$CF$_3$ | Ph(2-F) | |
| 3-237 | Me | Me | H | 6-OCH$_2$CF$_3$ | Ph(2,6-F$_2$) | |
| 3-238 | Me | Me | H | 6-OCH$_2$CF$_3$ | Ph(2-Cl) | |
| 3-239 | Me | Me | H | 6-OCH$_2$CF$_3$ | Ph(2-Me) | |
| 3-240 | Me | Me | H | 6-OCH$_2$CF$_3$ | Ph(2-CF$_3$) | |
| 3-241 | Me | Me | H | 6-OCH$_2$CF$_3$ | Ph(2-F-6-Cl) | |
| 3-242 | Me | Me | H | 6-CN | Ph(2-F) | |
| 3-243 | Me | Me | H | 6-CN | Ph(2,6-F$_2$) | |
| 3-244 | Me | Me | H | 6-CN | Ph(2-Cl) | |
| 3-245 | Me | Me | H | 6-CN | Ph(2-Me) | |
| 3-246 | Me | Me | H | 6-CN | Ph(2-CF$_3$) | |
| 3-247 | Me | Me | H | 6-CN | Ph(2-F-6-Cl) | |
| 3-248 | Me | Me | H | 7-Cl | Ph(2-F) | |
| 3-249 | Me | Me | H | 7-Cl | Ph(2,6-F$_2$) | |
| 3-250 | Me | Me | H | 7-Cl | Ph(2-Cl) | |
| 3-251 | Me | Me | H | 7-Cl | Ph(2-Me) | |
| 3-252 | Me | Me | H | 7-Cl | Ph(2-CF$_3$) | |
| 3-253 | Me | Me | H | 7-Cl | Ph(2-F-6-Cl) | |
| 3-254 | Me | Me | H | 7-Br | Ph(2-F) | |
| 3-255 | Me | Me | H | 7-Br | Ph(2,6-F$_2$) | |
| 3-256 | Me | Me | H | 7-Br | Ph(2-Cl) | |
| 3-257 | Me | Me | H | 7-Br | Ph(2-Me) | |
| 3-258 | Me | Me | H | 7-Br | Ph(2-CF$_3$) | |
| 3-259 | Me | Me | H | 7-Br | Ph(2-F-6-Cl) | |
| 3-260 | Me | Me | H | 7-CF$_3$ | Ph(2-F) | |
| 3-261 | Me | Me | H | 7-CF$_3$ | Ph(2,6-F$_2$) | |
| 3-262 | Me | Me | H | 7-CF$_3$ | Ph(2-Cl) | |
| 3-263 | Me | Me | H | 7-CF$_3$ | Ph(2-Me) | |

TABLE 3-continued

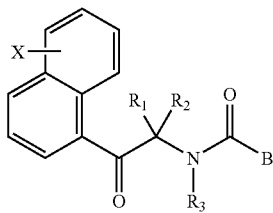

| Compound No. | $R_1$ | $R_2$ | $R_3$ | X | B | Physical properties (mp ° C.) |
|---|---|---|---|---|---|---|
| 3-264 | Me | Me | H | 7-$CF_3$ | Ph(2-$CF_3$) | |
| 3-265 | Me | Me | H | 7-$CF_3$ | Ph(2-F-6-Cl) | |
| 3-266 | Me | Me | H | 7-$OCF_3$ | Ph(2-F) | |
| 3-267 | Me | Me | H | 7-$OCF_3$ | Ph(2,6-$F_2$) | |
| 3-268 | Me | Me | H | 7-$OCF_3$ | Ph(2-Cl) | |
| 3-269 | Me | Me | H | 7-$OCF_3$ | Ph(2-Me) | |
| 3-270 | Me | Me | H | 7-$OCF_3$ | Ph(2-$CF_3$) | |
| 3-271 | Me | Me | H | 7-$OCF_3$ | Ph(2-F-6-Cl) | |
| 3-272 | Me | Me | H | 7-$OCHF_2$ | Ph(2-F) | |
| 3-273 | Me | Me | H | 7-$OCHF_2$ | Ph(2,6-$F_2$) | |
| 3-274 | Me | Me | H | 7-$OCHF_2$ | Ph(2-Cl) | |
| 3-275 | Me | Me | H | 7-$OCHF_2$ | Ph(2-Me) | |
| 3-276 | Me | Me | H | 7-$OCHF_2$ | Ph(2-$CF_3$) | |
| 3-277 | Me | Me | H | 7-$OCHF_2$ | Ph(2-F-6-Cl) | |
| 3-278 | Me | Me | H | 7-$OCH_2CF_3$ | Ph(2-F) | |
| 3-279 | Me | Me | H | 7-$OCH_2CF_3$ | Ph(2,6-$F_2$) | |
| 3-280 | Me | Me | H | 7-$OCH_2CF_3$ | Ph(2-Cl) | |
| 3-281 | Me | Me | H | 7-$OCH_2CF_3$ | Ph(2-Me) | |
| 3-282 | Me | Me | H | 7-$OCH_2CF_3$ | Ph(2-$CF_3$) | |
| 3-283 | Me | Me | H | 7-$OCH_2CF_3$ | Ph(2-F-6-Cl) | |
| 3-284 | Me | Me | H | 7-CN | Ph(2-F) | |
| 3-285 | Me | Me | H | 7-CN | Ph(2,6-$F_2$) | |
| 3-286 | Me | Me | H | 7-CN | Ph(2-Cl) | |
| 3-287 | Me | Me | H | 7-CN | Ph(2-Me) | |
| 3-288 | Me | Me | H | 7-CN | Ph(2-$CF_3$) | |
| 3-289 | Me | Me | H | 7-CN | Ph(2-F-6-Cl) | |
| 3-290 | Me | Me | H | 2-Me-4-Cl | Ph(2-F) | |
| 3-291 | Me | Me | H | 2-Me-4-Cl | Ph(2,6-$F_2$) | |
| 3-292 | Me | Me | H | 2-Me-4-Cl | Ph(2-Cl) | |
| 3-293 | Me | Me | H | 2-Me-4-Cl | Ph(2-Me) | |
| 3-294 | Me | Me | H | 2-Me-4-Cl | Ph(2-$CF_3$) | |
| 3-295 | Me | Me | H | 2-Me-4-Cl | Ph(2-F-6-Cl) | |
| 3-296 | Me | Me | H | 3-Me-4-Cl | Ph(2-F) | |
| 3-297 | Me | Me | H | 3-Me-4-Cl | Ph(2,6-$F_2$) | |
| 3-298 | Me | Me | H | 3-Me-4-Cl | Ph(2-Cl) | |
| 3-299 | Me | Me | H | 3-Me-4-Cl | Ph(2-Me) | |
| 3-300 | Me | Me | H | 3-Me-4-Cl | Ph(2-$CF_3$) | |
| 3-301 | Me | Me | H | 3-Me-4-Cl | Ph(2-F-6-Cl) | |
| 3-302 | Me | Me | H | 5-Me-6-Cl | Ph(2-F) | |
| 3-303 | Me | Me | H | 5-Me-6-Cl | Ph(2,6-$F_2$) | |
| 3-304 | Me | Me | H | 5-Me-6-Cl | Ph(2-Cl) | |
| 3-305 | Me | Me | H | 5-Me-6-Cl | Ph(2-Me) | |
| 3-306 | Me | Me | H | 5-Me-6-Cl | Ph(2-$CF_3$) | |
| 3-307 | Me | Me | H | 5-Me-6-Cl | Ph(2-F-6-Cl) | |
| 3-308 | Me | Me | H | 6-Me-5-Cl | Ph(2-F) | |
| 3-309 | Me | Me | H | 6-Me-5-Cl | Ph(2,6-$F_2$) | |
| 3-310 | Me | Me | H | 6-Me-5-Cl | Ph(2-Cl) | |
| 3-311 | Me | Me | H | 6-Me-5-Cl | Ph(2-Me) | |
| 3-312 | Me | Me | H | 6-Me-5-Cl | Ph(2-$CF_3$) | |
| 3-313 | Me | Me | H | 6-Me-5-Cl | Ph(2-F-6-Cl) | |
| 3-314 | Me | Me | H | 2-Me-4-Br | Ph(2-F) | |
| 3-315 | Me | Me | H | 2-Me-4-Br | Ph(2,6-$F_2$) | |
| 3-316 | Me | Me | H | 2-Me-4-Br | Ph(2-Cl) | |
| 3-317 | Me | Me | H | 2-Me-4-Br | Ph(2-Me) | |
| 3-318 | Me | Me | H | 2-Me-4-Br | Ph(2-$CF_3$) | |
| 3-319 | Me | Me | H | 2-Me-4-Br | Ph(2-F-6-Cl) | |
| 3-320 | Me | Me | H | 3-Me-4-Br | Ph(2-F) | |
| 3-321 | Me | Me | H | 3-Me-4-Br | Ph(2,6-$F_2$) | |
| 3-322 | Me | Me | H | 3-Me-4-Br | Ph(2-Cl) | |
| 3-323 | Me | Me | H | 3-Me-4-Br | Ph(2-Me) | |
| 3-324 | Me | Me | H | 3-Me-4-Br | Ph(2-$CF_3$) | |
| 3-325 | Me | Me | H | 3-Me-4-Br | Ph(2-F-6-Cl) | |
| 3-326 | Me | Me | H | 5-Me-6-Br | Ph(2-F) | |
| 3-327 | Me | Me | H | 5-Me-6-Br | Ph(2,6-$F_2$) | |
| 3-328 | Me | Me | H | 5-Me-6-Br | Ph(2-Cl) | |
| 3-329 | Me | Me | H | 5-Me-6-Br | Ph(2-Me) | |

TABLE 3-continued

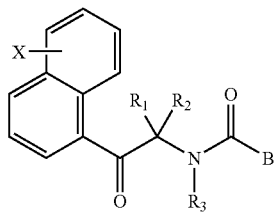

| Compound No. | $R_1$ | $R_2$ | $R_3$ | X | B | Physical properties (mp ° C.) |
|---|---|---|---|---|---|---|
| 3-330 | Me | Me | H | 5-Me-6-Br | Ph(2-CF$_3$) | |
| 3-331 | Me | Me | H | 5-Me-6-Br | Ph(2-F-6-Cl) | |
| 3-332 | Me | Me | H | 6-Me-5-Br | Ph(2-F) | |
| 3-333 | Me | Me | H | 6-Me-5-Br | Ph(2,6-F$_2$) | |
| 3-334 | Me | Me | H | 6-Me-5-Br | Ph(2-Cl) | |
| 3-335 | Me | Me | H | 6-Me-5-Br | Ph(2-Me) | |
| 3-336 | Me | Me | H | 6-Me-5-Br | Ph(2-CF$_3$) | |
| 3-337 | Me | Me | H | 6-Me-5-Br | Ph(2-F-6-Cl) | |
| 3-338 | Me | Me | H | 2-Me-4-CF$_3$ | Ph(2-F) | |
| 3-339 | Me | Me | H | 2-Me-4-CF$_3$ | Ph(2,6-F$_2$) | |
| 3-340 | Me | Me | H | 2-Me-4-CF$_3$ | Ph(2-Cl) | |
| 3-341 | Me | Me | H | 2-Me-4-CF$_3$ | Ph(2-Me) | |
| 3-342 | Me | Me | H | 2-Me-4-CF$_3$ | Ph(2-CF$_3$) | |
| 3-343 | Me | Me | H | 2-Me-4-CF$_3$ | Ph(2-F-6-Cl) | |
| 3-344 | Me | Me | H | 3-Me-4-CF$_3$ | Ph(2-F) | |
| 3-345 | Me | Me | H | 3-Me-4-CF$_3$ | Ph(2,6-F$_2$) | |
| 3-346 | Me | Me | H | 3-Me-4-CF$_3$ | Ph(2-Cl) | |
| 3-347 | Me | Me | H | 3-Me-4-CF$_3$ | Ph(2-Me) | |
| 3-348 | Me | Me | H | 3-Me-4-CF$_3$ | Ph(2-CF$_3$) | |
| 3-349 | Me | Me | H | 3-Me-4-CF$_3$ | Ph(2-F-6-Cl) | |
| 3-350 | Me | Me | H | 5-Me-6-CF$_3$ | Ph(2-F) | |
| 3-351 | Me | Me | H | 5-Me-6-CF$_3$ | Ph(2,6-F$_2$) | |
| 3-352 | Me | Me | H | 5-Me-6-CF$_3$ | Ph(2-Cl) | |
| 3-353 | Me | Me | H | 5-Me-6-CF$_3$ | Ph(2-Me) | |
| 3-354 | Me | Me | H | 5-Me-6-CF$_3$ | Ph(2-CF$_3$) | |
| 3-355 | Me | Me | H | 5-Me-6-CF$_3$ | Ph(2-F-6-Cl) | |
| 3-356 | Me | Me | H | 6-Me-5-CF$_3$ | Ph(2-F) | |
| 3-357 | Me | Me | H | 6-Me-5-CF$_3$ | Ph(2,6-F$_2$) | |
| 3-358 | Me | Me | H | 6-Me-5-CF$_3$ | Ph(2-Cl) | |
| 3-359 | Me | Me | H | 6-Me-5-CF$_3$ | Ph(2-Me) | |
| 3-360 | Me | Me | H | 6-Me-5-CF$_3$ | Ph(2-CF$_3$) | |
| 3-361 | Me | Me | H | 6-Me-5-CF$_3$ | Ph(2-F-6-Cl) | |
| 3-362 | Me | Me | H | 2-Me-4-OCF$_3$ | Ph(2-F) | |
| 3-363 | Me | Me | H | 2-Me-4-OCF$_3$ | Ph(2,6-F$_2$) | |
| 3-364 | Me | Me | H | 2-Me-4-OCF$_3$ | Ph(2-Cl) | |
| 3-365 | Me | Me | H | 2-Me-4-OCF$_3$ | Ph(2-Me) | |
| 3-366 | Me | Me | H | 2-Me-4-OCF$_3$ | Ph(2-CF$_3$) | |
| 3-367 | Me | Me | H | 2-Me-4-OCF$_3$ | Ph(2-F-6-Cl) | |
| 3-368 | Me | Me | H | 3-Me-4-OCF$_3$ | Ph(2-F) | |
| 3-369 | Me | Me | H | 3-Me-4-OCF$_3$ | Ph(2,6-F$_2$) | |
| 3-370 | Me | Me | H | 3-Me-4-OCF$_3$ | Ph(2-Cl) | |
| 3-371 | Me | Me | H | 3-Me-4-OCF$_3$ | Ph(2-Me) | |
| 3-372 | Me | Me | H | 3-Me-4-OCF$_3$ | Ph(2-CF$_3$) | |
| 3-373 | Me | Me | H | 3-Me-4-OCF$_3$ | Ph(2-F-6-Cl) | |
| 3-374 | Me | Me | H | 5-Me-6-OCF$_3$ | Ph(2-F) | |
| 3-375 | Me | Me | H | 5-Me-6-OCF$_3$ | Ph(2,6-F$_2$) | |
| 3-376 | Me | Me | H | 5-Me-6-OCF$_3$ | Ph(2-Cl) | |
| 3-377 | Me | Me | H | 5-Me-6-OCF$_3$ | Ph(2-Me) | |
| 3-378 | Me | Me | H | 5-Me-6-OCF$_3$ | Ph(2-CF$_3$) | |
| 3-379 | Me | Me | H | 5-Me-6-OCF$_3$ | Ph(2-F-6-Cl) | |
| 3-380 | Me | Me | H | 6-Me-5-OCF$_3$ | Ph(2-F) | |
| 3-381 | Me | Me | H | 6-Me-5-OCF$_3$ | Ph(2,6-F$_2$) | |
| 3-382 | Me | Me | H | 6-Me-5-OCF$_3$ | Ph(2-Cl) | |
| 3-383 | Me | Me | H | 6-Me-5-OCF$_3$ | Ph(2-Me) | |
| 3-384 | Me | Me | H | 6-Me-5-OCF$_3$ | Ph(2-CF$_3$) | |
| 3-385 | Me | Me | H | 6-Me-5-OCF$_3$ | Ph(2-F-6-Cl) | |
| 3-386 | Me | Me | H | 2-Me-4-OCHF$_2$ | Ph(2-F) | |
| 3-387 | Me | Me | H | 2-Me-4-OCHF$_2$ | Ph(2,6-F$_2$) | |
| 3-388 | Me | Me | H | 2-Me-4-OCHF$_2$ | Ph(2-Cl) | |
| 3-389 | Me | Me | H | 2-Me-4-OCHF$_2$ | Ph(2-Me) | |
| 3-390 | Me | Me | H | 2-Me-4-OCHF$_2$ | Ph(2-CF$_3$) | |
| 3-391 | Me | Me | H | 2-Me-4-OCHF$_2$ | Ph(2-F-6-Cl) | |
| 3-392 | Me | Me | H | 3-Me-4-OCHF$_2$ | Ph(2-F) | |
| 3-393 | Me | Me | H | 3-Me-4-OCHF$_2$ | Ph(2,6-F$_2$) | |
| 3-394 | Me | Me | H | 3-Me-4-OCHF$_2$ | Ph(2-Cl) | |
| 3-395 | Me | Me | H | 3-Me-4-OCHF$_2$ | Ph(2-Me) | |

TABLE 3-continued

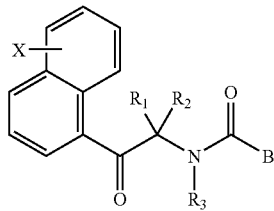

| Compound No. | R$_1$ | R$_2$ | R$_3$ | X | B | Physical properties (mp ° C.) |
|---|---|---|---|---|---|---|
| 3-396 | Me | Me | H | 3-Me-4-OCHF$_2$ | Ph(2-CF$_3$) | |
| 3-397 | Me | Me | H | 3-Me-4-OCHF$_2$ | Ph(2-F-6-Cl) | |
| 3-398 | Me | Me | H | 5-Me-6-OCHF$_2$ | Ph(2-F) | |
| 3-399 | Me | Me | H | 5-Me-6-OCHF$_2$ | Ph(2,6-F$_2$) | |
| 3-400 | Me | Me | H | 5-Me-6-OCHF$_2$ | Ph(2-Cl) | |
| 3-401 | Me | Me | H | 5-Me-6-OCHF$_2$ | Ph(2-Me) | |
| 3-402 | Me | Me | H | 5-Me-6-OCHF$_2$ | Ph(2-CF$_3$) | |
| 3-403 | Me | Me | H | 5-Me-6-OCHF$_2$ | Ph(2-F-6-Cl) | |
| 3-404 | Me | Me | H | 6-Me-5-OCHF$_2$ | Ph(2-F) | |
| 3-405 | Me | Me | H | 6-Me-5-OCHF$_2$ | Ph(2,6-F$_2$) | |
| 3-406 | Me | Me | H | 6-Me-5-OCHF$_2$ | Ph(2-Cl) | |
| 3-407 | Me | Me | H | 6-Me-5-OCHF$_2$ | Ph(2-Me) | |
| 3-408 | Me | Me | H | 6-Me-5-OCHF$_2$ | Ph(2-CF$_3$) | |
| 3-409 | Me | Me | H | 6-Me-5-OCHF$_2$ | Ph(2-F-6-Cl) | |
| 3-410 | Me | Me | H | 2-Me-4-OCH$_2$CF$_3$ | Ph(2-F) | |
| 3-411 | Me | Me | H | 2-Me-4-OCH$_2$CF$_3$ | Ph(2,6-F$_2$) | |
| 3-412 | Me | Me | H | 2-Me-4-OCH$_2$CF$_3$ | Ph(2-Cl) | |
| 3-413 | Me | Me | H | 2-Me-4-OCH$_2$CF$_3$ | Ph(2-Me) | |
| 3-414 | Me | Me | H | 2-Me-4-OCH$_2$CF$_3$ | Ph(2-CF$_3$) | |
| 3-415 | Me | Me | H | 2-Me-4-OCH$_2$CF$_3$ | Ph(2-F-6-Cl) | |
| 3-416 | Me | Me | H | 3-Me-4-OCH$_2$CF$_3$ | Ph(2-F) | |
| 3-417 | Me | Me | H | 3-Me-4-OCH$_2$CF$_3$ | Ph(2,6-F$_2$) | |
| 3-418 | Me | Me | H | 3-Me-4-OCH$_2$CF$_3$ | Ph(2-Cl) | |
| 3-419 | Me | Me | H | 3-Me-4-OCH$_2$CF$_3$ | Ph(2-Me) | |
| 3-420 | Me | Me | H | 3-Me-4-OCH$_2$CF$_3$ | Ph(2-CF$_3$) | |
| 3-421 | Me | Me | H | 3-Me-4-OCH$_2$CF$_3$ | Ph(2-F-6-Cl) | |
| 3-422 | Me | Me | H | 5-Me-6-OCH$_2$CF$_3$ | Ph(2-F) | |
| 3-423 | Me | Me | H | 5-Me-6-OCH$_2$CF$_3$ | Ph(2,6-F$_2$) | |
| 3-424 | Me | Me | H | 5-Me-6-OCH$_2$CF$_3$ | Ph(2-Cl) | |
| 3-425 | Me | Me | H | 5-Me-6-OCH$_2$CF$_3$ | Ph(2-Me) | |
| 3-426 | Me | Me | H | 5-Me-6-OCH$_2$CF$_3$ | Ph(2-CF$_3$) | |
| 3-427 | Me | Me | H | 5-Me-6-OCH$_2$CF$_3$ | Ph(2-F-6-Cl) | |
| 3-428 | Me | Me | H | 6-Me-5-OCH$_2$CF$_3$ | Ph(2-F) | |
| 3-429 | Me | Me | H | 6-Me-5-OCH$_2$CF$_3$ | Ph(2,6-F$_2$) | |
| 3-430 | Me | Me | H | 6-Me-5-OCH$_2$CF$_3$ | Ph(2-Cl) | |
| 3-431 | Me | Me | H | 6-Me-5-OCH$_2$CF$_3$ | Ph(2-Me) | |
| 3-432 | Me | Me | H | 6-Me-5-OCH$_2$CF$_3$ | Ph(2-CF$_3$) | |
| 3-433 | Me | Me | H | 6-Me-5-OCH$_2$CF$_3$ | Ph(2-F-6-Cl) | |
| 3-434 | Me | Me | H | 2,4-Cl$_2$ | Ph(2-F) | |
| 3-435 | Me | Me | H | 2,4-Cl$_2$ | Ph(2,6-F$_2$) | |
| 3-436 | Me | Me | H | 2,4-Cl$_2$ | Ph(2-Cl) | |
| 3-437 | Me | Me | H | 2,4-Cl$_2$ | Ph(2-Me) | |
| 3-438 | Me | Me | H | 2,4-Cl$_2$ | Ph(2-CF$_3$) | |
| 3-439 | Me | Me | H | 2,4-Cl$_2$ | Ph(2-F-6-Cl) | |
| 3-440 | Me | Me | H | 3,4-Cl$_2$ | Ph(2-F) | |
| 3-441 | Me | Me | H | 3,4-Cl$_2$ | Ph(2,6-F$_2$) | |
| 3-442 | Me | Me | H | 3,4-Cl$_2$ | Ph(2-Cl) | |
| 3-443 | Me | Me | H | 3,4-Cl$_2$ | Ph(2-Me) | |
| 3-444 | Me | Me | H | 3,4-Cl$_2$ | Ph(2-CF$_3$) | |
| 3-445 | Me | Me | H | 3,4-Cl$_2$ | Ph(2-F-6-Cl) | |
| 3-446 | Me | Me | H | 5,6-Cl$_2$ | Ph(2-F) | |
| 3-447 | Me | Me | H | 5,6-Cl$_2$ | Ph(2,6-F$_2$) | |
| 3-448 | Me | Me | H | 5,6-Cl$_2$ | Ph(2-Cl) | |
| 3-449 | Me | Me | H | 5,6-Cl$_2$ | Ph(2-Me) | |
| 3-450 | Me | Me | H | 5,6-Cl$_2$ | Ph(2-CF$_3$) | |
| 3-451 | Me | Me | H | 5,6-Cl$_2$ | Ph(2-F-6-Cl) | |
| 3-452 | Me | Me | H | 2-Cl-4-Br | Ph(2-F) | |
| 3-453 | Me | Me | H | 2-Cl-4-Br | Ph(2,6-F$_2$) | |
| 3-454 | Me | Me | H | 2-Cl-4-Br | Ph(2-Cl) | |
| 3-455 | Me | Me | H | 2-Cl-4-Br | Ph(2-Me) | |
| 3-456 | Me | Me | H | 2-Cl-4-Br | Ph(2-CF$_3$) | |
| 3-457 | Me | Me | H | 2-Cl-4-Br | Ph(2-F-6-Cl) | |
| 3-458 | Me | Me | H | 3-Cl-4-Br | Ph(2-F) | |
| 3-459 | Me | Me | H | 3-Cl-4-Br | Ph(2,6-F$_2$) | |
| 3-460 | Me | Me | H | 3-Cl-4-Br | Ph(2-Cl) | |
| 3-461 | Me | Me | H | 3-Cl-4-Br | Ph(2-Me) | |

TABLE 3-continued

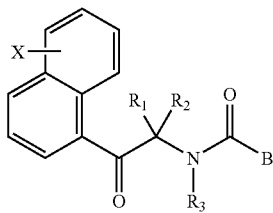

| Compound No. | $R_1$ | $R_2$ | $R_3$ | X | B | Physical properties (mp ° C.) |
|---|---|---|---|---|---|---|
| 3-462 | Me | Me | H | 3-Cl-4-Br | Ph(2-CF$_3$) | |
| 3-463 | Me | Me | H | 3-Cl-4-Br | Ph(2-F-6-Cl) | |
| 3-464 | Me | Me | H | 5-Cl-6-Br | Ph(2-F) | |
| 3-465 | Me | Me | H | 5-Cl-6-Br | Ph(2,6-F$_2$) | |
| 3-466 | Me | Me | H | 5-Cl-6-Br | Ph(2-Cl) | |
| 3-467 | Me | Me | H | 5-Cl-6-Br | Ph(2-Me) | |
| 3-468 | Me | Me | H | 5-Cl-6-Br | Ph(2-CF$_3$) | |
| 3-469 | Me | Me | H | 5-Cl-6-Br | Ph(2-F-6-Cl) | |
| 3-470 | Me | Me | H | 6-Cl-5-Br | Ph(2-F) | |
| 3-471 | Me | Me | H | 6-Cl-5-Br | Ph(2,6-F$_2$) | |
| 3-472 | Me | Me | H | 6-Cl-5-Br | Ph(2-Cl) | |
| 3-473 | Me | Me | H | 6-Cl-5-Br | Ph(2-Me) | |
| 3-474 | Me | Me | H | 6-Cl-5-Br | Ph(2-CF$_3$) | |
| 3-475 | Me | Me | H | 6-Cl-5-Br | Ph(2-F-6-Cl) | |
| 3-476 | Me | Me | H | 2-Cl-4-CF$_3$ | Ph(2-F) | |
| 3-477 | Me | Me | H | 2-Cl-4-CF$_3$ | Ph(2,6-F$_2$) | |
| 3-478 | Me | Me | H | 2-Cl-4-CF$_3$ | Ph(2-Cl) | |
| 3-479 | Me | Me | H | 2-Cl-4-CF$_3$ | Ph(2-Me) | |
| 3-480 | Me | Me | H | 2-Cl-4-CF$_3$ | Ph(2-CF$_3$) | |
| 3-481 | Me | Me | H | 2-Cl-4-CF$_3$ | Ph(2-F-6-Cl) | |
| 3-482 | Me | Me | H | 3-Cl-4-CF$_3$ | Ph(2-F) | |
| 3-483 | Me | Me | H | 3-Cl-4-CF$_3$ | Ph(2,6-F$_2$) | |
| 3-484 | Me | Me | H | 3-Cl-4-CF$_3$ | Ph(2-Cl) | |
| 3-485 | Me | Me | H | 3-Cl-4-CF$_3$ | Ph(2-Me) | |
| 3-486 | Me | Me | H | 3-Cl-4-CF$_3$ | Ph(2-CF$_3$) | |
| 3-487 | Me | Me | H | 3-Cl-4-CF$_3$ | Ph(2-F-6-Cl) | |
| 3-488 | Me | Me | H | 3-Cl-6-CF$_3$ | Ph(2-F) | |
| 3-489 | Me | Me | H | 3-Cl-6-CF$_3$ | Ph(2,6-F$_2$) | |
| 3-490 | Me | Me | H | 3-Cl-6-CF$_3$ | Ph(2-Cl) | |
| 3-491 | Me | Me | H | 3-Cl-6-CF$_3$ | Ph(2-Me) | |
| 3-492 | Me | Me | H | 3-Cl-6-CF$_3$ | Ph(2-CF$_3$) | |
| 3-493 | Me | Me | H | 3-Cl-6-CF$_3$ | Ph(2-F-6-Cl) | |
| 3-494 | Me | Me | H | 6-Cl-5-CF$_3$ | Ph(2-F) | |
| 3-495 | Me | Me | H | 6-Cl-5-CF$_3$ | Ph(2,6-F$_2$) | |
| 3-496 | Me | Me | H | 6-Cl-5-CF$_3$ | Ph(2-Cl) | |
| 3-497 | Me | Me | H | 6-Cl-5-CF$_3$ | Ph(2-Me) | |
| 3-498 | Me | Me | H | 6-Cl-5-CF$_3$ | Ph(2-CF$_3$) | |
| 3-499 | Me | Me | H | 6-Cl-5-CF$_3$ | Ph(2-F-6-Cl) | |
| 3-500 | Me | Me | H | 2-Cl-4-OCF$_3$ | Ph(2-F) | |
| 3-501 | Me | Me | H | 2-Cl-4-OCF$_3$ | Ph(2,6-F$_2$) | |
| 3-502 | Me | Me | H | 2-Cl-4-OCF$_3$ | Ph(2-Cl) | |
| 3-503 | Me | Me | H | 2-Cl-4-OCF$_3$ | Ph(2-Me) | |
| 3-504 | Me | Me | H | 2-Cl-4-OCF$_3$ | Ph(2-CF$_3$) | |
| 3-505 | Me | Me | H | 2-Cl-4-OCF$_3$ | Ph(2-F-6-Cl) | |
| 3-506 | Me | Me | H | 3-Cl-4-OCF$_3$ | Ph(2-F) | |
| 3-507 | Me | Me | H | 3-Cl-4-OCF$_3$ | Ph(2,6-F$_2$) | |
| 3-508 | Me | Me | H | 3-Cl-4-OCF$_3$ | Ph(2-Cl) | |
| 3-509 | Me | Me | H | 3-Cl-4-OCF$_3$ | Ph(2-Me) | |
| 3-510 | Me | Me | H | 3-Cl-4-OCF$_3$ | Ph(2-CF$_3$) | |
| 3-511 | Me | Me | H | 3-Cl-4-OCF$_3$ | Ph(2-F-6-Cl) | |
| 3-512 | Me | Me | H | 5-Cl-6-OCF$_3$ | Ph(2-F) | |
| 3-513 | Me | Me | H | 5-Cl-6-OCF$_3$ | Ph(2,6-F$_2$) | |
| 3-514 | Me | Me | H | 5-Cl-6-OCF$_3$ | Ph(2-Cl) | |
| 3-515 | Me | Me | H | 5-Cl-6-OCF$_3$ | Ph(2-Me) | |
| 3-516 | Me | Me | H | 5-Cl-6-OCF$_3$ | Ph(2-CF$_3$) | |
| 3-517 | Me | Me | H | 5-Cl-6-OCF$_3$ | Ph(2-F-6-Cl) | |
| 3-518 | Me | Me | H | 6-Cl-5-OCF$_3$ | Ph(2-F) | |
| 3-519 | Me | Me | H | 6-Cl-5-OCF$_3$ | Ph(2,6-F$_2$) | |
| 3-520 | Me | Me | H | 6-Cl-5-OCF$_3$ | Ph(2-Cl) | |
| 3-521 | Me | Me | H | 6-Cl-5-OCF$_3$ | Ph(2-Me) | |
| 3-522 | Me | Me | H | 6-Cl-5-OCF$_3$ | Ph(2-CF$_3$) | |
| 3-523 | Me | Me | H | 6-Cl-5-OCF$_3$ | Ph(2-F-6-Cl) | |
| 3-524 | Me | Me | H | 2-Cl-4-OCHF$_2$ | Ph(2-F) | |
| 3-525 | Me | Me | H | 2-Cl-4-OCHF$_2$ | Ph(2,6-F$_2$) | |
| 3-526 | Me | Me | H | 2-Cl-4-OCHF$_2$ | Ph(2-Cl) | |
| 3-527 | Me | Me | H | 2-Cl-4-OCHF$_2$ | Ph(2-Me) | |

TABLE 3-continued

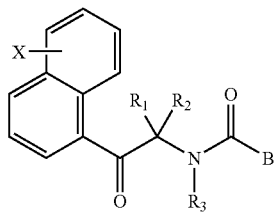

| Compound No. | $R_1$ | $R_2$ | $R_3$ | X | B | Physical properties (mp ° C.) |
|---|---|---|---|---|---|---|
| 3-528 | Me | Me | H | 2-Cl-4-OCHF$_2$ | Ph(2-CF$_3$) | |
| 3-529 | Me | Me | H | 2-Cl-4-OCHF$_2$ | Ph(2-F-6-Cl) | |
| 3-530 | Me | Me | H | 3-Cl-4-OCHF$_2$ | Ph(2-F) | |
| 3-531 | Me | Me | H | 3-Cl-4-OCHF$_2$ | Ph(2,6-F$_2$) | |
| 3-532 | Me | Me | H | 3-Cl-4-OCHF$_2$ | Ph(2-Cl) | |
| 3-533 | Me | Me | H | 3-Cl-4-OCHF$_2$ | Ph(2-Me) | |
| 3-534 | Me | Me | H | 3-Cl-4-OCHF$_2$ | Ph(2-CF$_3$) | |
| 3-535 | Me | Me | H | 3-Cl-4-OCHF$_2$ | Ph(2-F-6-Cl) | |
| 3-536 | Me | Me | H | 5-Cl-6-OCHF$_2$ | Ph(2-F) | |
| 3-537 | Me | Me | H | 5-Cl-6-OCHF$_2$ | Ph(2,6-F$_2$) | |
| 3-538 | Me | Me | H | 5-Cl-6-OCHF$_2$ | Ph(2-Cl) | |
| 3-539 | Me | Me | H | 5-Cl-6-OCHF$_2$ | Ph(2-Me) | |
| 3-540 | Me | Me | H | 5-Cl-6-OCHF$_2$ | Ph(2-CF$_3$) | |
| 3-541 | Me | Me | H | 5-Cl-6-OCHF$_2$ | Ph(2-F-6-Cl) | |
| 3-542 | Me | Me | H | 6-Cl-5-OCHF$_2$ | Ph(2-F) | |
| 3-543 | Me | Me | H | 6-Cl-5-OCHF$_2$ | Ph(2,6-F$_2$) | |
| 3-544 | Me | Me | H | 6-Cl-5-OCHF$_2$ | Ph(2-Cl) | |
| 3-545 | Me | Me | H | 6-Cl-5-OCHF$_2$ | Ph(2-Me) | |
| 3-546 | Me | Me | H | 6-Cl-5-OCHF$_2$ | Ph(2-CF$_3$) | |
| 3-547 | Me | Me | H | 6-Cl-5-OCHF$_2$ | Ph(2-F-6-Cl) | |
| 3-548 | Me | Me | H | 2-Cl-4-OCH$_2$CF$_3$ | Ph(2-F) | |
| 3-549 | Me | Me | H | 2-Cl-4-OCH$_2$CF$_3$ | Ph(2,6-F$_2$) | |
| 3-550 | Me | Me | H | 2-Cl-4-OCH$_2$CF$_3$ | Ph(2-Cl) | |
| 3-551 | Me | Me | H | 2-Cl-4-OCH$_2$CF$_3$ | Ph(2-Me) | |
| 3-552 | Me | Me | H | 2-Cl-4-OCH$_2$CF$_3$ | Ph(2-CF$_3$) | |
| 3-553 | Me | Me | H | 2-Cl-4-OCH$_2$CF$_3$ | Ph(2-F-6-Cl) | |
| 3-554 | Me | Me | H | 3-Cl-4-OCH$_2$CF$_3$ | Ph(2-F) | |
| 3-555 | Me | Me | H | 3-Cl-4-OCH$_2$CF$_3$ | Ph(2,6-F$_2$) | |
| 3-556 | Me | Me | H | 3-Cl-4-OCH$_2$CF$_3$ | Ph(2-Cl) | |
| 3-557 | Me | Me | H | 3-Cl-4-OCH$_2$CF$_3$ | Ph(2-Me) | |
| 3-558 | Me | Me | H | 3-Cl-4-OCH$_2$CF$_3$ | Ph(2-CF$_3$) | |
| 3-559 | Me | Me | H | 3-Cl-4-OCH$_2$CF$_3$ | Ph(2-F-6-Cl) | |
| 3-560 | Me | Me | H | 5-Cl-6-OCH$_2$CF$_3$ | Ph(2-F) | |
| 3-561 | Me | Me | H | 5-Cl-6-OCH$_2$CF$_3$ | Ph(2,6-F$_2$) | |
| 3-562 | Me | Me | H | 5-Cl-6-OCH$_2$CF$_3$ | Ph(2-Cl) | |
| 3-563 | Me | Me | H | 5-Cl-6-OCH$_2$CF$_3$ | Ph(2-Me) | |
| 3-564 | Me | Me | H | 5-Cl-6-OCH$_2$CF$_3$ | Ph(2-CF$_3$) | |
| 3-565 | Me | Me | H | 5-Cl-6-OCH$_2$CF$_3$ | Ph(2-F-6-Cl) | |
| 3-566 | Me | Me | H | 6-Cl-5-OCH$_2$CF$_3$ | Ph(2-F) | |
| 3-567 | Me | Me | H | 6-Cl-5-OCH$_2$CF$_3$ | Ph(2,6-F$_2$) | |
| 3-568 | Me | Me | H | 6-Cl-5-OCH$_2$CF$_3$ | Ph(2-Cl) | |
| 3-569 | Me | Me | H | 6-Cl-5-OCH$_2$CF$_3$ | Ph(2-Me) | |
| 3-570 | Me | Me | H | 6-Cl-5-OCH$_2$CF$_3$ | Ph(2-CF$_3$) | |
| 3-571 | Me | Me | H | 6-Cl-5-OCH$_2$CF$_3$ | Ph(2-F-6-Cl) | |

TABLE 4

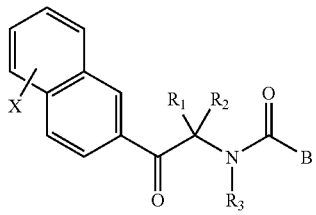

| Compound No. | $R_1$ | $R_2$ | $R_3$ | X | B | Physical properties (mp ° C.) |
|---|---|---|---|---|---|---|
| 4-1 | Me | Me | H | H | Ph | |
| 4-2 | Me | Me | H | H | Ph(2-F) | 114-116 |
| 4-3 | Me | Me | H | H | Ph(2-Cl) | |

TABLE 4-continued

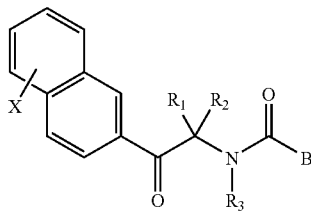

| Compound No. | R₁ | R₂ | R₃ | X | B | Physical properties (mp °C.) |
|---|---|---|---|---|---|---|
| 4-4 | Me | Me | H | H | Ph(2-OMe) | |
| 4-5 | Me | Me | H | H | Ph(2,6-F₂) | 170-172 |
| 4-6 | Me | Me | H | H | Ph(2,6-Cl₂) | |
| 4-7 | Me | Me | H | H | Ph(2,6-OMe₂) | 128-130 |
| 4-8 | Me | Me | H | 6-Cl | Ph | |
| 4-9 | Me | Me | H | 6-Cl | Ph(2-F) | |
| 4-10 | Me | Me | H | 6-Cl | Ph(2-Cl) | |
| 4-11 | Me | Me | H | 6-Cl | Ph(2,6-F₂) | |
| 4-12 | Me | Me | H | 6-Cl | Ph(2,6-Cl₂) | |
| 4-13 | Me | Me | H | 6-Br | Ph | |
| 4-14 | Me | Me | H | 6-Br | Ph(2-F) | |
| 4-15 | Me | Me | H | 6-Br | Ph(2-Cl) | |
| 4-16 | Me | Me | H | 6-Br | Ph(2,6-F₂) | |
| 4-17 | Me | Me | H | 6-Br | Ph(2,6-Cl₂) | |
| 4-18 | Me | Me | H | 6-CF₃ | Ph(2,6-F₂) | |
| 4-19 | Me | Me | H | 6-CN | Ph(2,6-F₂) | |
| 4-20 | Me | CN | H | H | Ph(2,6-F₂) | |
| 4-21 | Me | CO₂Et | H | H | Ph(2,6-F₂) | |
| 4-22 | Me | CN | H | 6-Cl | Ph(2,6-F₂) | |
| 4-23 | Me | CO₂Et | H | 6-Cl | Ph(2,6-F₂) | |
| 4-24 | Me | Et | H | H | Ph(2,6-F₂) | |
| 4-25 | Me | Me | COMe | H | Ph(2,6-F₂) | |
| 4-26 | Me | Me | CH₂OMe | H | Ph(2,6-F₂) | |
| 4-27 | Me | Me | H | H | 1-naphthyl | |
| 4-28 | Me | Me | H | H | 2-naphthyl | |
| 4-29 | Me | Me | H | H | 2-thienyl | |
| 4-30 | Me | Me | H | H | 3-thienyl | |
| 4-31 | Me | Me | H | H | 2-pyrazinyl | |
| 4-32 | Me | Me | H | H | 2-pyridyl | |
| 4-33 | Me | Me | H | H | 3-pyridyl | |
| 4-34 | Me | Me | H | H | 4-trifluoromethyl-3-pyridyl | 156-158 |
| 4-35 | Me | Me | H | H | 4-pyridyl | |
| 4-36 | Me | Me | H | H | 2-furyl | |
| 4-37 | Me | Me | H | H | 3-furyl | |
| 4-38 | Me | Me | H | 1-Cl | Ph(2-F) | |
| 4-39 | Me | Me | H | 1-Cl | Ph(2,6-F₂) | |
| 4-40 | Me | Me | H | 1-Cl | Ph(2-Cl) | |
| 4-41 | Me | Me | H | 1-Cl | Ph(2-Me) | |
| 4-42 | Me | Me | H | 1-Cl | Ph(2-CF₃) | |
| 4-43 | Me | Me | H | 1-Cl | Ph(2-F-6-Cl) | |
| 4-44 | Me | Me | H | 1-Me | Ph(2-F) | |
| 4-45 | Me | Me | H | 1-Me | Ph(2,6-F₂) | |
| 4-46 | Me | Me | H | 1-Me | Ph(2-Cl) | |
| 4-47 | Me | Me | H | 1-Me | Ph(2-Me) | |
| 4-48 | Me | Me | H | 1-Me | Ph(2-CF₃) | |
| 4-49 | Me | Me | H | 1-Me | Ph(2-F-6-Cl) | |
| 4-50 | Me | Me | H | 3-Cl | Ph(2-F) | |
| 4-51 | Me | Me | H | 3-Cl | Ph(2,6-F₂) | |
| 4-52 | Me | Me | H | 3-Cl | Ph(2-Cl) | |
| 4-53 | Me | Me | H | 3-Cl | Ph(2-Me) | |
| 4-54 | Me | Me | H | 3-Cl | Ph(2-CF₃) | |
| 4-55 | Me | Me | H | 3-Cl | Ph(2-F-6-Cl) | |
| 4-56 | Me | Me | H | 3-Me | Ph(2-F) | |
| 4-57 | Me | Me | H | 3-Me | Ph(2,6-F₂) | |
| 4-58 | Me | Me | H | 3-Me | Ph(2-Cl) | |
| 4-59 | Me | Me | H | 3-Me | Ph(2-Me) | |
| 4-60 | Me | Me | H | 3-Me | Ph(2-CF₃) | |
| 4-61 | Me | Me | H | 3-Me | Ph(2-F-6-Cl) | |
| 4-62 | Me | Me | H | 3-CF₃ | Ph(2-F) | |
| 4-63 | Me | Me | H | 3-CF₃ | Ph(2,6-F₂) | |
| 4-64 | Me | Me | H | 3-CF₃ | Ph(2-Cl) | |
| 4-65 | Me | Me | H | 3-CF₃ | Ph(2-Me) | |
| 4-66 | Me | Me | H | 3-CF₃ | Ph(2-CF₃) | |
| 4-67 | Me | Me | H | 3-CF₃ | Ph(2-F-6-Cl) | |
| 4-68 | Me | Me | H | 4-CF₃ | Ph(2-F) | |

TABLE 4-continued

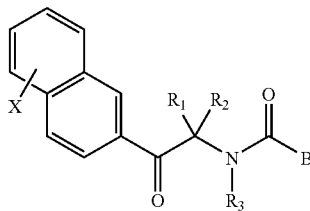

| Compound No. | $R_1$ | $R_2$ | $R_3$ | X | B | Physical properties (mp ° C.) |
|---|---|---|---|---|---|---|
| 4-69 | Me | Me | H | 4-$CF_3$ | Ph(2,6-$F_2$) | |
| 4-70 | Me | Me | H | 4-$CF_3$ | Ph(2-Cl) | |
| 4-71 | Me | Me | H | 4-$CF_3$ | Ph(2-Me) | |
| 4-72 | Me | Me | H | 4-$CF_3$ | Ph(2-$CF_3$) | |
| 4-73 | Me | Me | H | 4-$CF_3$ | Ph(2-F-6-Cl) | |
| 4-74 | Me | Me | H | 3-CN | Ph(2-F) | |
| 4-75 | Me | Me | H | 3-CN | Ph(2,6-$F_2$) | |
| 4-76 | Me | Me | H | 3-CN | Ph(2-Cl) | |
| 4-77 | Me | Me | H | 3-CN | Ph(2-Me) | |
| 4-78 | Me | Me | H | 3-CN | Ph(2-$CF_3$) | |
| 4-79 | Me | Me | H | 3-CN | Ph(2-F-6-Cl) | |
| 4-80 | Me | Me | H | 4-CN | Ph(2-F) | |
| 4-81 | Me | Me | H | 4-CN | Ph(2,6-$F_2$) | |
| 4-82 | Me | Me | H | 4-CN | Ph(2-Cl) | |
| 4-83 | Me | Me | H | 4-CN | Ph(2-Me) | |
| 4-84 | Me | Me | H | 4-CN | Ph(2-$CF_3$) | |
| 4-85 | Me | Me | H | 4-CN | Ph(2-F-6-Cl) | |

TABLE 5

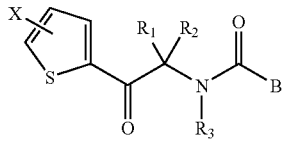

| Compound No. | $R_1$ | $R_2$ | $R_3$ | X | B | Physical properties (mp ° C.) |
|---|---|---|---|---|---|---|
| 5-1 | Me | Me | H | H | Ph | |
| 5-2 | Me | Me | H | H | Ph(2-F) | |
| 5-3 | Me | Me | H | H | Ph(2-Cl) | |
| 5-4 | Me | Me | H | H | Ph(2-OMe) | |
| 5-5 | Me | Me | H | H | Ph(2,6-$F_2$) | 108-110 |
| 5-6 | Me | Me | H | H | Ph(2,6-$Cl_2$) | |
| 5-7 | Me | Me | H | H | Ph(2,6-$OMe_2$) | |
| 5-8 | Me | Me | H | 5-Cl | Ph | |
| 5-9 | Me | Me | H | 5-Cl | Ph(2-F) | 127-130 |
| 5-10 | Me | Me | H | 5-Cl | Ph(2-Cl) | |
| 5-11 | Me | Me | H | 5-Cl | Ph(2,6-$F_2$) | 129-131 |
| 5-12 | Me | Me | H | 5-Cl | Ph(2,6-$Cl_2$) | |
| 5-13 | Me | Me | H | 5-Br | Ph | |
| 5-14 | Me | Me | H | 5-Br | Ph(2-F) | 141-142 |
| 5-15 | Me | Me | H | 5-Br | Ph(2-Cl) | |
| 5-16 | Me | Me | H | 5-Br | Ph(2,6-$F_2$) | 145-147 |
| 5-17 | Me | Me | H | 5-Br | Ph(2,6-$Cl_2$) | |
| 5-18 | Me | Me | H | 5-$CF_3$ | Ph(2,6-$F_2$) | |
| 5-19 | Me | Me | H | 5-CN | Ph(2,6-$F_2$) | |
| 5-20 | Me | Me | H | 3-Me | Ph(2,6-$F_2$) | 124-127 |
| 5-21 | Me | CN | H | H | Ph(2,6-$F_2$) | |
| 5-22 | Me | $CO_2Et$ | H | H | Ph(2,6-$F_2$) | |
| 5-23 | Me | CN | H | 5-Cl | Ph(2,6-$F_2$) | |
| 5-24 | Me | $CO_2Et$ | H | 5-Cl | Ph(2,6-$F_2$) | |
| 5-25 | Me | Et | H | H | Ph(2,6-$F_2$) | |
| 5-26 | Me | Me | COMe | H | Ph(2,6-$F_2$) | |
| 5-27 | Me | Me | $CH_2OMe$ | H | Ph(2,6-$F_2$) | |
| 5-28 | Me | Me | H | H | 1-naphthyl | |
| 5-29 | Me | Me | H | H | 2-naphthyl | |
| 5-30 | Me | Me | H | H | 2-thienyl | |
| 5-31 | Me | Me | H | H | 3-thienyl | |
| 5-32 | Me | Me | H | H | 2-pyrazinyl | |
| 5-33 | Me | Me | H | H | 2-pyridyl | |

TABLE 5-continued

| Compound No. | R₁ | R₂ | R₃ | X | B | Physical properties (mp ° C.) |
|---|---|---|---|---|---|---|
| 5-34 | Me | Me | H | H | 3-pyridyl | |
| 5-35 | Me | Me | H | H | 4-trifluoromethyl-3-pyridyl | |
| 5-36 | Me | Me | H | H | 4-pyridyl | |
| 5-37 | Me | Me | H | H | 2-furyl | |
| 5-38 | Me | Me | H | H | 3-furyl | |
| 5-39 | Me | Me | H | 3-Br | Ph(2,6-F₂) | |
| 5-40 | Me | Me | H | 3-CF₃ | Ph(2,6-F₂) | |
| 5-41 | Me | Me | H | 3-CN | Ph(2,6-F₂) | |
| 5-42 | Me | Me | H | 5-Me | Ph(2,6-F₂) | |
| 5-43 | Me | Me | H | 5-OSO₂CF₃ | Ph(2-F) | |
| 5-44 | Me | Me | H | 5-OSO₂CF₃ | Ph(2,6-F₂) | |
| 5-45 | Me | Me | H | 5-OCH₂CF₃ | Ph(2-F) | |
| 5-46 | Me | Me | H | 5-OCH₂CF₃ | Ph(2,6-F₂) | |
| 5-47 | Me | Me | H | 3-Cl | Ph(2-F) | |
| 5-48 | Me | Me | H | 3-Cl | Ph(2,6-F₂) | |
| 5-49 | Me | Me | H | 3-Cl | Ph(2-Cl) | |
| 5-50 | Me | Me | H | 3-Cl | Ph(2-Me) | |
| 5-51 | Me | Me | H | 3-Cl | Ph(2-CF₃) | |
| 5-52 | Me | Me | H | 3-Cl | Ph(2-F-6-Cl) | |
| 5-53 | Me | Me | H | 4-Cl | Ph(2-F) | |
| 5-54 | Me | Me | H | 4-Cl | Ph(2,6-F₂) | |
| 5-55 | Me | Me | H | 4-Cl | Ph(2-Cl) | |
| 5-56 | Me | Me | H | 4-Cl | Ph(2-Me) | |
| 5-57 | Me | Me | H | 4-Cl | Ph(2-CF₃) | |
| 5-58 | Me | Me | H | 4-Cl | Ph(2-F-6-Cl) | |
| 5-59 | Me | Me | H | 3-Br | Ph(2-F) | |
| 5-60 | Me | Me | H | 3-Br | Ph(2,6-F₂) | |
| 5-61 | Me | Me | H | 3-Br | Ph(2-Cl) | |
| 5-62 | Me | Me | H | 3-Br | Ph(2-Me) | |
| 5-63 | Me | Me | H | 3-Br | Ph(2-CF₃) | |
| 5-64 | Me | Me | H | 3-Br | Ph(2-F-6-Cl) | |
| 5-65 | Me | Me | H | 4-Br | Ph(2-F) | 120-123 |
| 5-66 | Me | Me | H | 4-Br | Ph(2,6-F₂) | 218-220 |
| 5-67 | Me | Me | H | 4-Br | Ph(2-Cl) | |
| 5-68 | Me | Me | H | 4-Br | Ph(2-Me) | |
| 5-69 | Me | Me | H | 4-Br | Ph(2-CF₃) | |
| 5-70 | Me | Me | H | 4-Br | Ph(2-F-6-Cl) | |
| 5-71 | Me | Me | H | 3-CF₃ | Ph(2-F) | |
| 5-72 | Me | Me | H | 3-CF₃ | Ph(2,6-F₂) | |
| 5-73 | Me | Me | H | 3-CF₃ | Ph(2-Cl) | |
| 5-74 | Me | Me | H | 3-CF₃ | Ph(2-Me) | |
| 5-75 | Me | Me | H | 3-CF₃ | Ph(2-CF₃) | |
| 5-76 | Me | Me | H | 3-CF₃ | Ph(2-F-6-Cl) | |
| 5-77 | Me | Me | H | 4-CF₃ | Ph(2-F) | |
| 5-78 | Me | Me | H | 4-CF₃ | Ph(2,6-F₂) | |
| 5-79 | Me | Me | H | 4-CF₃ | Ph(2-Cl) | |
| 5-80 | Me | Me | H | 4-CF₃ | Ph(2-Me) | |
| 5-81 | Me | Me | H | 4-CF₃ | Ph(2-CF₃) | |
| 5-82 | Me | Me | H | 4-CF₃ | Ph(2-F-6-Cl) | |
| 5-83 | Me | Me | H | 5-CF₃ | Ph(2-F) | |
| 5-84 | Me | Me | H | 5-CF₃ | Ph(2-Cl) | |
| 5-85 | Me | Me | H | 5-CF₃ | Ph(2,6-Cl₂) | |
| 5-86 | Me | Me | H | 3-CN | Ph(2-F) | |
| 5-87 | Me | Me | H | 3-CN | Ph(2,6-F₂) | |
| 5-88 | Me | Me | H | 3-CN | Ph(2-Cl) | |
| 5-89 | Me | Me | H | 3-CN | Ph(2-Me) | |
| 5-90 | Me | Me | H | 3-CN | Ph(2-CF₃) | |
| 5-91 | Me | Me | H | 3-CN | Ph(2-F-6-Cl) | |
| 5-92 | Me | Me | H | 4-CN | Ph(2-F) | |
| 5-93 | Me | Me | H | 4-CN | Ph(2,6-F₂) | |
| 5-94 | Me | Me | H | 4-CN | Ph(2-Cl) | |
| 5-95 | Me | Me | H | 4-CN | Ph(2-Me) | |
| 5-96 | Me | Me | H | 4-CN | Ph(2-CF₃) | |
| 5-97 | Me | Me | H | 4-CN | Ph(2-F-6-Cl) | |
| 5-98 | Me | Me | H | 5-CN | Ph(2-F) | |
| 5-99 | Me | Me | H | 5-CN | Ph(2-Cl) | |
| 5-100 | Me | Me | H | 5-CN | Ph(2,6-Cl₂) | |
| 5-101 | Me | Me | H | 3-OCF₃ | Ph(2-F) | |

TABLE 5-continued

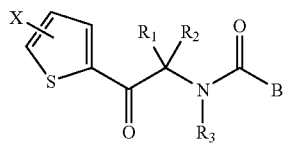

| Compound No. | R₁ | R₂ | R₃ | X | B | Physical properties (mp ° C.) |
|---|---|---|---|---|---|---|
| 5-102 | Me | Me | H | 3-OCF₃ | Ph(2,6-F₂) | |
| 5-103 | Me | Me | H | 3-OCF₃ | Ph(2-Cl) | |
| 5-104 | Me | Me | H | 3-OCF₃ | Ph(2-Me) | |
| 5-105 | Me | Me | H | 3-OCF₃ | Ph(2-CF₃) | |
| 5-106 | Me | Me | H | 3-OCF₃ | Ph(2-F-6-Cl) | |
| 5-107 | Me | Me | H | 4-OCF₃ | Ph(2-F) | |
| 5-108 | Me | Me | H | 4-OCF₃ | Ph(2,6-F₂) | |
| 5-109 | Me | Me | H | 4-OCF₃ | Ph(2-Cl) | |
| 5-110 | Me | Me | H | 4-OCF₃ | Ph(2-Me) | |
| 5-111 | Me | Me | H | 4-OCF₃ | Ph(2-CF₃) | |
| 5-112 | Me | Me | H | 4-OCF₃ | Ph(2-F-6-Cl) | |
| 5-113 | Me | Me | H | 5-OCF₃ | Ph(2-F) | |
| 5-114 | Me | Me | H | 5-OCF₃ | Ph(2,6-F₂) | |
| 5-115 | Me | Me | H | 5-OCF₃ | Ph(2-Cl) | |
| 5-116 | Me | Me | H | 5-OCF₃ | Ph(2-Me) | |
| 5-117 | Me | Me | H | 5-OCF₃ | Ph(2-CF₃) | |
| 5-118 | Me | Me | H | 5-OCF₃ | Ph(2-F-6-Cl) | |
| 5-119 | Me | Me | H | 3-OCHF₂ | Ph(2-F) | |
| 5-120 | Me | Me | H | 3-OCHF₂ | Ph(2,6-F₂) | |
| 5-121 | Me | Me | H | 3-OCHF₂ | Ph(2-Cl) | |
| 5-122 | Me | Me | H | 3-OCHF₂ | Ph(2-Me) | |
| 5-123 | Me | Me | H | 3-OCHF₂ | Ph(2-CF₃) | |
| 5-124 | Me | Me | H | 3-OCHF₂ | Ph(2-F-6-Cl) | |
| 5-125 | Me | Me | H | 4-OCHF₂ | Ph(2-F) | |
| 5-126 | Me | Me | H | 4-OCHF₂ | Ph(2,6-F₂) | |
| 5-127 | Me | Me | H | 4-OCHF₂ | Ph(2-Cl) | |
| 5-128 | Me | Me | H | 4-OCHF₂ | Ph(2-Me) | |
| 5-129 | Me | Me | H | 4-OCHF₂ | Ph(2-CF₃) | |
| 5-130 | Me | Me | H | 4-OCHF₂ | Ph(2-F-6-Cl) | |
| 5-131 | Me | Me | H | 5-OCHF₂ | Ph(2-F) | |
| 5-132 | Me | Me | H | 5-OCHF₂ | Ph(2,6-F₂) | |
| 5-133 | Me | Me | H | 5-OCHF₂ | Ph(2-Cl) | |
| 5-134 | Me | Me | H | 5-OCHF₂ | Ph(2-Me) | |
| 5-135 | Me | Me | H | 5-OCHF₂ | Ph(2-CF₃) | |
| 5-136 | Me | Me | H | 5-OCHF₂ | Ph(2-F-6-Cl) | |
| 5-137 | Me | Me | H | 3-OCH₂CF₃ | Ph(2-F) | |
| 5-138 | Me | Me | H | 3-OCH₂CF₃ | Ph(2,6-F₂) | |
| 5-139 | Me | Me | H | 3-OCH₂CF₃ | Ph(2-Cl) | |
| 5-140 | Me | Me | H | 3-OCH₂CF₃ | Ph(2-Me) | |
| 5-141 | Me | Me | H | 3-OCH₂CF₃ | Ph(2-CF₃) | |
| 5-142 | Me | Me | H | 3-OCH₂CF₃ | Ph(2-F-6-Cl) | |
| 5-143 | Me | Me | H | 4-OCH₂CF₃ | Ph(2-F) | |
| 5-144 | Me | Me | H | 4-OCH₂CF₃ | Ph(2,6-F₂) | |
| 5-145 | Me | Me | H | 4-OCH₂CF₃ | Ph(2-Cl) | |
| 5-146 | Me | Me | H | 4-OCH₂CF₃ | Ph(2-Me) | |
| 5-147 | Me | Me | H | 4-OCH₂CF₃ | Ph(2-CF₃) | |
| 5-148 | Me | Me | H | 4-OCH₂CF₃ | Ph(2-F-6-Cl) | |
| 5-149 | Me | Me | H | 5-OCH₂CF₃ | Ph(2-F) | |
| 5-150 | Me | Me | H | 5-OCH₂CF₃ | Ph(2,6-F₂) | |
| 5-151 | Me | Me | H | 5-OCH₂CF₃ | Ph(2-Cl) | |
| 5-152 | Me | Me | H | 5-OCH₂CF₃ | Ph(2-Me) | |
| 5-153 | Me | Me | H | 5-OCH₂CF₃ | Ph(2-CF₃) | |
| 5-154 | Me | Me | H | 5-OCH₂CF₃ | Ph(2-F-6-Cl) | |
| 5-155 | Me | Me | H | 5-Cl | 4-trifluoromethyl-3-pyridyl | 179-182 |
| 5-156 | Me | Me | H | 4,5-Br₂ | Ph(2,6-F₂) | 128-130 |
| 5-157 | Me | Me | H | 4,5-Br₂ | Ph(2-F) | 173-175 |
| 5-158 | Me | Me | H | 3-Me-4-Cl | Ph(2-F) | |
| 5-159 | Me | Me | H | 3-Me-4-Cl | Ph(2,6-F₂) | |
| 5-160 | Me | Me | H | 3-Me-4-Cl | Ph(2-Cl) | |
| 5-161 | Me | Me | H | 3-Me-4-Cl | Ph(2-Me) | |
| 5-162 | Me | Me | H | 3-Me-4-Cl | Ph(2-CF₃) | |
| 5-163 | Me | Me | H | 3-Me-4-Cl | Ph(2-F-6-Cl) | |
| 5-164 | Me | Me | H | 3-Me-5-Cl | Ph(2-F) | |
| 5-165 | Me | Me | H | 3-Me-5-Cl | Ph(2,6-F₂) | |
| 5-166 | Me | Me | H | 3-Me-5-Cl | Ph(2-Cl) | |
| 5-167 | Me | Me | H | 3-Me-5-Cl | Ph(2-Me) | |
| 5-168 | Me | Me | H | 3-Me-5-Cl | Ph(2-CF₃) | |
| 5-169 | Me | Me | H | 3-Me-5-Cl | Ph(2-F-6-Cl) | |

TABLE 5-continued

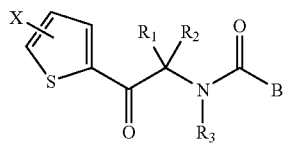

| Compound No. | R₁ | R₂ | R₃ | X | B | Physical properties (mp ° C.) |
|---|---|---|---|---|---|---|
| 5-170 | Me | Me | H | 3-Me-4-Br | Ph(2-F) | |
| 5-171 | Me | Me | H | 3-Me-4-Br | Ph(2,6-F$_2$) | |
| 5-172 | Me | Me | H | 3-Me-4-Br | Ph(2-Cl) | |
| 5-173 | Me | Me | H | 3-Me-4-Br | Ph(2-Me) | |
| 5-174 | Me | Me | H | 3-Me-4-Br | Ph(2-CF$_3$) | |
| 5-175 | Me | Me | H | 3-Me-4-Br | Ph(2-F-6-Cl) | |
| 5-176 | Me | Me | H | 3-Me-5-Br | Ph(2-F) | |
| 5-177 | Me | Me | H | 3-Me-5-Br | Ph(2,6-F$_2$) | |
| 5-178 | Me | Me | H | 3-Me-5-Br | Ph(2-Cl) | |
| 5-179 | Me | Me | H | 3-Me-5-Br | Ph(2-Me) | |
| 5-180 | Me | Me | H | 3-Me-5-Br | Ph(2-CF$_3$) | |
| 5-181 | Me | Me | H | 3-Me-5-Br | Ph(2-F-6-Cl) | |
| 5-182 | Me | Me | H | 3-Me-4-CF$_3$ | Ph(2-F) | |
| 5-183 | Me | Me | H | 3-Me-4-CF$_3$ | Ph(2,6-F$_2$) | |
| 5-184 | Me | Me | H | 3-Me-4-CF$_3$ | Ph(2-Cl) | |
| 5-185 | Me | Me | H | 3-Me-4-CF$_3$ | Ph(2-Me) | |
| 5-186 | Me | Me | H | 3-Me-4-CF$_3$ | Ph(2-CF$_3$) | |
| 5-187 | Me | Me | H | 3-Me-4-CF$_3$ | Ph(2-F-6-Cl) | |
| 5-188 | Me | Me | H | 3-Me-5-CF$_3$ | Ph(2-F) | |
| 5-189 | Me | Me | H | 3-Me-5-CF$_3$ | Ph(2,6-F$_2$) | |
| 5-190 | Me | Me | H | 3-Me-5-CF$_3$ | Ph(2-Cl) | |
| 5-191 | Me | Me | H | 3-Me-5-CF$_3$ | Ph(2-Me) | |
| 5-192 | Me | Me | H | 3-Me-5-CF$_3$ | Ph(2-CF$_3$) | |
| 5-193 | Me | Me | H | 3-Me-5-CF$_3$ | Ph(2-F-6-Cl) | |
| 5-194 | Me | Me | H | 3-Me-4-OCF$_3$ | Ph(2-F) | |
| 5-195 | Me | Me | H | 3-Me-4-OCF$_3$ | Ph(2,6-F$_2$) | |
| 5-196 | Me | Me | H | 3-Me-4-OCF$_3$ | Ph(2-Cl) | |
| 5-197 | Me | Me | H | 3-Me-4-OCF$_3$ | Ph(2-Me) | |
| 5-198 | Me | Me | H | 3-Me-4-OCF$_3$ | Ph(2-CF$_3$) | |
| 5-199 | Me | Me | H | 3-Me-4-OCF$_3$ | Ph(2-F-6-Cl) | |
| 5-200 | Me | Me | H | 3-Me-5-OCF$_3$ | Ph(2-F) | |
| 5-201 | Me | Me | H | 3-Me-5-OCF$_3$ | Ph(2,6-F$_2$) | |
| 5-202 | Me | Me | H | 3-Me-5-OCF$_3$ | Ph(2-Cl) | |
| 5-203 | Me | Me | H | 3-Me-5-OCF$_3$ | Ph(2-Me) | |
| 5-204 | Me | Me | H | 3-Me-5-OCF$_3$ | Ph(2-CF$_3$) | |
| 5-205 | Me | Me | H | 3-Me-5-OCF$_3$ | Ph(2-F-6-Cl) | |
| 5-206 | Me | Me | H | 3-Me-4-OCHF$_2$ | Ph(2-F) | |
| 5-207 | Me | Me | H | 3-Me-4-OCHF$_2$ | Ph(2,6-F$_2$) | |
| 5-208 | Me | Me | H | 3-Me-4-OCHF$_2$ | Ph(2-Cl) | |
| 5-209 | Me | Me | H | 3-Me-4-OCHF$_2$ | Ph(2-Me) | |
| 5-210 | Me | Me | H | 3-Me-4-OCHF$_2$ | Ph(2-CF$_3$) | |
| 5-211 | Me | Me | H | 3-Me-4-OCHF$_2$ | Ph(2-F-6-Cl) | |
| 5-212 | Me | Me | H | 3-Me-5-OCHF$_2$ | Ph(2-F) | |
| 5-213 | Me | Me | H | 3-Me-5-OCHF$_2$ | Ph(2,6-F$_2$) | |
| 5-214 | Me | Me | H | 3-Me-5-OCHF$_2$ | Ph(2-Cl) | |
| 5-215 | Me | Me | H | 3-Me-5-OCHF$_2$ | Ph(2-Me) | |
| 5-216 | Me | Me | H | 3-Me-5-OCHF$_2$ | Ph(2-CF$_3$) | |
| 5-217 | Me | Me | H | 3-Me-5-OCHF$_2$ | Ph(2-F-6-Cl) | |
| 5-218 | Me | Me | H | 3-Me-4-OCH$_2$CF$_3$ | Ph(2-F) | |
| 5-219 | Me | Me | H | 3-Me-4-OCH$_2$CF$_3$ | Ph(2,6-F$_2$) | |
| 5-220 | Me | Me | H | 3-Me-4-OCH$_2$CF$_3$ | Ph(2-Cl) | |
| 5-221 | Me | Me | H | 3-Me-4-OCH$_2$CF$_3$ | Ph(2-Me) | |
| 5-222 | Me | Me | H | 3-Me-4-OCH$_2$CF$_3$ | Ph(2-CF$_3$) | |
| 5-223 | Me | Me | H | 3-Me-4-OCH$_2$CF$_3$ | Ph(2-F-6-Cl) | |
| 5-224 | Me | Me | H | 3-Me-5-OCH$_2$CF$_3$ | Ph(2-F) | |
| 5-225 | Me | Me | H | 3-Me-5-OCH$_2$CF$_3$ | Ph(2,6-F$_2$) | |
| 5-226 | Me | Me | H | 3-Me-5-OCH$_2$CF$_3$ | Ph(2-Cl) | |
| 5-227 | Me | Me | H | 3-Me-5-OCH$_2$CF$_3$ | Ph(2-Me) | |
| 5-228 | Me | Me | H | 3-Me-5-OCH$_2$CF$_3$ | Ph(2-CF$_3$) | |
| 5-229 | Me | Me | H | 3-Me-5-OCH$_2$CF$_3$ | Ph(2-F-6-Cl) | |
| 5-230 | Me | Me | H | 3,5-Cl$_2$ | Ph(2-F) | |
| 5-231 | Me | Me | H | 3,5-Cl$_2$ | Ph(2,6-F$_2$) | |
| 5-232 | Me | Me | H | 3,5-Cl$_2$ | Ph(2-Cl) | |
| 5-233 | Me | Me | H | 3,5-Cl$_2$ | Ph(2-Me) | |
| 5-234 | Me | Me | H | 3,5-Cl$_2$ | Ph(2-CF$_3$) | |
| 5-235 | Me | Me | H | 3,5-Cl$_2$ | Ph(2-F-6-Cl) | |
| 5-236 | Me | Me | H | 3-Cl-5-Br | Ph(2-F) | |
| 5-237 | Me | Me | H | 3-Cl-5-Br | Ph(2,6-F$_2$) | |
| 5-238 | Me | Me | H | 3-Cl-5-Br | Ph(2-Cl) | |

TABLE 5-continued

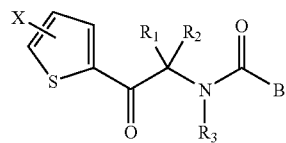

| Compound No. | R₁ | R₂ | R₃ | X | B | Physical properties (mp ° C.) |
|---|---|---|---|---|---|---|
| 5-239 | Me | Me | H | 3-Cl-5-Br | Ph(2-Me) | |
| 5-240 | Me | Me | H | 3-Cl-5-Br | Ph(2-CF₃) | |
| 5-241 | Me | Me | H | 3-Cl-5-Br | Ph(2-F-6-Cl) | |
| 5-242 | Me | Me | H | 3-Cl-5-CF₃ | Ph(2-F) | |
| 5-243 | Me | Me | H | 3-Cl-5-CF₃ | Ph(2,6-F₂) | |
| 5-244 | Me | Me | H | 3-Cl-5-CF₃ | Ph(2-Cl) | |
| 5-245 | Me | Me | H | 3-Cl-5-CF₃ | Ph(2-Me) | |
| 5-246 | Me | Me | H | 3-Cl-5-CF₃ | Ph(2-CF₃) | |
| 5-247 | Me | Me | H | 3-Cl-5-CF₃ | Ph(2-F-6-Cl) | |
| 5-248 | Me | Me | H | 3-Cl-5-OCF₃ | Ph(2-F) | |
| 5-249 | Me | Me | H | 3-Cl-5-OCF₃ | Ph(2,6-F₂) | |
| 5-250 | Me | Me | H | 3-Cl-5-OCF₃ | Ph(2-Cl) | |
| 5-251 | Me | Me | H | 3-Cl-5-OCF₃ | Ph(2-Me) | |
| 5-252 | Me | Me | H | 3-Cl-5-OCF₃ | Ph(2-CF₃) | |
| 5-253 | Me | Me | H | 3-Cl-5-OCF₃ | Ph(2-F-6-Cl) | |
| 5-254 | Me | Me | H | 3-Cl-5-OCHF₂ | Ph(2-F) | |
| 5-255 | Me | Me | H | 3-Cl-5-OCHF₂ | Ph(2,6-F₂) | |
| 5-256 | Me | Me | H | 3-Cl-5-OCHF₂ | Ph(2-Cl) | |
| 5-257 | Me | Me | H | 3-Cl-5-OCHF₂ | Ph(2-Me) | |
| 5-258 | Me | Me | H | 3-Cl-5-OCHF₂ | Ph(2-CF₃) | |
| 5-259 | Me | Me | H | 3-Cl-5-OCHF₂ | Ph(2-F-6-Cl) | |
| 5-260 | Me | Me | H | 3-Cl-5-OCH₂CF₃ | Ph(2-F) | |
| 5-261 | Me | Me | H | 3-Cl-5-OCH₂CF₃ | Ph(2,6-F₂) | |
| 5-262 | Me | Me | H | 3-Cl-5-OCH₂CF₃ | Ph(2-Cl) | |
| 5-263 | Me | Me | H | 3-Cl-5-OCH₂CF₃ | Ph(2-Me) | |
| 5-264 | Me | Me | H | 3-Cl-5-OCH₂CF₃ | Ph(2-CF₃) | |
| 5-265 | Me | Me | H | 3-Cl-5-OCH₂CF₃ | Ph(2-F-6-Cl) | |

TABLE 6

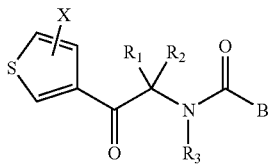

| Compound No. | R₁ | R₂ | R₃ | X | B | Physical properties (mp ° C.) |
|---|---|---|---|---|---|---|
| 6-1 | Me | Me | H | H | Ph | |
| 6-2 | Me | Me | H | H | Ph(2-F) | |
| 6-3 | Me | Me | H | H | Ph(2-Cl) | |
| 6-4 | Me | Me | H | H | Ph(2-OMe) | |
| 6-5 | Me | Me | H | H | Ph(2,6-F₂) | 139-142 |
| 6-6 | Me | Me | H | H | Ph(2,6-Cl₂) | |
| 6-7 | Me | Me | H | H | Ph(2,6-OMe₂) | |
| 6-8 | Me | Me | H | 2-Cl | Ph | |
| 6-9 | Me | Me | H | 2-Cl | Ph(2-F) | |
| 6-10 | Me | Me | H | 2-Cl | Ph(2-Cl) | |
| 6-11 | Me | Me | H | 2-Cl | Ph(2,6-F₂) | |
| 6-12 | Me | Me | H | 2-Cl | Ph(2,6-Cl₂) | |
| 6-13 | Me | Me | H | 2-Br | Ph | |
| 6-14 | Me | Me | H | 2-Br | Ph(2-F) | |
| 6-15 | Me | Me | H | 2-Br | Ph(2-Cl) | |
| 6-16 | Me | Me | H | 2-Br | Ph(2,6-F₂) | |
| 6-17 | Me | Me | H | 2-Br | Ph(2,6-Cl₂) | |
| 6-18 | Me | Me | H | 2-CF₃ | Ph(2,6-F₂) | |
| 6-19 | Me | Me | H | 2-CN | Ph(2,6-F₂) | |
| 6-20 | Me | CN | H | H | Ph(2,6-F₂) | |
| 6-21 | Me | CO₂Et | H | H | Ph(2,6-F₂) | |
| 6-22 | Me | CN | H | 2-Cl | Ph(2,6-F₂) | |
| 6-23 | Me | CO₂Et | H | 2-Cl | Ph(2,6-F₂) | |
| 6-24 | Me | Et | H | H | Ph(2,6-F₂) | |

TABLE 6-continued

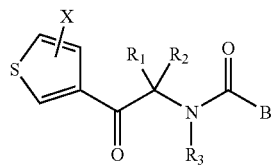

| Compound No. | $R_1$ | $R_2$ | $R_3$ | X | B | Physical properties (mp ° C.) |
|---|---|---|---|---|---|---|
| 6-25 | Me | Me | COMe | H | Ph(2,6-$F_2$) | |
| 6-26 | Me | Me | $CH_2OMe$ | H | Ph(2,6-$F_2$) | |
| 6-27 | Me | Me | H | H | 1-naphthyl | |
| 6-28 | Me | Me | H | H | 2-naphthyl | |
| 6-29 | Me | Me | H | H | 2-thienyl | |
| 6-30 | Me | Me | H | H | 3-thienyl | |
| 6-31 | Me | Me | H | H | 2-pyrazinyl | |
| 6-32 | Me | Me | H | H | 2-pyridyl | |
| 6-33 | Me | Me | H | H | 3-pyridyl | |
| 6-34 | Me | Me | H | H | 4-trifluoromethyl-3-pyridyl | |
| 6-35 | Me | Me | H | H | 4-pyridyl | |
| 6-36 | Me | Me | H | H | 2-furyl | |
| 6-37 | Me | Me | H | H | 3-furyl | |
| 6-38 | Me | Me | H | 4-Cl | Ph(2-F) | |
| 6-39 | Me | Me | H | 4-Cl | Ph(2,6-$F_2$) | |
| 6-40 | Me | Me | H | 4-Cl | Ph(2-Cl) | |
| 6-41 | Me | Me | H | 4-Cl | Ph(2-Me) | |
| 6-42 | Me | Me | H | 4-Cl | Ph(2-$CF_3$) | |
| 6-43 | Me | Me | H | 4-Cl | Ph(2-F-6-Cl) | |
| 6-44 | Me | Me | H | 5-Cl | Ph(2-F) | |
| 6-45 | Me | Me | H | 5-Cl | Ph(2,6-$F_2$) | |
| 6-46 | Me | Me | H | 5-Cl | Ph(2-Cl) | |
| 6-47 | Me | Me | H | 5-Cl | Ph(2-Me) | |
| 6-48 | Me | Me | H | 5-Cl | Ph(2-$CF_3$) | |
| 6-49 | Me | Me | H | 5-Cl | Ph(2-F-6-Cl) | |
| 6-50 | Me | Me | H | 5-Br | Ph(2-F) | |
| 6-51 | Me | Me | H | 5-Br | Ph(2,6-$F_2$) | |
| 6-52 | Me | Me | H | 5-Br | Ph(2-Cl) | |
| 6-53 | Me | Me | H | 5-Br | Ph(2-Me) | |
| 6-54 | Me | Me | H | 5-Br | Ph(2-$CF_3$) | |
| 6-55 | Me | Me | H | 5-Br | Ph(2-F-6-Cl) | |
| 6-56 | Me | Me | H | 2-Me | Ph(2-F) | |
| 6-57 | Me | Me | H | 2-Me | Ph(2,6-$F_2$) | |
| 6-58 | Me | Me | H | 2-Me | Ph(2-Cl) | |
| 6-59 | Me | Me | H | 2-Me | Ph(2-Me) | |
| 6-60 | Me | Me | H | 2-Me | Ph(2-$CF_3$) | |
| 6-61 | Me | Me | H | 2-Me | Ph(2-F-6-Cl) | |
| 6-62 | Me | Me | H | 4-Me | Ph(2-F) | |
| 6-63 | Me | Me | H | 4-Me | Ph(2,6-$F_2$) | |
| 6-64 | Me | Me | H | 4-Me | Ph(2-Cl) | |
| 6-65 | Me | Me | H | 4-Me | Ph(2-Me) | |
| 6-66 | Me | Me | H | 4-Me | Ph(2-$CF_3$) | |
| 6-67 | Me | Me | H | 4-Me | Ph(2-F-6-Cl) | |
| 6-68 | Me | Me | H | 5-$CF_3$ | Ph(2-F) | |
| 6-69 | Me | Me | H | 5-$CF_3$ | Ph(2,6-$F_2$) | |
| 6-70 | Me | Me | H | 5-$CF_3$ | Ph(2-Cl) | |
| 6-71 | Me | Me | H | 5-$CF_3$ | Ph(2-Me) | |
| 6-72 | Me | Me | H | 5-$CF_3$ | Ph(2-$CF_3$) | |
| 6-73 | Me | Me | H | 5-$CF_3$ | Ph(2-F-6-Cl) | |
| 6-74 | Me | Me | H | 5-$OCF_3$ | Ph(2-F) | |
| 6-75 | Me | Me | H | 5-$OCF_3$ | Ph(2,6-$F_2$) | |
| 6-76 | Me | Me | H | 5-$OCF_3$ | Ph(2-Cl) | |
| 6-77 | Me | Me | H | 5-$OCF_3$ | Ph(2-Me) | |
| 6-78 | Me | Me | H | 5-$OCF_3$ | Ph(2-$CF_3$) | |
| 6-79 | Me | Me | H | 5-$OCF_3$ | Ph(2-F-6-Cl) | |
| 6-80 | Me | Me | H | 5-$OCHF_2$ | Ph(2-F) | |
| 6-81 | Me | Me | H | 5-$OCHF_2$ | Ph(2,6-$F_2$) | |
| 6-82 | Me | Me | H | 5-$OCHF_2$ | Ph(2-Cl) | |
| 6-83 | Me | Me | H | 5-$OCHF_2$ | Ph(2-Me) | |
| 6-84 | Me | Me | H | 5-$OCHF_2$ | Ph(2-$CF_3$) | |
| 6-85 | Me | Me | H | 5-$OCHF_2$ | Ph(2-F-6-Cl) | |
| 6-86 | Me | Me | H | 5-$OCH_2CF_3$ | Ph(2-F) | |
| 6-87 | Me | Me | H | 5-$OCH_2CF_3$ | Ph(2,6-$F_2$) | |
| 6-88 | Me | Me | H | 5-$OCH_2CF_3$ | Ph(2-Cl) | |
| 6-89 | Me | Me | H | 5-$OCH_2CF_3$ | Ph(2-Me) | |
| 6-90 | Me | Me | H | 5-$OCH_2CF_3$ | Ph(2-$CF_3$) | |
| 6-91 | Me | Me | H | 5-$OCH_2CF_3$ | Ph(2-F-6-Cl) | |

TABLE 6-continued

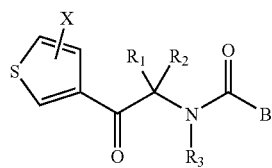

| Compound No. | R₁ | R₂ | R₃ | X | B | Physical properties (mp ° C.) |
|---|---|---|---|---|---|---|
| 6-92 | Me | Me | H | 2,5-Cl₂ | Ph(2-F) | |
| 6-93 | Me | Me | H | 2,5-Cl₂ | Ph(2,6-F₂) | |
| 6-94 | Me | Me | H | 2,5-Cl₂ | Ph(2-Cl) | |
| 6-95 | Me | Me | H | 2,5-Cl₂ | Ph(2-Me) | |
| 6-96 | Me | Me | H | 2,5-Cl₂ | Ph(2-CF₃) | |
| 6-97 | Me | Me | H | 2,5-Cl₂ | Ph(2-F-6-Cl) | |
| 6-98 | Me | Me | H | 4,5-Cl₂ | Ph(2-F) | |
| 6-99 | Me | Me | H | 4,5-Cl₂ | Ph(2,6-F₂) | |
| 6-100 | Me | Me | H | 4,5-Cl₂ | Ph(2-Cl) | |
| 6-101 | Me | Me | H | 4,5-Cl₂ | Ph(2-Me) | |
| 6-102 | Me | Me | H | 4,5-Cl₂ | Ph(2-CF₃) | |
| 6-103 | Me | Me | H | 4,5-Cl₂ | Ph(2-F-6-Cl) | |
| 6-104 | Me | Me | H | 2-Cl-5-Br | Ph(2-F) | |
| 6-105 | Me | Me | H | 2-Cl-5-Br | Ph(2,6-F₂) | |
| 6-106 | Me | Me | H | 2-Cl-5-Br | Ph(2-Cl) | |
| 6-107 | Me | Me | H | 2-Cl-5-Br | Ph(2-Me) | |
| 6-108 | Me | Me | H | 2-Cl-5-Br | Ph(2-CF₃) | |
| 6-109 | Me | Me | H | 2-Cl-5-Br | Ph(2-F-6-Cl) | |
| 6-110 | Me | Me | H | 4-Cl-5-Br | Ph(2-F) | |
| 6-111 | Me | Me | H | 4-Cl-5-Br | Ph(2,6-F₂) | |
| 6-112 | Me | Me | H | 4-Cl-5-Br | Ph(2-Cl) | |
| 6-113 | Me | Me | H | 4-Cl-5-Br | Ph(2-Me) | |
| 6-114 | Me | Me | H | 4-Cl-5-Br | Ph(2-CF₃) | |
| 6-115 | Me | Me | H | 4-Cl-5-Br | Ph(2-F-6-Cl) | |
| 6-116 | Me | Me | H | 2-Cl-5-CF₃ | Ph(2-F) | |
| 6-117 | Me | Me | H | 2-Cl-5-CF₃ | Ph(2,6-F₂) | |
| 6-118 | Me | Me | H | 2-Cl-5-CF₃ | Ph(2-Cl) | |
| 6-119 | Me | Me | H | 2-Cl-5-CF₃ | Ph(2-Me) | |
| 6-120 | Me | Me | H | 2-Cl-5-CF₃ | Ph(2-CF₃) | |
| 6-121 | Me | Me | H | 2-Cl-5-CF₃ | Ph(2-F-6-Cl) | |
| 6-122 | Me | Me | H | 4-Cl-5-CF₃ | Ph(2-F) | |
| 6-123 | Me | Me | H | 4-Cl-5-CF₃ | Ph(2,6-F₂) | |
| 6-124 | Me | Me | H | 4-Cl-5-CF₃ | Ph(2-Cl) | |
| 6-125 | Me | Me | H | 4-Cl-5-CF₃ | Ph(2-Me) | |
| 6-126 | Me | Me | H | 4-Cl-5-CF₃ | Ph(2-CF₃) | |
| 6-127 | Me | Me | H | 4-Cl-5-CF₃ | Ph(2-F-6-Cl) | |
| 6-128 | Me | Me | H | 2-Cl-5-OCF₃ | Ph(2-F) | |
| 6-129 | Me | Me | H | 2-Cl-5-OCF₃ | Ph(2,6-F₂) | |
| 6-130 | Me | Me | H | 2-Cl-5-OCF₃ | Ph(2-Cl) | |
| 6-131 | Me | Me | H | 2-Cl-5-OCF₃ | Ph(2-Me) | |
| 6-132 | Me | Me | H | 2-Cl-5-OCF₃ | Ph(2-CF₃) | |
| 6-133 | Me | Me | H | 2-Cl-5-OCF₃ | Ph(2-F-6-Cl) | |
| 6-134 | Me | Me | H | 4-Cl-5-OCF₃ | Ph(2-F) | |
| 6-135 | Me | Me | H | 4-Cl-5-OCF₃ | Ph(2,6-F₂) | |
| 6-136 | Me | Me | H | 4-Cl-5-OCF₃ | Ph(2-Cl) | |
| 6-137 | Me | Me | H | 4-Cl-5-OCF₃ | Ph(2-Me) | |
| 6-138 | Me | Me | H | 4-Cl-5-OCF₃ | Ph(2-CF₃) | |
| 6-139 | Me | Me | H | 4-Cl-5-OCF₃ | Ph(2-F-6-Cl) | |
| 6-140 | Me | Me | H | 2-Cl-5-OCHF₂ | Ph(2-F) | |
| 6-141 | Me | Me | H | 2-Cl-5-OCHF₂ | Ph(2,6-F₂) | |
| 6-142 | Me | Me | H | 2-Cl-5-OCHF₂ | Ph(2-Cl) | |
| 6-143 | Me | Me | H | 2-Cl-5-OCHF₂ | Ph(2-Me) | |
| 6-144 | Me | Me | H | 2-Cl-5-OCHF₂ | Ph(2-CF₃) | |
| 6-145 | Me | Me | H | 2-Cl-5-OCHF₂ | Ph(2-F-6-Cl) | |
| 6-146 | Me | Me | H | 4-Cl-5-OCHF₂ | Ph(2-F) | |
| 6-147 | Me | Me | H | 4-Cl-5-OCHF₂ | Ph(2,6-F₂) | |
| 6-148 | Me | Me | H | 4-Cl-5-OCHF₂ | Ph(2-Cl) | |
| 6-149 | Me | Me | H | 4-Cl-5-OCHF₂ | Ph(2-Me) | |
| 6-150 | Me | Me | H | 4-Cl-5-OCHF₂ | Ph(2-CF₃) | |
| 6-151 | Me | Me | H | 4-Cl-5-OCHF₂ | Ph(2-F-6-Cl) | |
| 6-152 | Me | Me | H | 2-Cl-5-OCH₂CF₃ | Ph(2-F) | |
| 6-153 | Me | Me | H | 2-Cl-5-OCH₂CF₃ | Ph(2,6-F₂) | |
| 6-154 | Me | Me | H | 2-Cl-5-OCH₂CF₃ | Ph(2-Cl) | |
| 6-155 | Me | Me | H | 2-Cl-5-OCH₂CF₃ | Ph(2-Me) | |
| 6-156 | Me | Me | H | 2-Cl-5-OCH₂CF₃ | Ph(2-CF₃) | |
| 6-157 | Me | Me | H | 2-Cl-5-OCH₂CF₃ | Ph(2-F-6-Cl) | |
| 6-158 | Me | Me | H | 4-Cl-5-OCH₂CF₃ | Ph(2-F) | |

TABLE 6-continued

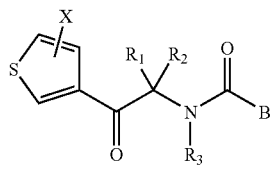

| Compound No. | R₁ | R₂ | R₃ | X | B | Physical properties (mp °C.) |
|---|---|---|---|---|---|---|
| 6-159 | Me | Me | H | 4-Cl-5-OCH$_2$CF$_3$ | Ph(2,6-F$_2$) | |
| 6-160 | Me | Me | H | 4-Cl-5-OCH$_2$CF$_3$ | Ph(2-Cl) | |
| 6-161 | Me | Me | H | 4-Cl-5-OCH$_2$CF$_3$ | Ph(2-Me) | |
| 6-162 | Me | Me | H | 4-Cl-5-OCH$_2$CF$_3$ | Ph(2-CF$_3$) | |
| 6-163 | Me | Me | H | 4-Cl-5-OCH$_2$CF$_3$ | Ph(2-F-6-Cl) | |
| 6-164 | Me | Me | H | 2-Me-5-Cl | Ph(2-F) | |
| 6-165 | Me | Me | H | 2-Me-5-Cl | Ph(2,6-F$_2$) | |
| 6-166 | Me | Me | H | 2-Me-5-Cl | Ph(2-Cl) | |
| 6-167 | Me | Me | H | 2-Me-5-Cl | Ph(2-Me) | |
| 6-168 | Me | Me | H | 2-Me-5-Cl | Ph(2-CF$_3$) | |
| 6-169 | Me | Me | H | 2-Me-5-Cl | Ph(2-F-6-Cl) | |
| 6-170 | Me | Me | H | 4-Me-5-Cl | Ph(2-F) | |
| 6-171 | Me | Me | H | 4-Me-5-Cl | Ph(2,6-F$_2$) | |
| 6-172 | Me | Me | H | 4-Me-5-Cl | Ph(2-Cl) | |
| 6-173 | Me | Me | H | 4-Me-5-Cl | Ph(2-Me) | |
| 6-174 | Me | Me | H | 4-Me-5-Cl | Ph(2-CF$_3$) | |
| 6-175 | Me | Me | H | 4-Me-5-Cl | Ph(2-F-6-Cl) | |
| 6-176 | Me | Me | H | 2-Me-5-Br | Ph(2-F) | |
| 6-177 | Me | Me | H | 2-Me-5-Br | Ph(2,6-F$_2$) | |
| 6-178 | Me | Me | H | 2-Me-5-Br | Ph(2-Cl) | |
| 6-179 | Me | Me | H | 2-Me-5-Br | Ph(2-Me) | |
| 6-180 | Me | Me | H | 2-Me-5-Br | Ph(2-CF$_3$) | |
| 6-181 | Me | Me | H | 2-Me-5-Br | Ph(2-F-6-Cl) | |
| 6-182 | Me | Me | H | 4-Me-5-Br | Ph(2-F) | |
| 6-183 | Me | Me | H | 4-Me-5-Br | Ph(2,6-F$_2$) | |
| 6-184 | Me | Me | H | 4-Me-5-Br | Ph(2-Cl) | |
| 6-185 | Me | Me | H | 4-Me-5-Br | Ph(2-Me) | |
| 6-186 | Me | Me | H | 4-Me-5-Br | Ph(2-CF$_3$) | |
| 6-187 | Me | Me | H | 4-Me-5-Br | Ph(2-F-6-Cl) | |
| 6-188 | Me | Me | H | 2-Me-5-CF$_3$ | Ph(2-F) | |
| 6-189 | Me | Me | H | 2-Me-5-CF$_3$ | Ph(2,6-F$_2$) | |
| 6-190 | Me | Me | H | 2-Me-5-CF$_3$ | Ph(2-Cl) | |
| 6-191 | Me | Me | H | 2-Me-5-CF$_3$ | Ph(2-Me) | |
| 6-192 | Me | Me | H | 2-Me-5-CF$_3$ | Ph(2-CF$_3$) | |
| 6-193 | Me | Me | H | 2-Me-5-CF$_3$ | Ph(2-F-6-Cl) | |
| 6-194 | Me | Me | H | 4-Me-5-CF$_3$ | Ph(2-F) | |
| 6-195 | Me | Me | H | 4-Me-5-CF$_3$ | Ph(2,6-F$_2$) | |
| 6-196 | Me | Me | H | 4-Me-5-CF$_3$ | Ph(2-Cl) | |
| 6-197 | Me | Me | H | 4-Me-5-CF$_3$ | Ph(2-Me) | |
| 6-198 | Me | Me | H | 4-Me-5-CF$_3$ | Ph(2-CF$_3$) | |
| 6-199 | Me | Me | H | 4-Me-5-CF$_3$ | Ph(2-F-6-Cl) | |
| 6-200 | Me | Me | H | 2-Me-5-OCF$_3$ | Ph(2-F) | |
| 6-201 | Me | Me | H | 2-Me-5-OCF$_3$ | Ph(2,6-F$_2$) | |
| 6-202 | Me | Me | H | 2-Me-5-OCF$_3$ | Ph(2-Cl) | |
| 6-203 | Me | Me | H | 2-Me-5-OCF$_3$ | Ph(2-Me) | |
| 6-204 | Me | Me | H | 2-Me-5-OCF$_3$ | Ph(2-CF$_3$) | |
| 6-205 | Me | Me | H | 2-Me-5-OCF$_3$ | Ph(2-F-6-Cl) | |
| 6-206 | Me | Me | H | 4-Me-5-OCF$_3$ | Ph(2-F) | |
| 6-207 | Me | Me | H | 4-Me-5-OCF$_3$ | Ph(2,6-F$_2$) | |
| 6-208 | Me | Me | H | 4-Me-5-OCF$_3$ | Ph(2-Cl) | |
| 6-209 | Me | Me | H | 4-Me-5-OCF$_3$ | Ph(2-Me) | |
| 6-210 | Me | Me | H | 4-Me-5-OCF$_3$ | Ph(2-CF$_3$) | |
| 6-211 | Me | Me | H | 4-Me-5-OCF$_3$ | Ph(2-F-6-Cl) | |
| 6-212 | Me | Me | H | 2-Me-5-OCHF$_2$ | Ph(2-F) | |
| 6-213 | Me | Me | H | 2-Me-5-OCHF$_2$ | Ph(2,6-F$_2$) | |
| 6-214 | Me | Me | H | 2-Me-5-OCHF$_2$ | Ph(2-Cl) | |
| 6-215 | Me | Me | H | 2-Me-5-OCHF$_2$ | Ph(2-Me) | |
| 6-216 | Me | Me | H | 2-Me-5-OCHF$_2$ | Ph(2-CF$_3$) | |
| 6-217 | Me | Me | H | 2-Me-5-OCHF$_2$ | Ph(2-F-6-Cl) | |
| 6-218 | Me | Me | H | 4-Me-5-OCHF$_2$ | Ph(2-F) | |
| 6-219 | Me | Me | H | 4-Me-5-OCHF$_2$ | Ph(2,6-F$_2$) | |
| 6-220 | Me | Me | H | 4-Me-5-OCHF$_2$ | Ph(2-Cl) | |
| 6-221 | Me | Me | H | 4-Me-5-OCHF$_2$ | Ph(2-Me) | |
| 6-222 | Me | Me | H | 4-Me-5-OCHF$_2$ | Ph(2-CF$_3$) | |
| 6-223 | Me | Me | H | 4-Me-5-OCHF$_2$ | Ph(2-F-6-Cl) | |
| 6-224 | Me | Me | H | 2-Me-5-OCH$_2$CF$_3$ | Ph(2-F) | |
| 6-225 | Me | Me | H | 2-Me-5-OCH$_2$CF$_3$ | Ph(2,6-F$_2$) | |

TABLE 6-continued

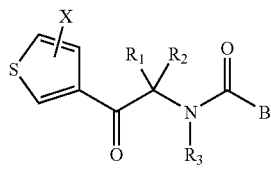

| Compound No. | R$_1$ | R$_2$ | R$_3$ | X | B | Physical properties (mp ° C.) |
|---|---|---|---|---|---|---|
| 6-226 | Me | Me | H | 2-Me-5-OCH$_2$CF$_3$ | Ph(2-Cl) | |
| 6-227 | Me | Me | H | 2-Me-5-OCH$_2$CF$_3$ | Ph(2-Me) | |
| 6-228 | Me | Me | H | 2-Me-5-OCH$_2$CF$_3$ | Ph(2-CF$_3$) | |
| 6-229 | Me | Me | H | 2-Me-5-OCH$_2$CF$_3$ | Ph(2-F-6-Cl) | |
| 6-230 | Me | Me | H | 4-Me-5-OCH$_2$CF$_3$ | Ph(2-F) | |
| 6-231 | Me | Me | H | 4-Me-5-OCH$_2$CF$_3$ | Ph(2,6-F$_2$) | |
| 6-232 | Me | Me | H | 4-Me-5-OCH$_2$CF$_3$ | Ph(2-Cl) | |
| 6-233 | Me | Me | H | 4-Me-5-OCH$_2$CF$_3$ | Ph(2-Me) | |
| 6-234 | Me | Me | H | 4-Me-5-OCH$_2$CF$_3$ | Ph(2-CF$_3$) | |
| 6-235 | Me | Me | H | 4-Me-5-OCH$_2$CF$_3$ | Ph(2-F-6-Cl) | |

TABLE 7

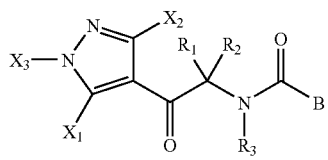

| Compound No. | R$_1$ | R$_2$ | R$_3$ | X$_1$ | X$_2$ | X$_3$ | B | Physical properties (mp ° C.) |
|---|---|---|---|---|---|---|---|---|
| 7-1 | Me | Me | H | Me | Me | Me | Ph(2-Cl) | |
| 7-2 | Me | Me | H | Me | Me | Me | Ph(4-Cl) | |
| 7-3 | Me | Me | H | Me | Me | Me | Ph(2-CF$_3$) | |
| 7-4 | Me | Me | H | Me | Me | Me | Ph(4-CF$_3$) | |
| 7-5 | Me | Me | H | Me | Me | Me | Ph(2-F) | |
| 7-6 | Me | Me | H | Me | Me | Me | Ph(2,6-F$_2$) | |
| 7-7 | Me | Me | H | Me | Me | Me | Ph(2,6-(OMe)$_2$) | |
| 7-8 | Me | Me | H | Cl | Cl | Me | Ph(2-Cl) | |
| 7-9 | Me | Me | H | Cl | Cl | Me | Ph(4-Cl) | |
| 7-10 | Me | Me | H | Cl | Cl | Me | Ph(2-CF$_3$) | |
| 7-11 | Me | Me | H | Cl | Cl | Me | Ph(4-CF$_3$) | |
| 7-12 | Me | Me | H | Cl | Cl | Me | Ph(2-F) | |
| 7-13 | Me | Me | H | Cl | Cl | Me | Ph(2,6-F$_2$) | |
| 7-14 | Me | Me | H | Cl | Me | Me | Ph(2-Cl) | |
| 7-15 | Me | Me | H | Cl | Me | Me | Ph(4-Cl) | |
| 7-16 | Me | Me | H | Cl | Me | Me | Ph(2-CF$_3$) | |
| 7-17 | Me | Me | H | Cl | Me | Me | Ph(4-CF$_3$) | |
| 7-18 | Me | Me | H | Cl | Me | Me | Ph(2-F) | |
| 7-19 | Me | Me | H | Cl | Me | Me | Ph(2,6-F$_2$) | |
| 7-20 | Me | Me | H | Cl | CF$_3$ | Me | Ph(2-Cl) | |
| 7-21 | Me | Me | H | Cl | CF$_3$ | Me | Ph(4-Cl) | |
| 7-22 | Me | Me | H | Cl | CF$_3$ | Me | Ph(2-CF$_3$) | |
| 7-23 | Me | Me | H | Cl | CF$_3$ | Me | Ph(4-CF$_3$) | |
| 7-24 | Me | Me | H | Cl | CF$_3$ | Me | Ph(2-F) | |
| 7-25 | Me | Me | H | Cl | CF$_3$ | Me | Ph(2,6-F$_2$) | |
| 7-26 | Me | Me | H | Me | H | Me | Ph(2-F) | |
| 7-27 | Me | Me | H | Me | H | Me | Ph(2,6-F$_2$) | |
| 7-28 | Me | Me | H | Me | H | Me | Ph(2-Cl) | |
| 7-29 | Me | Me | H | Me | H | Me | Ph(2-Me) | |
| 7-30 | Me | Me | H | Me | H | Me | Ph(2-CF$_3$) | |
| 7-31 | Me | Me | H | Me | H | Me | Ph(2-F-6-Cl) | |
| 7-32 | Me | Me | H | H | Me | Me | Ph(2-F) | |
| 7-33 | Me | Me | H | H | Me | Me | Ph(2,6-F$_2$) | |
| 7-34 | Me | Me | H | H | Me | Me | Ph(2-Cl) | |
| 7-35 | Me | Me | H | H | Me | Me | Ph(2-Me) | |
| 7-36 | Me | Me | H | H | Me | Me | Ph(2-CF$_3$) | |
| 7-37 | Me | Me | H | H | Me | Me | Ph(2-F-6-Cl) | |
| 7-38 | Me | Me | H | H | H | H | Ph(2-F) | |
| 7-39 | Me | Me | H | H | H | H | Ph(2,6-F$_2$) | |

TABLE 7-continued

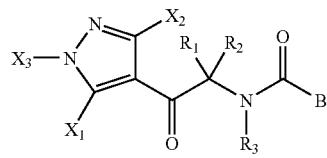

| Compound No. | $R_1$ | $R_2$ | $R_3$ | $X_1$ | $X_2$ | $X_3$ | B | Physical properties (mp ° C.) |
|---|---|---|---|---|---|---|---|---|
| 7-40 | Me | Me | H | H | H | H | Ph(2-Cl) | |
| 7-41 | Me | Me | H | H | H | H | Ph(2-Me) | |
| 7-42 | Me | Me | H | H | H | H | Ph(2-CF$_3$) | |
| 7-43 | Me | Me | H | H | H | H | Ph(2-F-6-Cl) | |
| 7-44 | Me | Me | H | Me | H | H | Ph(2-F) | |
| 7-45 | Me | Me | H | Me | H | H | Ph(2,6-F$_2$) | |
| 7-46 | Me | Me | H | Me | H | H | Ph(2-Cl) | |
| 7-47 | Me | Me | H | Me | H | H | Ph(2-Me) | |
| 7-48 | Me | Me | H | Me | H | H | Ph(2-CF$_3$) | |
| 7-49 | Me | Me | H | Me | H | H | Ph(2-F-6-Cl) | |
| 7-50 | Me | Me | H | Cl | H | H | Ph(2-F) | |
| 7-51 | Me | Me | H | Cl | H | H | Ph(2,6-F$_2$) | |
| 7-52 | Me | Me | H | Cl | H | H | Ph(2-Cl) | |
| 7-53 | Me | Me | H | Cl | H | H | Ph(2-Me) | |
| 7-54 | Me | Me | H | Cl | H | H | Ph(2-CF$_3$) | |
| 7-55 | Me | Me | H | Cl | H | H | Ph(2-F-6-Cl) | |
| 7-56 | Me | Me | H | H | Me | H | Ph(2-F) | |
| 7-57 | Me | Me | H | H | Me | H | Ph(2,6-F$_2$) | |
| 7-58 | Me | Me | H | H | Me | H | Ph(2-Cl) | |
| 7-59 | Me | Me | H | H | Me | H | Ph(2-Me) | |
| 7-60 | Me | Me | H | H | Me | H | Ph(2-CF$_3$) | |
| 7-61 | Me | Me | H | H | Me | H | Ph(2-F-6-Cl) | |
| 7-62 | Me | Me | H | H | Cl | H | Ph(2-F) | |
| 7-63 | Me | Me | H | H | Cl | H | Ph(2,6-F$_2$) | |
| 7-64 | Me | Me | H | H | Cl | H | Ph(2-Cl) | |
| 7-65 | Me | Me | H | H | Cl | H | Ph(2-Me) | |
| 7-66 | Me | Me | H | H | Cl | H | Ph(2-CF$_3$) | |
| 7-67 | Me | Me | H | H | Cl | H | Ph(2-F-6-Cl) | |
| 7-68 | Me | Me | H | H | H | Et | Ph(2-F) | |
| 7-69 | Me | Me | H | H | H | Et | Ph(2,6-F$_2$) | |
| 7-70 | Me | Me | H | H | H | Et | Ph(2-Cl) | |
| 7-71 | Me | Me | H | H | H | Et | Ph(2-Me) | |
| 7-72 | Me | Me | H | H | H | Et | Ph(2-CF$_3$) | |
| 7-73 | Me | Me | H | H | H | Et | Ph(2-F-6-Cl) | |
| 7-74 | Me | Me | H | Me | H | Et | Ph(2-F) | |
| 7-75 | Me | Me | H | Me | H | Et | Ph(2,6-F$_2$) | |
| 7-76 | Me | Me | H | Me | H | Et | Ph(2-Cl) | |
| 7-77 | Me | Me | H | Me | H | Et | Ph(2-Me) | |
| 7-78 | Me | Me | H | Me | H | Et | Ph(2-CF$_3$) | |
| 7-79 | Me | Me | H | Me | H | Et | Ph(2-F-6-Cl) | |
| 7-80 | Me | Me | H | Cl | H | Et | Ph(2-F) | |
| 7-81 | Me | Me | H | Cl | H | Et | Ph(2,6-F$_2$) | |
| 7-82 | Me | Me | H | Cl | H | Et | Ph(2-Cl) | |
| 7-83 | Me | Me | H | Cl | H | Et | Ph(2-Me) | |
| 7-84 | Me | Me | H | Cl | H | Et | Ph(2-CF$_3$) | |
| 7-85 | Me | Me | H | Cl | H | Et | Ph(2-F-6-Cl) | |
| 7-86 | Me | Me | H | H | Me | Et | Ph(2-F) | |
| 7-87 | Me | Me | H | H | Me | Et | Ph(2,6-F$_2$) | |
| 7-88 | Me | Me | H | H | Me | Et | Ph(2-Cl) | |
| 7-89 | Me | Me | H | H | Me | Et | Ph(2-Me) | |
| 7-90 | Me | Me | H | H | Me | Et | Ph(2-CF$_3$) | |
| 7-91 | Me | Me | H | H | Me | Et | Ph(2-F-6-Cl) | |
| 7-92 | Me | Me | H | H | Cl | Et | Ph(2-F) | |
| 7-93 | Me | Me | H | H | Cl | Et | Ph(2,6-F$_2$) | |
| 7-94 | Me | Me | H | H | Cl | Et | Ph(2-Cl) | |
| 7-95 | Me | Me | H | H | Cl | Et | Ph(2-Me) | |
| 7-96 | Me | Me | H | H | Cl | Et | Ph(2-CF$_3$) | |
| 7-97 | Me | Me | H | H | Cl | Et | Ph(2-F-6-Cl) | |
| 7-98 | Me | Me | H | H | H | Ph | Ph(2-F) | |
| 7-99 | Me | Me | H | H | H | Ph | Ph(2,6-F$_2$) | |
| 7-100 | Me | Me | H | H | H | Ph | Ph(2-Cl) | |
| 7-101 | Me | Me | H | H | H | Ph | Ph(2-Me) | |
| 7-102 | Me | Me | H | H | H | Ph | Ph(2-CF$_3$) | |
| 7-103 | Me | Me | H | H | H | Ph | Ph(2-F-6-Cl) | |
| 7-104 | Me | Me | H | Me | H | Ph | Ph(2-F) | |
| 7-105 | Me | Me | H | Me | H | Ph | Ph(2,6-F$_2$) | |
| 7-106 | Me | Me | H | Me | H | Ph | Ph(2-Cl) | |

TABLE 7-continued

| Compound No. | R₁ | R₂ | R₃ | X₁ | X₂ | X₃ | B | Physical properties (mp ° C.) |
|---|---|---|---|---|---|---|---|---|
| 7-107 | Me | Me | H | Me | H | Ph | Ph(2-Me) | |
| 7-108 | Me | Me | H | Me | H | Ph | Ph(2-CF₃) | |
| 7-109 | Me | Me | H | Me | H | Ph | Ph(2-F-6-Cl) | |
| 7-110 | Me | Me | H | Cl | H | Ph | Ph(2-F) | |
| 7-111 | Me | Me | H | Cl | H | Ph | Ph(2,6-F₂) | |
| 7-112 | Me | Me | H | Cl | H | Ph | Ph(2-Cl) | |
| 7-113 | Me | Me | H | Cl | H | Ph | Ph(2-Me) | |
| 7-114 | Me | Me | H | Cl | H | Ph | Ph(2-CF₃) | |
| 7-115 | Me | Me | H | Cl | H | Ph | Ph(2-F-6-Cl) | |
| 7-116 | Me | Me | H | H | Me | Ph | Ph(2-F) | |
| 7-117 | Me | Me | H | H | Me | Ph | Ph(2,6-F₂) | |
| 7-118 | Me | Me | H | H | Me | Ph | Ph(2-Cl) | |
| 7-119 | Me | Me | H | H | Me | Ph | Ph(2-Me) | |
| 7-120 | Me | Me | H | H | Me | Ph | Ph(2-CF₃) | |
| 7-121 | Me | Me | H | H | Me | Ph | Ph(2-F-6-Cl) | |
| 7-122 | Me | Me | H | H | Cl | Ph | Ph(2-F) | |
| 7-123 | Me | Me | H | H | Cl | Ph | Ph(2,6-F₂) | |
| 7-124 | Me | Me | H | H | Cl | Ph | Ph(2-Cl) | |
| 7-125 | Me | Me | H | H | Cl | Ph | Ph(2-Me) | |
| 7-126 | Me | Me | H | H | Cl | Ph | Ph(2-CF₃) | |
| 7-127 | Me | Me | H | H | Cl | Ph | Ph(2-F-6-Cl) | |
| 7-128 | Me | Me | H | H | H | Ph(4-Cl) | Ph(2-F) | |
| 7-129 | Me | Me | H | H | H | Ph(4-Cl) | Ph(2,6-F₂) | |
| 7-130 | Me | Me | H | H | H | Ph(4-Cl) | Ph(2-Cl) | |
| 7-131 | Me | Me | H | H | H | Ph(4-Cl) | Ph(2-Me) | |
| 7-132 | Me | Me | H | H | H | Ph(4-Cl) | Ph(2-CF₃) | |
| 7-133 | Me | Me | H | H | H | Ph(4-Cl) | Ph(2-F-6-Cl) | |
| 7-134 | Me | Me | H | Me | H | Ph(4-Cl) | Ph(2-F) | |
| 7-135 | Me | Me | H | Me | H | Ph(4-Cl) | Ph(2,6-F₂) | |
| 7-136 | Me | Me | H | Me | H | Ph(4-Cl) | Ph(2-Cl) | |
| 7-137 | Me | Me | H | Me | H | Ph(4-Cl) | Ph(2-Me) | |
| 7-138 | Me | Me | H | Me | H | Ph(4-Cl) | Ph(2-CF₃) | |
| 7-139 | Me | Me | H | Me | H | Ph(4-Cl) | Ph(2-F-6-Cl) | |
| 7-140 | Me | Me | H | Cl | H | Ph(4-Cl) | Ph(2-F) | |
| 7-141 | Me | Me | H | Cl | H | Ph(4-Cl) | Ph(2,6-F₂) | |
| 7-142 | Me | Me | H | Cl | H | Ph(4-Cl) | Ph(2-Cl) | |
| 7-143 | Me | Me | H | Cl | H | Ph(4-Cl) | Ph(2-Me) | |
| 7-144 | Me | Me | H | Cl | H | Ph(4-Cl) | Ph(2-CF₃) | |
| 7-145 | Me | Me | H | Cl | H | Ph(4-Cl) | Ph(2-F-6-Cl) | |
| 7-146 | Me | Me | H | H | Me | Ph(4-Cl) | Ph(2-F) | |
| 7-147 | Me | Me | H | H | Me | Ph(4-Cl) | Ph(2,6-F₂) | |
| 7-148 | Me | Me | H | H | Me | Ph(4-Cl) | Ph(2-Cl) | |
| 7-149 | Me | Me | H | H | Me | Ph(4-Cl) | Ph(2-Me) | |
| 7-150 | Me | Me | H | H | Me | Ph(4-Cl) | Ph(2-CF₃) | |
| 7-151 | Me | Me | H | H | Me | Ph(4-Cl) | Ph(2-F-6-Cl) | |
| 7-152 | Me | Me | H | H | Cl | Ph(4-Cl) | Ph(2-F) | |
| 7-153 | Me | Me | H | H | Cl | Ph(4-Cl) | Ph(2,6-F₂) | |
| 7-154 | Me | Me | H | H | Cl | Ph(4-Cl) | Ph(2-Cl) | |
| 7-155 | Me | Me | H | H | Cl | Ph(4-Cl) | Ph(2-Me) | |
| 7-156 | Me | Me | H | H | Cl | Ph(4-Cl) | Ph(2-CF₃) | |
| 7-157 | Me | Me | H | H | Cl | Ph(4-Cl) | Ph(2-F-6-Cl) | |
| 7-158 | Me | Me | H | H | H | Ph(4-CF₃) | Ph(2-F) | |
| 7-159 | Me | Me | H | H | H | Ph(4-CF₃) | Ph(2,6-F₂) | |
| 7-160 | Me | Me | H | H | H | Ph(4-CF₃) | Ph(2-Cl) | |
| 7-161 | Me | Me | H | H | H | Ph(4-CF₃) | Ph(2-Me) | |
| 7-162 | Me | Me | H | H | H | Ph(4-CF₃) | Ph(2-CF₃) | |
| 7-163 | Me | Me | H | H | H | Ph(4-CF₃) | Ph(2-F-6-Cl) | |
| 7-164 | Me | Me | H | Me | H | Ph(4-CF₃) | Ph(2-F) | |
| 7-165 | Me | Me | H | Me | H | Ph(4-CF₃) | Ph(2,6-F₂) | |
| 7-166 | Me | Me | H | Me | H | Ph(4-CF₃) | Ph(2-Cl) | |
| 7-167 | Me | Me | H | Me | H | Ph(4-CF₃) | Ph(2-Me) | |
| 7-168 | Me | Me | H | Me | H | Ph(4-CF₃) | Ph(2-CF₃) | |
| 7-169 | Me | Me | H | Me | H | Ph(4-CF₃) | Ph(2-F-6-Cl) | |
| 7-170 | Me | Me | H | Cl | H | Ph(4-CF₃) | Ph(2-F) | |
| 7-171 | Me | Me | H | Cl | H | Ph(4-CF₃) | Ph(2,6-F₂) | |
| 7-172 | Me | Me | H | Cl | H | Ph(4-CF₃) | Ph(2-Cl) | |
| 7-173 | Me | Me | H | Cl | H | Ph(4-CF₃) | Ph(2-Me) | |

TABLE 7-continued

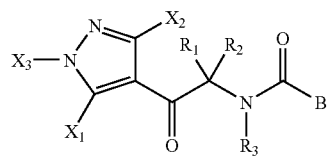

| Compound No. | R₁ | R₂ | R₃ | X₁ | X₂ | X₃ | B | Physical properties (mp ° C.) |
|---|---|---|---|---|---|---|---|---|
| 7-174 | Me | Me | H | Cl | H | Ph(4-CF₃) | Ph(2-CF₃) | |
| 7-175 | Me | Me | H | Cl | H | Ph(4-CF₃) | Ph(2-F-6-Cl) | |
| 7-176 | Me | Me | H | H | Me | Ph(4-CF₃) | Ph(2-F) | |
| 7-177 | Me | Me | H | H | Me | Ph(4-CF₃) | Ph(2,6-F₂) | |
| 7-178 | Me | Me | H | H | Me | Ph(4-CF₃) | Ph(2-Cl) | |
| 7-179 | Me | Me | H | H | Me | Ph(4-CF₃) | Ph(2-Me) | |
| 7-180 | Me | Me | H | H | Me | Ph(4-CF₃) | Ph(2-CF₃) | |
| 7-181 | Me | Me | H | H | Me | Ph(4-CF₃) | Ph(2-F-6-Cl) | |
| 7-182 | Me | Me | H | H | Cl | Ph(4-CF₃) | Ph(2-F) | |
| 7-183 | Me | Me | H | H | Cl | Ph(4-CF₃) | Ph(2,6-F₂) | |
| 7-184 | Me | Me | H | H | Cl | Ph(4-CF₃) | Ph(2-Cl) | |
| 7-185 | Me | Me | H | H | Cl | Ph(4-CF₃) | Ph(2-Me) | |
| 7-186 | Me | Me | H | H | Cl | Ph(4-CF₃) | Ph(2-CF₃) | |
| 7-187 | Me | Me | H | H | Cl | Ph(4-CF₃) | Ph(2-F-6-Cl) | |

TABLE 8

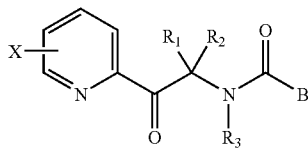

| Compound No. | R₁ | R₂ | R₃ | X | B | Physical properties (mp ° C.) |
|---|---|---|---|---|---|---|
| 8-1 | Me | Me | H | H | Ph | |
| 8-2 | Me | Me | H | H | Ph(2-F) | 44-45 |
| 8-3 | Me | Me | H | H | Ph(2-Cl) | |
| 8-4 | Me | Me | H | H | Ph(2-OMe) | |
| 8-5 | Me | Me | H | H | Ph(2,6-F₂) | 112-114 |
| 8-6 | Me | Me | H | H | Ph(2,6-Cl₂) | |
| 8-7 | Me | Me | H | H | Ph(2,6-OMe₂) | |
| 8-8 | Me | Me | H | 6-Cl | Ph | |
| 8-9 | Me | Me | H | 6-Cl | Ph(2-F) | |
| 8-10 | Me | Me | H | 6-Cl | Ph(2-Cl) | |
| 8-11 | Me | Me | H | 6-Cl | Ph(2,6-F₂) | |
| 8-12 | Me | Me | H | 6-Cl | Ph(2,6-Cl₂) | |
| 8-13 | Me | Me | H | 6-Br | Ph | |
| 8-14 | Me | Me | H | 6-Br | Ph(2-F) | |
| 8-15 | Me | Me | H | 6-Br | Ph(2-Cl) | |
| 8-16 | Me | Me | H | 6-Br | Ph(2,6-F₂) | |
| 8-17 | Me | Me | H | 6-Br | Ph(2,6-Cl₂) | |
| 8-18 | Me | Me | H | 6-CF₃ | Ph(2,6-F₂) | |
| 8-19 | Me | Me | H | 6-CN | Ph(2,6-F₂) | |
| 8-20 | Me | CN | H | H | Ph(2,6-F₂) | |
| 8-21 | Me | CO₂Et | H | H | Ph(2,6-F₂) | |
| 8-22 | Me | CN | H | 6-Cl | Ph(2,6-F₂) | |
| 8-23 | Me | CO₂Et | H | 6-Cl | Ph(2,6-F₂) | |
| 8-24 | Me | Et | H | H | Ph(2,6-F₂) | |
| 8-25 | Me | Me | COMe | H | Ph(2,6-F₂) | |
| 8-26 | Me | Me | CH₂OMe | H | Ph(2,6-F₂) | |
| 8-27 | Me | Me | H | H | 1-naphthyl | |
| 8-28 | Me | Me | H | H | 2-naphthyl | |
| 8-29 | Me | Me | H | H | 2-thienyl | |
| 8-30 | Me | Me | H | H | 3-thienyl | |
| 8-31 | Me | Me | H | H | 2-pyrazinyl | |
| 8-32 | Me | Me | H | H | 2-pyridyl | |
| 8-33 | Me | Me | H | H | 3-pyridyl | |
| 8-34 | Me | Me | H | H | 4-trifluoro methyl-3-pyridyl | |
| 8-35 | Me | Me | H | H | 4-pyridyl | |
| 8-36 | Me | Me | H | H | 2-furyl | |

TABLE 8-continued

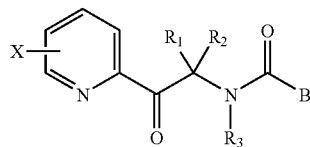

| Compound No. | R₁ | R₂ | R₃ | X | B | Physical properties (mp ° C.) |
|---|---|---|---|---|---|---|
| 8-37 | Me | Me | H | H | 3-furyl | |
| 8-38 | Me | Me | H | 5-Cl | Ph(2-F) | |
| 8-39 | Me | Me | H | 5-Cl | Ph(2,6-F₂) | |
| 8-40 | Me | Me | H | 5-Br | Ph(2-F) | |
| 8-41 | Me | Me | H | 5-Br | Ph(2,6-F₂) | |
| 8-42 | Me | Me | H | 5-CF₃ | Ph(2-F) | |
| 8-43 | Me | Me | H | 5-CF₃ | Ph(2,6-F₂) | 116-119 |
| 8-44 | Me | Me | H | 5-OSO₂CF₃ | Ph(2-F) | |
| 8-45 | Me | Me | H | 5-OSO₂CF₃ | Ph(2,6-F₂) | |
| 8-46 | Me | Me | H | 5-OCH₂CF₃ | Ph(2-F) | |
| 8-47 | Me | Me | H | 5-OCH₂CF₃ | Ph(2,6-F₂) | |
| 8-48 | Me | Me | H | 3-Cl | Ph(2-F) | |
| 8-49 | Me | Me | H | 3-Cl | Ph(2,6-F₂) | |
| 8-50 | Me | Me | H | 3-Cl | Ph(2-Cl) | |
| 8-51 | Me | Me | H | 3-Cl | Ph(2-Me) | |
| 8-52 | Me | Me | H | 3-Cl | Ph(2-CF₃) | |
| 8-53 | Me | Me | H | 3-Cl | Ph(2-F-6-Cl) | |
| 8-54 | Me | Me | H | 3-Me | Ph(2-F) | |
| 8-55 | Me | Me | H | 3-Me | Ph(2,6-F₂) | |
| 8-56 | Me | Me | H | 3-Me | Ph(2-Cl) | |
| 8-57 | Me | Me | H | 3-Me | Ph(2-Me) | |
| 8-58 | Me | Me | H | 3-Me | Ph(2-CF₃) | |
| 8-59 | Me | Me | H | 3-Me | Ph(2-F-6-Cl) | |
| 8-60 | Me | Me | H | 5-Me | Ph(2-F) | |
| 8-61 | Me | Me | H | 5-Me | Ph(2,6-F₂) | |
| 8-62 | Me | Me | H | 5-Me | Ph(2-Cl) | |
| 8-63 | Me | Me | H | 5-Me | Ph(2-Me) | |
| 8-64 | Me | Me | H | 5-Me | Ph(2-CF₃) | |
| 8-65 | Me | Me | H | 5-Me | Ph(2-F-6-Cl) | |
| 8-66 | Me | Me | H | 6-Me | Ph(2-F) | |
| 8-67 | Me | Me | H | 6-Me | Ph(2,6-F₂) | |
| 8-68 | Me | Me | H | 6-Me | Ph(2-Cl) | |
| 8-69 | Me | Me | H | 6-Me | Ph(2-Me) | |
| 8-70 | Me | Me | H | 6-Me | Ph(2-CF₃) | |
| 8-71 | Me | Me | H | 6-Me | Ph(2-F-6-Cl) | |
| 8-72 | Me | Me | H | 5-OCF₃ | Ph(2-F) | |
| 8-73 | Me | Me | H | 5-OCF₃ | Ph(2,6-F₂) | |
| 8-74 | Me | Me | H | 5-OCF₃ | Ph(2-Cl) | |
| 8-75 | Me | Me | H | 5-OCF₃ | Ph(2-Me) | |
| 8-76 | Me | Me | H | 5-OCF₃ | Ph(2-CF₃) | |
| 8-77 | Me | Me | H | 5-OCF₃ | Ph(2-F-6-Cl) | |
| 8-78 | Me | Me | H | 6-OCF₃ | Ph(2-F) | |
| 8-79 | Me | Me | H | 6-OCF₃ | Ph(2,6-F₂) | |
| 8-80 | Me | Me | H | 6-OCF₃ | Ph(2-Cl) | |
| 8-81 | Me | Me | H | 6-OCF₃ | Ph(2-Me) | |
| 8-82 | Me | Me | H | 6-OCF₃ | Ph(2-CF₃) | |
| 8-83 | Me | Me | H | 6-OCF₃ | Ph(2-F-6-Cl) | |
| 8-84 | Me | Me | H | 5-OCHF₂ | Ph(2-F) | |
| 8-85 | Me | Me | H | 5-OCHF₂ | Ph(2,6-F₂) | |
| 8-86 | Me | Me | H | 5-OCHF₂ | Ph(2-Cl) | |
| 8-87 | Me | Me | H | 5-OCHF₂ | Ph(2-Me) | |
| 8-88 | Me | Me | H | 5-OCHF₂ | Ph(2-CF₃) | |
| 8-89 | Me | Me | H | 5-OCHF₂ | Ph(2-F-6-Cl) | |
| 8-90 | Me | Me | H | 6-OCHF₂ | Ph(2-F) | |
| 8-91 | Me | Me | H | 6-OCHF₂ | Ph(2,6-F₂) | |
| 8-92 | Me | Me | H | 6-OCHF₂ | Ph(2-Cl) | |
| 8-93 | Me | Me | H | 6-OCHF₂ | Ph(2-Me) | |
| 8-94 | Me | Me | H | 6-OCHF₂ | Ph(2-CF₃) | |
| 8-95 | Me | Me | H | 6-OCHF₂ | Ph(2-F-6-Cl) | |
| 8-96 | Me | Me | H | 3,5-Cl₂ | Ph(2-F) | |
| 8-97 | Me | Me | H | 3,5-Cl₂ | Ph(2,6-F₂) | |
| 8-98 | Me | Me | H | 3,5-Cl₂ | Ph(2-Cl) | |
| 8-99 | Me | Me | H | 3,5-Cl₂ | Ph(2-Me) | |
| 8-100 | Me | Me | H | 3,5-Cl₂ | Ph(2-CF₃) | |
| 8-101 | Me | Me | H | 3,5-Cl₂ | Ph(2-F-6-Cl) | |
| 8-102 | Me | Me | H | 4,5-Cl₂ | Ph(2-F) | |
| 8-103 | Me | Me | H | 4,5-Cl₂ | Ph(2,6-F₂) | |
| 8-104 | Me | Me | H | 4,5-Cl₂ | Ph(2-Cl) | |
| 8-105 | Me | Me | H | 4,5-Cl₂ | Ph(2-Me) | |

TABLE 8-continued

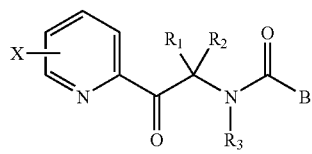

| Compound No. | $R_1$ | $R_2$ | $R_3$ | X | B | Physical properties (mp ° C.) |
|---|---|---|---|---|---|---|
| 8-106 | Me | Me | H | 4,5-Cl$_2$ | Ph(2-CF$_3$) | |
| 8-107 | Me | Me | H | 4,5-Cl$_2$ | Ph(2-F-6-Cl) | |
| 8-108 | Me | Me | H | 3-Cl-5-Br | Ph(2-F) | |
| 8-109 | Me | Me | H | 3-Cl-5-Br | Ph(2,6-F$_2$) | |
| 8-110 | Me | Me | H | 3-Cl-5-Br | Ph(2-Cl) | |
| 8-111 | Me | Me | H | 3-Cl-5-Br | Ph(2-Me) | |
| 8-112 | Me | Me | H | 3-Cl-5-Br | Ph(2-CF$_3$) | |
| 8-113 | Me | Me | H | 3-Cl-5-Br | Ph(2-F-6-Cl) | |
| 8-114 | Me | Me | H | 4-Cl-5-Br | Ph(2-F) | |
| 8-115 | Me | Me | H | 4-Cl-5-Br | Ph(2,6-F$_2$) | |
| 8-116 | Me | Me | H | 4-Cl-5-Br | Ph(2-Cl) | |
| 8-117 | Me | Me | H | 4-Cl-5-Br | Ph(2-Me) | |
| 8-118 | Me | Me | H | 4-Cl-5-Br | Ph(2-CF$_3$) | |
| 8-119 | Me | Me | H | 4-Cl-5-Br | Ph(2-F-6-Cl) | |
| 8-120 | Me | Me | H | 3-Cl-5-CF$_3$ | Ph(2-F) | |
| 8-121 | Me | Me | H | 3-Cl-5-CF$_3$ | Ph(2,6-F$_2$) | 159-162 |
| 8-122 | Me | Me | H | 3-Cl-5-CF$_3$ | Ph(2-Cl) | |
| 8-123 | Me | Me | H | 3-Cl-5-CF$_3$ | Ph(2-Me) | |
| 8-124 | Me | Me | H | 3-Cl-5-CF$_3$ | Ph(2-CF$_3$) | |
| 8-125 | Me | Me | H | 3-Cl-5-CF$_3$ | Ph(2-F-6-Cl) | |
| 8-126 | Me | Me | H | 4-Cl-5-CF$_3$ | Ph(2-F) | |
| 8-127 | Me | Me | H | 4-Cl-5-CF$_3$ | Ph(2,6-F$_2$) | |
| 8-128 | Me | Me | H | 4-Cl-5-CF$_3$ | Ph(2-Cl) | |
| 8-129 | Me | Me | H | 4-Cl-5-CF$_3$ | Ph(2-Me) | |
| 8-130 | Me | Me | H | 4-Cl-5-CF$_3$ | Ph(2-CF$_3$) | |
| 8-131 | Me | Me | H | 4-Cl-5-CF$_3$ | Ph(2-F-6-Cl) | |
| 8-132 | Me | Me | H | 3-Cl-5-OCF$_3$ | Ph(2-F) | |
| 8-133 | Me | Me | H | 3-Cl-5-OCF$_3$ | Ph(2,6-F$_2$) | |
| 8-134 | Me | Me | H | 3-Cl-5-OCF$_3$ | Ph(2-Cl) | |
| 8-135 | Me | Me | H | 3-Cl-5-OCF$_3$ | Ph(2-Me) | |
| 8-136 | Me | Me | H | 3-Cl-5-OCF$_3$ | Ph(2-CF$_3$) | |
| 8-137 | Me | Me | H | 3-Cl-5-OCF$_3$ | Ph(2-F-6-Cl) | |
| 8-138 | Me | Me | H | 4-Cl-5-OCF$_3$ | Ph(2-F) | |
| 8-139 | Me | Me | H | 4-Cl-5-OCF$_3$ | Ph(2,6-F$_2$) | |
| 8-140 | Me | Me | H | 4-Cl-5-OCF$_3$ | Ph(2-Cl) | |
| 8-141 | Me | Me | H | 4-Cl-5-OCF$_3$ | Ph(2-Me) | |
| 8-142 | Me | Me | H | 4-Cl-5-OCF$_3$ | Ph(2-CF$_3$) | |
| 8-143 | Me | Me | H | 4-Cl-5-OCF$_3$ | Ph(2-F-6-Cl) | |
| 8-144 | Me | Me | H | 3-Cl-5-OCHF$_2$ | Ph(2-F) | |
| 8-145 | Me | Me | H | 3-Cl-5-OCHF$_2$ | Ph(2,6-F$_2$) | |
| 8-146 | Me | Me | H | 3-Cl-5-OCHF$_2$ | Ph(2-Cl) | |
| 8-147 | Me | Me | H | 3-Cl-5-OCHF$_2$ | Ph(2-Me) | |
| 8-148 | Me | Me | H | 3-Cl-5-OCHF$_2$ | Ph(2-CF$_3$) | |
| 8-149 | Me | Me | H | 3-Cl-5-OCHF$_2$ | Ph(2-F-6-Cl) | |
| 8-150 | Me | Me | H | 4-Cl-5-OCHF$_2$ | Ph(2-F) | |
| 8-151 | Me | Me | H | 4-Cl-5-OCHF$_2$ | Ph(2,6-F$_2$) | |
| 8-152 | Me | Me | H | 4-Cl-5-OCHF$_2$ | Ph(2-Cl) | |
| 8-153 | Me | Me | H | 4-Cl-5-OCHF$_2$ | Ph(2-Me) | |
| 8-154 | Me | Me | H | 4-Cl-5-OCHF$_2$ | Ph(2-CF$_3$) | |
| 8-155 | Me | Me | H | 4-Cl-5-OCHF$_2$ | Ph(2-F-6-Cl) | |
| 8-156 | Me | Me | H | 3-Cl-5-OCH$_2$CF$_3$ | Ph(2-F) | |
| 8-157 | Me | Me | H | 3-Cl-5-OCH$_2$CF$_3$ | Ph(2,6-F$_2$) | |
| 8-158 | Me | Me | H | 3-Cl-5-OCH$_2$CF$_3$ | Ph(2-Cl) | |
| 8-159 | Me | Me | H | 3-Cl-5-OCH$_2$CF$_3$ | Ph(2-Me) | |
| 8-160 | Me | Me | H | 3-Cl-5-OCH$_2$CF$_3$ | Ph(2-CF$_3$) | |
| 8-161 | Me | Me | H | 3-Cl-5-OCH$_2$CF$_3$ | Ph(2-F-6-Cl) | |
| 8-162 | Me | Me | H | 4-Cl-5-OCH$_2$CF$_3$ | Ph(2-F) | |
| 8-163 | Me | Me | H | 4-Cl-5-OCH$_2$CF$_3$ | Ph(2,6-F$_2$) | |
| 8-164 | Me | Me | H | 4-Cl-5-OCH$_2$CF$_3$ | Ph(2-Cl) | |
| 8-165 | Me | Me | H | 4-Cl-5-OCH$_2$CF$_3$ | Ph(2-Me) | |
| 8-166 | Me | Me | H | 4-Cl-5-OCH$_2$CF$_3$ | Ph(2-CF$_3$) | |
| 8-167 | Me | Me | H | 4-Cl-5-OCH$_2$CF$_3$ | Ph(2-F-6-Cl) | |
| 8-168 | Me | Me | H | 3-Me-5-Cl | Ph(2-F) | |
| 8-169 | Me | Me | H | 3-Me-5-Cl | Ph(2,6-F$_2$) | |
| 8-170 | Me | Me | H | 3-Me-5-Cl | Ph(2-Cl) | |
| 8-171 | Me | Me | H | 3-Me-5-Cl | Ph(2-Me) | |
| 8-172 | Me | Me | H | 3-Me-5-Cl | Ph(2-CF$_3$) | |
| 8-173 | Me | Me | H | 3-Me-5-Cl | Ph(2-F-6-Cl) | |
| 8-174 | Me | Me | H | 4-Me-5-Cl | Ph(2-F) | |

TABLE 8-continued

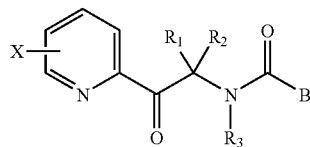

| Compound No. | R₁ | R₂ | R₃ | X | B | Physical properties (mp ° C.) |
|---|---|---|---|---|---|---|
| 8-175 | Me | Me | H | 4-Me-5-Cl | Ph(2,6-F₂) | |
| 8-176 | Me | Me | H | 4-Me-5-Cl | Ph(2-Cl) | |
| 8-177 | Me | Me | H | 4-Me-5-Cl | Ph(2-Me) | |
| 8-173 | Me | Me | H | 4-Me-5-Cl | Ph(2-CF₃) | |
| 8-179 | Me | Me | H | 4-Me-5-Cl | Ph(2-F-6-Cl) | |
| 8-180 | Me | Me | H | 3-Me-5-Br | Ph(2-F) | |
| 8-181 | Me | Me | H | 3-Me-5-Br | Ph(2,6-F₂) | |
| 8-182 | Me | Me | H | 3-Me-5-Br | Ph(2-Cl) | |
| 8-183 | Me | Me | H | 3-Me-5-Br | Ph(2-Me) | |
| 8-184 | Me | Me | H | 3-Me-5-Br | Ph(2-CF₃) | |
| 8-185 | Me | Me | H | 3-Me-5-Br | Ph(2-F-6-Cl) | |
| 8-186 | Me | Me | H | 4-Me-5-Br | Ph(2-F) | |
| 8-187 | Me | Me | H | 4-Me-5-Br | Ph(2,6-F₂) | |
| 8-188 | Me | Me | H | 4-Me-5-Br | Ph(2-Cl) | |
| 8-189 | Me | Me | H | 4-Me-5-Br | Ph(2-Me) | |
| 8-190 | Me | Me | H | 4-Me-5-Br | Ph(2-CF₃) | |
| 8-191 | Me | Me | H | 4-Me-5-Br | Ph(2-F-6-Cl) | |
| 8-192 | Me | Me | H | 3-Me-5-CF₃ | Ph(2-F) | |
| 8-193 | Me | Me | H | 3-Me-5-CF₃ | Ph(2,6-F₂) | |
| 8-194 | Me | Me | H | 3-Me-5-CF₃ | Ph(2-Cl) | |
| 8-195 | Me | Me | H | 3-Me-5-CF₃ | Ph(2-Me) | |
| 8-196 | Me | Me | H | 3-Me-5-CF₃ | Ph(2-CF₃) | |
| 8-197 | Me | Me | H | 3-Me-5-CF₃ | Ph(2-F-6-Cl) | |
| 8-198 | Me | Me | H | 4-Me-5-CF₃ | Ph(2-F) | |
| 8-199 | Me | Me | H | 4-Me-5-CF₃ | Ph(2,6-F₂) | |
| 8-200 | Me | Me | H | 4-Me-5-CF₃ | Ph(2-Cl) | |
| 8-201 | Me | Me | H | 4-Me-5-CF₃ | Ph(2-Me) | |
| 8-202 | Me | Me | H | 4-Me-5-CF₃ | Ph(2-CF₃) | |
| 8-203 | Me | Me | H | 4-Me-5-CF₃ | Ph(2-F-6-Cl) | |
| 8-204 | Me | Me | H | 3-Me-5-OCF₃ | Ph(2-F) | |
| 8-205 | Me | Me | H | 3-Me-5-OCF₃ | Ph(2,6-F₂) | |
| 8-206 | Me | Me | H | 3-Me-5-OCF₃ | Ph(2-Cl) | |
| 8-207 | Me | Me | H | 3-Me-5-OCF₃ | Ph(2-Me) | |
| 8-208 | Me | Me | H | 3-Me-5-OCF₃ | Ph(2-CF₃) | |
| 8-209 | Me | Me | H | 3-Me-5-OCF₃ | Ph(2-F-6-Cl) | |
| 8-210 | Me | Me | H | 4-Me-5-OCF₃ | Ph(2-F) | |
| 8-211 | Me | Me | H | 4-Me-5-OCF₃ | Ph(2,6-F₂) | |
| 8-212 | Me | Me | H | 4-Me-5-OCF₃ | Ph(2-Cl) | |
| 8-213 | Me | Me | H | 4-Me-5-OCF₃ | Ph(2-Me) | |
| 8-214 | Me | Me | H | 4-Me-5-OCF₃ | Ph(2-CF₃) | |
| 8-215 | Me | Me | H | 4-Me-5-OCF₃ | Ph(2-F-6-Cl) | |
| 8-216 | Me | Me | H | 3-Me-5-OCHF₂ | Ph(2-F) | |
| 8-217 | Me | Me | H | 3-Me-5-OCHF₂ | Ph(2,6-F₂) | |
| 8-218 | Me | Me | H | 3-Me-5-OCHF₂ | Ph(2-Cl) | |
| 8-219 | Me | Me | H | 3-Me-5-OCHF₂ | Ph(2-Me) | |
| 8-220 | Me | Me | H | 3-Me-5-OCHF₂ | Ph(2-CF₃) | |
| 8-221 | Me | Me | H | 3-Me-5-OCHF₂ | Ph(2-F-6-Cl) | |
| 8-222 | Me | Me | H | 4-Me-5-OCHF₂ | Ph(2-F) | |
| 8-223 | Me | Me | H | 4-Me-5-OCHF₂ | Ph(2,6-F₂) | |
| 8-224 | Me | Me | H | 4-Me-5-OCHF₂ | Ph(2-Cl) | |
| 8-225 | Me | Me | H | 4-Me-5-OCHF₂ | Ph(2-Me) | |
| 8-226 | Me | Me | H | 4-Me-5-OCHF₂ | Ph(2-CF₃) | |
| 8-227 | Me | Me | H | 4-Me-5-OCHF₂ | Ph(2-F-6-Cl) | |
| 8-228 | Me | Me | H | 3-Me-5-OCH₂CF₃ | Ph(2-F) | |
| 8-229 | Me | Me | H | 3-Me-5-OCH₂CF₃ | Ph(2,6-F₂) | |
| 8-230 | Me | Me | H | 3-Me-5-OCH₂CF₃ | Ph(2-Cl) | |
| 8-231 | Me | Me | H | 3-Me-5-OCH₂CF₃ | Ph(2-Me) | |
| 8-232 | Me | Me | H | 3-Me-5-OCH₂CF₃ | Ph(2-CF₃) | |
| 8-233 | Me | Me | H | 3-Me-5-OCH₂CF₃ | Ph(2-F-6-Cl) | |
| 8-234 | Me | Me | H | 4-Me-5-OCH₂CF₃ | Ph(2-F) | |
| 8-235 | Me | Me | H | 4-Me-5-OCH₂CF₃ | Ph(2,6-F₂) | |
| 8-236 | Me | Me | H | 4-Me-5-OCH₂CF₃ | Ph(2-Cl) | |
| 8-237 | Me | Me | H | 4-Me-5-OCH₂CF₃ | Ph(2-Me) | |
| 8-238 | Me | Me | H | 4-Me-5-OCH₂CF₃ | Ph(2-CF₃) | |
| 8-239 | Me | Me | H | 4-Me-5-OCH₂CF₃ | Ph(2-F-6-Cl) | |

TABLE 9

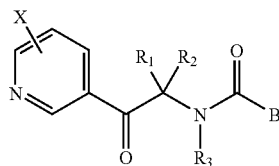

| Compound No. | R$_1$ | R$_2$ | R$_3$ | X | B | Physical properties (mp ° C.) |
|---|---|---|---|---|---|---|
| 9-1 | Me | Me | H | H | Ph | |
| 9-2 | Me | Me | H | H | Ph(2-F) | |
| 9-3 | Me | Me | H | H | Ph(2-Cl) | |
| 9-4 | Me | Me | H | H | Ph(2-OMe) | |
| 9-5 | Me | Me | H | H | Ph(2,6-F$_2$) | 223-226 |
| 9-6 | Me | Me | H | H | Ph(2,6-Cl$_2$) | |
| 9-7 | Me | Me | H | H | Ph(2,6-OMe$_2$) | |
| 9-8 | Me | Me | H | 6-Cl | Ph | |
| 9-9 | Me | Me | H | 6-Cl | Ph(2-F) | |
| 9-10 | Me | Me | H | 6-Cl | Ph(2-Cl) | |
| 9-11 | Me | Me | H | 6-Cl | Ph(2,6-F$_2$) | |
| 9-12 | Me | Me | H | 6-Cl | Ph(2,6-Cl$_2$) | |
| 9-13 | Me | Me | H | 6-Br | Ph | |
| 9-14 | Me | Me | H | 6-Br | Ph(2-F) | |
| 9-15 | Me | Me | H | 6-Br | Ph(2-Cl) | |
| 9-16 | Me | Me | H | 6-Br | Ph(2,6-F$_2$) | |
| 9-17 | Me | Me | H | 6-Br | Ph(2,6-Cl$_2$) | |
| 9-18 | Me | Me | H | 6-CF$_3$ | Ph(2,6-F$_2$) | |
| 9-19 | Me | Me | H | 6-CN | Ph(2,6-F$_2$) | |
| 9-20 | Me | CN | H | H | Ph(2,6-F$_2$) | |
| 9-21 | Me | CO$_2$Et | H | H | Ph(2,6-F$_2$) | |
| 9-22 | Me | CN | H | 6-Cl | Ph(2,6-F$_2$) | |
| 9-23 | Me | CO$_2$Et | H | 6-Cl | Ph(2,6-F$_2$) | |
| 9-24 | Me | Et | H | H | Ph(2,6-F$_2$) | |
| 9-25 | Me | Me | COMe | H | Ph(2,6-F$_2$) | |
| 9-26 | Me | Me | CH$_2$OMe | H | Ph(2,6-F$_2$) | |
| 9-27 | Me | Me | H | H | 1-naphthyl | |
| 9-28 | Me | Me | H | H | 2-naphthyl | |
| 9-29 | Me | Me | H | H | 2-thienyl | |
| 9-30 | Me | Me | H | H | 3-thienyl | |
| 9-31 | Me | Me | H | H | 2-pyrazinyl | |
| 9-32 | Me | Me | H | H | 2-pyridyl | |
| 9-33 | Me | Me | H | H | 3-pyridyl | |
| 9-34 | Me | Me | H | H | 4-trifluoromethyl-3-pyridyl | |
| 9-35 | Me | Me | H | H | 4-pyridyl | |
| 9-36 | Me | Me | H | H | 2-furyl | |
| 9-37 | Me | Me | H | H | 3-furyl | |
| 9-38 | Me | Me | H | 6-OSO$_2$CF$_3$ | Ph(2-F) | |
| 9-39 | Me | Me | H | 6-OSO$_2$CF$_3$ | Ph(2,6-F$_2$) | |
| 9-40 | Me | Me | H | 6-OCH$_2$CF$_3$ | Ph(2-F) | |
| 9-41 | Me | Me | H | 6-OCH$_2$CF$_3$ | Ph(2,6-F$_2$) | |
| 9-42 | Me | Me | H | 2-Cl | Ph(2-F) | |
| 9-43 | Me | Me | H | 2-Cl | Ph(2,6-F$_2$) | |
| 9-44 | Me | Me | H | 2-Cl | Ph(2-Cl) | |
| 9-45 | Me | Me | H | 2-Cl | Ph(2-Me) | |
| 9-46 | Me | Me | H | 2-Cl | Ph(2-CF$_3$) | |
| 9-47 | Me | Me | H | 2-Cl | Ph(2-F-6-Cl) | |
| 9-48 | Me | Me | H | 4-Cl | Ph(2-F) | |
| 9-49 | Me | Me | H | 4-Cl | Ph(2,6-F$_2$) | |
| 9-50 | Me | Me | H | 4-Cl | Ph(2-Cl) | |
| 9-51 | Me | Me | H | 4-Cl | Ph(2-Me) | |
| 9-52 | Me | Me | H | 4-Cl | Ph(2-CF$_3$) | |
| 9-53 | Me | Me | H | 4-Cl | Ph(2-F-6-Cl) | |
| 9-54 | Me | Me | H | 5-Cl | Ph(2-F) | |
| 9-55 | Me | Me | H | 5-Cl | Ph(2,6-F$_2$) | |
| 9-56 | Me | Me | H | 5-Cl | Ph(2-Cl) | |
| 9-57 | Me | Me | H | 5-Cl | Ph(2-Me) | |
| 9-58 | Me | Me | H | 5-Cl | Ph(2-CF$_3$) | |
| 9-59 | Me | Me | H | 5-Cl | Ph(2-F-6-Cl) | |
| 9-60 | Me | Me | H | 5-Br | Ph(2-F) | |
| 9-61 | Me | Me | H | 5-Br | Ph(2,6-F$_2$) | |
| 9-62 | Me | Me | H | 5-Br | Ph(2-Cl) | |
| 9-63 | Me | Me | H | 5-Br | Ph(2-Me) | |
| 9-64 | Me | Me | H | 5-Br | Ph(2-CF$_3$) | |
| 9-65 | Me | Me | H | 5-Br | Ph(2-F-6-Cl) | |
| 9-66 | Me | Me | H | 2-Me | Ph(2-F) | |
| 9-67 | Me | Me | H | 2-Me | Ph(2,6-F$_2$) | |

TABLE 9-continued

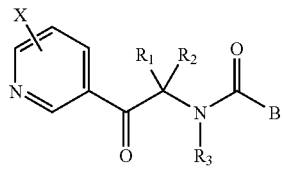

| Compound No. | R₁ | R₂ | R₃ | X | B | Physical properties (mp ° C.) |
|---|---|---|---|---|---|---|
| 9-68 | Me | Me | H | 2-Me | Ph(2-Cl) | |
| 9-69 | Me | Me | H | 2-Me | Ph(2-Me) | |
| 9-70 | Me | Me | H | 2-Me | Ph(2-CF₃) | |
| 9-71 | Me | Me | H | 2-Me | Ph(2-F-6-Cl) | |
| 9-72 | Me | Me | H | 4-Me | Ph(2-F) | |
| 9-73 | Me | Me | H | 4-Me | Ph(2,6-F₂) | |
| 9-74 | Me | Me | H | 4-Me | Ph(2-Cl) | |
| 9-75 | Me | Me | H | 4-Me | Ph(2-Me) | |
| 9-76 | Me | Me | H | 4-Me | Ph(2-CF₃) | |
| 9-77 | Me | Me | H | 4-Me | Ph(2-F-6-Cl) | |
| 9-78 | Me | Me | H | 5-Me | Ph(2-F) | |
| 9-79 | Me | Me | H | 5-Me | Ph(2,6-F₂) | |
| 9-80 | Me | Me | H | 5-Me | Ph(2-Cl) | |
| 9-81 | Me | Me | H | 5-Me | Ph(2-Me) | |
| 9-82 | Me | Me | H | 5-Me | Ph(2-CF₃) | |
| 9-83 | Me | Me | H | 5-Me | Ph(2-F-6-Cl) | |
| 9-84 | Me | Me | H | 6-Me | Ph(2-F) | |
| 9-85 | Me | Me | H | 6-Me | Ph(2,6-F₂) | |
| 9-86 | Me | Me | H | 6-Me | Ph(2-Cl) | |
| 9-87 | Me | Me | H | 6-Me | Ph(2-Me) | |
| 9-88 | Me | Me | H | 6-Me | Ph(2-CF₃) | |
| 9-89 | Me | Me | H | 6-Me | Ph(2-F-6-Cl) | |
| 9-90 | Me | Me | H | 5-CN | Ph(2-F) | |
| 9-91 | Me | Me | H | 5-CN | Ph(2,6-F₂) | |
| 9-92 | Me | Me | H | 5-CN | Ph(2-Cl) | |
| 9-93 | Me | Me | H | 5-CN | Ph(2-Me) | |
| 9-94 | Me | Me | H | 5-CN | Ph(2-CF₃) | |
| 9-95 | Me | Me | H | 5-CN | Ph(2-F-6-Cl) | |
| 9-96 | Me | Me | H | 5-CF₃ | Ph(2-F) | |
| 9-97 | Me | Me | H | 5-CF₃ | Ph(2,6-F₂) | |
| 9-98 | Me | Me | H | 5-CF₃ | Ph(2-Cl) | |
| 9-99 | Me | Me | H | 5-CF₃ | Ph(2-Me) | |
| 9-100 | Me | Me | H | 5-CF₃ | Ph(2-CF₃) | |
| 9-101 | Me | Me | H | 5-CF₃ | Ph(2-F-6-Cl) | |
| 9-102 | Me | Me | H | 5-OCF₃ | Ph(2-F) | |
| 9-103 | Me | Me | H | 5-OCF₃ | Ph(2,6-F₂) | |
| 9-104 | Me | Me | H | 5-OCF₃ | Ph(2-Cl) | |
| 9-105 | Me | Me | H | 5-OCF₃ | Ph(2-Me) | |
| 9-106 | Me | Me | H | 5-OCF₃ | Ph(2-CF₃) | |
| 9-107 | Me | Me | H | 5-OCF₃ | Ph(2-F-6-Cl) | |
| 9-108 | Me | Me | H | 6-OCF₃ | Ph(2-F) | |
| 9-109 | Me | Me | H | 6-OCF₃ | Ph(2,6-F₂) | |
| 9-110 | Me | Me | H | 6-OCF₃ | Ph(2-Cl) | |
| 9-111 | Me | Me | H | 6-OCF₃ | Ph(2-Me) | |
| 9-112 | Me | Me | H | 6-OCF₃ | Ph(2-CF₃) | |
| 9-113 | Me | Me | H | 6-OCF₃ | Ph(2-F-6-Cl) | |
| 9-114 | Me | Me | H | 5-OCHF₂ | Ph(2-F) | |
| 9-115 | Me | Me | H | 5-OCHF₂ | Ph(2,6-F₂) | |
| 9-116 | Me | Me | H | 5-OCHF₂ | Ph(2-Cl) | |
| 9-117 | Me | Me | H | 5-OCHF₂ | Ph(2-Me) | |
| 9-118 | Me | Me | H | 5-OCHF₂ | Ph(2-CF₃) | |
| 9-119 | Me | Me | H | 5-OCHF₂ | Ph(2-F-6-Cl) | |
| 9-120 | Me | Me | H | 6-OCHF₂ | Ph(2-F) | |
| 9-121 | Me | Me | H | 6-OCHF₂ | Ph(2,6-F₂) | |
| 9-122 | Me | Me | H | 6-OCHF₂ | Ph(2-Cl) | |
| 9-123 | Me | Me | H | 6-OCHF₂ | Ph(2-Me) | |
| 9-124 | Me | Me | H | 6-OCHF₂ | Ph(2-CF₃) | |
| 9-125 | Me | Me | H | 6-OCHF₂ | Ph(2-F-6-Cl) | |
| 9-126 | Me | Me | H | 2,6-Cl₂ | Ph(2-F) | |
| 9-127 | Me | Me | H | 2,6-Cl₂ | Ph(2,6-F₂) | |
| 9-128 | Me | Me | H | 2,6-Cl₂ | Ph(2-Cl) | |
| 9-129 | Me | Me | H | 2,6-Cl₂ | Ph(2-Me) | |
| 9-130 | Me | Me | H | 2,6-Cl₂ | Ph(2-CF₃) | |
| 9-131 | Me | Me | H | 2,6-Cl₂ | Ph(2-F-6-Cl) | |
| 9-132 | Me | Me | H | 4,6-Cl₂ | Ph(2-F) | |
| 9-133 | Me | Me | H | 4,6-Cl₂ | Ph(2,6-F₂) | |
| 9-134 | Me | Me | H | 4,6-Cl₂ | Ph(2-Cl) | |

TABLE 9-continued

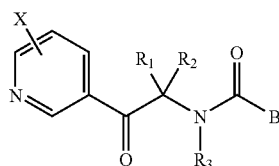

| Compound No. | R₁ | R₂ | R₃ | X | B | Physical properties (mp ° C.) |
|---|---|---|---|---|---|---|
| 9-135 | Me | Me | H | 4,6-Cl₂ | Ph(2-Me) | |
| 9-136 | Me | Me | H | 4,6-Cl₂ | Ph(2-CF₃) | |
| 9-137 | Me | Me | H | 4,6-Cl₂ | Ph(2-F-6-Cl) | |
| 9-138 | Me | Me | H | 5,6-Cl₂ | Ph(2-F) | |
| 9-139 | Me | Me | H | 5,6-Cl₂ | Ph(2,6-F₂) | |
| 9-140 | Me | Me | H | 5,6-Cl₂ | Ph(2-Cl) | |
| 9-141 | Me | Me | H | 5,6-Cl₂ | Ph(2-Me) | |
| 9-142 | Me | Me | H | 5,6-Cl₂ | Ph(2-CF₃) | |
| 9-143 | Me | Me | H | 5,6-Cl₂ | Ph(2-F-6-Cl) | |
| 9-144 | Me | Me | H | 2-Cl-6-Br | Ph(2-F) | |
| 9-145 | Me | Me | H | 2-Cl-6-Br | Ph(2,6-F₂) | |
| 9-146 | Me | Me | H | 2-Cl-6-Br | Ph(2-Cl) | |
| 9-147 | Me | Me | H | 2-Cl-6-Br | Ph(2-Me) | |
| 9-148 | Me | Me | H | 2-Cl-6-Br | Ph(2-CF₃) | |
| 9-149 | Me | Me | H | 2-Cl-6-Br | Ph(2-F-6-Cl) | |
| 9-150 | Me | Me | H | 4-Cl-6-Br | Ph(2-F) | |
| 9-151 | Me | Me | H | 4-Cl-6-Br | Ph(2,6-F₂) | |
| 9-152 | Me | Me | H | 4-Cl-6-Br | Ph(2-Cl) | |
| 9-153 | Me | Me | H | 4-Cl-6-Br | Ph(2-Me) | |
| 9-154 | Me | Me | H | 4-Cl-6-Br | Ph(2-CF₃) | |
| 9-155 | Me | Me | H | 4-Cl-6-Br | Ph(2-F-6-Cl) | |
| 9-156 | Me | Me | H | 5-Cl-6-Br | Ph(2-F) | |
| 9-157 | Me | Me | H | 5-Cl-6-Br | Ph(2,6-F₂) | |
| 9-158 | Me | Me | H | 5-Cl-6-Br | Ph(2-Cl) | |
| 9-159 | Me | Me | H | 5-Cl-6-Br | Ph(2-Me) | |
| 9-160 | Me | Me | H | 5-Cl-6-Br | Ph(2-CF₃) | |
| 9-161 | Me | Me | H | 5-Cl-6-Br | Ph(2-F-6-Cl) | |
| 9-162 | Me | Me | H | 2-Cl-6-CF₃ | Ph(2-F) | |
| 9-163 | Me | Me | H | 2-Cl-6-CF₃ | Ph(2,6-F₂) | |
| 9-164 | Me | Me | H | 2-Cl-6-CF₃ | Ph(2-Cl) | |
| 9-165 | Me | Me | H | 2-Cl-6-CF₃ | Ph(2-Me) | |
| 9-166 | Me | Me | H | 2-Cl-6-CF₃ | Ph(2-CF₃) | |
| 9-167 | Me | Me | H | 2-Cl-6-CF₃ | Ph(2-F-6-Cl) | |
| 9-168 | Me | Me | H | 4-Cl-6-CF₃ | Ph(2-F) | |
| 9-169 | Me | Me | H | 4-Cl-6-CF₃ | Ph(2,6-F₂) | |
| 9-170 | Me | Me | H | 4-Cl-6-CF₃ | Ph(2-Cl) | |
| 9-171 | Me | Me | H | 4-Cl-6-CF₃ | Ph(2-Me) | |
| 9-172 | Me | Me | H | 4-Cl-6-CF₃ | Ph(2-CF₃) | |
| 9-173 | Me | Me | H | 4-Cl-6-CF₃ | Ph(2-F-6-Cl) | |
| 9-174 | Me | Me | H | 5-Cl-6-CF₃ | Ph(2-F) | |
| 9-175 | Me | Me | H | 5-Cl-6-CF₃ | Ph(2,6-F₂) | |
| 9-176 | Me | Me | H | 5-Cl-6-CF₃ | Ph(2-Cl) | |
| 9-177 | Me | Me | H | 5-Cl-6-CF₃ | Ph(2-Me) | |
| 9-178 | Me | Me | H | 5-Cl-6-CF₃ | Ph(2-CF₃) | |
| 9-179 | Me | Me | H | 5-Cl-6-CF₃ | Ph(2-F-6-Cl) | |
| 9-180 | Me | Me | H | 2-Cl-6-OCF₃ | Ph(2-F) | |
| 9-181 | Me | Me | H | 2-Cl-6-OCF₃ | Ph(2,6-F₂) | |
| 9-182 | Me | Me | H | 2-Cl-6-OCF₃ | Ph(2-Cl) | |
| 9-183 | Me | Me | H | 2-Cl-6-OCF₃ | Ph(2-Me) | |
| 9-184 | Me | Me | H | 2-Cl-6-OCF₃ | Ph(2-CF₃) | |
| 9-185 | Me | Me | H | 2-Cl-6-OCF₃ | Ph(2-F-6-Cl) | |
| 9-186 | Me | Me | H | 4-Cl-6-OCF₃ | Ph(2-F) | |
| 9-187 | Me | Me | H | 4-Cl-6-OCF₃ | Ph(2,6-F₂) | |
| 9-188 | Me | Me | H | 4-Cl-6-OCF₃ | Ph(2-Cl) | |
| 9-189 | Me | Me | H | 4-Cl-6-OCF₃ | Ph(2-Me) | |
| 9-190 | Me | Me | H | 4-Cl-6-OCF₃ | Ph(2-CF₃) | |
| 9-191 | Me | Me | H | 4-Cl-6-OCF₃ | Ph(2-F-6-Cl) | |
| 9-192 | Me | Me | H | 5-Cl-6-OCF₃ | Ph(2-F) | |
| 9-193 | Me | Me | H | 5-Cl-6-OCF₃ | Ph(2,6-F₂) | |
| 9-194 | Me | Me | H | 5-Cl-6-OCF₃ | Ph(2-Cl) | |
| 9-195 | Me | Me | H | 5-Cl-6-OCF₃ | Ph(2-Me) | |
| 9-196 | Me | Me | H | 5-Cl-6-OCF₃ | Ph(2-CF₃) | |
| 9-197 | Me | Me | H | 5-Cl-6-OCF₃ | Ph(2-F-6-Cl) | |
| 9-198 | Me | Me | H | 2-Cl-6-OCHF₂ | Ph(2-F) | |
| 9-199 | Me | Me | H | 2-Cl-6-OCHF₂ | Ph(2,6-F₂) | |
| 9-200 | Me | Me | H | 2-Cl-6-OCHF₂ | Ph(2-Cl) | |
| 9-201 | Me | Me | H | 2-Cl-6-OCHF₂ | Ph(2-Me) | |

TABLE 9-continued

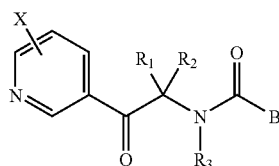

| Compound No. | R$_1$ | R$_2$ | R$_3$ | X | B | Physical properties (mp ° C.) |
|---|---|---|---|---|---|---|
| 9-202 | Me | Me | H | 2-Cl-6-OCHF$_2$ | Ph(2-CF$_3$) | |
| 9-203 | Me | Me | H | 2-Cl-6-OCHF$_2$ | Ph(2-F-6-Cl) | |
| 9-204 | Me | Me | H | 4-Cl-6-OCHF$_2$ | Ph(2-F) | |
| 9-205 | Me | Me | H | 4-Cl-6-OCHF$_2$ | Ph(2,6-F$_2$) | |
| 9-206 | Me | Me | H | 4-Cl-6-OCHF$_2$ | Ph(2-Cl) | |
| 9-207 | Me | Me | H | 4-Cl-6-OCHF$_2$ | Ph(2-Me) | |
| 9-208 | Me | Me | H | 4-Cl-6-OCHF$_2$ | Ph(2-CF$_3$) | |
| 9-209 | Me | Me | H | 4-Cl-6-OCHF$_2$ | Ph(2-F-6-Cl) | |
| 9-210 | Me | Me | H | 5-Cl-6-OCHF$_2$ | Ph(2-F) | |
| 9-211 | Me | Me | H | 5-Cl-6-OCHF$_2$ | Ph(2,6-F$_2$) | |
| 9-212 | Me | Me | H | 5-Cl-6-OCHF$_2$ | Ph(2-Cl) | |
| 9-213 | Me | Me | H | 5-Cl-6-OCHF$_2$ | Ph(2-Me) | |
| 9-214 | Me | Me | H | 5-Cl-6-OCHF$_2$ | Ph(2-CF$_3$) | |
| 9-215 | Me | Me | H | 5-Cl-6-OCHF$_2$ | Ph(2-F-6-Cl) | |
| 9-216 | Me | Me | H | 2-Cl-6-OCH$_2$CF$_3$ | Ph(2-F) | |
| 9-217 | Me | Me | H | 2-Cl-6-OCH$_2$CF$_3$ | Ph(2,6-F$_2$) | |
| 9-218 | Me | Me | H | 2-Cl-6-OCH$_2$CF$_3$ | Ph(2-Cl) | |
| 9-219 | Me | Me | H | 2-Cl-6-OCH$_2$CF$_3$ | Ph(2-Me) | |
| 9-220 | Me | Me | H | 2-Cl-6-OCH$_2$CF$_3$ | Ph(2-CF$_3$) | |
| 9-221 | Me | Me | H | 2-Cl-6-OCH$_2$CF$_3$ | Ph(2-F-6-Cl) | |
| 9-222 | Me | Me | H | 4-Cl-6-OCH$_2$CF$_3$ | Ph(2-F) | |
| 9-223 | Me | Me | H | 4-Cl-6-OCH$_2$CF$_3$ | Ph(2,6-F$_2$) | |
| 9-224 | Me | Me | H | 4-Cl-6-OCH$_2$CF$_3$ | Ph(2-Cl) | |
| 9-225 | Me | Me | H | 4-Cl-6-OCH$_2$CF$_3$ | Ph(2-Me) | |
| 9-226 | Me | Me | H | 4-Cl-6-OCH$_2$CF$_3$ | Ph(2-CF$_3$) | |
| 9-227 | Me | Me | H | 4-Cl-6-OCH$_2$CF$_3$ | Ph(2-F-6-Cl) | |
| 9-228 | Me | Me | H | 5-Cl-6-OCH$_2$CF$_3$ | Ph(2-F) | |
| 9-229 | Me | Me | H | 5-Cl-6-OCH$_2$CF$_3$ | Ph(2,6-F$_2$) | |
| 9-230 | Me | Me | H | 5-Cl-6-OCH$_2$CF$_3$ | Ph(2-Cl) | |
| 9-231 | Me | Me | H | 5-Cl-6-OCH$_2$CF$_3$ | Ph(2-Me) | |
| 9-232 | Me | Me | H | 5-Cl-6-OCH$_2$CF$_3$ | Ph(2-CF$_3$) | |
| 9-233 | Me | Me | H | 5-Cl-6-OCH$_2$CF$_3$ | Ph(2-F-6-Cl) | |
| 9-234 | Me | Me | H | 2-Me-6-Cl | Ph(2-F) | |
| 9-235 | Me | Me | H | 2-Me-6-Cl | Ph(2,6-F$_2$) | |
| 9-236 | Me | Me | H | 2-Me-6-Cl | Ph(2-Cl) | |
| 9-237 | Me | Me | H | 2-Me-6-Cl | Ph(2-Me) | |
| 9-238 | Me | Me | H | 2-Me-6-Cl | Ph(2-CF$_3$) | |
| 9-239 | Me | Me | H | 2-Me-6-Cl | Ph(2-F-6-Cl) | |
| 9-240 | Me | Me | H | 4-Me-6-Cl | Ph(2-F) | |
| 9-241 | Me | Me | H | 4-Me-6-Cl | Ph(2,6-F$_2$) | |
| 9-242 | Me | Me | H | 4-Me-6-Cl | Ph(2-Cl) | |
| 9-243 | Me | Me | H | 4-Me-6-Cl | Ph(2-Me) | |
| 9-244 | Me | Me | H | 4-Me-6-Cl | Ph(2-CF$_3$) | |
| 9-245 | Me | Me | H | 4-Me-6-Cl | Ph(2-F-6-Cl) | |
| 9-246 | Me | Me | H | 5-Me-6-Cl | Ph(2-F) | |
| 9-247 | Me | Me | H | 5-Me-6-Cl | Ph(2,6-F$_2$) | |
| 9-248 | Me | Me | H | 5-Me-6-Cl | Ph(2-Cl) | |
| 9-249 | Me | Me | H | 5-Me-6-Cl | Ph(2-Me) | |
| 9-250 | Me | Me | H | 5-Me-6-Cl | Ph(2-CF$_3$) | |
| 9-251 | Me | Me | H | 5-Me-6-Cl | Ph(2-F-6-Cl) | |
| 9-252 | Me | Me | H | 2-Me-6-Br | Ph(2-F) | |
| 9-253 | Me | Me | H | 2-Me-6-Br | Ph(2,6-F$_2$) | |
| 9-254 | Me | Me | H | 2-Me-6-Br | Ph(2-Cl) | |
| 9-255 | Me | Me | H | 2-Me-6-Br | Ph(2-Me) | |
| 9-256 | Me | Me | H | 2-Me-6-Br | Ph(2-CF$_3$) | |
| 9-257 | Me | Me | H | 2-Me-6-Br | Ph(2-F-6-Cl) | |
| 9-258 | Me | Me | H | 4-Me-6-Br | Ph(2-F) | |
| 9-259 | Me | Me | H | 4-Me-6-Br | Ph(2,6-F$_2$) | |
| 9-260 | Me | Me | H | 4-Me-6-Br | Ph(2-Cl) | |
| 9-261 | Me | Me | H | 4-Me-6-Br | Ph(2-Me) | |
| 9-262 | Me | Me | H | 4-Me-6-Br | Ph(2-CF$_3$) | |
| 9-263 | Me | Me | H | 4-Me-6-Br | Ph(2-F-6-Cl) | |
| 9-264 | Me | Me | H | 5-Me-6-Br | Ph(2-F) | |
| 9-265 | Me | Me | H | 5-Me-6-Br | Ph(2,6-F$_2$) | |
| 9-266 | Me | Me | H | 5-Me-6-Br | Ph(2-Cl) | |
| 9-267 | Me | Me | H | 5-Me-6-Br | Ph(2-Me) | |
| 9-268 | Me | Me | H | 5-Me-6-Br | Ph(2-CF$_3$) | |

TABLE 9-continued

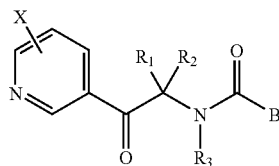

| Compound No. | R₁ | R₂ | R₃ | X | B | Physical properties (mp ° C.) |
|---|---|---|---|---|---|---|
| 9-269 | Me | Me | H | 5-Me-6-Br | Ph(2-F-6-Cl) | |
| 9-270 | Me | Me | H | 2-Me-6-CF₃ | Ph(2-F) | |
| 9-271 | Me | Me | H | 2-Me-6-CF₃ | Ph(2,6-F₂) | |
| 9-272 | Me | Me | H | 2-Me-6-CF₃ | Ph(2-Cl) | |
| 9-273 | Me | Me | H | 2-Me-6-CF₃ | Ph(2-Me) | |
| 9-274 | Me | Me | H | 2-Me-6-CF₃ | Ph(2-CF₃) | |
| 9-275 | Me | Me | H | 2-Me-6-CF₃ | Ph(2-F-6-Cl) | |
| 9-276 | Me | Me | H | 4-Me-6-CF₃ | Ph(2-F) | |
| 9-277 | Me | Me | H | 4-Me-6-CF₃ | Ph(2,6-F₂) | |
| 9-278 | Me | Me | H | 4-Me-6-CF₃ | Ph(2-Cl) | |
| 9-279 | Me | Me | H | 4-Me-6-CF₃ | Ph(2-Me) | |
| 9-280 | Me | Me | H | 4-Me-6-CF₃ | Ph(2-CF₃) | |
| 9-281 | Me | Me | H | 4-Me-6-CF₃ | Ph(2-F-6-Cl) | |
| 9-282 | Me | Me | H | 5-Me-6-CF₃ | Ph(2-F) | |
| 9-283 | Me | Me | H | 5-Me-6-CF₃ | Ph(2,6-F₂) | |
| 9-284 | Me | Me | H | 5-Me-6-CF₃ | Ph(2-Cl) | |
| 9-285 | Me | Me | H | 5-Me-6-CF₃ | Ph(2-Me) | |
| 9-286 | Me | Me | H | 5-Me-6-CF₃ | Ph(2-CF₃) | |
| 9-287 | Me | Me | H | 5-Me-6-CF₃ | Ph(2-F-6-Cl) | |
| 9-288 | Me | Me | H | 2-Me-6-OCF₃ | Ph(2-F) | |
| 9-289 | Me | Me | H | 2-Me-6-OCF₃ | Ph(2,6-F₂) | |
| 9-290 | Me | Me | H | 2-Me-6-OCF₃ | Ph(2-Cl) | |
| 9-291 | Me | Me | H | 2-Me-6-OCF₃ | Ph(2-Me) | |
| 9-292 | Me | Me | H | 2-Me-6-OCF₃ | Ph(2-CF₃) | |
| 9-293 | Me | Me | H | 2-Me-6-OCF₃ | Ph(2-F-6-Cl) | |
| 9-294 | Me | Me | H | 4-Me-6-OCF₃ | Ph(2-F) | |
| 9-295 | Me | Me | H | 4-Me-6-OCF₃ | Ph(2,6-F₂) | |
| 9-296 | Me | Me | H | 4-Me-6-OCF₃ | Ph(2-Cl) | |
| 9-297 | Me | Me | H | 4-Me-6-OCF₃ | Ph(2-Me) | |
| 9-298 | Me | Me | H | 4-Me-6-OCF₃ | Ph(2-CF₃) | |
| 9-299 | Me | Me | H | 4-Me-6-OCF₃ | Ph(2-F-6-Cl) | |
| 9-300 | Me | Me | H | 5-Me-6-OCF₃ | Ph(2-F) | |
| 9-301 | Me | Me | H | 5-Me-6-OCF₃ | Ph(2,6-F₂) | |
| 9-302 | Me | Me | H | 5-Me-6-OCF₃ | Ph(2-Cl) | |
| 9-303 | Me | Me | H | 5-Me-6-OCF₃ | Ph(2-Me) | |
| 9-304 | Me | Me | H | 5-Me-6-OCF₃ | Ph(2-CF₃) | |
| 9-305 | Me | Me | H | 5-Me-6-OCF₃ | Ph(2-F-6-Cl) | |
| 9-306 | Me | Me | H | 2-Me-6-OCHF₂ | Ph(2-F) | |
| 9-307 | Me | Me | H | 2-Me-6-OCHF₂ | Ph(2,6-F₂) | |
| 9-308 | Me | Me | H | 2-Me-6-OCHF₂ | Ph(2-Cl) | |
| 9-309 | Me | Me | H | 2-Me-6-OCHF₂ | Ph(2-Me) | |
| 9-310 | Me | Me | H | 2-Me-6-OCHF₂ | Ph(2-CF₃) | |
| 9-311 | Me | Me | H | 2-Me-6-OCHF₂ | Ph(2-F-6-Cl) | |
| 9-312 | Me | Me | H | 4-Me-6-OCHF₂ | Ph(2-F) | |
| 9-313 | Me | Me | H | 4-Me-6-OCHF₂ | Ph(2,6-F₂) | |
| 9-314 | Me | Me | H | 4-Me-6-OCHF₂ | Ph(2-Cl) | |
| 9-315 | Me | Me | H | 4-Me-6-OCHF₂ | Ph(2-Me) | |
| 9-316 | Me | Me | H | 4-Me-6-OCHF₂ | Ph(2-CF₃) | |
| 9-317 | Me | Me | H | 4-Me-6-OCHF₂ | Ph(2-F-6-Cl) | |
| 9-318 | Me | Me | H | 5-Me-6-OCHF₂ | Ph(2-F) | |
| 9-319 | Me | Me | H | 5-Me-6-OCHF₂ | Ph(2,6-F₂) | |
| 9-320 | Me | Me | H | 5-Me-6-OCHF₂ | Ph(2-Cl) | |
| 9-321 | Me | Me | H | 5-Me-6-OCHF₂ | Ph(2-Me) | |
| 9-322 | Me | Me | H | 5-Me-6-OCHF₂ | Ph(2-CF₃) | |
| 9-323 | Me | Me | H | 5-Me-6-OCHF₂ | Ph(2-F-6-Cl) | |
| 9-324 | Me | Me | H | 2-Me-6-OCH₂CF₃ | Ph(2-F) | |
| 9-325 | Me | Me | H | 2-Me-6-OCH₂CF₃ | Ph(2,6-F₂) | |
| 9-326 | Me | Me | H | 2-Me-6-OCH₂CF₃ | Ph(2-Cl) | |
| 9-327 | Me | Me | H | 2-Me-6-OCH₂CF₃ | Ph(2-Me) | |
| 9-328 | Me | Me | H | 2-Me-6-OCH₂CF₃ | Ph(2-CF₃) | |
| 9-329 | Me | Me | H | 2-Me-6-OCH₂CF₃ | Ph(2-F-6-Cl) | |
| 9-330 | Me | Me | H | 4-Me-6-OCH₂CF₃ | Ph(2-F) | |
| 9-331 | Me | Me | H | 4-Me-6-OCH₂CF₃ | Ph(2,6-F₂) | |
| 9-332 | Me | Me | H | 4-Me-6-OCH₂CF₃ | Ph(2-Cl) | |
| 9-333 | Me | Me | H | 4-Me-6-OCH₂CF₃ | Ph(2-Me) | |
| 9-334 | Me | Me | H | 4-Me-6-OCH₂CF₃ | Ph(2-CF₃) | |
| 9-335 | Me | Me | H | 4-Me-6-OCH₂CF₃ | Ph(2-F-6-Cl) | |

TABLE 9-continued

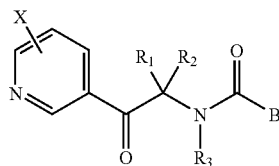

| Compound No. | $R_1$ | $R_2$ | $R_3$ | X | B | Physical properties (mp ° C.) |
|---|---|---|---|---|---|---|
| 9-336 | Me | Me | H | 5-Me-6-OCH$_2$CF$_3$ | Ph(2-F) | |
| 9-337 | Me | Me | H | 5-Me-6-OCH$_2$CF$_3$ | Ph(2,6-F$_2$) | |
| 9-338 | Me | Me | H | 5-Me-6-OCH$_2$CF$_3$ | Ph(2-Cl) | |
| 9-339 | Me | Me | H | 5-Me-6-OCH$_2$CF$_3$ | Ph(2-Me) | |
| 9-340 | Me | Me | H | 5-Me-6-OCH$_2$CF$_3$ | Ph(2-CF$_3$) | |
| 9-341 | Me | Me | H | 5-Me-6-OCH$_2$CF$_3$ | Ph(2-F-6-Cl) | |

TABLE 10

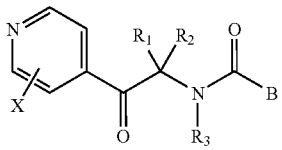

| Compound No. | $R_1$ | $R_2$ | $R_3$ | X | B | Physical properties (mp ° C.) |
|---|---|---|---|---|---|---|
| 10-1 | Me | Me | H | H | Ph | |
| 10-2 | Me | Me | H | H | Ph(2-F) | |
| 10-3 | Me | Me | H | H | Ph(2-Cl) | |
| 10-4 | Me | Me | H | H | Ph(2-OMe) | |
| 10-5 | Me | Me | H | H | Ph(2,6-F$_2$) | 155-157 |
| 10-6 | Me | Me | H | H | Ph(2,6-Cl$_2$) | |
| 10-7 | Me | Me | H | H | Ph(2,6-OMe$_2$) | |
| 10-8 | Me | Me | H | 2-Cl | Ph | |
| 10-9 | Me | Me | H | 2-Cl | Ph(2-F) | |
| 10-10 | Me | Me | H | 2-Cl | Ph(2-Cl) | |
| 10-11 | Me | Me | H | 2-Cl | Ph(2,6-F$_2$) | |
| 10-12 | Me | Me | H | 2-Cl | Ph(2,6-Cl$_2$) | |
| 10-13 | Me | Me | H | 2-Br | Ph | |
| 10-14 | Me | Me | H | 2-Br | Ph(2-F) | |
| 10-15 | Me | Me | H | 2-Br | Ph(2-Cl) | |
| 10-16 | Me | Me | H | 2-Br | Ph(2,6-F$_2$) | |
| 10-17 | Me | Me | H | 2-Br | Ph(2,6-Cl$_2$) | |
| 10-18 | Me | Me | H | 2-CF$_3$ | Ph(2,6-F$_2$) | |
| 10-19 | Me | Me | H | 2-CN | Ph(2,6-F$_2$) | |
| 10-20 | Me | CN | H | H | Ph(2,6-F$_2$) | |
| 10-21 | Me | CO$_2$Et | H | H | Ph(2,6-F$_2$) | |
| 10-22 | Me | CN | H | 2-Cl | Ph(2,6-F$_2$) | |
| 10-23 | Me | CO$_2$Et | H | 2-Cl | Ph(2,6-F$_2$) | |
| 10-24 | Me | Et | H | H | Ph(2,6-F$_2$) | |
| 10-25 | Me | Me | COMe | H | Ph(2,6-F$_2$) | |
| 10-26 | Me | Me | CH$_2$OMe | H | Ph(2,6-F$_2$) | |
| 10-27 | Me | Me | H | H | 1-naphthyl | |
| 10-28 | Me | Me | H | H | 2-naphthyl | |
| 10-29 | Me | Me | H | H | 2-thienyl | |
| 10-30 | Me | Me | H | H | 3-thienyl | |
| 10-31 | Me | Me | H | H | 2-pyrazinyl | |
| 10-32 | Me | Me | H | H | 2-pyridyl | |
| 10-33 | Me | Me | H | H | 3-pyridyl | |
| 10-34 | Me | Me | H | H | 4-trifluoromethyl-3-pyridyl | |
| 10-35 | Me | Me | H | H | 4-pyridyl | |
| 10-36 | Me | Me | H | H | 2-furyl | |
| 10-37 | Me | Me | H | H | 3-furyl | |
| 10-38 | Me | Me | H | 3-Cl | Ph(2-F) | |
| 10-39 | Me | Me | H | 3-Cl | Ph(2,6-F$_2$) | |
| 10-40 | Me | Me | H | 3-Cl | Ph(2-Cl) | |
| 10-41 | Me | Me | H | 3-Cl | Ph(2-Me) | |

TABLE 10-continued

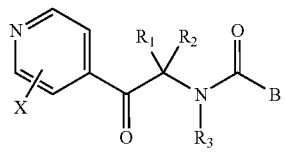

| Compound No. | R$_1$ | R$_2$ | R$_3$ | X | B | Physical properties (mp ° C.) |
|---|---|---|---|---|---|---|
| 10-42 | Me | Me | H | 3-Cl | Ph(2-CF$_3$) | |
| 10-43 | Me | Me | H | 3-Cl | Ph(2-F-6-Cl) | |
| 10-44 | Me | Me | H | 3-Br | Ph(2-F) | |
| 10-45 | Me | Me | H | 3-Br | Ph(2,6-F$_2$) | |
| 10-46 | Me | Me | H | 3-Br | Ph(2-Cl) | |
| 10-47 | Me | Me | H | 3-Br | Ph(2-Me) | |
| 10-48 | Me | Me | H | 3-Br | Ph(2-CF$_3$) | |
| 10-49 | Me | Me | H | 3-Br | Ph(2-F-6-Cl) | |
| 10-50 | Me | Me | H | 2-Me | Ph(2-F) | |
| 10-51 | Me | Me | H | 2-Me | Ph(2,6-F$_2$) | |
| 10-52 | Me | Me | H | 2-Me | Ph(2-Cl) | |
| 10-53 | Me | Me | H | 2-Me | Ph(2-Me) | |
| 10-54 | Me | Me | H | 2-Me | Ph(2-CF$_3$) | |
| 10-55 | Me | Me | H | 2-Me | Ph(2-F-6-Cl) | |
| 10-56 | Me | Me | H | 3-Me | Ph(2-F) | |
| 10-57 | Me | Me | H | 3-Me | Ph(2,6-F$_2$) | |
| 10-58 | Me | Me | H | 3-Me | Ph(2-Cl) | |
| 10-59 | Me | Me | H | 3-Me | Ph(2-Me) | |
| 10-60 | Me | Me | H | 3-Me | Ph(2-CF$_3$) | |
| 10-61 | Me | Me | H | 3-Me | Ph(2-F-6-Cl) | |
| 10-62 | Me | Me | H | 3-CN | Ph(2-F) | |
| 10-63 | Me | Me | H | 3-CN | Ph(2,6-F$_2$) | |
| 10-64 | Me | Me | H | 3-CN | Ph(2-Cl) | |
| 10-65 | Me | Me | H | 3-CN | Ph(2-Me) | |
| 10-66 | Me | Me | H | 3-CN | Ph(2-CF$_3$) | |
| 10-67 | Me | Me | H | 3-CN | Ph(2-F-6-Cl) | |
| 10-68 | Me | Me | H | 3-CF$_3$ | Ph(2-F) | |
| 10-69 | Me | Me | H | 3-CF$_3$ | Ph(2,6-F$_2$) | |
| 10-70 | Me | Me | H | 3-CF$_3$ | Ph(2-Cl) | |
| 10-71 | Me | Me | H | 3-CF$_3$ | Ph(2-Me) | |
| 10-72 | Me | Me | H | 3-CF$_3$ | Ph(2-CF$_3$) | |
| 10-73 | Me | Me | H | 3-CF$_3$ | Ph(2-F-6-Cl) | |
| 10-74 | Me | Me | H | 2-OCF$_3$ | Ph(2-F) | |
| 10-75 | Me | Me | H | 2-OCF$_3$ | Ph(2,6-F$_2$) | |
| 10-76 | Me | Me | H | 2-OCF$_3$ | Ph(2-Cl) | |
| 10-77 | Me | Me | H | 2-OCF$_3$ | Ph(2-Me) | |
| 10-78 | Me | Me | H | 2-OCF$_3$ | Ph(2-CF$_3$) | |
| 10-79 | Me | Me | H | 2-OCF$_3$ | Ph(2-F-6-Cl) | |
| 10-80 | Me | Me | H | 3-OCF$_3$ | Ph(2-F) | |
| 10-81 | Me | Me | H | 3-OCF$_3$ | Ph(2,6-F$_2$) | |
| 10-82 | Me | Me | H | 3-OCF$_3$ | Ph(2-Cl) | |
| 10-83 | Me | Me | H | 3-OCF$_3$ | Ph(2-Me) | |
| 10-84 | Me | Me | H | 3-OCF$_3$ | Ph(2-CF$_3$) | |
| 10-85 | Me | Me | H | 3-OCF$_3$ | Ph(2-F-6-Cl) | |
| 10-86 | Me | Me | H | 2-OCHF$_2$ | Ph(2-F) | |
| 10-87 | Me | Me | H | 2-OCHF$_2$ | Ph(2,6-F$_2$) | |
| 10-88 | Me | Me | H | 2-OCHF$_2$ | Ph(2-Cl) | |
| 10-89 | Me | Me | H | 2-OCHF$_2$ | Ph(2-Me) | |
| 10-90 | Me | Me | H | 2-OCHF$_2$ | Ph(2-CF$_3$) | |
| 10-91 | Me | Me | H | 2-OCHF$_2$ | Ph(2-F-6-Cl) | |
| 10-92 | Me | Me | H | 3-OCHF$_2$ | Ph(2-F) | |
| 10-93 | Me | Me | H | 3-OCHF$_2$ | Ph(2,6-F$_2$) | |
| 10-94 | Me | Me | H | 3-OCHF$_2$ | Ph(2-Cl) | |
| 10-95 | Me | Me | H | 3-OCHF$_2$ | Ph(2-Me) | |
| 10-96 | Me | Me | H | 3-OCHF$_2$ | Ph(2-CF$_3$) | |
| 10-97 | Me | Me | H | 3-OCHF$_2$ | Ph(2-F-6-Cl) | |
| 10-98 | Me | Me | H | 2-CF$_3$-3-Cl | Ph(2-F) | |
| 10-99 | Me | Me | H | 2-CF$_3$-3-Cl | Ph(2,6-F$_2$) | |
| 10-100 | Me | Me | H | 2-CF$_3$-3-Cl | Ph(2-Cl) | |
| 10-101 | Me | Me | H | 2-CF$_3$-3-Cl | Ph(2-Me) | |
| 10-102 | Me | Me | H | 2-CF$_3$-3-Cl | Ph(2-CF$_3$) | |
| 10-103 | Me | Me | H | 2-CF$_3$-3-Cl | Ph(2-F-6-Cl) | |
| 10-104 | Me | Me | H | 2-CF$_3$-3-Me | Ph(2-F) | |
| 10-105 | Me | Me | H | 2-CF$_3$-3-Me | Ph(2,6-F$_2$) | |
| 10-106 | Me | Me | H | 2-CF$_3$-3-Me | Ph(2-Cl) | |
| 10-107 | Me | Me | H | 2-CF$_3$-3-Me | Ph(2-Me) | |
| 10-108 | Me | Me | H | 2-CF$_3$-3-Me | Ph(2-CF$_3$) | |

TABLE 10-continued

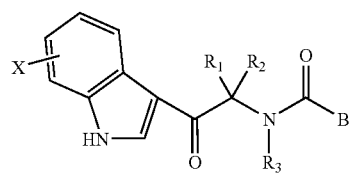

| Compound No. | $R_1$ | $R_2$ | $R_3$ | X | B | Physical properties (mp °C.) |
|---|---|---|---|---|---|---|
| 10-109 | Me | Me | H | 2-CF$_3$-3-Me | Ph(2-F-6-Cl) | |
| 10-110 | Me | Me | H | 2-OMe-3-Cl | Ph(2-F) | |
| 10-111 | Me | Me | H | 2-OMe-3-Cl | Ph(2,6-F$_2$) | |
| 10-112 | Me | Me | H | 2-OMe-3-Cl | Ph(2-Cl) | |
| 10-113 | Me | Me | H | 2-OMe-3-Cl | Ph(2-Me) | |
| 10-114 | Me | Me | H | 2-OMe-3-Cl | Ph(2-CF$_3$) | |
| 10-115 | Me | Me | H | 2-OMe-3-Cl | Ph(2-F-6-Cl) | |
| 10-116 | Me | Me | H | 2-OMe-3-Me | Ph(2-F) | |
| 10-117 | Me | Me | H | 2-OMe-3-Me | Ph(2,6-F$_2$) | |
| 10-118 | Me | Me | H | 2-OMe-3-Me | Ph(2-Cl) | |
| 10-119 | Me | Me | H | 2-OMe-3-Me | Ph(2-Me) | |
| 10-120 | Me | Me | H | 2-OMe-3-Me | Ph(2-CF$_3$) | |
| 10-121 | Me | Me | H | 2-OMe-3-Me | Ph(2-F-6-Cl) | |
| 10-122 | Me | Me | H | 2-OCF$_3$-3-Cl | Ph(2-F) | |
| 10-123 | Me | Me | H | 2-OCF$_3$-3-Cl | Ph(2,6-F$_2$) | |
| 10-124 | Me | Me | H | 2-OCF$_3$-3-Cl | Ph(2-Cl) | |
| 10-125 | Me | Me | H | 2-OCF$_3$-3-Cl | Ph(2-Me) | |
| 10-126 | Me | Me | H | 2-OCF$_3$-3-Cl | Ph(2-CF$_3$) | |
| 10-127 | Me | Me | H | 2-OCF$_3$-3-Cl | Ph(2-F-6-Cl) | |
| 10-128 | Me | Me | H | 2-OCF$_3$-3-Me | Ph(2-F) | |
| 10-129 | Me | Me | H | 2-OCF$_3$-3-Me | Ph(2,6-F$_2$) | |
| 10-130 | Me | Me | H | 2-OCF$_3$-3-Me | Ph(2-Cl) | |
| 10-131 | Me | Me | H | 2-OCF$_3$-3-Me | Ph(2-Me) | |
| 10-132 | Me | Me | H | 2-OCF$_3$-3-Me | Ph(2-CF$_3$) | |
| 10-133 | Me | Me | H | 2-OCF$_3$-3-Me | Ph(2-F-6-Cl) | |
| 10-134 | Me | Me | H | 2-OCHF$_2$-3-Cl | Ph(2-F) | |
| 10-135 | Me | Me | H | 2-OCHF$_2$-3-Cl | Ph(2,6-F$_2$) | |
| 10-136 | Me | Me | H | 2-OCHF$_2$-3-Cl | Ph(2-Cl) | |
| 10-137 | Me | Me | H | 2-OCHF$_2$-3-Cl | Ph(2-Me) | |
| 10-138 | Me | Me | H | 2-OCHF$_2$-3-Cl | Ph(2-CF$_3$) | |
| 10-139 | Me | Me | H | 2-OCH$_2$-3-Cl | Ph(2-F-6-Cl) | |
| 10-140 | Me | Me | H | 2-OCHF$_2$-3-Me | Ph(2-F) | |
| 10-141 | Me | Me | H | 2-OCHF$_2$-3-Me | Ph(2,6-F$_2$) | |
| 10-142 | Me | Me | H | 2-OCHF$_2$-3-Me | Ph(2-Cl) | |
| 10-143 | Me | Me | H | 2-OCHF$_2$-3-Me | Ph(2-Me) | |
| 10-144 | Me | Me | H | 2-OCHF$_2$-3-Me | Ph(2-CF$_3$) | |
| 10-145 | Me | Me | H | 2-OCHF$_2$-3-Me | Ph(2-F-6-Cl) | |

TABLE 11

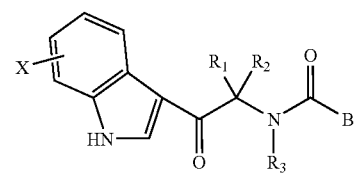

| Compound No. | $R_1$ | $R_2$ | $R_3$ | X | B | Physical properties (mp °C.) |
|---|---|---|---|---|---|---|
| 11-1 | Me | Me | H | H | Ph | |
| 11-2 | Me | Me | H | H | Ph(2-F) | 94-96 |
| 11-3 | Me | Me | H | H | Ph(2-Cl) | |
| 11-4 | Me | Me | H | H | Ph(2-OMe) | |
| 11-5 | Me | Me | H | H | Ph(2,6-F$_2$) | 119-121 |
| 11-6 | Me | Me | H | H | Ph(2,6-Cl$_2$) | |
| 11-7 | Me | Me | H | H | Ph(2,6-OMe$_2$) | |
| 11-8 | Me | Me | H | 6-Cl | Ph | |
| 11-9 | Me | Me | H | 6-Cl | Ph(2-F) | |
| 11-10 | Me | Me | H | 6-Cl | Ph(2-Cl) | |
| 11-11 | Me | Me | H | 6-Cl | Ph(2,6-F$_2$) | |
| 11-12 | Me | Me | H | 6-Cl | Ph(2,6-Cl$_2$) | |
| 11-13 | Me | Me | H | 6-Br | Ph | |
| 11-14 | Me | Me | H | 6-Br | Ph(2-F) | |
| 11-15 | Me | Me | H | 6-Br | Ph(2-Cl) | |
| 11-16 | Me | Me | H | 6-Br | Ph(2,6-F$_2$) | |

TABLE 11-continued

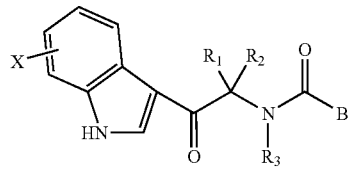

| Compound No. | R₁ | R₂ | R₃ | X | B | Physical properties (mp ° C.) |
|---|---|---|---|---|---|---|
| 11-17 | Me | Me | H | 6-Br | Ph(2,6-Cl₂) | |
| 11-18 | Me | Me | H | 6-CF₃ | Ph(2,6-F₂) | |
| 11-19 | Me | Me | H | 6-CN | Ph(2,6-F₂) | |
| 11-20 | Me | CN | H | H | Ph(2,6-F₂) | |
| 11-21 | Me | CO₂Et | H | H | Ph(2,6-F₂) | |
| 11-22 | Me | CN | H | 6-Cl | Ph(2,6-F₂) | |
| 11-23 | Me | CO₂Et | H | 6-Cl | Ph(2,6-F₂) | |
| 11-24 | Me | Et | H | H | Ph(2,6-F₂) | |
| 11-25 | Me | Me | COMe | H | Ph(2,6-F₂) | |
| 11-26 | Me | Me | CH₂OMe | H | Ph(2,6-F₂) | |
| 11-27 | Me | Me | H | H | 1-naphthyl | |
| 11-28 | Me | Me | H | H | 2-naphthyl | |
| 11-29 | Me | Me | H | H | 2-thienyl | |
| 11-30 | Me | Me | H | H | 3-thienyl | |
| 11-31 | Me | Me | H | H | 2-pyrazinyl | |
| 11-32 | Me | Me | H | H | 2-pyridyl | |
| 11-33 | Me | Me | H | H | 3-pyridyl | |
| 11-34 | Me | Me | H | H | 4-trifluoromethyl-3-pyridyl | |
| 11-35 | Me | Me | H | H | 4-pyridyl | |
| 11-36 | Me | Me | H | H | 2-furyl | |
| 11-37 | Me | Me | H | H | 3-furyl | |
| 11-38 | Me | Me | H | 2-Cl | Ph(2-F) | |
| 11-39 | Me | Me | H | 2-Cl | Ph(2,6-F₂) | |
| 11-40 | Me | Me | H | 2-Cl | Ph(2-Cl) | |
| 11-41 | Me | Me | H | 2-Cl | Ph(2-Me) | |
| 11-42 | Me | Me | H | 2-Cl | Ph(2-CF₃) | |
| 11-43 | Me | Me | H | 2-Cl | Ph(2-F-6-Cl) | |
| 11-44 | Me | Me | H | 2-Me | Ph(2-F) | |
| 11-45 | Me | Me | H | 2-Me | Ph(2,6-F₂) | |
| 11-46 | Me | Me | H | 2-Me | Ph(2-Cl) | |
| 11-47 | Me | Me | H | 2-Me | Ph(2-Me) | |
| 11-48 | Me | Me | H | 2-Me | Ph(2-CF₃) | |
| 11-49 | Me | Me | H | 2-Me | Ph(2-F-6-Cl) | |

TABLE 12

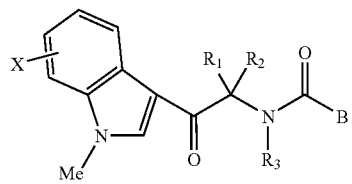

| Compound No. | R₁ | R₂ | R₃ | X | B | Physical Properties (mp ° C.) |
|---|---|---|---|---|---|---|
| 12-1 | Me | Me | H | H | Ph | |
| 12-2 | Me | Me | H | H | Ph(2-F) | 180-183 |
| 12-3 | Me | Me | H | H | Ph(2-Cl) | |
| 12-4 | Me | Me | H | H | Ph(2-OMe) | |
| 12-5 | Me | Me | H | H | Ph(2,6-F₂) | 246-250 |
| 12-6 | Me | Me | H | H | Ph(2,6-Cl₂) | |
| 12-7 | Me | Me | H | H | Ph(2,6-OMe₂) | |
| 12-8 | Me | Me | H | 6-Cl | Ph | |
| 12-9 | Me | Me | H | 6-Cl | Ph(2-F) | |
| 12-10 | Me | Me | H | 6-Cl | Ph(2-Cl) | |
| 12-11 | Me | Me | H | 6-Cl | Ph(2,6-F₂) | |

TABLE 12-continued

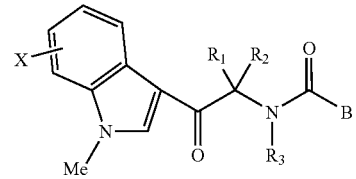

| Compound No. | R₁ | R₂ | R₃ | X | B | Physical Properties (mp ° C.) |
|---|---|---|---|---|---|---|
| 12-12 | Me | Me | H | 6-Cl | Ph(2,6-Cl₂) | |
| 12-13 | Me | Me | H | 6-Br | Ph | |
| 12-14 | Me | Me | H | 6-Br | Ph(2-F) | |
| 12-15 | Me | Me | H | 6-Br | Ph(2-Cl) | |
| 12-16 | Me | Me | H | 6-Br | Ph(2,6-F₂) | |
| 12-17 | Me | Me | H | 6-Br | Ph(2,6-Cl₂) | |
| 12-18 | Me | Me | H | 6-CF₃ | Ph(2,6-F₂) | |
| 12-19 | Me | Me | H | 6-CN | Ph(2,6-F₂) | |
| 12-20 | Me | CN | H | H | Ph(2,6-F₂) | |
| 12-21 | Me | CO₂Et | H | H | Ph(2,6-F₂) | |
| 12-22 | Me | CN | H | 6-Cl | Ph(2,6-F₂) | |
| 12-23 | Me | CO₂Et | H | 6-Cl | Ph(2,6-F₂) | |
| 12-24 | Me | Et | H | H | Ph(2,6-F₂) | |
| 12-25 | Me | Me | COMe | H | Ph(2,6-F₂) | |
| 12-26 | Me | Me | CH₂OMe | H | Ph(2,6-F₂) | |
| 12-27 | Me | Me | H | H | 1-naphthyl | |
| 12-28 | Me | Me | H | H | 2-naphthyl | |
| 12-29 | Me | Me | H | H | 2-thienyl | |
| 12-30 | Me | Me | H | H | 3-thienyl | |
| 12-31 | Me | Me | H | H | 2-pyrazinyl | |
| 12-32 | Me | Me | H | H | 2-pyridyl | |
| 12-33 | Me | Me | H | H | 3-pyridyl | |
| 12-34 | Me | Me | H | H | 4-trifluoromethyl-3-pyridyl | |
| 12-35 | Me | Me | H | H | 4-pyridyl | |
| 12-36 | Me | Me | H | H | 2-furyl | |
| 12-37 | Me | Me | H | H | 3-furyl | |
| 12-38 | Me | Me | H | 2-Cl | Ph(2-F) | |
| 12-39 | Me | Me | H | 2-Cl | Ph(2,6-F₂) | |
| 12-40 | Me | Me | H | 2-Cl | Ph(2-Cl) | |
| 12-41 | Me | Me | H | 2-Cl | Ph(2-Me) | |
| 12-42 | Me | Me | H | 2-Cl | Ph(2-CF₃) | |
| 12-43 | Me | Me | H | 2-Cl | Ph(2-F-6-Cl) | |
| 12-44 | Me | Me | H | 2-Me | Ph(2-F) | |
| 12-45 | Me | Me | H | 2-Me | Ph(2,6-F₂) | |
| 12-46 | Me | Me | H | 2-Me | Ph(2-Cl) | |
| 12-47 | Me | Me | H | 2-Me | Ph(2-Me) | |
| 12-48 | Me | Me | H | 2-Me | Ph(2-CF₃) | |
| 12-49 | Me | Me | H | 2-Me | Ph(2-F-6-Cl) | |

TABLE 13

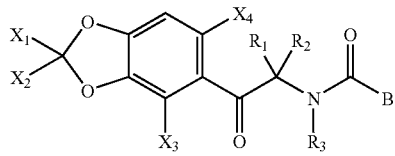

| Compound No. | R₁ | R₂ | R₃ | X₁ | X₂ | X₃ | X₄ | B | Physical properties (mp ° C.) |
|---|---|---|---|---|---|---|---|---|---|
| 13-1 | Me | Me | H | H | H | H | H | Ph | |
| 13-2 | Me | Me | H | H | H | H | H | Ph(2-Cl) | Oil |
| 13-3 | Me | Me | H | H | H | H | H | Ph(4-Cl) | |
| 13-4 | Me | Me | H | H | H | H | H | Ph(2-CF₃) | 164-167 |
| 13-5 | Me | Me | H | H | H | H | H | Ph(4-CF₃) | |
| 13-6 | Me | Me | H | H | H | H | H | Ph(2-F) | 116-121 |
| 13-7 | Me | Me | H | H | H | H | H | Ph(2,6-F₂) | 134-139 |

TABLE 13-continued

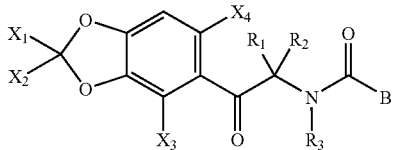

| Compound No. | R₁ | R₂ | R₃ | X₁ | X₂ | X₃ | X₄ | B | Physical properties (mp ° C.) |
|---|---|---|---|---|---|---|---|---|---|
| 13-8 | Me | Me | H | H | H | H | H | Ph(2-OCF₃) | |
| 13-9 | Me | Me | H | H | H | H | H | Ph(2-OCHF₂) | |
| 13-10 | Me | Me | H | H | H | H | H | Ph(2-OMe) | |
| 13-11 | Me | Me | H | H | H | H | H | Ph(2,6-(OMe)₂) | |
| 13-12 | Me | Me | H | F | F | H | H | Ph(2-NO₂) | |
| 13-13 | Me | Me | H | F | F | H | H | Ph | |
| 13-14 | Me | Me | H | F | F | H | H | Ph(2-Cl) | |
| 13-15 | Me | Me | H | F | F | H | H | Ph(4-Cl) | |
| 13-16 | Me | Me | H | F | F | H | H | Ph(2-CF₃) | |
| 13-17 | Me | Me | H | F | F | H | H | Ph(4-CF₃) | |
| 13-18 | Me | Me | H | F | F | H | H | Ph(2-F) | 114-117 |
| 13-19 | Me | Me | H | F | F | H | H | Ph(2,6-F₂) | 123-125 |
| 13-20 | Me | Me | H | F | F | H | H | Ph(2-OCF₃) | |
| 13-21 | Me | Me | H | F | F | H | H | Ph(2-OCHF₂) | |
| 13-22 | Me | Me | H | F | F | H | H | Ph(2-OMe) | |
| 13-23 | Me | Me | H | F | F | H | H | Ph(2,6-(OMe)₂) | |
| 13-24 | Me | Me | H | F | F | H | H | Ph(2-NO₂) | |
| 13-25 | Me | Me | H | F | F | H | H | Ph(2-SMe) | |
| 13-26 | Me | Me | H | H | H | Cl | H | Ph(2-F) | |
| 13-27 | Me | Me | H | H | H | Cl | H | Ph(2,6-F₂) | |
| 13-28 | Me | Me | H | H | H | Cl | H | Ph(2-Cl) | |
| 13-29 | Me | Me | H | H | H | Cl | H | Ph(2-Me) | |
| 13-30 | Me | Me | H | H | H | Cl | H | Ph(2-CF₃) | |
| 13-31 | Me | Me | H | H | H | Cl | H | Ph(2-F-6-Cl) | |
| 13-32 | Me | Me | H | H | H | Me | H | Ph(2-F) | |
| 13-33 | Me | Me | H | H | H | Me | H | Ph(2,6-F₂) | 133-135 |
| 13-34 | Me | Me | H | H | H | Me | H | Ph(2-Cl) | |
| 13-35 | Me | Me | H | H | H | Me | H | Ph(2-Me) | |
| 13-36 | Me | Me | H | H | H | Me | H | Ph(2-CF₃) | |
| 13-37 | Me | Me | H | H | H | Me | H | Ph(2-F-6-Cl) | |
| 13-38 | Me | Me | H | F | F | Cl | H | Ph(2-F) | |
| 13-39 | Me | Me | H | F | F | Cl | H | Ph(2,6-F₂) | |
| 13-40 | Me | Me | H | F | F | Cl | H | Ph(2-Cl) | |
| 13-41 | Me | Me | H | F | F | Cl | H | Ph(2-Me) | |
| 13-42 | Me | Me | H | F | F | Cl | H | Ph(2-CF₃) | |
| 13-43 | Me | Me | H | F | F | Cl | H | Ph(2-F-6-Cl) | |
| 13-44 | Me | Me | H | F | F | Me | H | Ph(2-F) | 105-108 |
| 13-45 | Me | Me | H | F | F | Me | H | Ph(2,6-F₂) | 178-180 |
| 13-46 | Me | Me | H | F | F | Me | H | Ph(2-Cl) | |
| 13-47 | Me | Me | H | F | F | Me | H | Ph(2-Me) | |
| 13-48 | Me | Me | H | F | F | Me | H | Ph(2-CF₃) | |
| 13-49 | Me | Me | H | F | F | Me | H | Ph(2-F-6-Cl) | |
| 13-50 | Me | Me | H | H | H | H | Me | Ph(2-F) | |
| 13-51 | Me | Me | H | H | H | H | Me | Ph(2,6-F₂) | |
| 13-52 | Me | Me | H | H | H | H | Me | Ph(2-Cl) | |
| 13-53 | Me | Me | H | H | H | H | Me | Ph(2-Me) | |
| 13-54 | Me | Me | H | H | H | H | Me | Ph(2-CF₃) | |
| 13-55 | Me | Me | H | H | H | H | Me | Ph(2-F-6-Cl) | |
| 13-56 | Me | Me | H | F | F | H | Me | Ph(2-F) | |
| 13-57 | Me | Me | H | F | F | H | Me | Ph(2,6-F₂) | |
| 13-58 | Me | Me | H | F | F | H | Me | Ph(2-Cl) | |
| 13-59 | Me | Me | H | F | F | H | Me | Ph(2-Me) | |
| 13-60 | Me | Me | H | F | F | H | Me | Ph(2-CF₃) | |
| 13-61 | Me | Me | H | F | F | H | Me | Ph(2-F-6-Cl) | |
| 13-62 | Me | Me | H | Me | Me | Me | H | Ph(2-F) | |
| 13-63 | Me | Me | H | Me | Me | Me | H | Ph(2,6-F₂) | |
| 13-64 | Me | Me | H | Me | Me | Me | H | Ph(2-Cl) | |
| 13-65 | Me | Me | H | Me | Me | Me | H | Ph(2-Me) | |
| 13-66 | Me | Me | H | Me | Me | Me | H | Ph(2-CF₃) | |
| 13-67 | Me | Me | H | Me | Me | Me | H | Ph(2-F-6-Cl) | |
| 13-68 | Me | Me | H | Me | Me | H | Me | Ph(2-F) | |
| 13-69 | Me | Me | H | Me | Me | H | Me | Ph(2,6-F₂) | |
| 13-70 | Me | Me | H | Me | Me | H | Me | Ph(2-Cl) | |
| 13-71 | Me | Me | H | Me | Me | H | Me | Ph(2-Me) | |

TABLE 13-continued

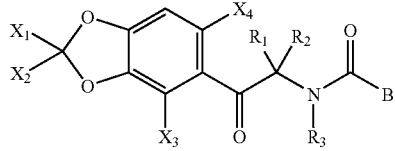

| Compound No. | R₁ | R₂ | R₃ | X₁ | X₂ | X₃ | X₄ | B | Physical properties (mp ° C.) |
|---|---|---|---|---|---|---|---|---|---|
| 13-72 | Me | Me | H | Me | Me | H | Me | Ph(2-CF₃) | |
| 13-73 | Me | Me | H | Me | Me | H | Me | Ph(2-F-6-Cl) | |
| 13-74 | Me | Me | H | H | H | H | Cl | Ph(2-F) | |
| 13-75 | Me | Me | H | H | H | H | Cl | Ph(2,6-F₂) | |
| 13-76 | Me | Me | H | H | H | H | Cl | Ph(2-Cl) | |
| 13-77 | Me | Me | H | H | H | H | Cl | Ph(2-Me) | |
| 13-78 | Me | Me | H | H | H | H | Cl | Ph(2-CF₃) | |
| 13-79 | Me | Me | H | H | H | H | Cl | Ph(2-F-6-Cl) | |
| 13-80 | Me | Me | H | F | F | H | Cl | Ph(2-F) | |
| 13-81 | Me | Me | H | F | F | H | Cl | Ph(2,6-F₂) | |
| 13-82 | Me | Me | H | F | F | H | Cl | Ph(2-Cl) | |
| 13-83 | Me | Me | H | F | F | H | Cl | Ph(2-Me) | |
| 13-84 | Me | Me | H | F | F | H | Cl | Ph(2-CF₃) | |
| 13-85 | Me | Me | H | F | F | H | Cl | Ph(2-F-6-Cl) | |
| 13-86 | Me | Me | H | Me | Me | Cl | H | Ph(2-F) | |
| 13-87 | Me | Me | H | Me | Me | Cl | H | Ph(2,6-F₂) | |
| 13-88 | Me | Me | H | Me | Me | Cl | H | Ph(2-Cl) | |
| 13-89 | Me | Me | H | Me | Me | Cl | H | Ph(2-Me) | |
| 13-90 | Me | Me | H | Me | Me | Cl | H | Ph(2-CF₃) | |
| 13-91 | Me | Me | H | Me | Me | Cl | H | Ph(2-F-6-Cl) | |
| 13-92 | Me | Me | H | Me | Me | H | Cl | Ph(2-F) | |
| 13-93 | Me | Me | H | Me | Me | H | Cl | Ph(2,6-F₂) | |
| 13-94 | Me | Me | H | Me | Me | H | Cl | Ph(2-Cl) | |
| 13-95 | Me | Me | H | Me | Me | H | Cl | Ph(2-Me) | |
| 13-96 | Me | Me | H | Me | Me | H | Cl | Ph(2-CF₃) | |
| 13-97 | Me | Me | H | Me | Me | H | Cl | Ph(2-F-6-Cl) | |

TABLE 14

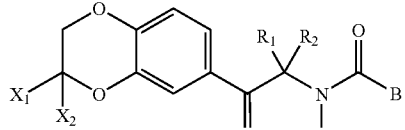

| Compound No. | R₁ | R₂ | R₃ | X₁ | X₂ | B | Physical properties (mp ° C.) |
|---|---|---|---|---|---|---|---|
| 14-1 | Me | Me | H | H | H | Ph | |
| 14-2 | Me | Me | H | H | H | Ph(2-Cl) | |
| 14-3 | Me | Me | H | H | H | Ph(4-Cl) | |
| 14-4 | Me | Me | H | H | H | Ph(2-CF₃) | |
| 14-5 | Me | Me | H | H | H | Ph(4-CF₃) | |
| 14-6 | Me | Me | H | H | H | Ph(2-F) | |
| 14-7 | Me | Me | H | H | H | Ph(2,6-F₂) | |
| 14-8 | Me | Me | H | H | H | Ph(2-OCF₃) | |
| 14-9 | Me | Me | H | H | H | Ph(2-OCHF₂) | |
| 14-10 | Me | Me | H | H | H | Ph(2-OMe) | |
| 14-11 | Me | Me | H | H | H | Ph(2,6-(OMe)₂) | |
| 14-12 | Me | Me | H | F | F | Ph(2-NO₂) | |
| 14-13 | Me | Me | H | F | F | Ph | |
| 14-14 | Me | Me | H | F | F | Ph(2-Cl) | |
| 14-15 | Me | Me | H | F | F | Ph(4-Cl) | |
| 14-16 | Me | Me | H | F | F | Ph(2-CF₃) | |
| 14-17 | Me | Me | H | F | F | Ph(4-CF₃) | |
| 14-18 | Me | Me | H | F | F | Ph(2-F) | |
| 14-19 | Me | Me | H | F | F | Ph(2,6-F₂) | |
| 14-20 | Me | Me | H | F | F | Ph(2-OCF₃) | |
| 14-21 | Me | Me | H | F | F | Ph(2-OCHF₂) | |
| 14-22 | Me | Me | H | F | F | Ph(2-OMe) | |

TABLE 14-continued

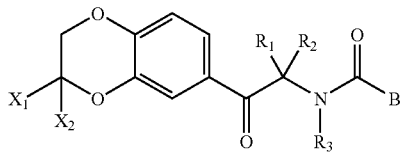

| Compound No. | R₁ | R₂ | R₃ | X₁ | X₂ | B | Physical properties (mp ° C.) |
|---|---|---|---|---|---|---|---|
| 14-23 | Me | Me | H | F | F | Ph(2,6-(OMe)₂) | |
| 14-24 | Me | Me | H | F | F | Ph(2-NO₂) | |
| 14-25 | Me | Me | H | F | F | Ph(2-SMe) | |

TABLE 15

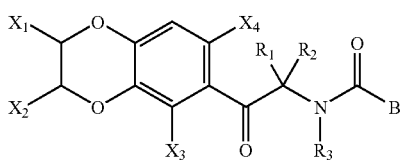

| Compound No. | R₁ | R₂ | R₃ | X₁ | X₂ | X₃ | X₄ | B | Physical properties (mp ° C.) |
|---|---|---|---|---|---|---|---|---|---|
| 15-1 | Me | Me | H | H | H | Me | H | Ph(2-F) | |
| 15-2 | Me | Me | H | H | H | Me | H | Ph(2,6-F₂) | |
| 15-3 | Me | Me | H | H | H | Me | H | Ph(2-Cl) | |
| 15-4 | Me | Me | H | H | H | Me | H | Ph(2-Me) | |
| 15-5 | Me | Me | H | H | H | Me | H | Ph(2-CF₃) | |
| 15-6 | Me | Me | H | H | H | Me | H | Ph(2-F-6-Cl) | |
| 15-7 | Me | Me | H | H | H | H | Me | Ph(2-F) | |
| 15-8 | Me | Me | H | H | H | H | Me | Ph(2,6-F₂) | |
| 15-9 | Me | Me | H | H | H | H | Me | Ph(2-Cl) | |
| 15-10 | Me | Me | H | H | H | H | Me | Ph(2-Me) | |
| 15-11 | Me | Me | H | H | H | H | Me | Ph(2-CF₃) | |
| 15-12 | Me | Me | H | H | H | H | Me | Ph(2-F-6-Cl) | |
| 15-13 | Me | Me | H | Me | H | H | H | Ph(2-F) | |
| 15-14 | Me | Me | H | Me | H | H | H | Ph(2,6-F₂) | |
| 15-15 | Me | Me | H | Me | H | H | H | Ph(2-Cl) | |
| 15-16 | Me | Me | H | Me | H | H | H | Ph(2-Me) | |
| 15-17 | Me | Me | H | Me | H | H | H | Ph(2-CF₃) | |
| 15-18 | Me | Me | H | Me | H | H | H | Ph(2-F-6-Cl) | |
| 15-19 | Me | Me | H | Me | H | Me | H | Ph(2-F) | |
| 15-20 | Me | Me | H | Me | H | Me | H | Ph(2,6-F₂) | |
| 15-21 | Me | Me | H | Me | H | Me | H | Ph(2-Cl) | |
| 15-22 | Me | Me | H | Me | H | Me | H | Ph(2-Me) | |
| 15-23 | Me | Me | H | Me | H | Me | H | Ph(2-CF₃) | |
| 15-24 | Me | Me | H | Me | H | Me | H | Ph(2-F-6-Cl) | |
| 15-25 | Me | Me | H | Me | H | H | Me | Ph(2-F) | |
| 15-26 | Me | Me | H | Me | H | H | Me | Ph(2,6-F₂) | |
| 15-27 | Me | Me | H | Me | H | H | Me | Ph(2-Cl) | |
| 15-28 | Me | Me | H | Me | H | H | Me | Ph(2-Me) | |
| 15-29 | Me | Me | H | Me | H | H | Me | Ph(2-CF₃) | |
| 15-30 | Me | Me | H | Me | H | H | Me | Ph(2-F-6-Cl) | |
| 15-31 | Me | Me | H | H | Me | H | H | Ph(2-F) | |
| 15-32 | Me | Me | H | H | Me | H | H | Ph(2,6-F₂) | |
| 15-33 | Me | Me | H | H | Me | H | H | Ph(2-Cl) | |
| 15-34 | Me | Me | H | H | Me | H | H | Ph(2-Me) | |
| 15-35 | Me | Me | H | H | Me | H | H | Ph(2-CF₃) | |
| 15-36 | Me | Me | H | H | Me | H | H | Ph(2-F-6-Cl) | |
| 15-37 | Me | Me | H | H | Me | Me | H | Ph(2-F) | |
| 15-38 | Me | Me | H | H | Me | Me | H | Ph(2,6-F₂) | |
| 15-39 | Me | Me | H | H | Me | Me | H | Ph(2-Cl) | |
| 15-40 | Me | Me | H | H | Me | Me | H | Ph(2-Me) | |

TABLE 15-continued

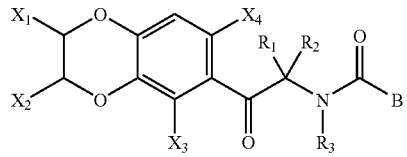

| Compound No. | R₁ | R₂ | R₃ | X₁ | X₂ | X₃ | X₄ | B | Physical properties (mp ° C.) |
|---|---|---|---|---|---|---|---|---|---|
| 15-41 | Me | Me | H | H | Me | Me | H | Ph(2-CF₃) | |
| 15-42 | Me | Me | H | H | Me | Me | H | Ph(2-F-6-Cl) | |
| 15-43 | Me | Me | H | H | Me | H | Me | Ph(2-F) | |
| 15-44 | Me | Me | H | H | Me | H | Me | Ph(2,6-F₂) | |
| 15-45 | Me | Me | H | H | Me | H | Me | Ph(2-Cl) | |
| 15-46 | Me | Me | H | H | Me | H | Me | Ph(2-Me) | |
| 15-47 | Me | Me | H | H | Me | H | Me | Ph(2-CF₃) | |
| 15-48 | Me | Me | H | H | Me | H | Me | Ph(2-F-6-Cl) | |
| 15-49 | Me | Me | H | H | H | Cl | H | Ph(2-F) | |
| 15-50 | Me | Me | H | H | H | Cl | H | Ph(2,6-F₂) | |
| 15-51 | Me | Me | H | H | H | Cl | H | Ph(2-Cl) | |
| 15-52 | Me | Me | H | H | H | Cl | H | Ph(2-Me) | |
| 15-53 | Me | Me | H | H | H | Cl | H | Ph(2-CF₃) | |
| 15-54 | Me | Me | H | H | H | Cl | H | Ph(2-F-6-Cl) | |
| 15-55 | Me | Me | H | H | H | H | Cl | Ph(2-F) | |
| 15-56 | Me | Me | H | H | H | H | Cl | Ph(2,6-F₂) | |
| 15-57 | Me | Me | H | H | H | H | Cl | Ph(2-Cl) | |
| 15-58 | Me | Me | H | H | H | H | Cl | Ph(2-Me) | |
| 15-59 | Me | Me | H | H | H | H | Cl | Ph(2-CF₃) | |
| 15-60 | Me | Me | H | H | H | H | Cl | Ph(2-F-6-Cl) | |
| 15-61 | Me | Me | H | Cl | H | H | H | Ph(2-F) | |
| 15-62 | Me | Me | H | Cl | H | H | H | Ph(2,6-F₂) | |
| 15-63 | Me | Me | H | Cl | H | H | H | Ph(2-Cl) | |
| 15-64 | Me | Me | H | Cl | H | H | H | Ph(2-Me) | |
| 15-65 | Me | Me | H | Cl | H | H | H | Ph(2-CF₃) | |
| 15-66 | Me | Me | H | Cl | H | H | H | Ph(2-F-6-Cl) | |
| 15-67 | Me | Me | H | Me | H | Cl | H | Ph(2-F) | |
| 15-68 | Me | Me | H | Me | H | Cl | H | Ph(2,6-F₂) | |
| 15-69 | Me | Me | H | Me | H | Cl | H | Ph(2-Cl) | |
| 15-70 | Me | Me | H | Me | H | Cl | H | Ph(2-Me) | |
| 15-71 | Me | Me | H | Me | H | Cl | H | Ph(2-CF₃) | |
| 15-72 | Me | Me | H | Me | H | Cl | H | Ph(2-F-6-Cl) | |
| 15-73 | Me | Me | H | Me | H | H | Cl | Ph(2-F) | |
| 15-74 | Me | Me | H | Me | H | H | Cl | Ph(2,6-F₂) | |
| 15-75 | Me | Me | H | Me | H | H | Cl | Ph(2-Cl) | |
| 15-76 | Me | Me | H | Me | H | H | Cl | Ph(2-Me) | |
| 15-77 | Me | Me | H | Me | H | H | Cl | Ph(2-CF₃) | |
| 15-78 | Me | Me | H | Me | H | H | Cl | Ph(2-F-6-Cl) | |
| 15-79 | Me | Me | H | H | Cl | H | H | Ph(2-F) | |
| 15-80 | Me | Me | H | H | Cl | H | H | Ph(2,6-F₂) | |
| 15-81 | Me | Me | H | H | Cl | H | H | Ph(2-Cl) | |
| 15-82 | Me | Me | H | H | Cl | H | H | Ph(2-Me) | |
| 15-83 | Me | Me | H | H | Cl | H | H | Ph(2-CF₃) | |
| 15-84 | Me | Me | H | H | Cl | H | H | Ph(2-F-6-Cl) | |
| 15-85 | Me | Me | H | H | Me | Cl | H | Ph(2-F) | |
| 15-86 | Me | Me | H | H | Me | Cl | H | Ph(2,6-F₂) | |
| 15-87 | Me | Me | H | H | Me | Cl | H | Ph(2-Cl) | |
| 15-88 | Me | Me | H | H | Me | Cl | H | Ph(2-Me) | |
| 15-89 | Me | Me | H | H | Me | Cl | H | Ph(2-CF₃) | |
| 15-90 | Me | Me | H | H | Me | Cl | H | Ph(2-F-6-Cl) | |
| 15-91 | Me | Me | H | H | Me | H | Cl | Ph(2-F) | |
| 15-92 | Me | Me | H | H | Me | H | Cl | Ph(2,6-F₂) | |
| 15-93 | Me | Me | H | H | Me | H | Cl | Ph(2-Cl) | |
| 15-94 | Me | Me | H | H | Me | H | Cl | Ph(2-Me) | |
| 15-95 | Me | Me | H | H | Me | H | Cl | Ph(2-CF₃) | |
| 15-96 | Me | Me | H | H | Me | H | Cl | Ph(2-F-6-Cl) | |

TABLE 16

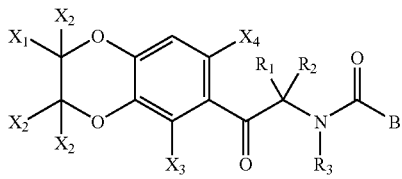

| Compound No. | R₁ | R₂ | R₃ | X₁ | X₂ | X₃ | X₄ | B | Physical properties (mp ° C.) |
|---|---|---|---|---|---|---|---|---|---|
| 16-1 | Me | Me | H | H | F | Me | H | Ph(2-F) | |
| 16-2 | Me | Me | H | H | F | Me | H | Ph(2,6-F₂) | |
| 16-3 | Me | Me | H | H | F | Me | H | Ph(2-Cl) | |
| 16-4 | Me | Me | H | H | F | Me | H | Ph(2-Me) | |
| 16-5 | Me | Me | H | H | F | Me | H | Ph(2-CF₃) | |
| 16-6 | Me | Me | H | H | F | Me | H | Ph(2-F-6-Cl) | |
| 16-7 | Me | Me | H | H | F | H | Me | Ph(2-F) | |
| 16-8 | Me | Me | H | H | F | H | Me | Ph(2,6-F₂) | |
| 16-9 | Me | Me | H | H | F | H | Me | Ph(2-Cl) | |
| 16-10 | Me | Me | H | H | F | H | Me | Ph(2-Me) | |
| 16-11 | Me | Me | H | H | F | H | Me | Ph(2-CF₃) | |
| 16-12 | Me | Me | H | H | F | H | Me | Ph(2-F-6-Cl) | |
| 16-13 | Me | Me | H | F | H | H | H | Ph(2-F) | |
| 16-14 | Me | Me | H | F | H | H | H | Ph(2,6-F₂) | |
| 16-15 | Me | Me | H | F | H | H | H | Ph(2-Cl) | |
| 16-16 | Me | Me | H | F | H | H | H | Ph(2-Me) | |
| 16-17 | Me | Me | H | F | H | H | H | Ph(2-CF₃) | |
| 16-18 | Me | Me | H | F | H | H | H | Ph(2-F-6-Cl) | |
| 16-19 | Me | Me | H | F | H | Me | H | Ph(2-F) | |
| 16-20 | Me | Me | H | F | H | Me | H | Ph(2,6-F₂) | |
| 16-21 | Me | Me | H | F | H | Me | H | Ph(2-Cl) | |
| 16-22 | Me | Me | H | F | H | Me | H | Ph(2-Me) | |
| 16-23 | Me | Me | H | F | H | Me | H | Ph(2-CF₃) | |
| 16-24 | Me | Me | H | F | H | Me | H | Ph(2-F-6-Cl) | |
| 16-25 | Me | Me | H | F | H | H | Me | Ph(2-F) | |
| 16-26 | Me | Me | H | F | H | H | Me | Ph(2,6-F₂) | |
| 16-27 | Me | Me | H | F | H | H | Me | Ph(2-Cl) | |
| 16-28 | Me | Me | H | F | H | H | Me | Ph(2-Me) | |
| 16-29 | Me | Me | H | F | H | H | Me | Ph(2-CF₃) | |
| 16-30 | Me | Me | H | F | H | H | Me | Ph(2-F-6-Cl) | |
| 16-31 | Me | Me | H | F | F | H | H | Ph(2-F) | |
| 16-32 | Me | Me | H | F | F | H | H | Ph(2,6-F₂) | 125-128 |
| 16-33 | Me | Me | H | F | F | H | H | Ph(2-Cl) | |
| 16-34 | Me | Me | H | F | F | H | H | Ph(2-Me) | |
| 16-35 | Me | Me | H | F | F | H | H | Ph(2-CF₃) | |
| 16-36 | Me | Me | H | F | F | H | H | Ph(2-F-6-Cl) | |
| 16-37 | Me | Me | H | F | F | Me | H | Ph(2-F) | 110-112 |
| 16-38 | Me | Me | H | F | F | Me | H | Ph(2,6-F₂) | 128-130 |
| 16-39 | Me | Me | H | F | F | Me | H | Ph(2-Cl) | |
| 16-40 | Me | Me | H | F | F | Me | H | Ph(2-Me) | |
| 16-41 | Me | Me | H | F | F | Me | H | Ph(2-CF₃) | |
| 16-42 | Me | Me | H | F | F | Me | H | Ph(2-F-6-Cl) | |
| 16-43 | Me | Me | H | F | F | H | Me | Ph(2-F) | |
| 16-44 | Me | Me | H | F | F | H | Me | Ph(2,6-F₂) | |
| 16-45 | Me | Me | H | F | F | H | Me | Ph(2-Cl) | |
| 16-46 | Me | Me | H | F | F | H | Me | Ph(2-Me) | |
| 16-47 | Me | Me | H | F | F | H | Me | Ph(2-CF₃) | |
| 16-48 | Me | Me | H | F | F | H | Me | Ph(2-F-6-Cl) | |
| 16-49 | Me | Me | H | H | F | Cl | H | Ph(2-F) | |
| 16-50 | Me | Me | H | H | F | Cl | H | Ph(2,6-F₂) | |
| 16-51 | Me | Me | H | H | F | Cl | H | Ph(2-Cl) | |
| 16-52 | Me | Me | H | H | F | Cl | H | Ph(2-Me) | |
| 16-53 | Me | Me | H | H | F | Cl | H | Ph(2-CF₃) | |
| 16-54 | Me | Me | H | H | F | Cl | H | Ph(2-F-6-Cl) | |
| 16-55 | Me | Me | H | H | F | H | Cl | Ph(2-F) | |
| 16-56 | Me | Me | H | H | F | H | Cl | Ph(2,6-F₂) | |
| 16-57 | Me | Me | H | H | F | H | Cl | Ph(2-Cl) | |
| 16-58 | Me | Me | H | H | F | H | Cl | Ph(2-Me) | |
| 16-59 | Me | Me | H | H | F | H | Cl | Ph(2-CF₃) | |
| 16-60 | Me | Me | H | H | F | H | Cl | Ph(2-F-6-Cl) | |
| 16-61 | Me | Me | H | F | H | Cl | H | Ph(2-F) | |
| 16-62 | Me | Me | H | F | H | Cl | H | Ph(2,6-F₂) | |
| 16-63 | Me | Me | H | F | H | Cl | H | Ph(2-Cl) | |
| 16-64 | Me | Me | H | F | H | Cl | H | Ph(2-Me) | |
| 16-65 | Me | Me | H | F | H | Cl | H | Ph(2-CF₃) | |
| 16-66 | Me | Me | H | F | H | Cl | H | Ph(2-F-6-Cl) | |
| 16-67 | Me | Me | H | F | H | H | Cl | Ph(2-F) | |
| 16-68 | Me | Me | H | F | H | H | Cl | Ph(2,6-F₂) | |
| 16-69 | Me | Me | H | F | H | H | Cl | Ph(2-Cl) | |
| 16-70 | Me | Me | H | F | H | H | Cl | Ph(2-Me) | |
| 16-71 | Me | Me | H | F | H | H | Cl | Ph(2-CF₃) | |
| 16-72 | Me | Me | H | F | H | H | Cl | Ph(2-F-6-Cl) | |
| 16-73 | Me | Me | H | F | F | Cl | H | Ph(2-F) | |
| 16-74 | Me | Me | H | F | F | Cl | H | Ph(2,6-F₂) | |
| 16-75 | Me | Me | H | F | F | Cl | H | Ph(2-Cl) | |
| 16-76 | Me | Me | H | F | F | Cl | H | Ph(2-Me) | |
| 16-77 | Me | Me | H | F | F | Cl | H | Ph(2-CF₃) | |
| 16-78 | Me | Me | H | F | F | Cl | H | Ph(2-F-6-Cl) | |
| 16-79 | Me | Me | H | F | F | H | Cl | Ph(2-F) | |
| 16-80 | Me | Me | H | F | F | H | Cl | Ph(2,6-F₂) | |
| 16-81 | Me | Me | H | F | F | H | Cl | Ph(2-Cl) | |
| 16-82 | Me | Me | H | F | F | H | Cl | Ph(2-Me) | |
| 16-83 | Me | Me | H | F | F | H | Cl | Ph(2-CF₃) | |
| 16-84 | Me | Me | H | F | F | H | Cl | Ph(2-F-6-Cl) | |

TABLE 17

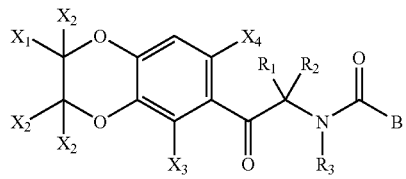

| Compound No. | R₁ | R₂ | R₃ | X₁ | X₂ | X₃ | X₄ | B | Physical properties (mp ° C.) |
|---|---|---|---|---|---|---|---|---|---|
| 17-1 | Me | Me | H | F | H | H | H | Ph(2-F) | |
| 17-2 | Me | Me | H | F | H | H | H | Ph(2,6-F₂) | |
| 17-3 | Me | Me | H | F | H | H | H | Ph(2-Cl) | |
| 17-4 | Me | Me | H | F | H | H | H | Ph(2-Me) | |
| 17-5 | Me | Me | H | F | H | H | H | Ph(2-CF₃) | |
| 17-6 | Me | Me | H | F | H | H | H | Ph(2-F-6-Cl) | |
| 17-7 | Me | Me | H | F | H | Me | H | Ph(2-F) | |
| 17-8 | Me | Me | H | F | H | Me | H | Ph(2,6-F₂) | |
| 17-9 | Me | Me | H | F | H | Me | H | Ph(2-Cl) | |
| 17-10 | Me | Me | H | F | H | Me | H | Ph(2-Me) | |
| 17-11 | Me | Me | H | F | H | Me | H | Ph(2-CF₃) | |
| 17-12 | Me | Me | H | F | H | Me | H | Ph(2-F-6-Cl) | |
| 17-13 | Me | Me | H | F | Cl | H | H | Ph(2-F) | |
| 17-14 | Me | Me | H | F | Cl | H | H | Ph(2,6-F₂) | |
| 17-15 | Me | Me | H | F | Cl | H | H | Ph(2-Cl) | |
| 17-16 | Me | Me | H | F | Cl | H | H | Ph(2-Me) | |
| 17-17 | Me | Me | H | F | Cl | H | H | Ph(2-CF₃) | |
| 17-18 | Me | Me | H | F | Cl | H | H | Ph(2-F-6-Cl) | |

TABLE 17-continued

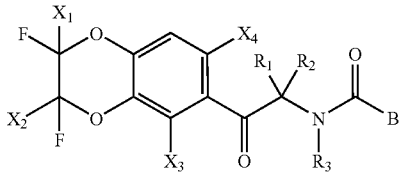

| Compound No. | R₁ | R₂ | R₃ | X₁ | X₂ | X₃ | X₄ | B | Physical properties (mp ° C.) |
|---|---|---|---|---|---|---|---|---|---|
| 17-19 | Me | Me | H | F | Cl | Me | H | Ph(2-F) | |
| 17-20 | Me | Me | H | F | Cl | Me | H | Ph(2,6-F₂) | |
| 17-21 | Me | Me | H | F | Cl | Me | H | Ph(2-Cl) | |
| 17-22 | Me | Me | H | F | Cl | Me | H | Ph(2-Me) | |
| 17-23 | Me | Me | H | F | Cl | Me | H | Ph(2-CF₃) | |
| 17-24 | Me | Me | H | F | Cl | Me | H | Ph(2-F-6-Cl) | |
| 17-25 | Me | Me | H | H | F | H | H | Ph(2-F) | |
| 17-26 | Me | Me | H | H | F | H | H | Ph(2,6-F₂) | |
| 17-27 | Me | Me | H | H | F | H | H | Ph(2-Cl) | |
| 17-28 | Me | Me | H | H | F | H | H | Ph(2-Me) | |
| 17-29 | Me | Me | H | H | F | H | H | Ph(2-CF₃) | |
| 17-30 | Me | Me | H | H | F | H | H | Ph(2-F-6-Cl) | |
| 17-31 | Me | Me | H | H | F | Me | H | Ph(2-F) | |
| 17-32 | Me | Me | H | H | F | Me | H | Ph(2,6-F₂) | |
| 17-33 | Me | Me | H | H | F | Me | H | Ph(2-Cl) | |
| 17-34 | Me | Me | H | H | F | Me | H | Ph(2-Me) | |
| 17-35 | Me | Me | H | H | F | Me | H | Ph(2-CF₃) | |
| 17-36 | Me | Me | H | H | F | Me | H | Ph(2-F-6-Cl) | |
| 17-37 | Me | Me | H | Cl | F | H | H | Ph(2-F) | |
| 17-38 | Me | Me | H | Cl | F | H | H | Ph(2,6-F₂) | |
| 17-39 | Me | Me | H | Cl | F | H | H | Ph(2-Cl) | |
| 17-40 | Me | Me | H | Cl | F | H | H | Ph(2-Me) | |
| 17-41 | Me | Me | H | Cl | F | H | H | Ph(2-CF₃) | |
| 17-42 | Me | Me | H | Cl | F | H | H | Ph(2-F-6-Cl) | |
| 17-43 | Me | Me | H | Cl | F | Me | H | Ph(2-F) | |
| 17-44 | Me | Me | H | Cl | F | Me | H | Ph(2,6-F₂) | |
| 17-45 | Me | Me | H | Cl | F | Me | H | Ph(2-Cl) | |
| 17-46 | Me | Me | H | Cl | F | Me | H | Ph(2-Me) | |
| 17-47 | Me | Me | H | Cl | F | Me | H | Ph(2-CF₃) | |
| 17-48 | Me | Me | H | Cl | F | Me | H | Ph(2-F-6-Cl) | |
| 17-49 | Me | Me | H | F | H | Cl | H | Ph(2-F) | |
| 17-50 | Me | Me | H | F | H | Cl | H | Ph(2,6-F₂) | |
| 17-51 | Me | Me | H | F | H | Cl | H | Ph(2-Cl) | |
| 17-52 | Me | Me | H | F | H | Cl | H | Ph(2-Me) | |
| 17-53 | Me | Me | H | F | H | Cl | H | Ph(2-CF₃) | |
| 17-54 | Me | Me | H | F | H | Cl | H | Ph(2-F-6-Cl) | |
| 17-55 | Me | Me | H | F | Cl | Cl | H | Ph(2-F) | |
| 17-56 | Me | Me | H | F | Cl | Cl | H | Ph(2,6-F₂) | |
| 17-57 | Me | Me | H | F | Cl | Cl | H | Ph(2-Cl) | |
| 17-58 | Me | Me | H | F | Cl | Cl | H | Ph(2-Me) | |
| 17-59 | Me | Me | H | F | Cl | Cl | H | Ph(2-CF₃) | |
| 17-60 | Me | Me | H | F | Cl | Cl | H | Ph(2-F-6-Cl) | |
| 17-61 | Me | Me | H | H | F | Cl | H | Ph(2-F) | |
| 17-62 | Me | Me | H | H | F | Cl | H | Ph(2,6-F₂) | |
| 17-63 | Me | Me | H | H | F | Cl | H | Ph(2-Cl) | |
| 17-64 | Me | Me | H | H | F | Cl | H | Ph(2-Me) | |
| 17-65 | Me | Me | H | H | F | Cl | H | Ph(2-CF₃) | |
| 17-66 | Me | Me | H | H | F | Cl | H | Ph(2-F-6-Cl) | |
| 17-67 | Me | Me | H | Cl | F | Cl | H | Ph(2-F) | |
| 17-68 | Me | Me | H | Cl | F | Cl | H | Ph(2,6-F₂) | |
| 17-69 | Me | Me | H | Cl | F | Cl | H | Ph(2-Cl) | |
| 17-70 | Me | Me | H | Cl | F | Cl | H | Ph(2-Me) | |
| 17-71 | Me | Me | H | Cl | F | Cl | H | Ph(2-CF₃) | |
| 17-72 | Me | Me | H | Cl | F | Cl | H | Ph(2-F-6-Cl) | |

TABLE 18

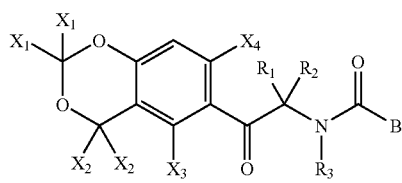

| Compound No. | R₁ | R₂ | R₃ | X₁ | X₂ | X₃ | X₄ | B | Physical properties (mp ° C.) |
|---|---|---|---|---|---|---|---|---|---|
| 18-1 | Me | Me | H | H | H | H | H | Ph(2-F) | |
| 18-2 | Me | Me | H | H | H | H | H | Ph(2,6-F₂) | |
| 18-3 | Me | Me | H | H | H | H | H | Ph(2-Cl) | |
| 18-4 | Me | Me | H | H | H | H | H | Ph(2-Me) | |
| 18-5 | Me | Me | H | H | H | H | H | Ph(2-CF₃) | |
| 18-6 | Me | Me | H | H | H | H | H | Ph(2-F-6-Cl) | |
| 18-7 | Me | Me | H | H | H | Me | H | Ph(2-F) | |
| 18-8 | Me | Me | H | H | H | Me | H | Ph(2,6-F₂) | |
| 18-9 | Me | Me | H | H | H | Me | H | Ph(2-Cl) | |
| 18-10 | Me | Me | H | H | H | Me | H | Ph(2-Me) | |
| 18-11 | Me | Me | H | H | H | Me | H | Ph(2-CF₃) | |
| 18-12 | Me | Me | H | H | H | Me | H | Ph(2-F-6-Cl) | |
| 18-13 | Me | Me | H | F | H | H | H | Ph(2-F) | |
| 18-14 | Me | Me | H | F | H | H | H | Ph(2,6-F₂) | |
| 18-15 | Me | Me | H | F | H | H | H | Ph(2-Cl) | |
| 18-16 | Me | Me | H | F | H | H | H | Ph(2-Me) | |
| 18-17 | Me | Me | H | F | H | H | H | Ph(2-CF₃) | |
| 18-18 | Me | Me | H | F | H | H | H | Ph(2-F-6-Cl) | |
| 18-19 | Me | Me | H | F | H | Me | H | Ph(2-F) | |
| 18-20 | Me | Me | H | F | H | Me | H | Ph(2,6-F₂) | |
| 18-21 | Me | Me | H | F | H | Me | H | Ph(2-Cl) | |
| 18-22 | Me | Me | H | F | H | Me | H | Ph(2-Me) | |
| 18-23 | Me | Me | H | F | H | Me | H | Ph(2-CF₃) | |
| 18-24 | Me | Me | H | F | H | Me | H | Ph(2-F-6-Cl) | |
| 18-25 | Me | Me | H | F | H | H | Me | Ph(2-F) | |
| 18-26 | Me | Me | H | F | H | H | Me | Ph(2,6-F₂) | |
| 18-27 | Me | Me | H | F | H | H | Me | Ph(2-Cl) | |
| 18-28 | Me | Me | H | F | H | H | Me | Ph(2-Me) | |
| 18-29 | Me | Me | H | F | H | H | Me | Ph(2-CF₃) | |
| 18-30 | Me | Me | H | F | H | H | Me | Ph(2-F-6-Cl) | |
| 18-31 | Me | Me | H | F | F | H | H | Ph(2-F) | |
| 18-32 | Me | Me | H | F | F | H | H | Ph(2,6-F₂) | |
| 18-33 | Me | Me | H | F | F | H | H | Ph(2-Cl) | |
| 18-34 | Me | Me | H | F | F | H | H | Ph(2-Me) | |
| 18-35 | Me | Me | H | F | F | H | H | Ph(2-CF₃) | |
| 18-36 | Me | Me | H | F | F | H | H | Ph(2-F-6-Cl) | |
| 18-37 | Me | Me | H | F | F | Me | H | Ph(2-F) | |
| 18-38 | Me | Me | H | F | F | Me | H | Ph(2,6-F₂) | |
| 18-39 | Me | Me | H | F | F | Me | H | Ph(2-Cl) | |
| 18-40 | Me | Me | H | F | F | Me | H | Ph(2-Me) | |
| 18-41 | Me | Me | H | F | F | Me | H | Ph(2-CF₃) | |
| 18-42 | Me | Me | H | F | F | Me | H | Ph(2-F-6-Cl) | |
| 18-43 | Me | Me | H | F | F | H | Me | Ph(2-F) | |
| 18-44 | Me | Me | H | F | F | H | Me | Ph(2,6-F₂) | |
| 18-45 | Me | Me | H | F | F | H | Me | Ph(2-Cl) | |
| 18-46 | Me | Me | H | F | F | H | Me | Ph(2-Me) | |
| 18-47 | Me | Me | H | F | F | H | Me | Ph(2-CF₃) | |
| 18-48 | Me | Me | H | F | F | H | Me | Ph(2-F-6-Cl) | |

TABLE 19

| Compound No. | R₁ | R₂ | R₃ | X₁ | X₂ | B | Physical properties (mp ° C.) |
|---|---|---|---|---|---|---|---|
| 19-1 | Me | Me | H | H | H | Ph(2-F) | |
| 19-2 | Me | Me | H | H | H | Ph(2,6-F₂) | |
| 19-3 | Me | Me | H | H | H | Ph(2-Cl) | |
| 19-4 | Me | Me | H | H | H | Ph(2-Me) | |
| 19-5 | Me | Me | H | H | H | Ph(2-CF₃) | |
| 19-6 | Me | Me | H | H | H | Ph(2-F-6-Cl) | |
| 19-7 | Me | Me | H | H | Cl | Ph(2-F) | |
| 19-8 | Me | Me | H | H | Cl | Ph(2,6-F₂) | |
| 19-9 | Me | Me | H | H | Cl | Ph(2-Cl) | |
| 19-10 | Me | Me | H | H | Cl | Ph(2-Me) | |
| 19-11 | Me | Me | H | H | Cl | Ph(2-CF₃) | |
| 19-12 | Me | Me | H | H | Cl | Ph(2-F-6-Cl) | |
| 19-13 | Me | Me | H | H | Me | Ph(2-F) | |
| 19-14 | Me | Me | H | H | Me | Ph(2,6-F₂) | |
| 19-15 | Me | Me | H | H | Me | Ph(2-Cl) | |
| 19-16 | Me | Me | H | H | Me | Ph(2-Me) | |
| 19-17 | Me | Me | H | H | Me | Ph(2-CF₃) | |
| 19-18 | Me | Me | H | H | Me | Ph(2-F-6-Cl) | |
| 19-19 | Me | Me | H | H | OMe | Ph(2-F) | |
| 19-20 | Me | Me | H | H | OMe | Ph(2,6-F₂) | |
| 19-21 | Me | Me | H | H | OMe | Ph(2-Cl) | |
| 19-22 | Me | Me | H | H | OMe | Ph(2-Me) | |
| 19-23 | Me | Me | H | H | OMe | Ph(2-CF₃) | |
| 19-24 | Me | Me | H | H | OMe | Ph(2-F-6-Cl) | |
| 19-25 | Me | Me | H | F | H | Ph(2-F) | |
| 19-26 | Me | Me | H | F | H | Ph(2,6-F₂) | |
| 19-27 | Me | Me | H | F | H | Ph(2-Cl) | |
| 19-28 | Me | Me | H | F | H | Ph(2-Me) | |
| 19-29 | Me | Me | H | F | H | Ph(2-CF₃) | |
| 19-30 | Me | Me | H | F | H | Ph(2-F-6-Cl) | |
| 19-31 | Me | Me | H | F | Cl | Ph(2-F) | |
| 19-32 | Me | Me | H | F | Cl | Ph(2,6-F₂) | |
| 19-33 | Me | Me | H | F | Cl | Ph(2-Cl) | |
| 19-34 | Me | Me | H | F | Cl | Ph(2-Me) | |
| 19-35 | Me | Me | H | F | Cl | Ph(2-CF₃) | |
| 19-36 | Me | Me | H | F | Cl | Ph(2-F-6-Cl) | |
| 19-37 | Me | Me | H | F | Me | Ph(2-F) | |
| 19-38 | Me | Me | H | F | Me | Ph(2,6-F₂) | |
| 19-39 | Me | Me | H | F | Me | Ph(2-Cl) | |
| 19-40 | Me | Me | H | F | Me | Ph(2-Me) | |
| 19-41 | Me | Me | H | F | Me | Ph(2-CF₃) | |
| 19-42 | Me | Me | H | F | Me | Ph(2-F-6-Cl) | |
| 19-43 | Me | Me | H | F | OMe | Ph(2-F) | |
| 19-44 | Me | Me | H | F | OMe | Ph(2,6-F₂) | |
| 19-45 | Me | Me | H | F | OMe | Ph(2-Cl) | |
| 19-46 | Me | Me | H | F | OMe | Ph(2-Me) | |
| 19-47 | Me | Me | H | F | OMe | Ph(2-CF₃) | |
| 19-48 | Me | Me | H | F | OMe | Ph(2-F-6-Cl) | |
| 19-49 | Me | Me | H | H | Br | Ph(2-F) | |
| 19-50 | Me | Me | H | H | Br | Ph(2,6-F₂) | |
| 19-51 | Me | Me | H | H | Br | Ph(2-Cl) | |
| 19-52 | Me | Me | H | H | Br | Ph(2-Me) | |
| 19-53 | Me | Me | H | H | Br | Ph(2-CF₃) | |
| 19-54 | Me | Me | H | H | Br | Ph(2-F-6-Cl) | |
| 19-55 | Me | Me | H | H | CF₃ | Ph(2-F) | |
| 19-56 | Me | Me | H | H | CF₃ | Ph(2,6-F₂) | |
| 19-57 | Me | Me | H | H | CF₃ | Ph(2-Cl) | |
| 19-58 | Me | Me | H | H | CF₃ | Ph(2-Me) | |
| 19-59 | Me | Me | H | H | CF₃ | Ph(2-CF₃) | |
| 19-60 | Me | Me | H | H | CF₃ | Ph(2-F-6-Cl) | |
| 19-61 | Me | Me | H | H | OCF₃ | Ph(2-F) | |
| 19-62 | Me | Me | H | H | OCF₃ | Ph(2,6-F₂) | |
| 19-63 | Me | Me | H | H | OCF₃ | Ph(2-Cl) | |
| 19-64 | Me | Me | H | H | OCF₃ | Ph(2-Me) | |
| 19-65 | Me | Me | H | H | OCF₃ | Ph(2-CF₃) | |
| 19-66 | Me | Me | H | H | OCF₃ | Ph(2-F-6-Cl) | |
| 19-67 | Me | Me | H | H | OCH₂CF₃ | Ph(2-F) | |
| 19-68 | Me | Me | H | H | OCH₂CF₃ | Ph(2,6-F₂) | |
| 19-69 | Me | Me | H | H | OCH₂CF₃ | Ph(2-Cl) | |
| 19-70 | Me | Me | H | H | OCH₂CF₃ | Ph(2-Me) | |
| 19-71 | Me | Me | H | H | OCH₂CF₃ | Ph(2-CF₃) | |
| 19-72 | Me | Me | H | H | OCH₂CF₃ | Ph(2-F-6-Cl) | |
| 19-73 | Me | Me | H | H | OCHF₂ | Ph(2-F) | |
| 19-74 | Me | Me | H | H | OCHF₂ | Ph(2,6-F₂) | |
| 19-75 | Me | Me | H | H | OCHF₂ | Ph(2-Cl) | |
| 19-76 | Me | Me | H | H | OCHF₂ | Ph(2-Me) | |
| 19-77 | Me | Me | H | H | OCHF₂ | Ph(2-CF₃) | |
| 19-78 | Me | Me | H | H | OCHF₂ | Ph(2-F-6-Cl) | |
| 19-79 | Me | Me | H | F | Br | Ph(2-F) | |
| 19-80 | Me | Me | H | F | Br | Ph(2,6-F₂) | |
| 19-81 | Me | Me | H | F | Br | Ph(2-Cl) | |
| 19-82 | Me | Me | H | F | Br | Ph(2-Me) | |
| 19-83 | Me | Me | H | F | Br | Ph(2-CF₃) | |
| 19-84 | Me | Me | H | F | Br | Ph(2-F-6-Cl) | |
| 19-85 | Me | Me | H | F | CF₃ | Ph(2-F) | |
| 19-86 | Me | Me | H | F | CF₃ | Ph(2,6-F₂) | |
| 19-87 | Me | Me | H | F | CF₃ | Ph(2-Cl) | |
| 19-88 | Me | Me | H | F | CF₃ | Ph(2-Me) | |
| 19-89 | Me | Me | H | F | CF₃ | Ph(2-CF₃) | |
| 19-90 | Me | Me | H | F | CF₃ | Ph(2-F-6-Cl) | |
| 19-91 | Me | Me | H | F | OCF₃ | Ph(2-F) | |
| 19-92 | Me | Me | H | F | OCF₃ | Ph(2,6-F₂) | |
| 19-93 | Me | Me | H | F | OCF₃ | Ph(2-Cl) | |
| 19-94 | Me | Me | H | F | OCF₃ | Ph(2-Me) | |
| 19-95 | Me | Me | H | F | OCF₃ | Ph(2-CF₃) | |
| 19-96 | Me | Me | H | F | OCF₃ | Ph(2-F-6-Cl) | |
| 19-97 | Me | Me | H | F | OCH₂CF₃ | Ph(2-F) | |
| 19-98 | Me | Me | H | F | OCH₂CF₃ | Ph(2,6-F₂) | |
| 19-99 | Me | Me | H | F | OCH₂CF₃ | Ph(2-Cl) | |
| 19-100 | Me | Me | H | F | OCH₂CF₃ | Ph(2-Me) | |
| 19-101 | Me | Me | H | F | OCH₂CF₃ | Ph(2-CF₃) | |
| 19-102 | Me | Me | H | F | OCH₂CF₃ | Ph(2-F-6-Cl) | |
| 19-103 | Me | Me | H | F | OCHF₂ | Ph(2-F) | |
| 19-104 | Me | Me | H | F | OCHF₂ | Ph(2,6-F₂) | |
| 19-105 | Me | Me | H | F | OCHF₂ | Ph(2-Cl) | |
| 19-106 | Me | Me | H | F | OCHF₂ | Ph(2-Me) | |
| 19-107 | Me | Me | H | F | OCHF₂ | Ph(2-CF₃) | |
| 19-108 | Me | Me | H | F | OCHF₂ | Ph(2-F-6-Cl) | |

TABLE 20

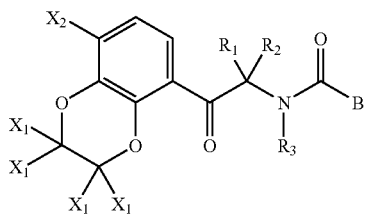

| Compound No. | R₁ | R₂ | R₃ | X₁ | X₂ | B | Physical properties (mp ° C.) |
|---|---|---|---|---|---|---|---|
| 20-1 | Me | Me | H | H | H | Ph(2-F) | |
| 20-2 | Me | Me | H | H | H | Ph(2,6-F₂) | |
| 20-3 | Me | Me | H | H | H | Ph(2-Cl) | |
| 20-4 | Me | Me | H | H | H | Ph(2-Me) | |
| 20-5 | Me | Me | H | H | H | Ph(2-CF₃) | |
| 20-6 | Me | Me | H | H | H | Ph(2-F-6-Cl) | |
| 20-7 | Me | Me | H | H | Cl | Ph(2-F) | |
| 20-8 | Me | Me | H | H | Cl | Ph(2,6-F₂) | |
| 20-9 | Me | Me | H | H | Cl | Ph(2-Cl) | |
| 20-10 | Me | Me | H | H | Cl | Ph(2-Me) | |
| 20-11 | Me | Me | H | H | Cl | Ph(2-CF₃) | |
| 20-12 | Me | Me | H | H | Cl | Ph(2-F-6-Cl) | |
| 20-13 | Me | Me | H | H | Me | Ph(2-F) | |
| 20-14 | Me | Me | H | H | Me | Ph(2,6-F₂) | |
| 20-15 | Me | Me | H | H | Me | Ph(2-Cl) | |
| 20-16 | Me | Me | H | H | Me | Ph(2-Me) | |
| 20-17 | Me | Me | H | H | Me | Ph(2-CF₃) | |
| 20-18 | Me | Me | H | H | Me | Ph(2-F-6-Cl) | |
| 20-19 | Me | Me | H | H | OMe | Ph(2-F) | |
| 20-20 | Me | Me | H | H | OMe | Ph(2,6-F₂) | |
| 20-21 | Me | Me | H | H | OMe | Ph(2-Cl) | |
| 20-22 | Me | Me | H | H | OMe | Ph(2-Me) | |
| 20-23 | Me | Me | H | H | OMe | Ph(2-CF₃) | |
| 20-24 | Me | Me | H | H | OMe | Ph(2-F-6-Cl) | |
| 20-25 | Me | Me | H | F | H | Ph(2-F) | |
| 20-26 | Me | Me | H | F | H | Ph(2,6-F₂) | |
| 20-27 | Me | Me | H | F | H | Ph(2-Cl) | |
| 20-28 | Me | Me | H | F | H | Ph(2-Me) | |
| 20-29 | Me | Me | H | F | H | Ph(2-CF₃) | |
| 20-30 | Me | Me | H | F | H | Ph(2-F-6-Cl) | |
| 20-31 | Me | Me | H | F | Cl | Ph(2-F) | |
| 20-32 | Me | Me | H | F | Cl | Ph(2,6-F₂) | |
| 20-33 | Me | Me | H | F | Cl | Ph(2-Cl) | |
| 20-34 | Me | Me | H | F | Cl | Ph(2-Me) | |
| 20-35 | Me | Me | H | F | Cl | Ph(2-CF₃) | |
| 20-36 | Me | Me | H | F | Cl | Ph(2-F-6-Cl) | |
| 20-37 | Me | Me | H | F | Me | Ph(2-F) | |
| 20-38 | Me | Me | H | F | Me | Ph(2,6-F₂) | |
| 20-39 | Me | Me | H | F | Me | Ph(2-Cl) | |
| 20-40 | Me | Me | H | F | Me | Ph(2-Me) | |
| 20-41 | Me | Me | H | F | Me | Ph(2-CF₃) | |
| 20-42 | Me | Me | H | F | Me | Ph(2-F-6-Cl) | |
| 20-43 | Me | Me | H | F | OMe | Ph(2-F) | |
| 20-44 | Me | Me | H | F | OMe | Ph(2,6-F₂) | |
| 20-45 | Me | Me | H | F | OMe | Ph(2-Cl) | |
| 20-46 | Me | Me | H | F | OMe | Ph(2-Me) | |
| 20-47 | Me | Me | H | F | OMe | Ph(2-CF₃) | |
| 20-48 | Me | Me | H | F | OMe | Ph(2-F-6-Cl) | |
| 20-49 | Me | Me | H | H | Br | Ph(2-F) | |
| 20-50 | Me | Me | H | H | Br | Ph(2,6-F₂) | |
| 20-51 | Me | Me | H | H | Br | Ph(2-Cl) | |
| 20-52 | Me | Me | H | H | Br | Ph(2-Me) | |
| 20-53 | Me | Me | H | H | Br | Ph(2-CF₃) | |
| 20-54 | Me | Me | H | H | Br | Ph(2-F-6-Cl) | |
| 20-55 | Me | Me | H | H | CF₃ | Ph(2-F) | |
| 20-56 | Me | Me | H | H | CF₃ | Ph(2,6-F₂) | |
| 20-57 | Me | Me | H | H | CF₃ | Ph(2-Cl) | |
| 20-58 | Me | Me | H | H | CF₃ | Ph(2-Me) | |
| 20-59 | Me | Me | H | H | CF₃ | Ph(2-CF₃) | |
| 20-60 | Me | Me | H | H | CF₃ | Ph(2-F-6-Cl) | |
| 20-61 | Me | Me | H | H | OCF₃ | Ph(2-F) | |
| 20-62 | Me | Me | H | H | OCF₃ | Ph(2,6-F₂) | |
| 20-63 | Me | Me | H | H | OCF₃ | Ph(2-Cl) | |
| 20-64 | Me | Me | H | H | OCF₃ | Ph(2-Me) | |
| 20-65 | Me | Me | H | H | OCF₃ | Ph(2-CF₃) | |
| 20-66 | Me | Me | H | H | OCF₃ | Ph(2-F-6-Cl) | |
| 20-67 | Me | Me | H | H | OCH₂CF₃ | Ph(2-F) | |
| 20-68 | Me | Me | H | H | OCH₂CF₃ | Ph(2,6-F₂) | |
| 20-69 | Me | Me | H | H | OCH₂CF₃ | Ph(2-Cl) | |
| 20-70 | Me | Me | H | H | OCH₂CF₃ | Ph(2-Me) | |
| 20-71 | Me | Me | H | H | OCH₂CF₃ | Ph(2-CF₃) | |
| 20-72 | Me | Me | H | H | OCH₂CF₃ | Ph(2-F-6-Cl) | |
| 20-73 | Me | Me | H | H | OCHF₂ | Ph(2-F) | |
| 20-74 | Me | Me | H | H | OCHF₂ | Ph(2,6-F₂) | |
| 20-75 | Me | Me | H | H | OCHF₂ | Ph(2-Cl) | |
| 20-76 | Me | Me | H | H | OCHF₂ | Ph(2-Me) | |
| 20-77 | Me | Me | H | H | OCHF₂ | Ph(2-CF₃) | |
| 20-78 | Me | Me | H | H | OCHF₂ | Ph(2-F-6-Cl) | |
| 20-79 | Me | Me | H | F | Br | Ph(2-F) | |
| 20-80 | Me | Me | H | F | Br | Ph(2,6-F₂) | |
| 20-81 | Me | Me | H | F | Br | Ph(2-Cl) | |
| 20-82 | Me | Me | H | F | Br | Ph(2-Me) | |
| 20-83 | Me | Me | H | F | Br | Ph(2-CF₃) | |
| 20-84 | Me | Me | H | F | Br | Ph(2-F-6-Cl) | |
| 20-85 | Me | Me | H | F | CF₃ | Ph(2-F) | |
| 20-86 | Me | Me | H | F | CF₃ | Ph(2,6-F₂) | |
| 20-87 | Me | Me | H | F | CF₃ | Ph(2-Cl) | |
| 20-88 | Me | Me | H | F | CF₃ | Ph(2-Me) | |
| 20-89 | Me | Me | H | F | CF₃ | Ph(2-CF₃) | |
| 20-90 | Me | Me | H | F | CF₃ | Ph(2-F-6-Cl) | |
| 20-91 | Me | Me | H | F | OCF₃ | Ph(2-F) | |
| 20-92 | Me | Me | H | F | OCF₃ | Ph(2,6-F₂) | |
| 20-93 | Me | Me | H | F | OCF₃ | Ph(2-Cl) | |
| 20-94 | Me | Me | H | F | OCF₃ | Ph(2-Me) | |
| 20-95 | Me | Me | H | F | OCF₃ | Ph(2-CF₃) | |
| 20-96 | Me | Me | H | F | OCF₃ | Ph(2-F-6-Cl) | |
| 20-97 | Me | Me | H | F | OCH₂CF₃ | Ph(2-F) | |
| 20-98 | Me | Me | H | F | OCH₂CF₃ | Ph(2,6-F₂) | |
| 20-99 | Me | Me | H | F | OCH₂CF₃ | Ph(2-Cl) | |
| 20-100 | Me | Me | H | F | OCH₂CF₃ | Ph(2-Me) | |
| 20-101 | Me | Me | H | F | OCH₂CF₃ | Ph(2-CF₃) | |
| 20-102 | Me | Me | H | F | OCH₂CF₃ | Ph(2-F-6-Cl) | |
| 20-103 | Me | Me | H | F | OCHF₂ | Ph(2-F) | |
| 20-104 | Me | Me | H | F | OCHF₂ | Ph(2,6-F₂) | |
| 20-105 | Me | Me | H | F | OCHF₂ | Ph(2-Cl) | |
| 20-106 | Me | Me | H | F | OCHF₂ | Ph(2-Me) | |
| 20-107 | Me | Me | H | F | OCHF₂ | Ph(2-CF₃) | |
| 20-108 | Me | Me | H | F | OCHF₂ | Ph(2-F-6-Cl) | |

TABLE 21

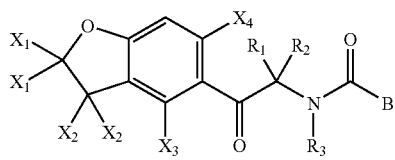

| Compound No. | R₁ | R₂ | R₃ | X₁ | X₂ | X₃ | X₄ | B | Physical properties (mp ° C.) |
|---|---|---|---|---|---|---|---|---|---|
| 21-1 | Me | Me | H | H | H | H | H | Ph(2-F) | |
| 21-2 | Me | Me | H | H | H | H | H | Ph(2,6-F₂) | |
| 21-3 | Me | Me | H | H | H | H | H | Ph(2-Cl) | |
| 21-4 | Me | Me | H | H | H | H | H | Ph(2-Me) | |

TABLE 21-continued

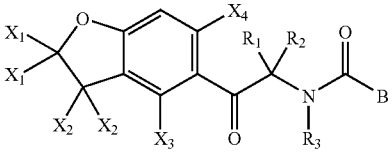

| Compound No. | R₁ | R₂ | R₃ | X₁ | X₂ | X₃ | X₄ | B | Physical properties (mp ° C.) |
|---|---|---|---|---|---|---|---|---|---|
| 21-5 | Me | Me | H | H | H | H | H | Ph(2-CF₃) | |
| 21-6 | Me | Me | H | H | H | H | H | Ph(2-F-6-Cl) | |
| 21-7 | Me | Me | H | H | H | Cl | H | Ph(2-F) | |
| 21-8 | Me | Me | H | H | H | Cl | H | Ph(2,6-F₂) | |
| 21-9 | Me | Me | H | H | H | Cl | H | Ph(2-Cl) | |
| 21-10 | Me | Me | H | H | H | Cl | H | Ph(2-Me) | |
| 21-11 | Me | Me | H | H | H | Cl | H | Ph(2-CF₃) | |
| 21-12 | Me | Me | H | H | H | Cl | H | Ph(2-F-6-Cl) | |
| 21-13 | Me | Me | H | H | H | Me | H | Ph(2-F) | |
| 21-14 | Me | Me | H | H | H | Me | H | Ph(2,6-F₂) | |
| 21-15 | Me | Me | H | H | H | Me | H | Ph(2-Cl) | |
| 21-16 | Me | Me | H | H | H | Me | H | Ph(2-Me) | |
| 21-17 | Me | Me | H | H | H | Me | H | Ph(2-CF₃) | |
| 21-18 | Me | Me | H | H | H | Me | H | Ph(2-F-6-Cl) | |
| 21-19 | Me | Me | H | H | H | H | Me | Ph(2-F) | |
| 21-20 | Me | Me | H | H | H | H | Me | Ph(2,6-F₂) | |
| 21-21 | Me | Me | H | H | H | H | Me | Ph(2-Cl) | |
| 21-22 | Me | Me | H | H | H | H | Me | Ph(2-Me) | |
| 21-23 | Me | Me | H | H | H | H | Me | Ph(2-CF₃) | |
| 21-24 | Me | Me | H | H | H | H | Me | Ph(2-F-6-Cl) | |
| 21-25 | Me | Me | H | F | F | H | H | Ph(2-F) | |
| 21-26 | Me | Me | H | F | F | H | H | Ph(2,6-F₂) | |
| 21-27 | Me | Me | H | F | F | H | H | Ph(2-Cl) | |
| 21-28 | Me | Me | H | F | F | H | H | Ph(2-Me) | |
| 21-29 | Me | Me | H | F | F | H | H | Ph(2-CF₃) | |
| 21-30 | Me | Me | H | F | F | H | H | Ph(2-F-6-Cl) | |
| 21-31 | Me | Me | H | F | F | Cl | H | Ph(2-F) | |
| 21-32 | Me | Me | H | F | F | Cl | H | Ph(2,6-F₂) | |
| 21-33 | Me | Me | H | F | F | Cl | H | Ph(2-Cl) | |
| 21-34 | Me | Me | H | F | F | Cl | H | Ph(2-Me) | |
| 21-35 | Me | Me | H | F | F | Cl | H | Ph(2-CF₃) | |
| 21-36 | Me | Me | H | F | F | Cl | H | Ph(2-F-6-Cl) | |
| 21-37 | Me | Me | H | F | F | Me | H | Ph(2-F) | |
| 21-38 | Me | Me | H | F | F | Me | H | Ph(2,6-F₂) | |
| 21-39 | Me | Me | H | F | F | Me | H | Ph(2-Cl) | |
| 21-40 | Me | Me | H | F | F | Me | H | Ph(2-Me) | |
| 21-41 | Me | Me | H | F | F | Me | H | Ph(2-CF₃) | |
| 21-42 | Me | Me | H | F | F | Me | H | Ph(2-F-6-Cl) | |
| 21-43 | Me | Me | H | F | F | H | Me | Ph(2-F) | |
| 21-44 | Me | Me | H | F | F | H | Me | Ph(2,6-F₂) | |
| 21-45 | Me | Me | H | F | F | H | Me | Ph(2-Cl) | |
| 21-46 | Me | Me | H | F | F | H | Me | Ph(2-Me) | |
| 21-47 | Me | Me | H | F | F | H | Me | Ph(2-CF₃) | |
| 21-48 | Me | Me | H | F | F | H | Me | Ph(2-F-6-Cl) | |
| 21-49 | Me | Me | H | Me | H | H | H | Ph(2-F) | |
| 21-50 | Me | Me | H | Me | H | H | H | Ph(2,6-F₂) | |
| 21-51 | Me | Me | H | Me | H | H | H | Ph(2-Cl) | |
| 21-52 | Me | Me | H | Me | H | H | H | Ph(2-Me) | |
| 21-53 | Me | Me | H | Me | H | H | H | Ph(2-CF₃) | |
| 21-54 | Me | Me | H | Me | H | H | H | Ph(2-F-6-Cl) | |
| 21-55 | Me | Me | H | Me | H | Me | H | Ph(2-F) | |
| 21-56 | Me | Me | H | Me | H | Me | H | Ph(2,6-F₂) | |
| 21-57 | Me | Me | H | Me | H | Me | H | Ph(2-Cl) | |
| 21-58 | Me | Me | H | Me | H | Me | H | Ph(2-Me) | |
| 21-59 | Me | Me | H | Me | H | Me | H | Ph(2-CF₃) | |
| 21-60 | Me | Me | H | Me | H | Me | H | Ph(2-F-6-Cl) | |
| 21-61 | Me | Me | H | Me | H | H | Me | Ph(2-F) | |
| 21-62 | Me | Me | H | Me | H | H | Me | Ph(2,6-F₂) | |
| 21-63 | Me | Me | H | Me | H | H | Me | Ph(2-Cl) | |
| 21-64 | Me | Me | H | Me | H | H | Me | Ph(2-Me) | |
| 21-65 | Me | Me | H | Me | H | H | Me | Ph(2-CF₃) | |
| 21-66 | Me | Me | H | Me | H | H | Me | Ph(2-F-6-Cl) | |
| 21-67 | Me | Me | H | F | H | H | H | Ph(2-F) | |
| 21-68 | Me | Me | H | F | H | H | H | Ph(2,6-F₂) | |
| 21-69 | Me | Me | H | F | H | H | H | Ph(2-Cl) | |
| 21-70 | Me | Me | H | F | H | H | H | Ph(2-Me) | |

TABLE 21-continued

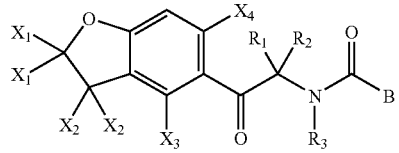

| Compound No. | R₁ | R₂ | R₃ | X₁ | X₂ | X₃ | X₄ | B | Physical properties (mp ° C.) |
|---|---|---|---|---|---|---|---|---|---|
| 21-71 | Me | Me | H | F | H | H | H | Ph(2-CF₃) | |
| 21-72 | Me | Me | H | F | H | H | H | Ph(2-F-6-Cl) | |
| 21-73 | Me | Me | H | H | F | H | H | Ph(2-F) | |
| 21-74 | Me | Me | H | H | F | H | H | Ph(2,6-F₂) | |
| 21-75 | Me | Me | H | H | F | H | H | Ph(2-Cl) | |
| 21-76 | Me | Me | H | H | F | H | H | Ph(2-Me) | |
| 21-77 | Me | Me | H | H | F | H | H | Ph(2-CF₃) | |
| 21-78 | Me | Me | H | H | F | H | H | Ph(2-F-6-Cl) | |
| 21-79 | Me | Me | H | F | H | Me | H | Ph(2-F) | |
| 21-80 | Me | Me | H | F | H | Me | H | Ph(2,6-F₂) | |
| 21-81 | Me | Me | H | F | H | Me | H | Ph(2-Cl) | |
| 21-82 | Me | Me | H | F | H | Me | H | Ph(2-Me) | |
| 21-83 | Me | Me | H | F | H | Me | H | Ph(2-CF₃) | |
| 21-84 | Me | Me | H | F | H | Me | H | Ph(2-F-6-Cl) | |
| 21-85 | Me | Me | H | H | F | Me | H | Ph(2-F) | |
| 21-86 | Me | Me | H | H | F | Me | H | Ph(2,6-F₂) | |
| 21-87 | Me | Me | H | H | F | Me | H | Ph(2-Cl) | |
| 21-88 | Me | Me | H | H | F | Me | H | Ph(2-Me) | |
| 21-89 | Me | Me | H | H | F | Me | H | Ph(2-CF₃) | |
| 21-90 | Me | Me | H | H | F | Me | H | Ph(2-F-6-Cl) | |
| 21-91 | Me | Me | H | F | H | H | Me | Ph(2-F) | |
| 21-92 | Me | Me | H | F | H | H | Me | Ph(2,6-F₂) | |
| 21-93 | Me | Me | H | F | H | H | Me | Ph(2-Cl) | |
| 21-94 | Me | Me | H | F | H | H | Me | Ph(2-Me) | |
| 21-95 | Me | Me | H | F | H | H | Me | Ph(2-CF₃) | |
| 21-96 | Me | Me | H | F | H | H | Me | Ph(2-F-6-Cl) | |
| 21-97 | Me | Me | H | H | F | H | Me | Ph(2-F) | |
| 21-98 | Me | Me | H | H | F | H | Me | Ph(2,6-F₂) | |
| 21-99 | Me | Me | H | H | F | H | Me | Ph(2-Cl) | |
| 21-100 | Me | Me | H | H | F | H | Me | Ph(2-Me) | |
| 21-101 | Me | Me | H | H | F | H | Me | Ph(2-CF₃) | |
| 21-102 | Me | Me | H | H | F | H | Me | Ph(2-F-6-Cl) | |
| 21-103 | Me | Me | H | F | H | Cl | H | Ph(2-F) | |
| 21-104 | Me | Me | H | F | H | Cl | H | Ph(2,6-F₂) | |
| 21-105 | Me | Me | H | F | H | Cl | H | Ph(2-Cl) | |
| 21-106 | Me | Me | H | F | H | Cl | H | Ph(2-Me) | |
| 21-107 | Me | Me | H | F | H | Cl | H | Ph(2-CF₃) | |
| 21-108 | Me | Me | H | F | H | Cl | H | Ph(2-F-6-Cl) | |
| 21-109 | Me | Me | H | H | F | Cl | H | Ph(2-F) | |
| 21-110 | Me | Me | H | H | F | Cl | H | Ph(2,6-F₂) | |
| 21-111 | Me | Me | H | H | F | Cl | H | Ph(2-Cl) | |
| 21-112 | Me | Me | H | H | F | Cl | H | Ph(2-Me) | |
| 21-113 | Me | Me | H | H | F | Cl | H | Ph(2-CF₃) | |
| 21-114 | Me | Me | H | H | F | Cl | H | Ph(2-F-6-Cl) | |
| 21-115 | Me | Me | H | F | H | H | Cl | Ph(2-F) | |
| 21-116 | Me | Me | H | F | H | H | Cl | Ph(2,6-F₂) | |
| 21-117 | Me | Me | H | F | H | H | Cl | Ph(2-Cl) | |
| 21-118 | Me | Me | H | F | H | H | Cl | Ph(2-Me) | |
| 21-119 | Me | Me | H | F | H | H | Cl | Ph(2-CF₃) | |
| 21-120 | Me | Me | H | F | H | H | Cl | Ph(2-F-6-Cl) | |
| 21-121 | Me | Me | H | H | F | H | Cl | Ph(2-F) | |
| 21-122 | Me | Me | H | H | F | H | Cl | Ph(2,6-F₂) | |
| 21-123 | Me | Me | H | H | F | H | Cl | Ph(2-Cl) | |
| 21-124 | Me | Me | H | H | F | H | Cl | Ph(2-Me) | |
| 21-125 | Me | Me | H | H | F | H | Cl | Ph(2-CF₃) | |
| 21-126 | Me | Me | H | H | F | H | Cl | Ph(2-F-6-Cl) | |
| 21-127 | Me | Me | H | Me | H | Cl | H | Ph(2-F) | |
| 21-128 | Me | Me | H | Me | H | Cl | H | Ph(2,6-F₂) | |
| 21-129 | Me | Me | H | Me | H | Cl | H | Ph(2-Cl) | |
| 21-130 | Me | Me | H | Me | H | Cl | H | Ph(2-Me) | |
| 21-131 | Me | Me | H | Me | H | Cl | H | Ph(2-CF₃) | |
| 21-132 | Me | Me | H | Me | H | Cl | H | Ph(2-F-6-Cl) | |
| 21-133 | Me | Me | H | Me | H | H | Cl | Ph(2-F) | |
| 21-134 | Me | Me | H | Me | H | H | Cl | Ph(2,6-F₂) | |
| 21-135 | Me | Me | H | Me | H | H | Cl | Ph(2-Cl) | |
| 21-136 | Me | Me | H | Me | H | H | Cl | Ph(2-Me) | |

TABLE 21-continued

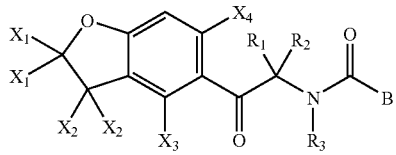

| Compound No. | R₁ | R₂ | R₃ | X₁ | X₂ | X₃ | X₄ | B | Physical properties (mp °C.) |
|---|---|---|---|---|---|---|---|---|---|
| 21-137 | Me | Me | H | Me | H | H | Cl | Ph(2-CF₃) | |
| 21-138 | Me | Me | H | Me | H | H | Cl | Ph(2-F-6-Cl) | |

TABLE 22

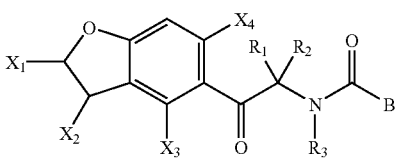

| Compound No. | R₁ | R₂ | R₃ | X₁ | X₂ | X₃ | X₄ | B | Physical properties (mp °C.) |
|---|---|---|---|---|---|---|---|---|---|
| 22-1  | Me | Me | H | Me | H  | H  | H  | Ph(2-F) | |
| 22-2  | Me | Me | H | Me | H  | H  | H  | Ph(2,6-F₂) | |
| 22-3  | Me | Me | H | Me | H  | H  | H  | Ph(2-Cl) | |
| 22-4  | Me | Me | H | Me | H  | H  | H  | Ph(2-Me) | |
| 22-5  | Me | Me | H | Me | H  | H  | H  | Ph(2-CF₃) | |
| 22-6  | Me | Me | H | Me | H  | H  | H  | Ph(2-F-6-Cl) | |
| 22-7  | Me | Me | H | Me | H  | Cl | H  | Ph(2-F) | |
| 22-8  | Me | Me | H | Me | H  | Cl | H  | Ph(2,6-F₂) | |
| 22-9  | Me | Me | H | Me | H  | Cl | H  | Ph(2-Cl) | |
| 22-10 | Me | Me | H | Me | H  | Cl | H  | Ph(2-Me) | |
| 22-11 | Me | Me | H | Me | H  | Cl | H  | Ph(2-CF₃) | |
| 22-12 | Me | Me | H | Me | H  | Cl | H  | Ph(2-F-6-Cl) | |
| 22-13 | Me | Me | H | Me | H  | Me | H  | Ph(2-F) | |
| 22-14 | Me | Me | H | Me | H  | Me | H  | Ph(2,6-F₂) | |
| 22-15 | Me | Me | H | Me | H  | Me | H  | Ph(2-Cl) | |
| 22-16 | Me | Me | H | Me | H  | Me | H  | Ph(2-Me) | |
| 22-17 | Me | Me | H | Me | H  | Me | H  | Ph(2-CF₃) | |
| 22-18 | Me | Me | H | Me | H  | Me | H  | Ph(2-F-6-Cl) | |
| 22-19 | Me | Me | H | Me | H  | H  | Me | Ph(2-F) | |
| 22-20 | Me | Me | H | Me | H  | H  | Me | Ph(2,6-F₂) | |
| 22-21 | Me | Me | H | Me | H  | H  | Me | Ph(2-Cl) | |
| 22-22 | Me | Me | H | Me | H  | H  | Me | Ph(2-Me) | |
| 22-23 | Me | Me | H | Me | H  | H  | Me | Ph(2-CF₃) | |
| 22-24 | Me | Me | H | Me | H  | H  | Me | Ph(2-F-6-Cl) | |
| 22-25 | Me | Me | H | H  | Me | H  | H  | Ph(2-F) | |
| 22-26 | Me | Me | H | H  | Me | H  | H  | Ph(2,6-F₂) | |
| 22-27 | Me | Me | H | H  | Me | H  | H  | ph(2-Cl) | |
| 22-28 | Me | Me | H | H  | Me | H  | H  | Ph(2-Me) | |
| 22-29 | Me | Me | H | H  | Me | H  | H  | Ph(2-CF₃) | |
| 22-30 | Me | Me | H | H  | Me | H  | H  | Ph(2-F-6-Cl) | |
| 22-31 | Me | Me | H | H  | Me | Cl | H  | Ph(2-F) | |
| 22-32 | Me | Me | H | H  | Me | Cl | H  | Ph(2,6-F₂) | |
| 22-33 | Me | Me | H | H  | Me | Cl | H  | Ph(2-Cl) | |
| 22-34 | Me | Me | H | H  | Me | Cl | H  | Ph(2-Me) | |
| 22-35 | Me | Me | H | H  | Me | Cl | H  | Ph(2-CF₃) | |
| 22-36 | Me | Me | H | H  | Me | Cl | H  | Ph(2-F-6-Cl) | |
| 22-37 | Me | Me | H | H  | Me | Me | H  | Ph(2-F) | |
| 22-38 | Me | Me | H | H  | Me | Me | H  | Ph(2,6-F₂) | |
| 22-39 | Me | Me | H | H  | Me | Me | H  | Ph(2-Cl) | |
| 22-40 | Me | Me | H | H  | Me | Me | H  | Ph(2-Me) | |
| 22-41 | Me | Me | H | H  | Me | Me | H  | Ph(2-CF₃) | |
| 22-42 | Me | Me | H | H  | Me | Me | H  | Ph(2-F-6-Cl) | |
| 22-43 | Me | Me | H | H  | Me | H  | Me | Ph(2-F) | |
| 22-44 | Me | Me | H | H  | Me | H  | Me | Ph(2,6-F₂) | |
| 22-45 | Me | Me | H | H  | Me | H  | Me | Ph(2-Cl) | |
| 22-46 | Me | Me | H | H  | Me | H  | Me | Ph(2-Me) | |

TABLE 22-continued

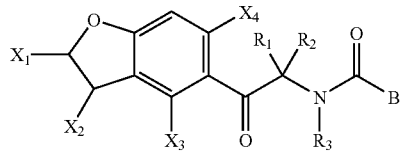

| Compound No. | R₁ | R₂ | R₃ | X₁ | X₂ | X₃ | X₄ | B | Physical properties (mp °C.) |
|---|---|---|---|---|---|---|---|---|---|
| 22-47 | Me | Me | H | H | Me | H | Me | Ph(2-CF₃) | |
| 22-48 | Me | Me | H | H | Me | H | Me | Ph(2-F-6-Cl) | |

TABLE 23

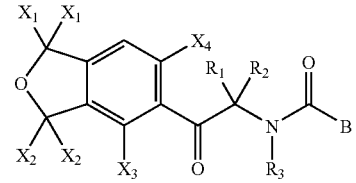

| Compound No. | R₁ | R₂ | R₃ | X₁ | X₂ | X₃ | X₄ | B | Physical properties (mp °C.) |
|---|---|---|---|---|---|---|---|---|---|
| 23-1  | Me | Me | H | H | H  | H  | H  | Ph(2-F) | |
| 23-2  | Me | Me | H | H | H  | H  | H  | Ph(2,6-F₂) | |
| 23-3  | Me | Me | H | H | H  | H  | H  | Ph(2-Cl) | |
| 23-4  | Me | Me | H | H | H  | H  | H  | Ph(2-Me) | |
| 23-5  | Me | Me | H | H | H  | H  | H  | Ph(2-CF₃) | |
| 23-6  | Me | Me | H | H | H  | H  | H  | Ph(2-F-6-Cl) | |
| 23-7  | Me | Me | H | H | H  | Cl | H  | Ph(2-F) | |
| 23-8  | Me | Me | H | H | H  | Cl | H  | Ph(2,6-F₂) | |
| 23-9  | Me | Me | H | H | H  | Cl | H  | Ph(2-Cl) | |
| 23-10 | Me | Me | H | H | H  | Cl | H  | Ph(2-Me) | |
| 23-11 | Me | Me | H | H | H  | Cl | H  | Ph(2-CF₃) | |
| 23-12 | Me | Me | H | H | H  | Cl | H  | Ph(2-F-6-Cl) | |
| 23-13 | Me | Me | H | H | H  | Me | H  | Ph(2-F) | |
| 23-14 | Me | Me | H | H | H  | Me | H  | Ph(2,6-F₂) | |
| 23-15 | Me | Me | H | H | H  | Me | H  | Ph(2-Cl) | |
| 23-16 | Me | Me | H | H | H  | Me | H  | Ph(2-Me) | |
| 23-17 | Me | Me | H | H | H  | Me | H  | Ph(2-CF₃) | |
| 23-18 | Me | Me | H | H | H  | Me | H  | Ph(2-F-6-Cl) | |
| 23-19 | Me | Me | H | H | H  | H  | Me | Ph(2-F) | |
| 23-20 | Me | Me | H | H | H  | H  | Me | Ph(2,6-F₂) | |
| 23-21 | Me | Me | H | H | H  | H  | Me | Ph(2-Cl) | |
| 23-22 | Me | Me | H | H | H  | H  | Me | Ph(2-Me) | |
| 23-23 | Me | Me | H | H | H  | H  | Me | Ph(2-CF₃) | |
| 23-24 | Me | Me | H | H | H  | H  | Me | Ph(2-F-6-Cl) | |
| 23-25 | Me | Me | H | F | F  | H  | H  | Ph(2-F) | |
| 23-26 | Me | Me | H | F | F  | H  | H  | Ph(2,6-F₂) | |
| 23-27 | Me | Me | H | F | F  | H  | H  | Ph(2-Cl) | |
| 23-28 | Me | Me | H | F | F  | H  | H  | Ph(2-Me) | |
| 23-29 | Me | Me | H | F | F  | H  | H  | Ph(2-CF₃) | |
| 23-30 | Me | Me | H | F | F  | H  | H  | Ph(2-F-6-Cl) | |
| 23-31 | Me | Me | H | F | F  | Cl | H  | Ph(2-F) | |
| 23-32 | Me | Me | H | F | F  | Cl | H  | Ph(2,6-F₂) | |
| 23-33 | Me | Me | H | F | F  | Cl | H  | Ph(2-Cl) | |
| 23-34 | Me | Me | H | F | F  | Cl | H  | Ph(2-Me) | |
| 23-35 | Me | Me | H | F | F  | Cl | H  | Ph(2-CF₃) | |
| 23-36 | Me | Me | H | F | F  | Cl | H  | Ph(2-F-6-Cl) | |
| 23-37 | Me | Me | H | F | F  | Me | H  | Ph(2-F) | |
| 23-38 | Me | Me | H | F | F  | Me | H  | Ph(2,6-F₂) | |
| 23-39 | Me | Me | H | F | F  | Me | H  | Ph(2-Cl) | |
| 23-40 | Me | Me | H | F | F  | Me | H  | Ph(2-Me) | |
| 23-41 | Me | Me | H | F | F  | Me | H  | Ph(2-CF₃) | |
| 23-42 | Me | Me | H | F | F  | Me | H  | Ph(2-F-6-Cl) | |
| 23-43 | Me | Me | H | F | F  | H  | Me | Ph(2-F) | |
| 23-44 | Me | Me | H | F | F  | H  | Me | Ph(2,6-F₂) | |
| 23-45 | Me | Me | H | F | F  | H  | Me | Ph(2-Cl) | |

TABLE 23-continued

| Compound No. | R₁ | R₂ | R₃ | X₁ | X₂ | X₃ | X₄ | B | Physical properties (mp ° C.) |
|---|---|---|---|---|---|---|---|---|---|
| 23-46 | Me | Me | H | F | F | H | Me | Ph(2-Me) | |
| 23-47 | Me | Me | H | F | F | H | Me | Ph(2-CF₃) | |
| 23-48 | Me | Me | H | F | F | H | Me | Ph(2-F-6-Cl) | |
| 23-49 | Me | Me | H | H | H | H | Cl | Ph(2-F) | |
| 23-50 | Me | Me | H | H | H | H | Cl | Ph(2,6-F₂) | |
| 23-51 | Me | Me | H | H | H | H | Cl | Ph(2-Cl) | |
| 23-52 | Me | Me | H | H | H | H | Cl | Ph(2-Me) | |
| 23-53 | Me | Me | H | H | H | H | Cl | Ph(2-CF₃) | |
| 23-54 | Me | Me | H | H | H | H | Cl | Ph(2-F-6-Cl) | |
| 23-55 | Me | Me | H | F | F | H | Cl | Ph(2-F) | |
| 23-56 | Me | Me | H | F | F | H | Cl | Ph(2,6-F₂) | |
| 23-57 | Me | Me | H | F | F | H | Cl | Ph(2-Cl) | |
| 23-58 | Me | Me | H | F | F | H | Cl | Ph(2-Me) | |
| 23-59 | Me | Me | H | F | F | H | Cl | Ph(2-CF₃) | |
| 23-60 | Me | Me | H | F | F | H | Cl | Ph(2-F-6-Cl) | |
| 23-61 | Me | Me | H | F | H | Cl | H | Ph(2-F) | |
| 23-62 | Me | Me | H | F | H | Cl | H | Ph(2,6-F₂) | |
| 23-63 | Me | Me | H | F | H | Cl | H | Ph(2-Cl) | |
| 23-64 | Me | Me | H | F | H | Cl | H | Ph(2-Me) | |
| 23-65 | Me | Me | H | F | H | Cl | H | Ph(2-CF₃) | |
| 23-66 | Me | Me | H | F | H | Cl | H | Ph(2-F-6-Cl) | |
| 23-67 | Me | Me | H | H | F | Cl | H | Ph(2-F) | |
| 23-68 | Me | Me | H | H | F | Cl | H | Ph(2,6-F₂) | |
| 23-69 | Me | Me | H | H | F | Cl | H | Ph(2-Cl) | |
| 23-70 | Me | Me | H | H | F | Cl | H | Ph(2-Me) | |
| 23-71 | Me | Me | H | H | F | Cl | H | Ph(2-CF₃) | |
| 23-72 | Me | Me | H | H | F | Cl | H | Ph(2-F-6-Cl) | |
| 23-73 | Me | Me | H | F | H | Me | H | Ph(2-F) | |
| 23-74 | Me | Me | H | F | H | Me | H | Ph(2,6-F₂) | |
| 23-75 | Me | Me | H | F | H | Me | H | Ph(2-Cl) | |
| 23-76 | Me | Me | H | F | H | Me | H | Ph(2-Me) | |
| 23-77 | Me | Me | H | F | H | Me | H | Ph(2-CF₃) | |
| 23-78 | Me | Me | H | F | H | Me | H | Ph(2-F-6-Cl) | |
| 23-79 | Me | Me | H | H | F | Me | H | Ph(2-F) | |
| 23-80 | Me | Me | H | H | F | Me | H | Ph(2,6-F₂) | |
| 23-81 | Me | Me | H | H | F | Me | H | Ph(2-Cl) | |
| 23-82 | Me | Me | H | H | F | Me | H | Ph(2-Me) | |
| 23-83 | Me | Me | H | H | F | Me | H | Ph(2-CF₃) | |
| 23-84 | Me | Me | H | H | F | Me | H | Ph(2-F-6-Cl) | |
| 23-85 | Me | Me | H | F | H | H | Cl | Ph(2-F) | |
| 23-86 | Me | Me | H | F | H | H | Cl | Ph(2,6-F₂) | |
| 23-87 | Me | Me | H | F | H | H | Cl | Ph(2-Cl) | |
| 23-88 | Me | Me | H | F | H | H | Cl | Ph(2-Me) | |
| 23-89 | Me | Me | H | F | H | H | Cl | Ph(2-CF₃) | |
| 23-90 | Me | Me | H | F | H | H | Cl | Ph(2-F-6-Cl) | |
| 23-91 | Me | Me | H | H | F | H | Me | Ph(2-F) | |
| 23-92 | Me | Me | H | H | F | H | Me | Ph(2,6-F₂) | |
| 23-93 | Me | Me | H | H | F | H | Me | Ph(2-Cl) | |
| 23-94 | Me | Me | H | H | F | H | Me | Ph(2-Me) | |
| 23-95 | Me | Me | H | H | F | H | Me | Ph(2-CF₃) | |
| 23-96 | Me | Me | H | H | F | H | Me | Ph(2-F-6-Cl) | |
| 23-97 | Me | Me | H | F | H | H | Me | Ph(2-F) | |
| 23-98 | Me | Me | H | F | H | H | Me | Ph(2,6-F₂) | |
| 23-99 | Me | Me | H | F | H | H | Me | Ph(2-Cl) | |
| 23-100 | Me | Me | H | F | H | H | Me | Ph(2-Me) | |
| 23-101 | Me | Me | H | F | H | H | Me | Ph(2-CF₃) | |
| 23-102 | Me | Me | H | F | H | H | Me | Ph(2-F-6-Cl) | |
| 23-103 | Me | Me | H | H | H | F | Me | Ph(2-F) | |
| 23-104 | Me | Me | H | H | H | F | Me | Ph(2,6-F₂) | |
| 23-105 | Me | Me | H | H | H | F | Me | Ph(2-Cl) | |
| 23-106 | Me | Me | H | H | H | F | Me | Ph(2-Me) | |
| 23-107 | Me | Me | H | H | H | F | Me | Ph(2-CF₃) | |
| 23-108 | Me | Me | H | H | H | F | Me | Ph(2-F-6-Cl) | |

TABLE 24

| Compound No. | R₁ | R₂ | R₃ | X₁ | X₂ | X₃ | X₄ | B | Physical properties (mp ° C.) |
|---|---|---|---|---|---|---|---|---|---|
| 24-1 | Me | Me | H | H | H | H | H | Ph(2-F) | |
| 24-2 | Me | Me | H | H | H | H | H | Ph(2,6-F₂) | |
| 24-3 | Me | Me | H | H | H | H | H | Ph(2-Cl) | |
| 24-4 | Me | Me | H | H | H | H | H | Ph(2-Me) | |
| 24-5 | Me | Me | H | H | H | H | H | Ph(2-CF₃) | |
| 24-6 | Me | Me | H | H | H | H | H | Ph(2-F-6-Cl) | |
| 24-7 | Me | Me | H | H | H | H | Me | Ph(2-F) | |
| 24-8 | Me | Me | H | H | H | H | Me | Ph(2,6-F₂) | |
| 24-9 | Me | Me | H | H | H | H | Me | Ph(2-Cl) | |
| 24-10 | Me | Me | H | H | H | H | Me | Ph(2-Me) | |
| 24-11 | Me | Me | H | H | H | H | Me | Ph(2-CF₃) | |
| 24-12 | Me | Me | H | H | H | H | Me | Ph(2-F-6-Cl) | |
| 24-13 | Me | Me | H | F | H | H | H | Ph(2-F) | |
| 24-14 | Me | Me | H | F | H | H | H | Ph(2,6-F₂) | |
| 24-15 | Me | Me | H | F | H | H | H | Ph(2-Cl) | |
| 24-16 | Me | Me | H | F | H | H | H | Ph(2-Me) | |
| 24-17 | Me | Me | H | F | H | H | H | Ph(2-CF₃) | |
| 24-18 | Me | Me | H | F | H | H | H | Ph(2-F-6-Cl) | |
| 24-19 | Me | Me | H | F | H | H | Me | Ph(2-F) | |
| 24-20 | Me | Me | H | F | H | H | Me | Ph(2,6-F₂) | |
| 24-21 | Me | Me | H | F | H | H | Me | Ph(2-Cl) | |
| 24-22 | Me | Me | H | F | H | H | Me | Ph(2-Me) | |
| 24-23 | Me | Me | H | F | H | H | Me | Ph(2-CF₃) | |
| 24-24 | Me | Me | H | F | H | H | Me | Ph(2-F-6-Cl) | |
| 24-25 | Me | Me | H | H | F | H | H | Ph(2-F) | |
| 24-26 | Me | Me | H | H | F | H | H | Ph(2,6-F₂) | |
| 24-27 | Me | Me | H | H | F | H | H | Ph(2-Cl) | |
| 24-28 | Me | Me | H | H | F | H | H | Ph(2-Me) | |
| 24-29 | Me | Me | H | H | F | H | H | Ph(2-CF₃) | |
| 24-30 | Me | Me | H | H | F | H | H | Ph(2-F-6-Cl) | |
| 24-31 | Me | Me | H | H | F | H | Me | Ph(2-F) | |
| 24-32 | Me | Me | H | H | F | H | Me | Ph(2,6-F₂) | |
| 24-33 | Me | Me | H | H | F | H | Me | Ph(2-Cl) | |
| 24-34 | Me | Me | H | H | F | H | Me | Ph(2-Me) | |
| 24-35 | Me | Me | H | H | F | H | Me | Ph(2-CF₃) | |
| 24-36 | Me | Me | H | H | F | H | Me | Ph(2-F-6-Cl) | |
| 24-37 | Me | Me | H | F | F | H | H | Ph(2-F) | |
| 24-38 | Me | Me | H | F | F | H | H | Ph(2,6-F₂) | |
| 24-39 | Me | Me | H | F | F | H | H | Ph(2-Cl) | |
| 24-40 | Me | Me | H | F | F | H | H | Ph(2-Me) | |
| 24-41 | Me | Me | H | F | F | H | H | Ph(2-CF₃) | |
| 24-42 | Me | Me | H | F | F | H | H | Ph(2-F-6-Cl) | |
| 24-43 | Me | Me | H | F | F | H | Me | Ph(2-F) | |
| 24-44 | Me | Me | H | F | F | H | Me | Ph(2,6-F₂) | |
| 24-45 | Me | Me | H | F | F | H | Me | Ph(2-Cl) | |
| 24-46 | Me | Me | H | F | F | H | Me | Ph(2-Me) | |
| 24-47 | Me | Me | H | F | F | H | Me | Ph(2-CF₃) | |
| 24-48 | Me | Me | H | F | F | H | Me | Ph(2-F-6-Cl) | |
| 24-49 | Me | Me | H | H | H | Me | Me | Ph(2-F) | |
| 24-50 | Me | Me | H | H | H | Me | Me | Ph(2,6-F₂) | |
| 24-51 | Me | Me | H | H | H | Me | Me | Ph(2-Cl) | |
| 24-52 | Me | Me | H | H | H | Me | Me | Ph(2-Me) | |
| 24-53 | Me | Me | H | H | H | Me | Me | Ph(2-CF₃) | |
| 24-54 | Me | Me | H | H | H | Me | Me | Ph(2-F-6-Cl) | |
| 24-55 | Me | Me | H | H | H | OMe | Me | Ph(2-F) | |
| 24-56 | Me | Me | H | H | H | OMe | Me | Ph(2,6-F₂) | |
| 24-57 | Me | Me | H | H | H | OMe | Me | Ph(2-Cl) | |
| 24-58 | Me | Me | H | H | H | OMe | Me | Ph(2-Me) | |
| 24-59 | Me | Me | H | H | H | OMe | Me | Ph(2-CF₃) | |
| 24-60 | Me | Me | H | H | H | OMe | Me | Ph(2-F-6-Cl) | |
| 24-61 | Me | Me | H | H | H | OH | Me | Ph(2-F) | |
| 24-62 | Me | Me | H | H | H | OH | Me | Ph(2,6-F₂) | |
| 24-63 | Me | Me | H | H | H | OH | Me | Ph(2-Cl) | |
| 24-64 | Me | Me | H | H | H | OH | Me | Ph(2-Me) | |
| 24-65 | Me | Me | H | H | H | OH | Me | Ph(2-CF₃) | |

TABLE 24-continued

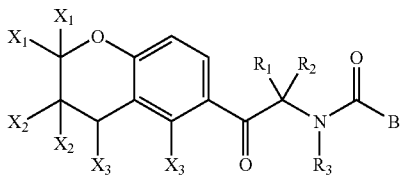

| Compound No. | R₁ | R₂ | R₃ | X₁ | X₂ | X₃ | X₄ | B |
|---|---|---|---|---|---|---|---|---|
| 24-66 | Me | Me | H | H | H | OH | Me | Ph(2-F-6-Cl) |
| 24-67 | Me | Me | H | Me | H | H | Me | Ph(2-F) |
| 24-68 | Me | Me | H | Me | H | H | Me | Ph(2,6-F₂) |
| 24-69 | Me | Me | H | Me | H | H | Me | Ph(2-Cl) |
| 24-70 | Me | Me | H | Me | H | H | Me | Ph(2-Me) |
| 24-71 | Me | Me | H | Me | H | H | Me | Ph(2-CF₃) |
| 24-72 | Me | Me | H | Me | H | H | Me | Ph(2-F-6-Cl) |
| 24-73 | Me | Me | H | H | H | H | Cl | Ph(2-F) |
| 24-74 | Me | Me | H | H | H | H | Cl | Ph(2,6-F₂) |
| 24-75 | Me | Me | H | H | H | H | Cl | Ph(2-Cl) |
| 24-76 | Me | Me | H | H | H | H | Cl | Ph(2-Me) |
| 24-77 | Me | Me | H | H | H | H | Cl | Ph(2-CF₃) |
| 24-78 | Me | Me | H | H | H | H | Cl | Ph(2-F-6-Cl) |
| 24-79 | Me | Me | H | F | H | H | Cl | Ph(2-F) |
| 24-80 | Me | Me | H | F | H | H | Cl | Ph(2,6-F₂) |
| 24-81 | Me | Me | H | F | H | H | Cl | Ph(2-Cl) |
| 24-82 | Me | Me | H | F | H | H | Cl | Ph(2-Me) |
| 24-83 | Me | Me | H | F | H | H | Cl | Ph(2-CF₃) |
| 24-84 | Me | Me | H | F | H | H | Cl | Ph(2-F-6-Cl) |
| 24-85 | Me | Me | H | H | F | H | Cl | Ph(2-F) |
| 24-86 | Me | Me | H | H | F | H | Cl | Ph(2,6-F₂) |
| 24-87 | Me | Me | H | H | F | H | Cl | Ph(2-Cl) |
| 24-88 | Me | Me | H | H | F | H | Cl | Ph(2-Me) |
| 24-89 | Me | Me | H | H | F | H | Cl | Ph(2-CF₃) |
| 24-90 | Me | Me | H | H | F | H | Cl | Ph(2-F-6-Cl) |
| 24-91 | Me | Me | H | F | F | H | Cl | Ph(2-F) |
| 24-92 | Me | Me | H | F | F | H | Cl | Ph(2,6-F₂) |
| 24-93 | Me | Me | H | F | F | H | Cl | Ph(2-Cl) |
| 24-94 | Me | Me | H | F | F | H | Cl | Ph(2-Me) |
| 24-95 | Me | Me | H | F | F | H | Cl | Ph(2-CF₃) |
| 24-96 | Me | Me | H | F | F | H | Cl | Ph(2-F-6-Cl) |
| 24-97 | Me | Me | H | H | H | Me | Cl | Ph(2-F) |
| 24-98 | Me | Me | H | H | H | Me | Cl | Ph(2,6-F₂) |
| 24-99 | Me | Me | H | H | H | Me | Cl | Ph(2-Cl) |
| 24-100 | Me | Me | H | H | H | Me | Cl | Ph(2-Me) |
| 24-101 | Me | Me | H | H | H | Me | Cl | Ph(2-CF₃) |
| 24-102 | Me | Me | H | H | H | Me | Cl | Ph(2-F-6-Cl) |
| 24-103 | Me | Me | H | H | H | OMe | Cl | Ph(2-F) |
| 24-104 | Me | Me | H | H | H | OMe | Cl | Ph(2,6-F₂) |
| 24-105 | Me | Me | H | H | H | OMe | Cl | Ph(2-Cl) |
| 24-106 | Me | Me | H | H | H | OMe | Cl | Ph(2-Me) |
| 24-107 | Me | Me | H | H | H | OMe | Cl | Ph(2-CF₃) |
| 24-108 | Me | Me | H | H | H | OMe | Cl | Ph(2-F-6-Cl) |
| 24-109 | Me | Me | H | H | H | OH | Cl | Ph(2-F) |
| 24-110 | Me | Me | H | H | H | OH | Cl | Ph(2,6-F₂) |
| 24-111 | Me | Me | H | H | H | OH | Cl | Ph(2-Cl) |
| 24-112 | Me | Me | H | H | H | OH | Cl | Ph(2-Me) |
| 24-113 | Me | Me | H | H | H | OH | Cl | Ph(2-CF₃) |
| 24-114 | Me | Me | H | H | H | OH | Cl | Ph(2-F-6-Cl) |
| 24-115 | Me | Me | H | Me | H | H | Cl | Ph(2-F) |
| 24-116 | Me | Me | H | Me | H | H | Cl | Ph(2,6-F₂) |
| 24-117 | Me | Me | H | Me | H | H | Cl | Ph(2-Cl) |
| 24-118 | Me | Me | H | Me | H | H | Cl | Ph(2-Me) |
| 24-119 | Me | Me | H | Me | H | H | Cl | Ph(2-CF₃) |
| 24-120 | Me | Me | H | Me | H | H | Cl | Ph(2-F-6-Cl) |

TABLE 25

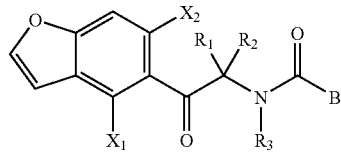

| Compound No. | R₁ | R₂ | R₃ | X₁ | X₂ | B |
|---|---|---|---|---|---|---|
| 25-1 | Me | Me | H | H | H | Ph(2-F) |
| 25-2 | Me | Me | H | H | H | Ph(2,6-F₂) |
| 25-3 | Me | Me | H | H | H | Ph(2-Cl) |
| 25-4 | Me | Me | H | H | H | Ph(2-Me) |
| 25-5 | Me | Me | H | H | H | Ph(2-CF₃) |
| 25-6 | Me | Me | H | H | H | Ph(2-F-6-Cl) |
| 25-7 | Me | Me | H | Cl | H | Ph(2-F) |
| 25-8 | Me | Me | H | Cl | H | Ph(2,6-F₂) |
| 25-9 | Me | Me | H | Cl | H | Ph(2-Cl) |
| 25-10 | Me | Me | H | Cl | H | Ph(2-Me) |
| 25-11 | Me | Me | H | Cl | H | Ph(2-CF₃) |
| 25-12 | Me | Me | H | Cl | H | Ph(2-F-6-Cl) |
| 25-13 | Me | Me | H | Me | H | Ph(2-F) |
| 25-14 | Me | Me | H | Me | H | Ph(2,6-F₂) |
| 25-15 | Me | Me | H | Me | H | Ph(2-Cl) |
| 25-16 | Me | Me | H | Me | H | Ph(2-Me) |
| 25-17 | Me | Me | H | Me | H | Ph(2-CF₃) |
| 25-18 | Me | Me | H | Me | H | Ph(2-F-6-Cl) |
| 25-19 | Me | Me | H | H | Cl | Ph(2-F) |
| 25-20 | Me | Me | H | H | Cl | Ph(2,6-F₂) |
| 25-21 | Me | Me | H | H | Cl | Ph(2-Cl) |
| 25-22 | Me | Me | H | H | Cl | Ph(2-Me) |
| 25-23 | Me | Me | H | H | Cl | Ph(2-CF₃) |
| 25-24 | Me | Me | H | H | Cl | Ph(2-F-6-Cl) |
| 25-25 | Me | Me | H | H | Me | Ph(2-F) |
| 25-26 | Me | Me | H | H | Me | Ph(2,6-F₂) |
| 25-27 | Me | Me | H | H | Me | Ph(2-Cl) |
| 25-28 | Me | Me | H | H | Me | Ph(2-Me) |
| 25-29 | Me | Me | H | H | Me | Ph(2-CF₃) |
| 25-30 | Me | Me | H | H | Me | Ph(2-F-6-Cl) |
| 25-31 | Me | Me | H | Me | Me | Ph(2-F) |
| 25-32 | Me | Me | H | Me | Me | Ph(2,6-F₂) |
| 25-33 | Me | Me | H | Me | Me | Ph(2-Cl) |
| 25-34 | Me | Me | H | Me | Me | Ph(2-Me) |
| 25-35 | Me | Me | H | Me | Me | Ph(2-CF₃) |
| 25-36 | Me | Me | H | Me | Me | Ph(2-F-6-Cl) |

TABLE 26

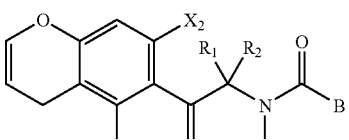

| Compound No. | R₁ | R₂ | R₃ | X₁ | X₂ | B |
|---|---|---|---|---|---|---|
| 26-1 | Me | Me | H | H | H | Ph(2-F) |
| 26-2 | Me | Me | H | H | H | Ph(2,6-F₂) |
| 26-3 | Me | Me | H | H | H | Ph(2-Cl) |
| 26-4 | Me | Me | H | H | H | Ph(2-Me) |
| 26-5 | Me | Me | H | H | H | Ph(2-CF₃) |
| 26-6 | Me | Me | H | H | H | Ph(2-F-6-Cl) |
| 26-7 | Me | Me | H | Cl | H | Ph(2-F) |
| 26-8 | Me | Me | H | Cl | H | Ph(2,6-F₂) |
| 26-9 | Me | Me | H | Cl | H | Ph(2-Cl) |
| 26-10 | Me | Me | H | Cl | H | Ph(2-Me) |
| 26-11 | Me | Me | H | Cl | H | Ph(2-CF₃) |
| 26-12 | Me | Me | H | Cl | H | Ph(2-F-6-Cl) |

TABLE 26-continued

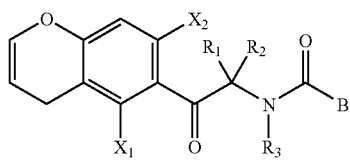

| Compound No. | R₁ | R₂ | R₃ | X₁ | X₂ | B | Physical properties (mp ° C.) |
|---|---|---|---|---|---|---|---|
| 26-13 | Me | Me | H | Me | H | Ph(2-F) | |
| 26-14 | Me | Me | H | Me | H | Ph(2,6-F₂) | |
| 26-15 | Me | Me | H | Me | H | Ph(2-Cl) | |
| 26-16 | Me | Me | H | Me | H | Ph(2-Me) | |
| 26-17 | Me | Me | H | Me | H | Ph(2-CF₃) | |
| 26-18 | Me | Me | H | Me | H | Ph(2-F-6-Cl) | |
| 26-19 | Me | Me | H | H | Cl | Ph(2-F) | |
| 26-20 | Me | Me | H | H | Cl | Ph(2,6-F₂) | |
| 26-21 | Me | Me | H | H | Cl | Ph(2-Cl) | |
| 26-22 | Me | Me | H | H | Cl | Ph(2-Me) | |
| 26-23 | Me | Me | H | H | Cl | Ph(2-CF₃) | |
| 26-24 | Me | Me | H | H | Cl | Ph(2-F-6-Cl) | |
| 26-25 | Me | Me | H | H | Me | Ph(2-F) | |
| 26-26 | Me | Me | H | H | Me | Ph(2,6-F₂) | |
| 26-27 | Me | Me | H | H | Me | Ph(2-Cl) | |
| 26-28 | Me | Me | H | H | Me | Ph(2-Me) | |
| 26-29 | Me | Me | H | H | Me | Ph(2-CF₃) | |
| 26-30 | Me | Me | H | H | Me | Ph(2-F-6-Cl) | |
| 26-31 | Me | Me | H | Me | Me | Ph(2-F) | |
| 26-32 | Me | Me | H | Me | Me | Ph(2,6-F₂) | |
| 26-33 | Me | Me | H | Me | Me | Ph(2-Cl) | |
| 26-34 | Me | Me | H | Me | Me | Ph(2-Me) | |
| 26-35 | Me | Me | H | Me | Me | Ph(2-CF₃) | |
| 26-36 | Me | Me | H | Me | Me | Ph(2-F-6-Cl) | |

TABLE 27

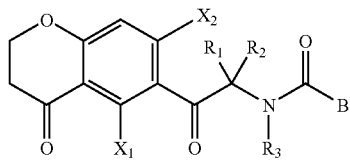

| Compound No. | R₁ | R₂ | R₃ | X₁ | X₂ | B | Physical properties (mp ° C.) |
|---|---|---|---|---|---|---|---|
| 27-1 | Me | Me | H | H | H | Ph(2-F) | |
| 27-2 | Me | Me | H | H | H | Ph(2,6-F₂) | |
| 27-3 | Me | Me | H | H | H | Ph(2-Cl) | |
| 27-4 | Me | Me | H | H | H | Ph(2-Me) | |
| 27-5 | Me | Me | H | H | H | Ph(2-CF₃) | |
| 27-6 | Me | Me | H | H | H | Ph(2-F-6-Cl) | |
| 27-7 | Me | Me | H | Cl | H | Ph(2-F) | |
| 27-8 | Me | Me | H | Cl | H | Ph(2,6-F₂) | |
| 27-9 | Me | Me | H | Cl | H | Ph(2-Cl) | |
| 27-10 | Me | Me | H | Cl | H | Ph(2-Me) | |
| 27-11 | Me | Me | H | Cl | H | Ph(2-CF₃) | |
| 27-12 | Me | Me | H | Cl | H | Ph(2-F-6-Cl) | |
| 27-13 | Me | Me | H | Me | H | Ph(2-F) | |
| 27-14 | Me | Me | H | Me | H | Ph(2,6-F₂) | |
| 27-15 | Me | Me | H | Me | H | Ph(2-Cl) | |
| 27-16 | Me | Me | H | Me | H | Ph(2-Me) | |
| 27-17 | Me | Me | H | Me | H | Ph(2-CF₃) | |
| 27-18 | Me | Me | H | Me | H | Ph(2-F-6-Cl) | |
| 27-19 | Me | Me | H | H | Cl | Ph(2-F) | |
| 27-20 | Me | Me | H | H | Cl | Ph(2,6-F₂) | |
| 27-21 | Me | Me | H | H | Cl | Ph(2-Cl) | |
| 27-22 | Me | Me | H | H | Cl | Ph(2-Me) | |
| 27-23 | Me | Me | H | H | Cl | Ph(2-CF₃) | |
| 27-24 | Me | Me | H | H | Cl | Ph(2-F-6-Cl) | |
| 27-25 | Me | Me | H | H | Me | Ph(2-F) | |

TABLE 27-continued

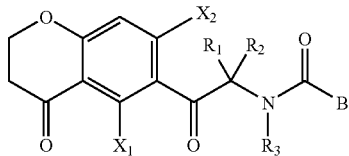

| Compound No. | R₁ | R₂ | R₃ | X₁ | X₂ | B | Physical properties (mp ° C.) |
|---|---|---|---|---|---|---|---|
| 27-26 | Me | Me | H | H | Me | Ph(2,6-F₂) | |
| 27-27 | Me | Me | H | H | Me | Ph(2-Cl) | |
| 27-28 | Me | Me | H | H | Me | Ph(2-Me) | |
| 27-29 | Me | Me | H | H | Me | Ph(2-CF₃) | |
| 27-30 | Me | Me | H | H | Me | Ph(2-F-6-Cl) | |
| 27-31 | Me | Me | H | Me | Me | Ph(2-F) | |
| 27-32 | Me | Me | H | Me | Me | Ph(2,6-F₂) | |
| 27-33 | Me | Me | H | Me | Me | Ph(2-Cl) | |
| 27-34 | Me | Me | H | Me | Me | Ph(2-Me) | |
| 27-35 | Me | Me | H | Me | Me | Ph(2-CF₃) | |
| 27-36 | Me | Me | H | Me | Me | Ph(2-F-6-Cl) | |

TABLE 28

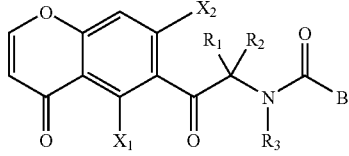

| Compound No. | R₁ | R₂ | R₃ | X₁ | X₂ | B | Physical properties (mp ° C.) |
|---|---|---|---|---|---|---|---|
| 28-1 | Me | Me | H | H | H | Ph(2-F) | |
| 28-2 | Me | Me | H | H | H | Ph(2,6-F₂) | |
| 28-3 | Me | Me | H | H | H | Ph(2-Cl) | |
| 28-4 | Me | Me | H | H | H | Ph(2-Me) | |
| 28-5 | Me | Me | H | H | H | Ph(2-CF₃) | |
| 28-6 | Me | Me | H | H | H | Ph(2-F-6-Cl) | |
| 28-7 | Me | Me | H | Cl | H | Ph(2-F) | |
| 28-8 | Me | Me | H | Cl | H | Ph(2,6-F₂) | |
| 28-9 | Me | Me | H | Cl | H | Ph(2-Cl) | |
| 28-10 | Me | Me | H | Cl | H | Ph(2-Me) | |
| 28-11 | Me | Me | H | Cl | H | Ph(2-CF₃) | |
| 28-12 | Me | Me | H | Cl | H | Ph(2-F-6-Cl) | |
| 28-13 | Me | Me | H | Me | H | Ph(2-F) | |
| 28-14 | Me | Me | H | Me | H | Ph(2,6-F₂) | |
| 28-15 | Me | Me | H | Me | H | Ph(2-Cl) | |
| 28-16 | Me | Me | H | Me | H | Ph(2-Me) | |
| 28-17 | Me | Me | H | Me | H | Ph(2-CF₃) | |
| 28-18 | Me | Me | H | Me | H | Ph(2-F-6-Cl) | |
| 28-19 | Me | Me | H | H | Cl | Ph(2-F) | |
| 28-20 | Me | Me | H | H | Cl | Ph(2,6-F₂) | |
| 28-21 | Me | Me | H | H | Cl | Ph(2-Cl) | |
| 28-22 | Me | Me | H | H | Cl | Ph(2-Me) | |
| 28-23 | Me | Me | H | H | Cl | Ph(2-CF₃) | |
| 28-24 | Me | Me | H | H | Cl | Ph(2-F-6-Cl) | |
| 28-25 | Me | Me | H | H | Me | Ph(2-F) | |
| 28-26 | Me | Me | H | H | Me | Ph(2,6-F₂) | |
| 28-27 | Me | Me | H | H | Me | Ph(2-Cl) | |
| 28-28 | Me | Me | H | H | Me | Ph(2-Me) | |
| 28-29 | Me | Me | H | H | Me | Ph(2-CF₃) | |
| 28-30 | Me | Me | H | H | Me | Ph(2-F-6-Cl) | |
| 28-31 | Me | Me | H | Me | Me | Ph(2-F) | |
| 28-32 | Me | Me | H | Me | Me | Ph(2,6-F₂) | |
| 28-33 | Me | Me | H | Me | Me | Ph(2-Cl) | |
| 28-34 | Me | Me | H | Me | Me | Ph(2-Me) | |
| 28-35 | Me | Me | H | Me | Me | Ph(2-CF₃) | |
| 28-36 | Me | Me | H | Me | Me | Ph(2-F-6-Cl) | |

TABLE 29

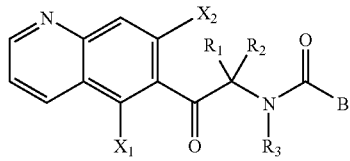

| Compound No. | R₁ | R₂ | R₃ | X₁ | X₂ | B | Physical properties (mp ° C.) |
|---|---|---|---|---|---|---|---|
| 29-1 | Me | Me | H | H | H | Ph(2-F) | |
| 29-2 | Me | Me | H | H | H | Ph(2,6-F₂) | |
| 29-3 | Me | Me | H | H | H | Ph(2-Cl) | |
| 29-4 | Me | Me | H | H | H | Ph(2-Me) | |
| 29-5 | Me | Me | H | H | H | Ph(2-CF₃) | |
| 29-6 | Me | Me | H | H | H | Ph(2-F-6-Cl) | |
| 29-7 | Me | Me | H | Cl | H | Ph(2-F) | |
| 29-8 | Me | Me | H | Cl | H | Ph(2,6-F₂) | |
| 29-9 | Me | Me | H | Cl | H | Ph(2-Cl) | |
| 29-10 | Me | Me | H | Cl | H | Ph(2-Me) | |
| 29-11 | Me | Me | H | Cl | H | Ph(2-CF₃) | |
| 29-12 | Me | Me | H | Cl | H | Ph(2-F-6-Cl) | |
| 29-13 | Me | Me | H | Me | H | Ph(2-F) | |
| 29-14 | Me | Me | H | Me | H | Ph(2,6-F₂) | |
| 29-15 | Me | Me | H | Me | H | Ph(2-Cl) | |
| 29-16 | Me | Me | H | Me | H | Ph(2-Me) | |
| 29-17 | Me | Me | H | Me | H | Ph(2-CF₃) | |
| 29-18 | Me | Me | H | Me | H | Ph(2-F-6-Cl) | |
| 29-19 | Me | Me | H | H | Cl | Ph(2-F) | |
| 29-20 | Me | Me | H | H | Cl | Ph(2,6-F₂) | |
| 29-21 | Me | Me | H | H | Cl | Ph(2-Cl) | |
| 29-22 | Me | Me | H | H | Cl | Ph(2-Me) | |
| 29-23 | Me | Me | H | H | Cl | Ph(2-CF₃) | |
| 29-24 | Me | Me | H | H | Cl | Ph(2-F-6-Cl) | |
| 29-25 | Me | Me | H | H | Me | Ph(2-F) | |
| 29-26 | Me | Me | H | H | Me | Ph(2,6-F₂) | |
| 29-27 | Me | Me | H | H | Me | Ph(2-Cl) | |
| 29-28 | Me | Me | H | H | Me | Ph(2-Me) | |
| 29-29 | Me | Me | H | H | Me | Ph(2-CF₃) | |
| 29-30 | Me | Me | H | H | Me | Ph(2-F-6-Cl) | |
| 29-31 | Me | Me | H | Me | Me | Ph(2-F) | |
| 29-32 | Me | Me | H | Me | Me | Ph(2,6-F₂) | |
| 29-33 | Me | Me | H | Me | Me | Ph(2-Cl) | |
| 29-34 | Me | Me | H | Me | Me | Ph(2-Me) | |
| 29-35 | Me | Me | H | Me | Me | Ph(2-CF₃) | |
| 29-36 | Me | Me | H | Me | Me | Ph(2-F-6-Cl) | |

TABLE 30

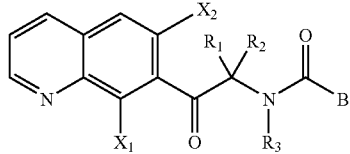

| Compound No. | R₁ | R₂ | R₃ | X₁ | X₂ | B | Physical properties (mp ° C.) |
|---|---|---|---|---|---|---|---|
| 30-1 | Me | Me | H | H | H | Ph(2-F) | |
| 30-2 | Me | Me | H | H | H | Ph(2,6-F₂) | |
| 30-3 | Me | Me | H | H | H | Ph(2-Cl) | |
| 30-4 | Me | Me | H | H | H | Ph(2-Me) | |
| 30-5 | Me | Me | H | H | H | Ph(2-CF₃) | |
| 30-6 | Me | Me | H | H | H | Ph(2-F-6-Cl) | |
| 30-7 | Me | Me | H | Cl | H | Ph(2-F) | |
| 30-8 | Me | Me | H | Cl | H | Ph(2,6-F₂) | |
| 30-9 | Me | Me | H | Cl | H | Ph(2-Cl) | |
| 30-10 | Me | Me | H | Cl | H | Ph(2-Me) | |
| 30-11 | Me | Me | H | Cl | H | Ph(2-CF₃) | |
| 30-12 | Me | Me | H | Cl | H | Ph(2-F-6-Cl) | |
| 30-13 | Me | Me | H | Me | H | Ph(2-F) | |
| 30-14 | Me | Me | H | Me | H | Ph(2,6-F₂) | |
| 30-15 | Me | Me | H | Me | H | Ph(2-Cl) | |
| 30-16 | Me | Me | H | Me | H | Ph(2-Me) | |
| 30-17 | Me | Me | H | Me | H | Ph(2-CF₃) | |
| 30-18 | Me | Me | H | Me | H | Ph(2-F-6-Cl) | |
| 30-19 | Me | Me | H | H | Cl | Ph(2-F) | |
| 30-20 | Me | Me | H | H | Cl | Ph(2,6-F₂) | |
| 30-21 | Me | Me | H | H | Cl | Ph(2-Cl) | |
| 30-22 | Me | Me | H | H | Cl | Ph(2-Me) | |
| 30-23 | Me | Me | H | H | Cl | Ph(2-CF₃) | |
| 30-24 | Me | Me | H | H | Cl | Ph(2-F-6-Cl) | |
| 30-25 | Me | Me | H | H | Me | Ph(2-F) | |
| 30-26 | Me | Me | H | H | Me | Ph(2,6-F₂) | |
| 30-27 | Me | Me | H | H | Me | Ph(2-Cl) | |
| 30-28 | Me | Me | H | H | Me | Ph(2-Me) | |
| 30-29 | Me | Me | H | H | Me | Ph(2-CF₃) | |
| 30-30 | Me | Me | H | H | Me | Ph(2-F-6-Cl) | |
| 30-31 | Me | Me | H | Me | Me | Ph(2-F) | |
| 30-32 | Me | Me | H | Me | Me | Ph(2,6-F₂) | |
| 30-33 | Me | Me | H | Me | Me | Ph(2-Cl) | |
| 30-34 | Me | Me | H | Me | Me | Ph(2-Me) | |
| 30-35 | Me | Me | H | Me | Me | Ph(2-CF₃) | |
| 30-36 | Me | Me | H | Me | Me | Ph(2-F-6-Cl) | |

TABLE 31

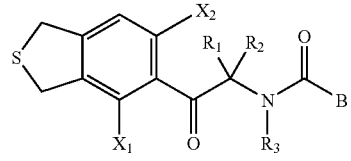

| Compound No. | R₁ | R₂ | R₃ | X₁ | X₂ | B | Physical properties (mp ° C.) |
|---|---|---|---|---|---|---|---|
| 31-1 | Me | Me | H | H | H | Ph(2-F) | |
| 31-2 | Me | Me | H | H | H | Ph(2,6-F₂) | |
| 31-3 | Me | Me | H | H | H | Ph(2-Cl) | |
| 31-4 | Me | Me | H | H | H | Ph(2-Me) | |
| 31-5 | Me | Me | H | H | H | Ph(2-CF₃) | |
| 31-6 | Me | Me | H | H | H | Ph(2-F-6-Cl) | |
| 31-7 | Me | Me | H | Cl | H | Ph(2-F) | |
| 31-8 | Me | Me | H | Cl | H | Ph(2,6-F₂) | |
| 31-9 | Me | Me | H | Cl | H | Ph(2-Cl) | |
| 31-10 | Me | Me | H | Cl | H | Ph(2-Me) | |
| 31-11 | Me | Me | H | Cl | H | Ph(2-CF₃) | |
| 31-12 | Me | Me | H | Cl | H | Ph(2-F-6-Cl) | |
| 31-13 | Me | Me | H | Me | H | Ph(2-F) | |
| 31-14 | Me | Me | H | Me | H | Ph(2,6-F₂) | |
| 31-15 | Me | Me | H | Me | H | Ph(2-Cl) | |
| 31-16 | Me | Me | H | Me | H | Ph(2-Me) | |
| 31-17 | Me | Me | H | Me | H | Ph(2-CF₃) | |
| 31-18 | Me | Me | H | Me | H | Ph(2-F-6-Cl) | |
| 31-19 | Me | Me | H | H | Cl | Ph(2-F) | |
| 31-20 | Me | Me | H | H | Cl | Ph(2,6-F₂) | |
| 31-21 | Me | Me | H | H | Cl | Ph(2-Cl) | |
| 31-22 | Me | Me | H | H | Cl | Ph(2-Me) | |
| 31-23 | Me | Me | H | H | Cl | Ph(2-CF₃) | |
| 31-24 | Me | Me | H | H | Cl | Ph(2-F-6-Cl) | |
| 31-25 | Me | Me | H | H | Me | Ph(2-F) | |
| 31-26 | Me | Me | H | H | Me | Ph(2,6-F₂) | |

TABLE 31-continued

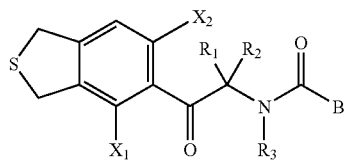

| Compound No. | R₁ | R₂ | R₃ | X₁ | X₂ | B | Physical properties (mp °C.) |
|---|---|---|---|---|---|---|---|
| 31-27 | Me | Me | H | H | Me | Ph(2-Cl) | |
| 31-28 | Me | Me | H | H | Me | Ph(2-Me) | |
| 31-29 | Me | Me | H | H | Me | Ph(2-CF₃) | |
| 31-30 | Me | Me | H | H | Me | Ph(2-F-6-Cl) | |
| 31-31 | Me | Me | H | Me | Me | Ph(2-F) | |
| 31-32 | Me | Me | H | Me | Me | Ph(2,6-F₂) | |
| 31-33 | Me | Me | H | Me | Me | Ph(2-Cl) | |
| 31-34 | Me | Me | H | Me | Me | Ph(2-Me) | |
| 31-35 | Me | Me | H | Me | Me | Ph(2-CF₃) | |
| 31-36 | Me | Me | H | Me | Me | Ph(2-F-6-Cl) | |

TABLE 32

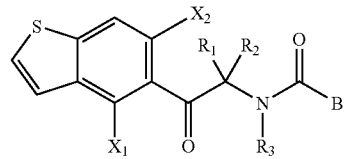

| Compound No. | R₁ | R₂ | R₃ | X₁ | X₂ | B | Physical properties (mp °C.) |
|---|---|---|---|---|---|---|---|
| 32-1 | Me | Me | H | H | H | Ph(2-F) | |
| 32-2 | Me | Me | H | H | H | Ph(2,6-F₂) | |
| 32-3 | Me | Me | H | H | H | Ph(2-Cl) | |
| 32-4 | Me | Me | H | H | H | Ph(2-Me) | |
| 32-5 | Me | Me | H | H | H | Ph(2-CF₃) | |
| 32-6 | Me | Me | H | H | H | Ph(2-F-6-Cl) | |
| 32-7 | Me | Me | H | Cl | H | Ph(2-F) | |
| 32-8 | Me | Me | H | Cl | H | Ph(2,6-F₂) | |
| 32-9 | Me | Me | H | Cl | H | Ph(2-Cl) | |
| 32-10 | Me | Me | H | Cl | H | Ph(2-Me) | |
| 32-11 | Me | Me | H | Cl | H | Ph(2-CF₃) | |
| 32-12 | Me | Me | H | Cl | H | Ph(2-F-6-Cl) | |
| 32-13 | Me | Me | H | Me | H | Ph(2-F) | |
| 32-14 | Me | Me | H | Me | H | Ph(2,6-F₂) | |
| 32-15 | Me | Me | H | Me | H | Ph(2-Cl) | |
| 32-16 | Me | Me | H | Me | H | Ph(2-Me) | |
| 32-17 | Me | Me | H | Me | H | Ph(2-CF₃) | |
| 32-18 | Me | Me | H | Me | H | Ph(2-F-6-Cl) | |
| 32-19 | Me | Me | H | H | Cl | Ph(2-F) | |
| 32-20 | Me | Me | H | H | Cl | Ph(2,6-F₂) | |
| 32-21 | Me | Me | H | H | Cl | Ph(2-Cl) | |
| 32-22 | Me | Me | H | H | Cl | Ph(2-Me) | |
| 32-23 | Me | Me | H | H | Cl | Ph(2-CF₃) | |
| 32-24 | Me | Me | H | H | Cl | Ph(2-F-6-Cl) | |
| 32-25 | Me | Me | H | H | Me | Ph(2-F) | |
| 32-26 | Me | Me | H | H | Me | Ph(2,6-F₂) | |
| 32-27 | Me | Me | H | H | Me | Ph(2-Cl) | |
| 32-28 | Me | Me | H | H | Me | Ph(2-Me) | |
| 32-29 | Me | Me | H | H | Me | Ph(2-CF₃) | |
| 32-30 | Me | Me | H | H | Me | Ph(2-F-6-Cl) | |
| 32-31 | Me | Me | H | Me | Me | Ph(2-F) | |
| 32-32 | Me | Me | H | Me | Me | Ph(2,6-F₂) | |
| 32-33 | Me | Me | H | Me | Me | Ph(2-Cl) | |
| 32-34 | Me | Me | H | Me | Me | Ph(2-Me) | |
| 32-35 | Me | Me | H | Me | Me | Ph(2-CF₃) | |
| 32-36 | Me | Me | H | Me | Me | Ph(2-F-6-Cl) | |

TABLE 33

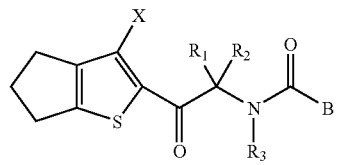

| Compound No. | R₁ | R₂ | R₃ | X | B | Physical properties (mp °C.) |
|---|---|---|---|---|---|---|
| 33-1 | Me | Me | H | H | Ph(2-F) | |
| 33-2 | Me | Me | H | H | Ph(2,6-F₂) | |
| 33-3 | Me | Me | H | H | Ph(2-Cl) | |
| 33-4 | Me | Me | H | H | Ph(2-Me) | |
| 33-5 | Me | Me | H | H | Ph(2-CF₃) | |
| 33-6 | Me | Me | H | H | Ph(2-F-6-Cl) | |
| 33-7 | Me | Me | H | Cl | Ph(2-F) | |
| 33-8 | Me | Me | H | Cl | Ph(2,6-F₂) | |
| 33-9 | Me | Me | H | Cl | Ph(2-Cl) | |
| 33-10 | Me | Me | H | Cl | Ph(2-Me) | |
| 33-11 | Me | Me | H | Cl | Ph(2-CF₃) | |
| 33-12 | Me | Me | H | Cl | Ph(2-F-6-Cl) | |
| 33-13 | Me | Me | H | Br | Ph(2-F) | |
| 33-14 | Me | Me | H | Br | Ph(2,6-F₂) | |
| 33-15 | Me | Me | H | Br | ph(2-Cl) | |
| 33-16 | Me | Me | H | Br | Ph(2-Me) | |
| 33-17 | Me | Me | H | Br | Ph(2-CF₃) | |
| 33-18 | Me | Me | H | Br | Ph(2-F-6-Cl) | |
| 33-19 | Me | Me | H | Me | Ph(2-F) | |
| 33-20 | Me | Me | H | Me | Ph(2,6-F₂) | |
| 33-21 | Me | Me | H | Me | Ph(2-Cl) | |
| 33-22 | Me | Me | H | Me | Ph(2-Me) | |
| 33-23 | Me | Me | H | Me | Ph(2-CF₃) | |
| 33-24 | Me | Me | H | Me | Ph(2-F-6-Cl) | |
| 33-25 | Me | Me | H | Et | Ph(2-F) | |
| 33-26 | Me | Me | H | Et | Ph(2,6-F₂) | |
| 33-27 | Me | Me | H | Et | Ph(2-Cl) | |
| 33-28 | Me | Me | H | Et | Ph(2-Me) | |
| 33-29 | Me | Me | H | Et | Ph(2-CF₃) | |
| 33-30 | Me | Me | H | Et | Ph(2-F-6-Cl) | |

TABLE 34

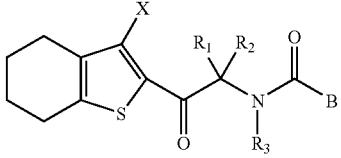

| Compound No. | R₁ | R₂ | R₃ | X | B | Physical properties (mp °C.) |
|---|---|---|---|---|---|---|
| 34-1 | Me | Me | H | H | Ph(2-F) | |
| 34-2 | Me | Me | H | H | Ph(2,6-F₂) | |
| 34-3 | Me | Me | H | H | Ph(2-Cl) | |
| 34-4 | Me | Me | H | H | Ph(2-Me) | |
| 34-5 | Me | Me | H | H | Ph(2-CF₃) | |
| 34-6 | Me | Me | H | H | Ph(2-F-6-Cl) | |
| 34-7 | Me | Me | H | Cl | Ph(2-F) | |
| 34-8 | Me | Me | H | Cl | Ph(2,6-F₂) | |
| 34-9 | Me | Me | H | Cl | Ph(2-Cl) | |
| 34-10 | Me | Me | H | Cl | Ph(2-Me) | |
| 34-11 | Me | Me | H | Cl | Ph(2-CF₃) | |
| 34-12 | Me | Me | H | Cl | Ph(2-F-6-Cl) | |
| 34-13 | Me | Me | H | Br | Ph(2-F) | |
| 34-14 | Me | Me | H | Br | Ph(2,6-F₂) | |
| 34-15 | Me | Me | H | Br | Ph(2-Cl) | |
| 34-16 | Me | Me | H | Br | Ph(2-Me) | |
| 34-17 | Me | Me | H | Br | Ph(2-CF₃) | |
| 34-18 | Me | Me | H | Br | Ph(2-F-6-Cl) | |
| 34-19 | Me | Me | H | Me | Ph(2-F) | |

TABLE 34-continued

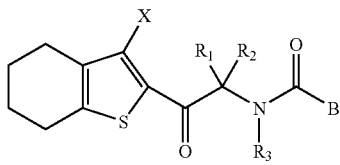

| Compound No. | R₁ | R₂ | R₃ | X | B | Physical properties (mp ° C.) |
|---|---|---|---|---|---|---|
| 34-20 | Me | Me | H | Me | Ph(2,6-F₂) | |
| 34-21 | Me | Me | H | Me | Ph(2-Cl) | |
| 34-22 | Me | Me | H | Me | Ph(2-Me) | |
| 34-23 | Me | Me | H | Me | Ph(2-CF₃) | |
| 34-24 | Me | Me | H | Me | Ph(2-F-6-Cl) | |
| 34-25 | Me | Me | H | Et | Ph(2-F) | |
| 34-26 | Me | Me | H | Et | Ph(2,6-F₂) | |
| 34-27 | Me | Me | H | Et | Ph(2-Cl) | |
| 34-28 | Me | Me | H | Et | Ph(2-Me) | |
| 34-29 | Me | Me | H | Et | Ph(2-CF₃) | |
| 34-30 | Me | Me | H | Et | Ph(2-F-6-Cl) | |

TABLE 35

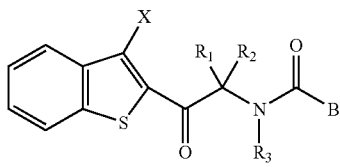

| Compound No. | R₁ | R₂ | R₃ | X | B | Physical properties (mp ° C.) |
|---|---|---|---|---|---|---|
| 35-1 | Me | Me | H | H | Ph(2-F) | |
| 35-2 | Me | Me | H | H | Ph(2,6-F₂) | |
| 35-3 | Me | Me | H | H | Ph(2-Cl) | |
| 35-4 | Me | Me | H | H | Ph(2-Me) | |
| 35-5 | Me | Me | H | H | Ph(2-CF₃) | |
| 35-6 | Me | Me | H | H | Ph(2-F-6-Cl) | |
| 35-7 | Me | Me | H | Cl | Ph(2-F) | |
| 35-8 | Me | Me | H | Cl | Ph(2,6-F₂) | |
| 35-9 | Me | Me | H | Cl | Ph(2-Cl) | |
| 35-10 | Me | Me | H | Cl | Ph(2-Me) | |
| 35-11 | Me | Me | H | Cl | Ph(2-CF₃) | |
| 35-12 | Me | Me | H | Cl | Ph(2-F-6-Cl) | |
| 35-13 | Me | Me | H | Br | Ph(2-F) | |
| 35-14 | Me | Me | H | Br | Ph(2,6-F₂) | |
| 35-15 | Me | Me | H | Br | Ph(2-Cl) | |
| 35-16 | Me | Me | H | Br | Ph(2-Me) | |
| 35-17 | Me | Me | H | Br | Ph(2-CF₃) | |
| 35-18 | Me | Me | H | Br | Ph(2-F-6-Cl) | |
| 35-19 | Me | Me | H | Me | Ph(2-F) | |
| 35-20 | Me | Me | H | Me | Ph(2,6-F₂) | |
| 35-21 | Me | Me | H | Me | Ph(2-Cl) | |
| 35-22 | Me | Me | H | Me | Ph(2-Me) | |
| 35-23 | Me | Me | H | Me | Ph(2-CF₃) | |
| 35-24 | Me | Me | H | Me | Ph(2-F-6-Cl) | |
| 35-25 | Me | Me | H | Et | Ph(2-F) | |
| 35-26 | Me | Me | H | Et | Ph(2,6-F₂) | |
| 35-27 | Me | Me | H | Et | Ph(2-Cl) | |
| 35-28 | Me | Me | H | Et | Ph(2-Me) | |
| 35-29 | Me | Me | H | Et | Ph(2-CF₃) | |
| 35-30 | Me | Me | H | Et | Ph(2-F-6-Cl) | |

TABLE 36

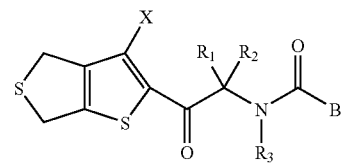

| Compound No. | R₁ | R₂ | R₃ | X | B | Physical properties (mp ° C.) |
|---|---|---|---|---|---|---|
| 36-1 | Me | Me | H | H | Ph(2-F) | |
| 36-2 | Me | Me | H | H | Ph(2,6-F₂) | |
| 36-3 | Me | Me | H | H | Ph(2-Cl) | |
| 36-4 | Me | Me | H | H | Ph(2-Me) | |
| 36-5 | Me | Me | H | H | Ph(2-CF₃) | |
| 36-6 | Me | Me | H | H | Ph(2-F-6-Cl) | |
| 36-7 | Me | Me | H | Cl | Ph(2-F) | |
| 36-8 | Me | Me | H | Cl | Ph(2,6-F₂) | |
| 36-9 | Me | Me | H | Cl | Ph(2-Cl) | |
| 36-10 | Me | Me | H | Cl | Ph(2-Me) | |
| 36-11 | Me | Me | H | Cl | Ph(2-CF₃) | |
| 36-12 | Me | Me | H | Cl | Ph(2-F-6-Cl) | |
| 36-13 | Me | Me | H | Br | Ph(2-F) | |
| 36-14 | Me | Me | H | Br | Ph(2,6-F₂) | |
| 36-15 | Me | Me | H | Br | Ph(2-Cl) | |
| 36-16 | Me | Me | H | Br | Ph(2-Me) | |
| 36-17 | Me | Me | H | Br | Ph(2-CF₃) | |
| 36-18 | Me | Me | H | Br | Ph(2-F-6-Cl) | |
| 36-19 | Me | Me | H | Me | Ph(2-F) | |
| 36-20 | Me | Me | H | Me | Ph(2,6-F₂) | |
| 36-21 | Me | Me | H | Me | Ph(2-Cl) | |
| 36-22 | Me | Me | H | Me | Ph(2-Me) | |
| 36-23 | Me | Me | H | Me | Ph(2-CF₃) | |
| 36-24 | Me | Me | H | Me | Ph(2-F-6-Cl) | |
| 36-25 | Me | Me | H | Et | Ph(2-F) | |
| 36-26 | Me | Me | H | Et | Ph(2,6-F₂) | |
| 36-27 | Me | Me | H | Et | Ph(2-Cl) | |
| 36-28 | Me | Me | H | Et | Ph(2-Me) | |
| 36-29 | Me | Me | H | Et | Ph(2-CF₃) | |
| 36-30 | Me | Me | H | Et | Ph(2-F-6-Cl) | |

TABLE 37

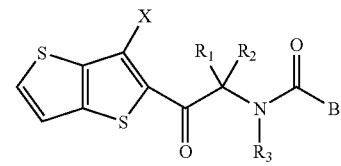

| Compound No. | R₁ | R₂ | R₃ | X | B | Physical properties (mp ° C.) |
|---|---|---|---|---|---|---|
| 37-1 | Me | Me | H | H | Ph(2-F) | |
| 37-2 | Me | Me | H | H | Ph(2,6-F₂) | |
| 37-3 | Me | Me | H | H | Ph(2-Cl) | |
| 37-4 | Me | Me | H | H | Ph(2-Me) | |
| 37-5 | Me | Me | H | H | Ph(2-CF₃) | |
| 37-6 | Me | Me | H | H | Ph(2-F-6-Cl) | |
| 37-7 | Me | Me | H | Cl | Ph(2-F) | |
| 37-8 | Me | Me | H | Cl | Ph(2,6-F₂) | |
| 37-9 | Me | Me | H | Cl | ph(2-Cl) | |
| 37-10 | Me | Me | H | Cl | Ph(2-Me) | |
| 37-11 | Me | Me | H | Cl | Ph(2-CF₃) | |
| 37-12 | Me | Me | H | Cl | Ph(2-F-6-Cl) | |
| 37-13 | Me | Me | H | Br | Ph(2-F) | |
| 37-14 | Me | Me | H | Br | Ph(2,6-F₂) | |
| 37-15 | Me | Me | H | Br | Ph(2-Cl) | |
| 37-16 | Me | Me | H | Br | Ph(2-Me) | |
| 37-17 | Me | Me | H | Br | Ph(2-CF₃) | |
| 37-18 | Me | Me | H | Br | Ph(2-F-6-Cl) | |
| 37-19 | Me | Me | H | Me | Ph(2-F) | |

TABLE 37-continued

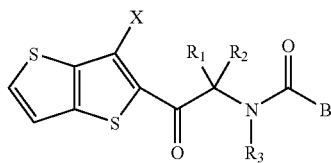

| Compound No. | R₁ | R₂ | R₃ | X | B | Physical properties (mp ° C.) |
|---|---|---|---|---|---|---|
| 37-20 | Me | Me | H | Me | Ph(2,6-F₂) | |
| 37-21 | Me | Me | H | Me | Ph(2-Cl) | |
| 37-22 | Me | Me | H | Me | Ph(2-Me) | |
| 37-23 | Me | Me | H | Me | Ph(2-CF₃) | |
| 37-24 | Me | Me | H | Me | Ph(2-F-6-Cl) | |
| 37-25 | Me | Me | H | Et | Ph(2-F) | |
| 37-26 | Me | Me | H | Et | Ph(2,6-F₂) | |
| 37-27 | Me | Me | H | Et | Ph(2-Cl) | |
| 37-28 | Me | Me | H | Et | Ph(2-Me) | |
| 37-29 | Me | Me | H | Et | Ph(2-CF₃) | |
| 37-30 | Me | Me | H | Et | Ph(2-F-6-Cl) | |

TABLE 38

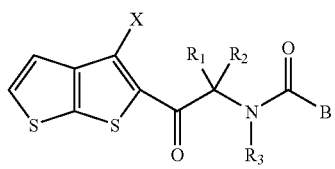

| Compound No. | R₁ | R₂ | R₃ | X | B | Physical properties (mp ° C.) |
|---|---|---|---|---|---|---|
| 38-1 | Me | Me | H | H | Ph(2-F) | |
| 38-2 | Me | Me | H | H | Ph(2,6-F₂) | |
| 38-3 | Me | Me | H | H | Ph(2-Cl) | |
| 38-4 | Me | Me | H | H | Ph(2-Me) | |
| 38-5 | Me | Me | H | H | Ph(2-CF₃) | |
| 38-6 | Me | Me | H | H | Ph(2-F-6-Cl) | |
| 38-7 | Me | Me | H | Cl | Ph(2-F) | |
| 38-8 | Me | Me | H | Cl | Ph(2,6-F₂) | |
| 38-9 | Me | Me | H | Cl | Ph(2-Cl) | |
| 38-10 | Me | Me | H | Cl | Ph(2-Me) | |
| 38-11 | Me | Me | H | Cl | Ph(2-CF₃) | |
| 38-12 | Me | Me | H | Cl | Ph(2-F-6-Cl) | |
| 38-13 | Me | Me | H | Br | Ph(2-F) | |
| 38-14 | Me | Me | H | Br | Ph(2,6-F₂) | |
| 38-15 | Me | Me | H | Br | Ph(2-Cl) | |
| 38-16 | Me | Me | H | Br | Ph(2-Me) | |
| 38-17 | Me | Me | H | Br | Ph(2-CF₃) | |
| 38-18 | Me | Me | H | Br | Ph(2-F-6-Cl) | |
| 38-19 | Me | Me | H | Me | Ph(2-F) | |
| 38-20 | Me | Me | H | Me | Ph(2,6-F₂) | |
| 38-21 | Me | Me | H | Me | Ph(2-Cl) | |
| 38-22 | Me | Me | H | Me | Ph(2-Me) | |
| 38-23 | Me | Me | H | Me | Ph(2-CF₃) | |
| 38-24 | Me | Me | H | Me | Ph(2-F-6-Cl) | |
| 38-25 | Me | Me | H | Et | Ph(2-F) | |
| 38-26 | Me | Me | H | Et | Ph(2,6-F₂) | |
| 38-27 | Me | Me | H | Et | Ph(2-Cl) | |
| 38-28 | Me | Me | H | Et | Ph(2-Me) | |
| 38-29 | Me | Me | H | Et | Ph(2-CF₃) | |
| 38-30 | Me | Me | H | Et | Ph(2-F-6-Cl) | |

TABLE 39

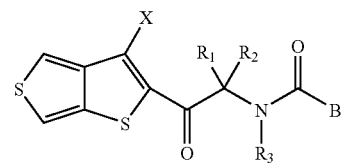

| Compound No. | R₁ | R₂ | R₃ | X | B | Physical properties (mp ° C.) |
|---|---|---|---|---|---|---|
| 39-1 | Me | Me | H | H | Ph(2-F) | |
| 39-2 | Me | Me | H | H | Ph(2,6-F₂) | |
| 39-3 | Me | Me | H | H | Ph(2-Cl) | |
| 39-4 | Me | Me | H | H | Ph(2-Me) | |
| 39-5 | Me | Me | H | H | Ph(2-CF₃) | |
| 39-6 | Me | Me | H | H | Ph(2-F-6-Cl) | |
| 39-7 | Me | Me | H | Cl | Ph(2-F) | |
| 39-8 | Me | Me | H | Cl | Ph(2,6-F₂) | |
| 39-9 | Me | Me | H | Cl | ph(2-Cl) | |
| 39-10 | Me | Me | H | Cl | Ph(2-Me) | |
| 39-11 | Me | Me | H | Cl | Ph(2-CF₃) | |
| 39-12 | Me | Me | H | Cl | Ph(2-F-6-Cl) | |
| 39-13 | Me | Me | H | Br | Ph(2-F) | |
| 39-14 | Me | Me | H | Br | Ph(2,6-F₂) | |
| 39-15 | Me | Me | H | Br | Ph(2-Cl) | |
| 39-16 | Me | Me | H | Br | Ph(2-Me) | |
| 39-17 | Me | Me | H | Br | Ph(2-CF₃) | |
| 39-18 | Me | Me | H | Br | Ph(2-F-6-Cl) | |
| 39-19 | Me | Me | H | Me | Ph(2-F) | |
| 39-20 | Me | Me | H | Me | Ph(2,6-F₂) | |
| 39-21 | Me | Me | H | Me | Ph(2-Cl) | |
| 39-22 | Me | Me | H | Me | Ph(2-Me) | |
| 39-23 | Me | Me | H | Me | Ph(2-CF₃) | |
| 39-24 | Me | Me | H | Me | Ph(2-F-6-Cl) | |
| 39-25 | Me | Me | H | Et | Ph(2-F) | |
| 39-26 | Me | Me | H | Et | Ph(2,6-F₂) | |
| 39-27 | Me | Me | H | Et | Ph(2-Cl) | |
| 39-28 | Me | Me | H | Et | Ph(2-Me) | |
| 39-29 | Me | Me | H | Et | Ph(2-CF₃) | |
| 39-30 | Me | Me | H | Et | Ph(2-F-6-Cl) | |

TABLE 40

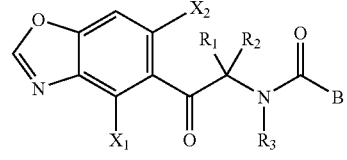

| Compound No. | R₁ | R₂ | R₃ | X₁ | X₂ | B | Physical properties (mp ° C.) |
|---|---|---|---|---|---|---|---|
| 40-1 | Me | Me | H | H | H | Ph(2-F) | |
| 40-2 | Me | Me | H | H | H | Ph(2,6-F₂) | |
| 40-3 | Me | Me | H | H | H | Ph(2-Cl) | |
| 40-4 | Me | Me | H | H | H | Ph(2-Me) | |
| 40-5 | Me | Me | H | H | H | Ph(2-CF₃) | |
| 40-6 | Me | Me | H | H | H | Ph(2-F-6-Cl) | |
| 40-7 | Me | Me | H | Cl | H | Ph(2-F) | |
| 40-8 | Me | Me | H | Cl | H | Ph(2,6-F₂) | |
| 40-9 | Me | Me | H | Cl | H | Ph(2-Cl) | |
| 40-10 | Me | Me | H | Cl | H | Ph(2-Me) | |
| 40-11 | Me | Me | H | Cl | H | Ph(2-CF₃) | |
| 40-12 | Me | Me | H | Cl | H | Ph(2-F-6-Cl) | |
| 40-13 | Me | Me | H | Me | H | Ph(2-F) | |
| 40-14 | Me | Me | H | Me | H | Ph(2,6-F₂) | |
| 40-15 | Me | Me | H | Me | H | Ph(2-Cl) | |
| 40-16 | Me | Me | H | Me | H | Ph(2-Me) | |
| 40-17 | Me | Me | H | Me | H | Ph(2-CF₃) | |
| 40-18 | Me | Me | H | Me | H | Ph(2-F-6-Cl) | |
| 40-19 | Me | Me | H | H | Cl | Ph(2-F) | |

TABLE 40-continued

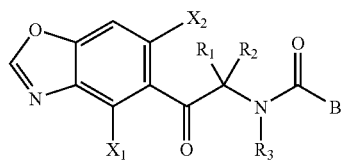

| Compound No. | R₁ | R₂ | R₃ | X₁ | X₂ | B | Physical properties (mp ° C.) |
|---|---|---|---|---|---|---|---|
| 40-20 | Me | Me | H | H | Cl | Ph(2,6-F₂) | |
| 40-21 | Me | Me | H | H | Cl | Ph(2-Cl) | |
| 40-22 | Me | Me | H | H | Cl | Ph(2-Me) | |
| 40-23 | Me | Me | H | H | Cl | Ph(2-CF₃) | |
| 40-24 | Me | Me | H | H | Cl | Ph(2-F-6-Cl) | |
| 40-25 | Me | Me | H | H | Me | Ph(2-F) | |
| 40-26 | Me | Me | H | H | Me | Ph(2,6-F₂) | |
| 40-27 | Me | Me | H | H | Me | Ph(2-Cl) | |
| 40-28 | Me | Me | H | H | Me | Ph(2-Me) | |
| 40-29 | Me | Me | H | H | Me | Ph(2-CF₃) | |
| 40-30 | Me | Me | H | H | Me | Ph(2-F-6-Cl) | |
| 40-31 | Me | Me | H | Me | Me | Ph(2-F) | |
| 40-32 | Me | Me | H | Me | Me | Ph(2,6-F₂) | |
| 40-33 | Me | Me | H | Me | Me | Ph(2-Cl) | |
| 40-34 | Me | Me | H | Me | Me | Ph(2-Me) | |
| 40-35 | Me | Me | H | Me | Me | Ph(2-CF₃) | |
| 40-36 | Me | Me | H | Me | Me | Ph(2-F-6-Cl) | |

TABLE 41

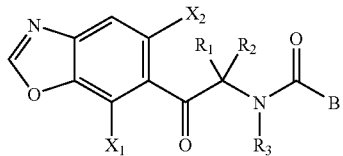

| Compound No. | R₁ | R₂ | R₃ | X₁ | X₂ | B | Physical properties (mp ° C.) |
|---|---|---|---|---|---|---|---|
| 41-1 | Me | Me | H | H | H | Ph(2-F) | |
| 41-2 | Me | Me | H | H | H | Ph(2,6-F₂) | |
| 41-3 | Me | Me | H | H | H | Ph(2-Cl) | |
| 41-4 | Me | Me | H | H | H | Ph(2-Me) | |
| 41-5 | Me | Me | H | H | H | Ph(2-CF₃) | |
| 41-6 | Me | Me | H | H | H | Ph(2-F-6-Cl) | |
| 41-7 | Me | Me | H | Cl | H | Ph(2-F) | |
| 41-8 | Me | Me | H | Cl | H | Ph(2,6-F₂) | |
| 41-9 | Me | Me | H | Cl | H | Ph(2-Cl) | |
| 41-10 | Me | Me | H | Cl | H | Ph(2-Me) | |
| 41-11 | Me | Me | H | Cl | H | Ph(2-CF₃) | |
| 41-12 | Me | Me | H | Cl | H | Ph(2-F-6-Cl) | |
| 41-13 | Me | Me | H | Me | H | Ph(2-F) | |
| 41-14 | Me | Me | H | Me | H | Ph(2,6-F₂) | |
| 41-15 | Me | Me | H | Me | H | Ph(2-Cl) | |
| 41-16 | Me | Me | H | Me | H | Ph(2-Me) | |
| 41-17 | Me | Me | H | Me | H | Ph(2-CF₃) | |
| 41-18 | Me | Me | H | Me | H | Ph(2-F-6-Cl) | |
| 41-19 | Me | Me | H | H | Cl | Ph(2-F) | |
| 41-20 | Me | Me | H | H | Cl | Ph(2,6-F₂) | |
| 41-21 | Me | Me | H | H | Cl | Ph(2-Cl) | |
| 41-22 | Me | Me | H | H | Cl | Ph(2-Me) | |
| 41-23 | Me | Me | H | H | Cl | Ph(2-CF₃) | |
| 41-24 | Me | Me | H | H | Cl | Ph(2-F-6-Cl) | |
| 41-25 | Me | Me | H | H | Me | Ph(2-F) | |
| 41-26 | Me | Me | H | H | Me | Ph(2,6-F₂) | |
| 41-27 | Me | Me | H | H | Me | Ph(2-Cl) | |
| 41-28 | Me | Me | H | H | Me | Ph(2-Me) | |
| 41-29 | Me | Me | H | H | Me | Ph(2-CF₃) | |
| 41-30 | Me | Me | H | H | Me | Ph(2-F-6-Cl) | |
| 41-31 | Me | Me | H | Me | Me | Ph(2-F) | |
| 41-32 | Me | Me | H | Me | Me | Ph(2,6-F₂) | |
| 41-33 | Me | Me | H | Me | Me | Ph(2-Cl) | |

TABLE 41-continued

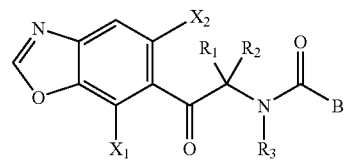

| Compound No. | R₁ | R₂ | R₃ | X₁ | X₂ | B | Physical properties (mp ° C.) |
|---|---|---|---|---|---|---|---|
| 41-34 | Me | Me | H | Me | Me | Ph(2-Me) | |
| 41-35 | Me | Me | H | Me | Me | Ph(2-CF₃) | |
| 41-36 | Me | Me | H | Me | Me | Ph(2-F-6-Cl) | |

TABLE 42

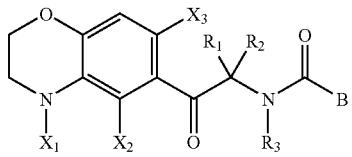

| Compound No. | R₁ | R₂ | R₃ | X₁ | X₂ | X₃ | B | Physical properties (mp ° C.) |
|---|---|---|---|---|---|---|---|---|
| 42-1 | Me | Me | H | H | H | H | Ph(2-F) | |
| 42-2 | Me | Me | H | H | H | H | Ph(2,6-F₂) | |
| 42-3 | Me | Me | H | H | H | H | Ph(2-Cl) | |
| 42-4 | Me | Me | H | H | H | H | Ph(2-Me) | |
| 42-5 | Me | Me | H | H | H | H | Ph(2-CF₃) | |
| 42-6 | Me | Me | H | H | H | H | Ph(2-F-6-Cl) | |
| 42-7 | Me | Me | H | H | Cl | H | Ph(2-F) | |
| 42-8 | Me | Me | H | H | Cl | H | Ph(2,6-F₂) | |
| 42-9 | Me | Me | H | H | Cl | H | Ph(2-Cl) | |
| 42-10 | Me | Me | H | H | Cl | H | Ph(2-Me) | |
| 42-11 | Me | Me | H | H | Cl | H | Ph(2-CF₃) | |
| 42-12 | Me | Me | H | H | Cl | H | Ph(2-F-6-Cl) | |
| 42-13 | Me | Me | H | H | Me | H | Ph(2-F) | |
| 42-14 | Me | Me | H | H | Me | H | Ph(2,6-F₂) | |
| 42-15 | Me | Me | H | H | Me | H | Ph(2-Cl) | |
| 42-16 | Me | Me | H | H | Me | H | Ph(2-Me) | |
| 42-17 | Me | Me | H | H | Me | H | Ph(2-CF₃) | |
| 42-18 | Me | Me | H | H | Me | H | Ph(2-F-6-Cl) | |
| 42-19 | Me | Me | H | H | H | Me | Ph(2-F) | |
| 42-20 | Me | Me | H | H | H | Me | Ph(2,6-F₂) | |
| 42-21 | Me | Me | H | H | H | Me | Ph(2-Cl) | |
| 42-22 | Me | Me | H | H | H | Me | Ph(2-Me) | |
| 42-23 | Me | Me | H | H | H | Me | Ph(2-CF₃) | |
| 42-24 | Me | Me | H | H | H | Me | Ph(2-F-6-Cl) | |
| 42-25 | Me | Me | H | Me | H | H | Ph(2-F) | |
| 42-26 | Me | Me | H | Me | H | H | Ph(2,6-F₂) | |
| 42-27 | Me | Me | H | Me | H | H | Ph(2-Cl) | |
| 42-28 | Me | Me | H | Me | H | H | Ph(2-Me) | |
| 42-29 | Me | Me | H | Me | H | H | Ph(2-CF₃) | |
| 42-30 | Me | Me | H | Me | H | H | Ph(2-F-6-Cl) | |
| 42-31 | Me | Me | H | Me | Cl | H | Ph(2-F) | |
| 42-32 | Me | Me | H | Me | Cl | H | Ph(2,6-F₂) | |
| 42-33 | Me | Me | H | Me | Cl | H | Ph(2-Cl) | |
| 42-34 | Me | Me | H | Me | Cl | H | Ph(2-Me) | |
| 42-35 | Me | Me | H | Me | Cl | H | Ph(2-CF₃) | |
| 42-36 | Me | Me | H | Me | Cl | H | Ph(2-F-6-Cl) | |
| 42-37 | Me | Me | H | Me | Me | H | Ph(2-F) | |
| 42-38 | Me | Me | H | Me | Me | H | Ph(2,6-F₂) | |
| 42-39 | Me | Me | H | Me | Me | H | Ph(2-Cl) | |
| 42-40 | Me | Me | H | Me | Me | H | Ph(2-Me) | |
| 42-41 | Me | Me | H | Me | Me | H | Ph(2-CF₃) | |
| 42-42 | Me | Me | H | Me | Me | H | Ph(2-F-6-Cl) | |
| 42-43 | Me | Me | H | Me | H | Me | Ph(2-F) | |
| 42-44 | Me | Me | H | Me | H | Me | Ph(2,6-F₂) | |
| 42-45 | Me | Me | H | Me | H | Me | Ph(2-Cl) | |
| 42-46 | Me | Me | H | Me | H | Me | Ph(2-Me) | |

TABLE 42-continued

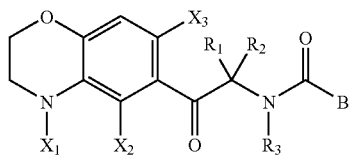

| Compound No. | R₁ | R₂ | R₃ | X₁ | X₂ | X₃ | B | Physical properties (mp ° C.) |
|---|---|---|---|---|---|---|---|---|
| 42-47 | Me | Me | H | Me | H | Me | Ph(2-CF₃) | |
| 42-48 | Me | Me | H | Me | H | Me | Ph(2-F-6-Cl) | |

TABLE 43

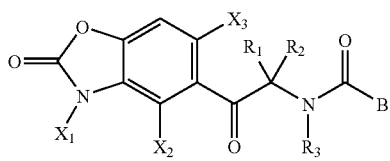

| Compound No. | R₁ | R₂ | R₃ | X₁ | X₂ | X₃ | B | Physical properties (mp ° C.) |
|---|---|---|---|---|---|---|---|---|
| 43-1 | Me | Me | H | H | H | H | Ph(2-F) | |
| 43-2 | Me | Me | H | H | H | H | Ph(2,6-F₂) | |
| 43-3 | Me | Me | H | H | H | H | Ph(2-Cl) | |
| 43-4 | Me | Me | H | H | H | H | Ph(2-Me) | |
| 43-5 | Me | Me | H | H | H | H | Ph(2-CF₃) | |
| 43-6 | Me | Me | H | H | H | H | Ph(2-F-6-Cl) | |
| 43-7 | Me | Me | H | H | Cl | H | Ph(2-F) | |
| 43-8 | Me | Me | H | H | Cl | H | Ph(2,6-F₂) | |
| 43-9 | Me | Me | H | H | Cl | H | Ph(2-Cl) | |
| 43-10 | Me | Me | H | H | Cl | H | Ph(2-Me) | |
| 43-11 | Me | Me | H | H | Cl | H | Ph(2-CF₃) | |
| 43-12 | Me | Me | H | H | Cl | H | Ph(2-F-6-Cl) | |
| 43-13 | Me | Me | H | H | Me | H | Ph(2-F) | |
| 43-14 | Me | Me | H | H | Me | H | Ph(2,6-F₂) | |
| 43-15 | Me | Me | H | H | Me | H | Ph(2-Cl) | |
| 43-16 | Me | Me | H | H | Me | H | Ph(2-Me) | |
| 43-17 | Me | Me | H | H | Me | H | Ph(2-CF₃) | |
| 43-18 | Me | Me | H | H | Me | H | Ph(2-F-6-Cl) | |
| 43-19 | Me | Me | H | H | H | Me | Ph(2-F) | |
| 43-20 | Me | Me | H | H | H | Me | Ph(2,6-F₂) | |
| 43-21 | Me | Me | H | H | H | Me | Ph(2-Cl) | |
| 43-22 | Me | Me | H | H | H | Me | Ph(2-Me) | |
| 43-23 | Me | Me | H | H | H | Me | Ph(2-CF₃) | |
| 43-24 | Me | Me | H | H | H | Me | Ph(2-F-6-Cl) | |
| 43-25 | Me | Me | H | Me | H | H | Ph(2-F) | |
| 43-26 | Me | Me | H | Me | H | H | Ph(2,6-F₂) | |
| 43-27 | Me | Me | H | Me | H | H | Ph(2-Cl) | |
| 43-28 | Me | Me | H | Me | H | H | Ph(2-Me) | |
| 43-29 | Me | Me | H | Me | H | H | Ph(2-CF₃) | |
| 43-30 | Me | Me | H | Me | H | H | Ph(2-F-6-Cl) | |
| 43-31 | Me | Me | H | Me | Cl | H | Ph(2-F) | |
| 43-32 | Me | Me | H | Me | Cl | H | Ph(2,6-F₂) | |
| 43-33 | Me | Me | H | Me | Cl | H | Ph(2-Cl) | |
| 43-34 | Me | Me | H | Me | Cl | H | Ph(2-Me) | |
| 43-35 | Me | Me | H | Me | Cl | H | Ph(2-CF₃) | |
| 43-36 | Me | Me | H | Me | Cl | H | Ph(2-F-6-Cl) | |
| 43-37 | Me | Me | H | Me | Me | H | Ph(2-F) | |
| 43-38 | Me | Me | H | Me | Me | H | Ph(2,6-F₂) | |
| 43-39 | Me | Me | H | Me | Me | H | Ph(2-Cl) | |
| 43-40 | Me | Me | H | Me | Me | H | Ph(2-Me) | |
| 43-41 | Me | Me | H | Me | Me | H | Ph(2-CF₃) | |
| 43-42 | Me | Me | H | Me | Me | H | Ph(2-F-6-Cl) | |
| 43-43 | Me | Me | H | Me | H | Me | Ph(2-F) | |
| 43-44 | Me | Me | H | Me | H | Me | Ph(2,6-F₂) | |
| 43-45 | Me | Me | H | Me | H | Me | Ph(2-Cl) | |
| 43-46 | Me | Me | H | Me | H | Me | Ph(2-Me) | |

TABLE 43-continued

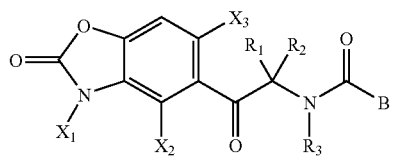

| Compound No. | R₁ | R₂ | R₃ | X₁ | X₂ | X₃ | B | Physical properties (mp ° C.) |
|---|---|---|---|---|---|---|---|---|
| 43-47 | Me | Me | H | Me | H | Me | Ph(2-CF₃) | |
| 43-48 | Me | Me | H | Me | H | Me | Ph(2-F-6-Cl) | |

TABLE 44

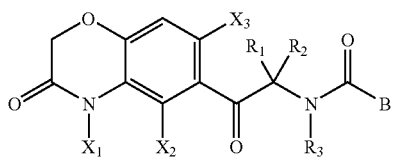

| Compound No. | R₁ | R₂ | R₃ | X₁ | X₂ | X₃ | B | Physical properties (mp ° C.) |
|---|---|---|---|---|---|---|---|---|
| 44-1 | Me | Me | H | H | H | H | Ph(2-F) | |
| 44-2 | Me | Me | H | H | H | H | Ph(2,6-F₂) | |
| 44-3 | Me | Me | H | H | H | H | Ph(2-Cl) | |
| 44-4 | Me | Me | H | H | H | H | Ph(2-Me) | |
| 44-5 | Me | Me | H | H | H | H | Ph(2-CF₃) | |
| 44-6 | Me | Me | H | H | H | H | Ph(2-F-6-Cl) | |
| 44-7 | Me | Me | H | H | Cl | H | Ph(2-F) | |
| 44-8 | Me | Me | H | H | Cl | H | Ph(2,6-F₂) | |
| 44-9 | Me | Me | H | H | Cl | H | Ph(2-Cl) | |
| 44-10 | Me | Me | H | H | Cl | H | Ph(2-Me) | |
| 44-11 | Me | Me | H | H | Cl | H | Ph(2-CF₃) | |
| 44-12 | Me | Me | H | H | Cl | H | Ph(2-F-6-Cl) | |
| 44-13 | Me | Me | H | H | Me | H | Ph(2-F) | |
| 44-14 | Me | Me | H | H | Me | H | Ph(2,6-F₂) | |
| 44-15 | Me | Me | H | H | Me | H | Ph(2-Cl) | |
| 44-16 | Me | Me | H | H | Me | H | Ph(2-Me) | |
| 44-17 | Me | Me | H | H | Me | H | Ph(2-CF₃) | |
| 44-18 | Me | Me | H | H | Me | H | Ph(2-F-6-Cl) | |
| 44-19 | Me | Me | H | H | H | Me | Ph(2-F) | |
| 44-20 | Me | Me | H | H | H | Me | Ph(2,6-F₂) | |
| 44-21 | Me | Me | H | H | H | Me | Ph(2-Cl) | |
| 44-22 | Me | Me | H | H | H | Me | Ph(2-Me) | |
| 44-23 | Me | Me | H | H | H | Me | Ph(2-CF₃) | |
| 44-24 | Me | Me | H | H | H | Me | Ph(2-F-6-Cl) | |
| 44-25 | Me | Me | H | Me | H | H | Ph(2-F) | |
| 44-26 | Me | Me | H | Me | H | H | Ph(2,6-F₂) | |
| 44-27 | Me | Me | H | Me | H | H | Ph(2-Cl) | |
| 44-28 | Me | Me | H | Me | H | H | Ph(2-Me) | |
| 44-29 | Me | Me | H | Me | H | H | Ph(2-CF₃) | |
| 44-30 | Me | Me | H | Me | H | H | Ph(2-F-6-Cl) | |
| 44-31 | Me | Me | H | Me | Cl | H | Ph(2-F) | |
| 44-32 | Me | Me | H | Me | Cl | H | Ph(2,6-F₂) | |
| 44-33 | Me | Me | H | Me | Cl | H | Ph(2-Cl) | |
| 44-34 | Me | Me | H | Me | Cl | H | Ph(2-Me) | |
| 44-35 | Me | Me | H | Me | Cl | H | Ph(2-CF₃) | |
| 44-36 | Me | Me | H | Me | Cl | H | Ph(2-F-6-Cl) | |
| 44-37 | Me | Me | H | Me | Me | H | Ph(2-F) | |
| 44-38 | Me | Me | H | Me | Me | H | Ph(2,6-F₂) | |
| 44-39 | Me | Me | H | Me | Me | H | Ph(2-Cl) | |
| 44-40 | Me | Me | H | Me | Me | H | Ph(2-Me) | |
| 44-41 | Me | Me | H | Me | Me | H | Ph(2-CF₃) | |
| 44-42 | Me | Me | H | Me | Me | H | Ph(2-F-6-Cl) | |
| 44-43 | Me | Me | H | Me | H | Me | Ph(2-F) | |
| 44-44 | Me | Me | H | Me | H | Me | Ph(2,6-F₂) | |
| 44-45 | Me | Me | H | Me | H | Me | Ph(2-Cl) | |
| 44-46 | Me | Me | H | Me | H | Me | Ph(2-Me) | |

TABLE 44-continued

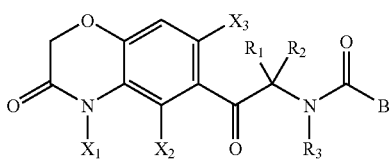

| Compound No. | R₁ | R₂ | R₃ | X₁ | X₂ | X₃ | B | Physical properties (mp °C.) |
|---|---|---|---|---|---|---|---|---|
| 44-47 | Me | Me | H | Me | H | Me | Ph(2-CF₃) | |
| 44-48 | Me | Me | H | Me | H | Me | Ph(2-F-6-Cl) | |

TABLE 45

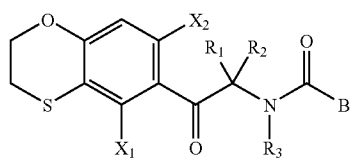

| Compound No. | R₁ | R₂ | R₃ | X₁ | X₂ | B | Physical properties (mp °C.) |
|---|---|---|---|---|---|---|---|
| 45-1 | Me | Me | H | H | H | Ph(2-F) | |
| 45-2 | Me | Me | H | H | H | Ph(2,6-F₂) | |
| 45-3 | Me | Me | H | H | H | Ph(2-Cl) | |
| 45-4 | Me | Me | H | H | H | Ph(2-Me) | |
| 45-5 | Me | Me | H | H | H | Ph(2-CF₃) | |
| 45-6 | Me | Me | H | H | H | Ph(2-F-6-Cl) | |
| 45-7 | Me | Me | H | Cl | H | Ph(2-F) | |
| 45-8 | Me | Me | H | Cl | H | Ph(2,6-F₂) | |
| 45-9 | Me | Me | H | Cl | H | Ph(2-Cl) | |
| 45-10 | Me | Me | H | Cl | H | Ph(2-Me) | |
| 45-11 | Me | Me | H | Cl | H | Ph(2-CF₃) | |
| 45-12 | Me | Me | H | Cl | H | Ph(2-F-6-Cl) | |
| 45-13 | Me | Me | H | Me | H | Ph(2-F) | |
| 45-14 | Me | Me | H | Me | H | Ph(2,6-F₂) | |
| 45-15 | Me | Me | H | Me | H | Ph(2-Cl) | |
| 45-16 | Me | Me | H | Me | H | Ph(2-Me) | |
| 45-17 | Me | Me | H | Me | H | Ph(2-CF₃) | |
| 45-18 | Me | Me | H | Me | H | Ph(2-F-6-Cl) | |
| 45-19 | Me | Me | H | H | Cl | Ph(2-F) | |
| 45-20 | Me | Me | H | H | Cl | Ph(2,6-F₂) | |
| 45-21 | Me | Me | H | H | Cl | Ph(2-Cl) | |
| 45-22 | Me | Me | H | H | Cl | Ph(2-Me) | |
| 45-23 | Me | Me | H | H | Cl | Ph(2-CF₃) | |
| 45-24 | Me | Me | H | H | Cl | Ph(2-F-6-Cl) | |
| 45-25 | Me | Me | H | H | Me | Ph(2-F) | |
| 45-26 | Me | Me | H | H | Me | Ph(2,6-F₂) | |
| 45-27 | Me | Me | H | H | Me | Ph(2-Cl) | |
| 45-28 | Me | Me | H | H | Me | Ph(2-Me) | |
| 45-29 | Me | Me | H | H | Me | Ph(2-CF₃) | |
| 45-30 | Me | Me | H | H | Me | Ph(2-F-6-Cl) | |
| 45-31 | Me | Me | H | Me | Me | Ph(2-F) | |
| 45-32 | Me | Me | H | Me | Me | Ph(2,6-F₂) | |
| 45-33 | Me | Me | H | Me | Me | Ph(2-Cl) | |
| 45-34 | Me | Me | H | Me | Me | Ph(2-Me) | |
| 45-35 | Me | Me | H | Me | Me | Ph(2-CF₃) | |
| 45-36 | Me | Me | H | Me | Me | Ph(2-F-6-Cl) | |

TABLE 46

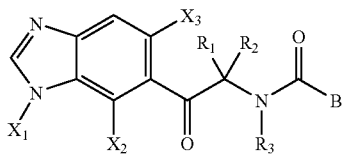

| Compound No. | R₁ | R₂ | R₃ | X₁ | X₂ | X₃ | B | Physical properties (mp °C.) |
|---|---|---|---|---|---|---|---|---|
| 46-1 | Me | Me | H | H | H | H | Ph(2-F) | |
| 46-2 | Me | Me | H | H | H | H | Ph(2,6-F₂) | |
| 46-3 | Me | Me | H | H | H | H | Ph(2-Cl) | |
| 46-4 | Me | Me | H | H | H | H | Ph(2-Me) | |
| 46-5 | Me | Me | H | H | H | H | Ph(2-CF₃) | |
| 46-6 | Me | Me | H | H | H | H | Ph(2-F-6-Cl) | |
| 46-7 | Me | Me | H | H | Cl | H | Ph(2-F) | |
| 46-8 | Me | Me | H | H | Cl | H | Ph(2,6-F₂) | |
| 46-9 | Me | Me | H | H | Cl | H | Ph(2-Cl) | |
| 46-10 | Me | Me | H | H | Cl | H | Ph(2-Me) | |
| 46-11 | Me | Me | H | H | Cl | H | Ph(2-CF₃) | |
| 46-12 | Me | Me | H | H | Cl | H | Ph(2-F-6-Cl) | |
| 46-13 | Me | Me | H | H | Me | H | Ph(2-F) | |
| 46-14 | Me | Me | H | H | Me | H | Ph(2,6-F₂) | |
| 46-15 | Me | Me | H | H | Me | H | Ph(2-Cl) | |
| 46-16 | Me | Me | H | H | Me | H | Ph(2-Me) | |
| 46-17 | Me | Me | H | H | Me | H | Ph(2-CF₃) | |
| 46-18 | Me | Me | H | H | Me | H | Ph(2-F-6-Cl) | |
| 46-19 | Me | Me | H | H | H | Me | Ph(2-F) | |
| 46-20 | Me | Me | H | H | H | Me | Ph(2,6-F₂) | |
| 46-21 | Me | Me | H | H | H | Me | Ph(2-Cl) | |
| 46-22 | Me | Me | H | H | H | Me | Ph(2-Me) | |
| 46-23 | Me | Me | H | H | H | Me | Ph(2-CF₃) | |
| 46-24 | Me | Me | H | H | H | Me | Ph(2-F-6-Cl) | |
| 46-25 | Me | Me | H | Me | H | H | Ph(2-F) | |
| 46-26 | Me | Me | H | Me | H | H | Ph(2,6-F₂) | |
| 46-27 | Me | Me | H | Me | H | H | Ph(2-Cl) | |
| 46-28 | Me | Me | H | Me | H | H | Ph(2-Me) | |
| 46-29 | Me | Me | H | Me | H | H | Ph(2-CF₃) | |
| 46-30 | Me | Me | H | Me | H | H | Ph(2-F-6-Cl) | |
| 46-31 | Me | Me | H | Me | Cl | H | Ph(2-F) | |
| 46-32 | Me | Me | H | Me | Cl | H | Ph(2,6-F₂) | |
| 46-33 | Me | Me | H | Me | Cl | H | Ph(2-Cl) | |
| 46-34 | Me | Me | H | Me | Cl | H | Ph(2-Me) | |
| 46-35 | Me | Me | H | Me | Cl | H | Ph(2-CF₃) | |
| 46-36 | Me | Me | H | Me | Cl | H | Ph(2-F-6-Cl) | |
| 46-37 | Me | Me | H | Me | Me | H | Ph(2-F) | |
| 46-38 | Me | Me | H | Me | Me | H | Ph(2,6-F₂) | |
| 46-39 | Me | Me | H | Me | Me | H | Ph(2-Cl) | |
| 46-40 | Me | Me | H | Me | Me | H | Ph(2-Me) | |
| 46-41 | Me | Me | H | Me | Me | H | Ph(2-CF₃) | |
| 46-42 | Me | Me | H | Me | Me | H | Ph(2-F-6-Cl) | |
| 46-43 | Me | Me | H | Me | H | Me | Ph(2-F) | |
| 46-44 | Me | Me | H | Me | H | Me | Ph(2,6-F₂) | |
| 46-45 | Me | Me | H | Me | H | Me | Ph(2-Cl) | |
| 46-46 | Me | Me | H | Me | H | Me | Ph(2-Me) | |
| 46-47 | Me | Me | H | Me | H | Me | Ph(2-CF₃) | |
| 46-48 | Me | Me | H | Me | H | Me | Ph(2-F-6-Cl) | |

TABLE 47

| Compound No. | R₁ | R₂ | R₃ | X₁ | X₂ | B | Physical properties (mp °C.) |
|---|---|---|---|---|---|---|---|
| 47-1 | Me | Me | H | H | H | Ph(2-F) | |
| 47-2 | Me | Me | H | H | H | Ph(2,6-F₂) | |
| 47-3 | Me | Me | H | H | H | Ph(2-Cl) | |

TABLE 47-continued

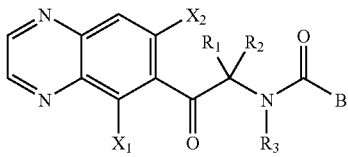

| Compound No. | R₁ | R₂ | R₃ | X₁ | X₂ | B | Physical properties (mp ° C.) |
|---|---|---|---|---|---|---|---|
| 47-4 | Me | Me | H | H | H | Ph(2-Me) | |
| 47-5 | Me | Me | H | H | H | Ph(2-CF₃) | |
| 47-6 | Me | Me | H | H | H | Ph(2-F-6-Cl) | |
| 47-7 | Me | Me | H | Cl | H | Ph(2-F) | |
| 47-8 | Me | Me | H | Cl | H | Ph(2,6-F₂) | |
| 47-9 | Me | Me | H | Cl | H | Ph(2-Cl) | |
| 47-10 | Me | Me | H | Cl | H | Ph(2-Me) | |
| 47-11 | Me | Me | H | Cl | H | Ph(2-CF₃) | |
| 47-12 | Me | Me | H | Cl | H | Ph(2-F-6-Cl) | |
| 47-13 | Me | Me | H | Me | H | Ph(2-F) | |
| 47-14 | Me | Me | H | Me | H | Ph(2,6-F₂) | |
| 47-15 | Me | Me | H | Me | H | Ph(2-Cl) | |
| 47-16 | Me | Me | H | Me | H | Ph(2-Me) | |
| 47-17 | Me | Me | H | Me | H | Ph(2-CF₃) | |
| 47-18 | Me | Me | H | Me | H | Ph(2-F-6-Cl) | |
| 47-19 | Me | Me | H | H | Cl | Ph(2-F) | |
| 47-20 | Me | Me | H | H | Cl | Ph(2,6-F₂) | |
| 47-21 | Me | Me | H | H | Cl | Ph(2-Cl) | |
| 47-22 | Me | Me | H | H | Cl | Ph(2-Me) | |
| 47-23 | Me | Me | H | H | Cl | Ph(2-CF₃) | |
| 47-24 | Me | Me | H | H | Cl | Ph(2-F-6-Cl) | |
| 47-25 | Me | Me | H | H | Me | Ph(2-F) | |
| 47-26 | Me | Me | H | H | Me | Ph(2,6-F₂) | |
| 47-27 | Me | Me | H | H | Me | Ph(2-Cl) | |
| 47-28 | Me | Me | H | H | Me | Ph(2-Me) | |
| 47-29 | Me | Me | H | H | Me | Ph(2-CF₃) | |
| 47-30 | Me | Me | H | H | Me | Ph(2-F-6-Cl) | |
| 47-31 | Me | Me | H | Me | Me | Ph(2-F) | |
| 47-32 | Me | Me | H | Me | Me | Ph(2,6-F₂) | |
| 47-33 | Me | Me | H | Me | Me | Ph(2-Cl) | |
| 47-34 | Me | Me | H | Me | Me | Ph(2-Me) | |
| 47-35 | Me | Me | H | Me | Me | Ph(2-CF₃) | |
| 47-36 | Me | Me | H | Me | Me | Ph(2-F-6-Cl) | |

TABLE 48

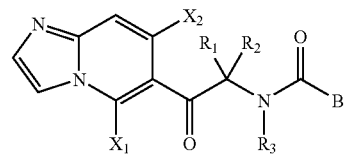

| Compound No. | R₁ | R₂ | R₃ | X₁ | X₂ | B | Physical properties (mp ° C.) |
|---|---|---|---|---|---|---|---|
| 48-1 | Me | Me | H | H | H | Ph(2-F) | |
| 48-2 | Me | Me | H | H | H | Ph(2,6-F₂) | |
| 48-3 | Me | Me | H | H | H | Ph(2-Cl) | |
| 48-4 | Me | Me | H | H | H | Ph(2-Me) | |
| 48-5 | Me | Me | H | H | H | Ph(2-CF₃) | |
| 48-6 | Me | Me | H | H | H | Ph(2-F-6-Cl) | |
| 48-7 | Me | Me | H | Cl | H | Ph(2-F) | |
| 48-8 | Me | Me | H | Cl | H | Ph(2,6-F₂) | |
| 48-9 | Me | Me | H | Cl | H | Ph(2-Cl) | |
| 48-10 | Me | Me | H | Cl | H | Ph(2-Me) | |
| 48-11 | Me | Me | H | Cl | H | Ph(2-CF₃) | |
| 48-12 | Me | Me | H | Cl | H | Ph(2-F-6-Cl) | |
| 48-13 | Me | Me | H | Me | H | Ph(2-F) | |
| 48-14 | Me | Me | H | Me | H | Ph(2,6-F₂) | |
| 48-15 | Me | Me | H | Me | H | Ph(2-Cl) | |

TABLE 48-continued

| Compound No. | R₁ | R₂ | R₃ | X₁ | X₂ | B | Physical properties (mp ° C.) |
|---|---|---|---|---|---|---|---|
| 48-16 | Me | Me | H | Me | H | Ph(2-Me) | |
| 48-17 | Me | Me | H | Me | H | Ph(2-CF₃) | |
| 48-18 | Me | Me | H | Me | H | Ph(2-F-6-Cl) | |
| 48-19 | Me | Me | H | H | Cl | Ph(2-F) | |
| 48-20 | Me | Me | H | H | Cl | Ph(2,6-F₂) | |
| 48-21 | Me | Me | H | H | Cl | Ph(2-Cl) | |
| 48-22 | Me | Me | H | H | Cl | Ph(2-Me) | |
| 48-23 | Me | Me | H | H | Cl | Ph(2-CF₃) | |
| 48-24 | Me | Me | H | H | Cl | Ph(2-F-6-Cl) | |
| 48-25 | Me | Me | H | H | Me | Ph(2-F) | |
| 48-26 | Me | Me | H | H | Me | Ph(2,6-F₂) | |
| 48-27 | Me | Me | H | H | Me | Ph(2-Cl) | |
| 48-28 | Me | Me | H | H | Me | Ph(2-Me) | |
| 48-29 | Me | Me | H | H | Me | Ph(2-CF₃) | |
| 48-30 | Me | Me | H | H | Me | Ph(2-F-6-Cl) | |
| 48-31 | Me | Me | H | Me | Me | Ph(2-F) | |
| 48-32 | Me | Me | H | Me | Me | Ph(2,6-F₂) | |
| 48-33 | Me | Me | H | Me | Me | Ph(2-Cl) | |
| 48-34 | Me | Me | H | Me | Me | Ph(2-Me) | |
| 48-35 | Me | Me | H | Me | Me | Ph(2-CF₃) | |
| 48-36 | Me | Me | H | Me | Me | Ph(2-F-6-Cl) | |

TABLE 49

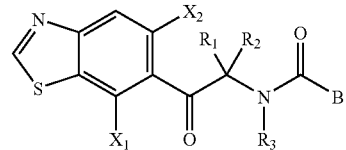

| Compound No. | R₁ | R₂ | R₃ | X₁ | X₂ | B | Physical properties (mp ° C.) |
|---|---|---|---|---|---|---|---|
| 49-1 | Me | Me | H | H | H | Ph(2-F) | |
| 49-2 | Me | Me | H | H | H | Ph(2,6-F₂) | |
| 49-3 | Me | Me | H | H | H | Ph(2-Cl) | |
| 49-4 | Me | Me | H | H | H | Ph(2-Me) | |
| 49-5 | Me | Me | H | H | H | Ph(2-CF₃) | |
| 49-6 | Me | Me | H | H | H | Ph(2-F-6-Cl) | |
| 49-7 | Me | Me | H | Cl | H | Ph(2-F) | |
| 49-8 | Me | Me | H | Cl | H | Ph(2,6-F₂) | |
| 49-9 | Me | Me | H | Cl | H | Ph(2-Cl) | |
| 49-10 | Me | Me | H | Cl | H | Ph(2-Me) | |
| 49-11 | Me | Me | H | Cl | H | Ph(2-CF₃) | |
| 49-12 | Me | Me | H | Cl | H | Ph(2-F-6-Cl) | |
| 49-13 | Me | Me | H | Me | H | Ph(2-F) | |
| 49-14 | Me | Me | H | Me | H | Ph(2,6-F₂) | |
| 49-15 | Me | Me | H | Me | H | Ph(2-Cl) | |
| 49-16 | Me | Me | H | Me | H | Ph(2-Me) | |
| 49-17 | Me | Me | H | Me | H | Ph(2-CF₃) | |
| 49-18 | Me | Me | H | Me | H | Ph(2-F-6-Cl) | |
| 49-19 | Me | Me | H | H | Cl | Ph(2-F) | |
| 49-20 | Me | Me | H | H | Cl | Ph(2,6-F₂) | |
| 49-21 | Me | Me | H | H | Cl | Ph(2-Cl) | |
| 49-22 | Me | Me | H | H | Cl | Ph(2-Me) | |
| 49-23 | Me | Me | H | H | Cl | Ph(2-CF₃) | |
| 49-24 | Me | Me | H | H | Cl | Ph(2-F-6-Cl) | |
| 49-25 | Me | Me | H | H | Me | Ph(2-F) | |
| 49-26 | Me | Me | H | H | Me | Ph(2,6-F₂) | |
| 49-27 | Me | Me | H | H | Me | Ph(2-Cl) | |

TABLE 49-continued

Structure: benzothiazole with N at top, S at left, X2 at top ring position, R1/R2 on CH connected to C(=O), then N(R3)-C(=O)-B; X1 at bottom position.

| Compound No. | R₁ | R₂ | R₃ | X₁ | X₂ | B | Physical properties (mp °C.) |
|---|---|---|---|---|---|---|---|
| 49-28 | Me | Me | H | H | Me | Ph(2-Me) | |
| 49-29 | Me | Me | H | H | Me | Ph(2-CF₃) | |
| 49-30 | Me | Me | H | H | Me | Ph(2-F-6-Cl) | |
| 49-31 | Me | Me | H | Me | Me | Ph(2-F) | |
| 49-32 | Me | Me | H | Me | Me | Ph(2,6-F₂) | |
| 49-33 | Me | Me | H | Me | Me | Ph(2-Cl) | |
| 49-34 | Me | Me | H | Me | Me | Ph(2-Me) | |
| 49-35 | Me | Me | H | Me | Me | Ph(2-CF₃) | |
| 49-36 | Me | Me | H | Me | Me | Ph(2-F-6-Cl) | |

TABLE 50

| Compound No. | R₁ | R₂ | R₃ | X₁ | X₂ | B | Physical properties (mp °C.) |
|---|---|---|---|---|---|---|---|
| 50-1 | Me | Me | H | H | H | Ph(2-F) | |
| 50-2 | Me | Me | H | H | H | Ph(2,6-F₂) | |
| 50-3 | Me | Me | H | H | H | Ph(2-Cl) | |
| 50-4 | Me | Me | H | H | H | Ph(2-Me) | |
| 50-5 | Me | Me | H | H | H | Ph(2-CF₃) | |
| 50-6 | Me | Me | H | H | H | Ph(2-F-6-Cl) | |
| 50-7 | Me | Me | H | Cl | H | Ph(2-F) | |
| 50-8 | Me | Me | H | Cl | H | Ph(2,6-F₂) | |
| 50-9 | Me | Me | H | Cl | H | Ph(2-Cl) | |
| 50-10 | Me | Me | H | Cl | H | Ph(2-Me) | |
| 50-11 | Me | Me | H | Cl | H | Ph(2-CF₃) | |
| 50-12 | Me | Me | H | Cl | H | Ph(2-F-6-Cl) | |
| 50-13 | Me | Me | H | Me | H | Ph(2-F) | |
| 50-14 | Me | Me | H | Me | H | Ph(2,6-F₂) | |
| 50-15 | Me | Me | H | Me | H | Ph(2-Cl) | |
| 50-16 | Me | Me | H | Me | H | Ph(2-Me) | |
| 50-17 | Me | Me | H | Me | H | Ph(2-CF₃) | |
| 50-18 | Me | Me | H | Me | H | Ph(2-F-6-Cl) | |
| 50-19 | Me | Me | H | H | Cl | Ph(2-F) | |
| 50-20 | Me | Me | H | H | Cl | Ph(2,6-F₂) | |
| 50-21 | Me | Me | H | H | Cl | Ph(2-Cl) | |
| 50-22 | Me | Me | H | H | Cl | Ph(2-Me) | |
| 50-23 | Me | Me | H | H | Cl | Ph(2-CF₃) | |
| 50-24 | Me | Me | H | H | Cl | Ph(2-F-6-Cl) | |
| 50-25 | Me | Me | H | H | Me | Ph(2-F) | |
| 50-26 | Me | Me | H | H | Me | Ph(2,6-F₂) | |
| 50-27 | Me | Me | H | H | Me | Ph(2-Cl) | |
| 50-28 | Me | Me | H | H | Me | Ph(2-Me) | |
| 50-29 | Me | Me | H | H | Me | Ph(2-CF₃) | |
| 50-30 | Me | Me | H | H | Me | Ph(2-F-6-Cl) | |
| 50-31 | Me | Me | H | Me | Me | Ph(2-F) | |
| 50-32 | Me | Me | H | Me | Me | Ph(2,6-F₂) | |
| 50-33 | Me | Me | H | Me | Me | Ph(2-Cl) | |
| 50-34 | Me | Me | H | Me | Me | Ph(2-Me) | |
| 50-35 | Me | Me | H | Me | Me | Ph(2-CF₃) | |
| 50-36 | Me | Me | H | Me | Me | Ph(2-F-6-Cl) | |

TABLE 51

| Compound No. | R₁ | R₂ | R₃ | X₁ | X₂ | B | Physical properties (mp °C.) |
|---|---|---|---|---|---|---|---|
| 51-1 | Me | Me | H | H | H | Ph(2-F) | 121-122 |
| 51-2 | Me | Me | H | H | H | Ph(2,6-F₂) | 147-148 |
| 51-3 | Me | Me | H | H | H | Ph(2-Cl) | |
| 51-4 | Me | Me | H | H | H | Ph(2-Me) | |
| 51-5 | Me | Me | H | H | H | Ph(2-CF₃) | |
| 51-6 | Me | Me | H | H | H | Ph(2-F-6-Cl) | |
| 51-7 | Me | Me | H | Me | H | Ph(2-F) | |
| 51-8 | Me | Me | H | Me | H | Ph(2,6-F₂) | |
| 51-9 | Me | Me | H | Me | H | Ph(2-Cl) | |
| 51-10 | Me | Me | H | Me | H | Ph(2-Me) | |
| 51-11 | Me | Me | H | Me | H | Ph(2-CF₃) | |
| 51-12 | Me | Me | H | Me | H | Ph(2-F-6-Cl) | |
| 51-13 | Me | Me | H | Me | Me | Ph(2-F) | |
| 51-14 | Me | Me | H | Me | Me | Ph(2,6-F₂) | |
| 51-15 | Me | Me | H | Me | Me | Ph(2-Cl) | |
| 51-16 | Me | Me | H | Me | Me | Ph(2-Me) | |
| 51-17 | Me | Me | H | Me | Me | Ph(2-CF₃) | |
| 51-18 | Me | Me | H | Me | Me | Ph(2-F-6-Cl) | |
| 51-19 | Me | Me | H | Me | Cl | Ph(2-F) | |
| 51-20 | Me | Me | H | Me | Cl | Ph(2,6-F₂) | |
| 51-21 | Me | Me | H | Me | Cl | Ph(2-Cl) | |
| 51-22 | Me | Me | H | Me | Cl | Ph(2-Me) | |
| 51-23 | Me | Me | H | Me | Cl | Ph(2-CF₃) | |
| 51-24 | Me | Me | H | Me | Cl | Ph(2-F-6-Cl) | |
| 51-25 | Me | Me | H | Me | Br | Ph(2-F) | |
| 51-26 | Me | Me | H | Me | Br | Ph(2,6-F₂) | |
| 51-27 | Me | Me | H | Me | Br | Ph(2-Cl) | |
| 51-28 | Me | Me | H | Me | Br | Ph(2-Me) | |
| 51-29 | Me | Me | H | Me | Br | Ph(2-CF₃) | |
| 51-30 | Me | Me | H | Me | Br | Ph(2-F-6-Cl) | |
| 51-31 | Me | Me | H | Me | CF₃ | Ph(2-F) | |
| 51-32 | Me | Me | H | Me | CF₃ | Ph(2,6-F₂) | |
| 51-33 | Me | Me | H | Me | CF₃ | Ph(2-Cl) | |
| 51-34 | Me | Me | H | Me | CF₃ | Ph(2-Me) | |
| 51-35 | Me | Me | H | Me | CF₃ | Ph(2-CF₃) | |
| 51-36 | Me | Me | H | Me | CF₃ | Ph(2-F-6-Cl) | |
| 51-37 | Me | Me | H | Me | OCF₃ | Ph(2-F) | |
| 51-38 | Me | Me | H | Me | OCF₃ | Ph(2,6-F₂) | |
| 51-39 | Me | Me | H | Me | OCF₃ | Ph(2-Cl) | |
| 51-40 | Me | Me | H | Me | OCF₃ | Ph(2-Me) | |
| 51-41 | Me | Me | H | Me | OCF₃ | Ph(2-CF₃) | |
| 51-42 | Me | Me | H | Me | OCF₃ | Ph(2-F-6-Cl) | |
| 51-43 | Me | Me | H | Me | OCHF₂ | Ph(2-F) | |
| 51-44 | Me | Me | H | Me | OCHF₂ | Ph(2,6-F₂) | |
| 51-45 | Me | Me | H | Me | OCHF₂ | Ph(2-Cl) | |
| 51-46 | Me | Me | H | Me | OCHF₂ | Ph(2-Me) | |
| 51-47 | Me | Me | H | Me | OCHF₂ | Ph(2-CF₃) | |
| 51-48 | Me | Me | H | Me | OCHF₂ | Ph(2-F-6-Cl) | |
| 51-49 | Me | Me | H | Me | OCH₂CF₃ | Ph(2-F) | |
| 51-50 | Me | Me | H | Me | OCH₂CF₃ | Ph(2,6-F₂) | |
| 51-51 | Me | Me | H | Me | OCH₂CF₃ | Ph(2-Cl) | |
| 51-52 | Me | Me | H | Me | OCH₂CF₃ | Ph(2-Me) | |
| 51-53 | Me | Me | H | Me | OCH₂CF₃ | Ph(2-CF₃) | |
| 51-54 | Me | Me | H | Me | OCH₂CF₃ | Ph(2-F-6-Cl) | |
| 51-55 | Me | Me | H | Cl | H | Ph(2-F) | |
| 51-56 | Me | Me | H | Cl | H | Ph(2,6-F₂) | |
| 51-57 | Me | Me | H | Cl | H | Ph(2-Cl) | |
| 51-58 | Me | Me | H | Cl | H | Ph(2-Me) | |
| 51-59 | Me | Me | H | Cl | H | Ph(2-CF₃) | |
| 51-60 | Me | Me | H | Cl | H | Ph(2-F-6-Cl) | |
| 51-61 | Me | Me | H | Cl | Me | Ph(2-F) | |
| 51-62 | Me | Me | H | Cl | Me | Ph(2,6-F₂) | |
| 51-63 | Me | Me | H | Cl | Me | Ph(2-Cl) | |
| 51-64 | Me | Me | H | Cl | Me | Ph(2-Me) | |
| 51-65 | Me | Me | H | Cl | Me | Ph(2-CF₃) | |
| 51-66 | Me | Me | H | Cl | Me | Ph(2-F-6-Cl) | |

TABLE 51-continued

![Structure: furan with X1, X2 substituents, R1, R2, R3, B groups]

| Compound No. | R₁ | R₂ | R₃ | X₁ | X₂ | B | Physical properties (mp ° C.) |
|---|---|---|---|---|---|---|---|
| 51-67 | Me | Me | H | Cl | Cl | Ph(2-F) | |
| 51-68 | Me | Me | H | Cl | Cl | Ph(2,6-F₂) | |
| 51-69 | Me | Me | H | Cl | Cl | Ph(2-Cl) | |
| 51-70 | Me | Me | H | Cl | Cl | Ph(2-Me) | |
| 51-71 | Me | Me | H | Cl | Cl | Ph(2-CF₃) | |
| 51-72 | Me | Me | H | Cl | Cl | Ph(2-F-6-Cl) | |
| 51-73 | Me | Me | H | Cl | Br | Ph(2-F) | |
| 51-74 | Me | Me | H | Cl | Br | Ph(2,6-F₂) | |
| 51-75 | Me | Me | H | Cl | Br | Ph(2-Cl) | |
| 51-76 | Me | Me | H | Cl | Br | Ph(2-Me) | |
| 51-77 | Me | Me | H | Cl | Br | Ph(2-CF₃) | |
| 51-78 | Me | Me | H | Cl | Br | Ph(2-F-6-Cl) | |
| 51-79 | Me | Me | H | Cl | CF₃ | Ph(2-F) | |
| 51-80 | Me | Me | H | Cl | CF₃ | Ph(2,6-F₂) | |
| 51-81 | Me | Me | H | Cl | CF₃ | Ph(2-Cl) | |
| 51-82 | Me | Me | H | Cl | CF₃ | Ph(2-Me) | |
| 51-83 | Me | Me | H | Cl | CF₃ | Ph(2-CF₃) | |
| 51-84 | Me | Me | H | Cl | CF₃ | Ph(2-F-6-Cl) | |
| 51-85 | Me | Me | H | Cl | OCF₃ | Ph(2-F) | |
| 51-86 | Me | Me | H | Cl | OCF₃ | Ph(2,6-F₂) | |
| 51-87 | Me | Me | H | Cl | OCF₃ | Ph(2-Cl) | |
| 51-88 | Me | Me | H | Cl | OCF₃ | Ph(2-Me) | |
| 51-89 | Me | Me | H | Cl | OCF₃ | Ph(2-CF₃) | |
| 51-90 | Me | Me | H | Cl | OCF₃ | Ph(2-F-6-Cl) | |
| 51-91 | Me | Me | H | Cl | OCHF₂ | Ph(2-F) | |
| 51-92 | Me | Me | H | Cl | OCHF₂ | Ph(2,6-F₂) | |
| 51-93 | Me | Me | H | Cl | OCHF₂ | Ph(2-Cl) | |
| 51-94 | Me | Me | H | Cl | OCHF₂ | Ph(2-Me) | |
| 51-95 | Me | Me | H | Cl | OCHF₂ | Ph(2-CF₃) | |
| 51-96 | Me | Me | H | Cl | OCHF₂ | Ph(2-F-6-Cl) | |
| 51-97 | Me | Me | H | Cl | OCH₂CF₃ | Ph(2-F) | |
| 51-98 | Me | Me | H | Cl | OCH₂CF₃ | Ph(2,6-F₂) | |
| 51-99 | Me | Me | H | Cl | OCH₂CF₃ | Ph(2-Cl) | |
| 51-100 | Me | Me | H | Cl | OCH₂CF₃ | Ph(2-Me) | |
| 51-101 | Me | Me | H | Cl | OCH₂CF₃ | Ph(2-CF₃) | |
| 51-102 | Me | Me | H | Cl | OCH₂CF₃ | Ph(2-F-6-Cl) | |

TABLE 52

![Structure: indane with X1, X2, X3 substituents, R1, R2, R3, B groups]

| Compound No. | R₁ | R₂ | R₃ | X₁ | X₂ | X₃ | B | Physical properties (mp ° C.) |
|---|---|---|---|---|---|---|---|---|
| 52-1 | Me | Me | H | H | H | H | Ph(2-F) | |
| 52-2 | Me | Me | H | H | H | H | Ph(2,6-F₂) | |
| 52-3 | Me | Me | H | H | H | H | Ph(2-Cl) | |
| 52-4 | Me | Me | H | H | H | H | Ph(2-Me) | |
| 52-5 | Me | Me | H | H | H | H | Ph(2-CF₃) | |
| 52-6 | Me | Me | H | H | H | H | Ph(2-F-6-Cl) | |
| 52-7 | Me | Me | H | H | Me | H | Ph(2-F) | |
| 52-8 | Me | Me | H | H | Me | H | Ph(2,6-F₂) | |
| 52-9 | Me | Me | H | H | Me | H | Ph(2-Cl) | |
| 52-10 | Me | Me | H | H | Me | H | Ph(2-Me) | |
| 52-11 | Me | Me | H | H | Me | H | Ph(2-CF₃) | |
| 52-12 | Me | Me | H | H | Me | H | Ph(2-F-6-Cl) | |
| 52-13 | Me | Me | H | H | H | Me | Ph(2-F) | |
| 52-14 | Me | Me | H | H | H | Me | Ph(2,6-F₂) | |
| 52-15 | Me | Me | H | H | H | Me | Ph(2-Cl) | |
| 52-16 | Me | Me | H | H | H | Me | Ph(2-Me) | |
| 52-17 | Me | Me | H | H | H | Me | Ph(2-CF₃) | |
| 52-18 | Me | Me | H | H | H | Me | Ph(2-F-6-Cl) | |
| 52-19 | Me | Me | H | F | H | H | Ph(2-F) | |
| 52-20 | Me | Me | H | F | H | H | Ph(2,6-F₂) | |
| 52-21 | Me | Me | H | F | H | H | Ph(2-Cl) | |
| 52-22 | Me | Me | H | F | H | H | Ph(2-Me) | |
| 52-23 | Me | Me | H | F | H | H | Ph(2-CF₃) | |
| 52-24 | Me | Me | H | F | H | H | Ph(2-F-6-Cl) | |
| 52-25 | Me | Me | H | F | Me | H | Ph(2-F) | |
| 52-26 | Me | Me | H | F | Me | H | Ph(2,6-F₂) | |
| 52-27 | Me | Me | H | F | Me | H | Ph(2-Cl) | |
| 52-28 | Me | Me | H | F | Me | H | Ph(2-Me) | |
| 52-29 | Me | Me | H | F | Me | H | Ph(2-CF₃) | |
| 52-30 | Me | Me | H | F | Me | H | Ph(2-F-6-Cl) | |
| 52-31 | Me | Me | H | F | Cl | H | Ph(2-F) | |
| 52-32 | Me | Me | H | F | Cl | H | Ph(2,6-F₂) | |
| 52-33 | Me | Me | H | F | Cl | H | Ph(2-Cl) | |
| 52-34 | Me | Me | H | F | Cl | H | Ph(2-Me) | |
| 52-35 | Me | Me | H | F | Cl | H | Ph(2-CF₃) | |
| 52-36 | Me | Me | H | F | Cl | H | Ph(2-F-6-Cl) | |
| 52-37 | Me | Me | H | F | H | Me | Ph(2-F) | |
| 52-38 | Me | Me | H | F | H | Me | Ph(2,6-F₂) | |
| 52-39 | Me | Me | H | F | H | Me | Ph(2-Cl) | |
| 52-40 | Me | Me | H | F | H | Me | Ph(2-Me) | |
| 52-41 | Me | Me | H | F | H | Me | Ph(2-CF₃) | |
| 52-42 | Me | Me | H | F | H | Me | Ph(2-F-6-Cl) | |
| 52-43 | Me | Me | H | H | Cl | H | Ph(2-F) | |
| 52-44 | Me | Me | H | H | Cl | H | Ph(2,6-F₂) | |
| 52-45 | Me | Me | H | H | Cl | H | Ph(2-Cl) | |
| 52-46 | Me | Me | H | H | Cl | H | Ph(2-Me) | |
| 52-47 | Me | Me | H | H | Cl | H | Ph(2-CF₃) | |
| 52-48 | Me | Me | H | H | Cl | H | Ph(2-F-6-Cl) | |
| 52-49 | Me | Me | H | H | H | Cl | Ph(2-F) | |
| 52-50 | Me | Me | H | H | H | Cl | Ph(2,6-F₂) | |
| 52-51 | Me | Me | H | H | H | Cl | Ph(2-Cl) | |
| 52-52 | Me | Me | H | H | H | Cl | Ph(2-Me) | |
| 52-53 | Me | Me | H | H | H | Cl | Ph(2-CF₃) | |
| 52-54 | Me | Me | H | H | H | Cl | Ph(2-F-6-Cl) | |
| 52-55 | Me | Me | H | F | H | Cl | Ph(2-F) | |
| 52-56 | Me | Me | H | F | H | Cl | Ph(2,6-F₂) | |
| 52-57 | Me | Me | H | F | H | Cl | Ph(2-Cl) | |
| 52-58 | Me | Me | H | F | H | Cl | Ph(2-Me) | |
| 52-59 | Me | Me | H | F | H | Cl | Ph(2-CF₃) | |
| 52-60 | Me | Me | H | F | H | Cl | Ph(2-F-6-Cl) | |

TABLE 53

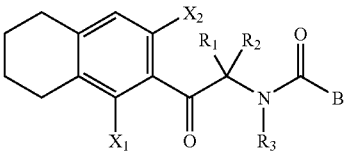

| Compound No. | R₁ | R₂ | R₃ | X₁ | X₂ | B | Physical properties (mp ° C.) |
|---|---|---|---|---|---|---|---|
| 53-1 | Me | Me | H | H | H | Ph(2-F) | |
| 53-2 | Me | Me | H | H | H | Ph(2,6-F$_2$) | |
| 53-3 | Me | Me | H | H | H | Ph(2-Cl) | |
| 53-4 | Me | Me | H | H | H | Ph(2-Me) | |
| 53-5 | Me | Me | H | H | H | Ph(2-CF$_3$) | |
| 53-6 | Me | Me | H | H | H | Ph(2-F-6-Cl) | |
| 53-7 | Me | Me | H | Cl | H | Ph(2-F) | |
| 53-8 | Me | Me | H | Cl | H | Ph(2,6-F$_2$) | |
| 53-9 | Me | Me | H | Cl | H | Ph(2-Cl) | |
| 53-10 | Me | Me | H | Cl | H | Ph(2-Me) | |
| 53-11 | Me | Me | H | Cl | H | Ph(2-CF$_3$) | |
| 53-12 | Me | Me | H | Cl | H | Ph(2-F-6-Cl) | |
| 53-13 | Me | Me | H | Me | H | Ph(2-F) | |
| 53-14 | Me | Me | H | Me | H | Ph(2,6-F$_2$) | |
| 53-15 | Me | Me | H | Me | H | Ph(2-Cl) | |
| 53-16 | Me | Me | H | Me | H | Ph(2-Me) | |
| 53-17 | Me | Me | H | Me | H | Ph(2-CF$_3$) | |
| 53-18 | Me | Me | H | Me | H | Ph(2-F-6-Cl) | |
| 53-19 | Me | Me | H | H | Cl | Ph(2-F) | |
| 53-20 | Me | Me | H | H | Cl | Ph(2,6-F$_2$) | |
| 53-21 | Me | Me | H | H | Cl | Ph(2-Cl) | |
| 53-22 | Me | Me | H | H | Cl | Ph(2-Me) | |
| 53-23 | Me | Me | H | H | Cl | Ph(2-CF$_3$) | |
| 53-24 | Me | Me | H | H | Cl | Ph(2-F-6-Cl) | |
| 53-25 | Me | Me | H | H | Me | Ph(2-F) | |
| 53-26 | Me | Me | H | H | Me | Ph(2,6-F$_2$) | |
| 53-27 | Me | Me | H | H | Me | Ph(2-Cl) | |
| 53-28 | Me | Me | H | H | Me | Ph(2-Me) | |
| 53-29 | Me | Me | H | H | Me | Ph(2-CF$_3$) | |
| 53-30 | Me | Me | H | H | Me | Ph(2-F-6-Cl) | |
| 53-31 | Me | Me | H | Me | Me | Ph(2-F) | |
| 53-32 | Me | Me | H | Me | Me | Ph(2,6-F$_2$) | |
| 53-33 | Me | Me | H | Me | Me | Ph(2-Cl) | |
| 53-34 | Me | Me | H | Me | Me | Ph(2-Me) | |
| 53-35 | Me | Me | H | Me | Me | Ph(2-CF$_3$) | |
| 53-36 | Me | Me | H | Me | Me | Ph(2-F-6-Cl) | |

Now, Test Examples will be described.

TEST EXAMPLE 1

Test on Southern Root-Knot Nematode (*Meloidgyne incognita*) (Soil Incorporation)

To 300 ml of the soil contaminated by southern root-knot nematode, 7 ml of a chemical solution having the concentration of the compound of the present invention adjusted to be 1600 ppm, is poured, followed by mixing so that the compound is uniformly dispersed. The treated soil is put into a pot (diameter: 9 cm, height: 8 cm), and then a tomato seedling in 2-leaf stage is transplanted and placed in a greenhouse. After three to four weeks from the transplantation of the tomato, the root knot index is determined based on the following standards. The compound of the present invention shows high controlling effects at a level of a root knot index of not more than 1. For example, the compound Nos. 1-25, 1-26, 1-73, 1-100, 1-122, 1-123, 1-125, 1-127, 1-130, 1-131, 1-133, 1-136, 1-137, 1-139, 1-140, 1-172, 1-173, 1-177, 5-5, 5-9, 5-11, 5-16, 5-20, 8-2, 8-5, 13-2, 13-4, 13-6, 13-7, 13-18, 13-19, 13-44, 13-45, 16-32, 16-37 and 16-38 were at a level of a root knot index of not more than 1.

| Root knot index | Degree of formation of root knots |
|---|---|
| 0 | No knot was formed |
| 1 | Knots were formed to a slight degree |
| 2 | Knots were formed to a moderate degree |
| 3 | Knots were formed to a heavy degree |
| 4 | Knots were formed to the heaviest degree |

TEST EXAMPLE 2

Test on Cobb Root-Lesion Nematode (*Pratylenchus penetrans*) (Soil Incorporation)

To 300 ml of the soil contaminated by Cobb root-lesion nematode, 7 ml of a chemical solution having the concentration of the compound of the present invention adjusted to be 1600 ppm, is poured, followed by mixing so that the compound is uniformly dispersed. The treated soil is put into a pot (diameter: 9 cm, height: 8 cm), and then 10 seeds of burdock are disseminated and placed in a greenhouse. After about two months from the dissemination of the burdock seeds, injury level of the roots is determined based on the following standards. The compound of the present invention shows high controlling effects at a level of an injury index of not more than 1. For example, the compound Nos. 13-19 and 13-45 were at a level of an injury index of not more than 1.

| Injury index | Injury level of roots |
|---|---|
| 0 | No injury |
| 1 | Slight injury |
| 2 | Moderate injury |
| 3 | Heavy injury |
| 4 | Heaviest injury |

TEST EXAMPLE 3

Test on Cobb Root-Lesion Nematode (Immersion Treatment)

To a test tube made of glass (DISPOSABLE CULTURE TUBE manufactured by IWAKI Co., Ltd: internal diameter: 10 mm, lengh: 75 mm), 1 ml of a chemical solution having the concentration of the compound of the present invention adjusted to be 40 ppm, is poured. 1 ml of water having about 100 of Cobb root-lesion nematodes is added thereto, followed by stirring gently. The final concentration of the compound of the present invention in the obtained solution is 20 ppm. Then, the top of the test tube is covered with a Para film (Manufactured by American National Can Co., Ltd) to obdurate, and then it is left at 25° C. After two days, the above solution is transferred to a slide glass (MICRO SLIDE GLASS manufactured by MATSUNAMI Co., Ltd: With plankton lattice lines), the number of inactive nematodes (including ones which do not move at least 10 seconds) and the number of active nematodes are counted by a microscope. The motility inhibition ratio (%) is calculated based on the following formula. As a result, the compound of the present invention shows high controlling effects at a level of a motility inhibition ratio (%) of not less than 70%. For example, the motility inhibition ratio of the compounds Nos. 13-45, 16-37 and 16-38 showed at a level of a motility inhibition ratio of not less than 70%.

Motility inhibition ratio (%)=The number of inactive nematodes/(The number of active nematodes+ The number of inactive nematodes)×100

TEST EXAMPLE 4

Test on Coccidia

*Eimeria tenella* of wild type is infected to chicks to obtain fresh immature oocysts, which are then exposed to a solution having a predetermined concentration of the compound of the present invention for 10 or 30 minutes. The exposed immature oocysts are subjected to centrifugal separation, and after removing the supernatant, a 2% potassium bichromate aqueous solution is added, followed by sporulation at 25° C. for 4 days, whereby good oosyst controlling effects are confirmed.

TEST EXAMPLE 5

Test on Dog Filarioidea

To a dog subcutaneously infected with dog filarioidea (*Dirofilaria immitis*), the compound of the present invention is orally administered. At the time of an autopsy after 200 days from the infection, the number of adults of dog filarioidea parasitic to the lung or heart of the treated animal is investigated, whereby good effects for controlling dog filarioidea is confirmed. Now, formulation Examples will be described.

FORMULATION EXAMPLE 1

| | |
|---|---|
| (1) Compound of the present invention | 20 parts by weight |
| (2) Clay | 72 parts by weight |
| (3) Sodium lignin sulfonate | 8 parts by weight |

The above components are uniformly mixed to obtain a wettable powder.

FORMULATION EXAMPLE 2

| | |
|---|---|
| (1) Compound of the present invention | 5 parts by weight |
| (2) Talc | 95 parts by weight |

The above components are uniformly mixed to obtain a dust.

FORMULATION EXAMPLE 3

| | |
|---|---|
| (1) Compound of the present invention | 20 parts by weight |
| (2) N,N'-dimethylacetamide | 20 parts by weight |
| (3) Polyoxyethylenealkylphenyl ether | 10 parts by weight |
| (4) Xylene | 50 parts by weight |

The above components are uniformly mixed and dissolved to obtain an emulsifiable concentrate.

FORMULATION EXAMPLE 4

| | |
|---|---|
| (1) Clay | 68 parts by weight |
| (2) Sodium lignin sulfonate | 2 parts by weight |
| (3) Polyoxyethylenealkylaryl sulfate | 5 parts by weight |
| (4) Fine silica powder | 25 parts by weight |

A mixture of the above components is mixed with compound of the present invention in a weight ratio of 4:1 to obtain a wettable powder.

FORMULATION EXAMPLE 5

| | |
|---|---|
| (1) Compound of the present invention | 50 parts by weight |
| (2) Oxylated polyalkylphenyl phosphate-triethanolamine | 2 parts by weight |
| (3) Silicone | 0.2 part by weight |
| (4) Water | 47.8 parts by weight |

The above components are uniformly mixed and pulverized to obtain a base liquid, and

| | |
|---|---|
| (5) Sodium polycarboxylate | 5 parts by weight |
| (6) Anhydrous sodium sulfate | 42.8 parts by weight | are added, and the mixture is uniformly mixed and dried to obtain water-dispersible granules.

FORMULATION EXAMPLE 6

| | |
|---|---|
| (1) Compound of the present invention | 5 parts by weight |
| (2) Polyoxyethyleneoctylphenyl ether | 1 part by weight |
| (3) polyoxyethylene phosphoric acid ester | 0.1 part by weight |
| (4) Granular calcium carbonate | 93.9 parts by weight |

The above components (1) to (3) are preliminarily uniformly mixed and diluted with a proper amount of acetone, and then the mixture is sprayed onto the component (4), and acetone is removed to obtain granules.

FORMULATION EXAMPLE 7

| | |
|---|---|
| (1) Compound of the present invention | 2.5 parts by weight |
| (2) N-methyl-2-pyrrolidone | 2.5 parts by weight |
| (3) Soybean oil | 95.0 parts by weight |

The above components are uniformly mixed and dissolved to obtain an ultra low volume formulation.

The invention claimed is:

1. An acid amide derivative of the formula (I) or a salt thereof:

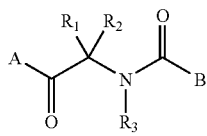
(I)

wherein A is a fused heterocyclic group which may be substituted by X, B is phenyl which may be substituted by Y, X is halogen, alkyl, haloalkyl, alkenyl, haloalkenyl, alkynyl, haloalkynyl, alkoxy, haloalkoxy, alkoxyalkoxy, haloalkoxyalkoxy, alkoxyhaloalkoxy, haloalkoxyhaloalkoxy, alkenyloxy, haloalkenyloxy, alkynyloxy, haloalkynyloxy, alkylthio, haloalkylthio, alkenylthio, haloalkenylthio, alkynylthio, haloalkynylthio, alkylsulfinyl, haloalkylsulfinyl, alkylsulfonyl, haloalkylsulfonyl, dialkylaminosulfonyl, nitro, cyano, phenyl which may be substituted by Y, phenoxy which may be substituted by Y, benzyloxy which may be substituted by Y, pyridyloxy which may be substituted by Y, —$OR_4$, —$SR_5$, —$NR_6$, $R_7$, —$CO_2R_8$, —$C(=O)NR_9$, $R_{10}$ or an unsaturated heterocyclic group (the unsaturated heterocyclic ring may be substituted by halogen, alkyl, haloalkyl, alkoxy or haloalkoxy), Y is halogen, alkyl, haloalkyl, alkoxy, haloalkoxy, alkylthio, haloalkylthio, alkylsulfinyl, haloalkylsulfinyl, alkylsulfonyl, haloalkylsulfonyl, dialkylaminosulfonyl, nitro, cyano, —$OR_4$, —$CO_2R_{11}$, —$CONR_{12}R_{13}$ or an unsaturated heterocyclic group (the unsaturated heterocyclic ring may be substituted by halogen, alkyl, haloalkyl, alkoxy or haloalkoxy), each of $R_1$ and $R_2$ is alkyl, cyano or —$CO_2R_{14}$, or $R_1$ and $R_2$ may together form a 3- to 6-membered saturated carbocyclic ring, $R_3$ is hydrogen, alkyl, alkoxyalkyl, alkylthioalkyl, —$COR_{15}$, —$S(O)mR_{16}$ or —$S(O)nNR_{17}R_{18}$, each of $R_4$ and $R_6$ is hydrogen, —$C(=W)R_{19}$, —$C(=W)OR_{20}$ —$C(=W)SR_{21}$, —$C(=W)NR_{22}R_{23}$, —$S(O)qR_{24}$ or —$S(O)rNR_{25}R_{26}$, $R_5$ is hydrogen, —$C(=W)R_{19}$, —$C(=W)OR_{20}$, —$C(=W)SR_{21}$ or —$C(=W)NR_{22}R_{23}$, $R_7$ is hydrogen, alkyl or haloalkyl, each of $R_8$, $R_9$, $R_{10}$, $R_{11}$, $R_{12}$, $R_{13}$ and $R_{14}$ is hydrogen or alkyl, $R_{15}$ is hydrogen, alkyl or alkoxy, each of $R_{16}$, $R_{17}$, $R_{18}$, $R_{19}$, $R_{20}$, $R_{21}$, $R_{22}$, $R_{23}$, $R_{24}$, $R_{25}$ and $R_{26}$ is alkyl, haloalkyl or phenyl (the phenyl which may be substituted by halogen, alkyl, haloalkyl, alkoxy or haloalkoxy), each of m, n, q and r is from 0 to 2, W is oxygen or sulfur.

2. The acid amide derivative or a salt thereof according to claim 1, wherein the fused heterocyclic group is a 8- to 10-membered fused heterocyclic group containing from 1 to 4 atoms of at least one type selected from the group consisting of O, S and N.

3. The acid amide derivative or a salt thereof according to claim 2, wherein the fused heterocyclic group is benzofuranyl, isobenzofuranyl, dihydrobenzofuranyl, dihydroisobenzofuranyl, benzothienyl, isobenzothienyl, dihydrobenzothienyl, dihydroisobenzothienyl, tetrahydrobenzothienyl, indolyl, isoindolyl, benzoxazolyl, benzothiazolyl, indazolyl, benzimidazolyl, benzodioxolanyl, benzodioxanyl, chromenyl, chromanyl, isochromanyl, chromonyl, chromanonyl, quinolyl, isoquinolyl, cinnolinyl, phthalazinyl, quinazolinyl, quinoxalinyl, indolizinyl, quinolizinyl, imidazopyridyl, naphthyridinyl, pteridinyl, dihydrobenzoxazinyl, dihydrobenzoxazolinonyl, dihydrobenzoxazinonyl or benzothioxanyl.

4. A process for producing an acid amide derivative of the formula (I) or a salt thereof:

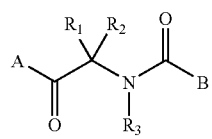
(I)

wherein A is a fused heterocyclic group which may be substituted by X, B is alkyl, cycloalkyl, phenyl which may be substituted by Y, X is halogen, alkyl, haloalkyl, alkenyl, haloalkenyl, alkynyl, haloalkynyl, alkoxy, haloalkoxy, alkoxyalkoxy, haloalkoxyalkoxy, alkoxyhaloalkoxy, haloalkoxyhaloalkoxy, alkenyloxy, haloalkenyloxy, alkynyloxy, haloalkynyloxy, alkylthio, haloalkylthio, alkenylthio, haloalkenylthio, alkynylthio, haloalkynylthio, alkylsulfinyl, haloalkylsulfinyl, alkylsulfonyl, haloalkylsulfonyl, dialkylaminosulfonyl, nitro, cyano, phenyl which may be substituted by Y, phenoxy which may be substituted by Y, benzyloxy which may be substituted by Y, pyridyloxy which may be substituted by Y, —$OR_4$, —$SR_5$, —$NR_6$, $R_7$, —$CO_2R_8$, —$C(=O)NR_9$, $R_{10}$ or an unsaturated heterocyclic group (the unsaturated heterocyclic ring may be substituted by halogen, alkyl, haloalkyl, alkoxy or haloalkoxy), Y is halogen, alkyl, haloalkyl, alkoxy, haloalkoxy, alkylthio, haloalkylthio, alkylsulfinyl, haloalkylsulfinyl, alkylsulfonyl, haloalkylsulfonyl, dialkylaminosulfonyl, nitro, cyano, —$OR_4$, —$CO_2R_{11}$, —$CONR_{12}R_{13}$ or an unsaturated heterocyclic group (the unsaturated heterocyclic ring may be substituted by halogen, alkyl, haloalkyl, alkoxy or haloalkoxy), each of $R_1$ and $R_2$ is alkyl, cyano or —$CO_2R_{14}$, or $R_1$ and $R_2$ may together form a 3- to 6-membered saturated carbocyclic ring, $R_3$ is hydrogen, alkyl, alkoxyalkyl, alkylthioalkyl, —$COR_{15}$, —$S(O)mR_{16}$ or —$S(O)nNR_{17}R_{18}$, each of $R_4$ and $R_6$ is hydrogen, —$C(=W)R_{19}$, —$C(=W)OR_{20}$, —$C(=W)SR_{21}$, —$C(=W)NR_{22}R_{23}$, —$S(O)qR_{24}$ or —$S(O)rNR_{25}R_{26}$, $R_5$ is hydrogen, —$C(=W)R_{19}$, —$C(=W)OR_{20}$, —$C(=W)SR_{21}$ or —$C(=W)NR_{22}R_{23}$, $R_7$ is hydrogen, alkyl or haloalkyl, each of $R_8$, $R_9$, $R_{10}$, $R_{11}$, $R_{12}$, $R_{13}$ and $R_{14}$ is hydrogen or alkyl, $R_{15}$ is hydrogen, alkyl or alkoxy, each of $R_{16}$, $R_{17}$, $R_{18}$, $R_{19}$, $R_{20}$, $R_{21}$, $R_{22}$, $R_{23}$, $R_{24}$, $R_{25}$ and $R_{26}$ is alkyl, haloalkyl or phenyl (the phenyl which may be substituted by halogen, alkyl, haloalkyl, alkoxy or haloalkoxy), each of m, n, q and r is from 0 to 2, W is oxygen or sulfur, which comprises (1) reacting a compound of the formula (II) or a salt thereof:

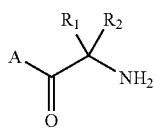

(II)

wherein A, R₁ and R₂ are as defined above, with a compound of the formula (III):

B—COZ (III)

wherein B is as defined above, and Z is hydroxy, alkoxy or halogen, or (2) reacting a compound of the formula (I-1):

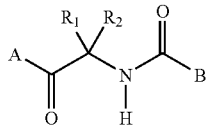

(I-1)

wherein A, B, R₁ and R₂ are as defined above, with a compound of the formula (IV):

R$_{3a}$-T (IV)

wherein R$_{3a}$ is alkyl, alkoxyalkyl, alkylthioalkyl, —COR$_{15}$, —S(O)mR$_{16}$ or —S(O)nNR$_{17}$R$_{18}$, R$_{15}$, R$_{16}$, R$_{17}$, R$_{18}$, m and n are as defined above, and T is halogen.

5. A pesticide which contains the acid amide derivative or a salt thereof as defined in claim 1, as an active ingredient.

6. An agricultural or horticultural pesticide which contains the acid amide derivative or a salt thereof as defined in claim 1, as an active ingredient.

7. An insecticide, miticide or nematicide which contains an acid amide derivative or a salt thereof as defined in claim 1, as an active ingredient.

8. A nematicide which contains an acid amide derivative or a salt thereof as defined in claim 1, as an active ingredient.

9. An agent for controlling parasites on animals, which contains an acid amide derivative or a salt thereof as defined in claim 1, as an active ingredient.

10. An agent for controlling parasites in the bodies of animals, which contains an acid amide derivative or a salt thereof as defined in claim 1, as an active ingredient.

11. A method for controlling a pest, which comprises using an effective amount of an acid amide derivative or a salt thereof as defined in claim 1.

* * * * *